US012202805B2

(12) United States Patent
Olenik et al.

(10) Patent No.: US 12,202,805 B2
(45) Date of Patent: Jan. 21, 2025

(54) PROCESS FOR PREPARING (5S)-{[2-(4-CARBOXYPHENYL)ETHYL] [2-(2-{[3-CHLORO-4'-(TRIFLUOROMETHYL) BIPHENYL-4-YL]METHOXY}PHENYL) ETHYL]AMINO]-5,6,7,8-TETRAHYDROQUINOLINE-2-CARBOXYLIC ACID AND ITS CRYSTALLINE FORMS FOR USE AS PHARMACEUTICALLY ACTIVE COMPOUND

(71) Applicants: Bayer Aktiengesellschaft, Leverkusen (DE); Bayer Pharma Aktiengesellschaft, Berlin (DE)

(72) Inventors: Britta Olenik, Bottrop (DE); Birgit Keil, Dusseldorf (DE); Bernd Rösler, Wuppertal (DE); Peter Fey, Wuppertal (DE); Heiko Schirmer, Solingen (DE); Guido Becker, Krefeld (DE); Julian Egger, Remscheid (DE); Clemens Bothe, Leverkusen (DE); Helene Faber, Dormagen (DE)

(73) Assignees: Bayer Aktiengesellschaft, Leverkusen (DE); Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 18/506,737

(22) Filed: Nov. 10, 2023

(65) Prior Publication Data

US 2024/0116874 A1     Apr. 11, 2024

Related U.S. Application Data

(63) Continuation of application No. PCT/EP2022/087952, filed on Dec. 28, 2022.

(30) Foreign Application Priority Data

Dec. 29, 2021   (EP) .................... 21218163

(51) Int. Cl.
| | |
|---|---|
| C07D 215/48 | (2006.01) |
| A61K 9/00 | (2006.01) |
| A61P 9/12 | (2006.01) |
| A61P 11/08 | (2006.01) |

(52) U.S. Cl.
CPC .......... *C07D 215/48* (2013.01); *A61K 9/0075* (2013.01); *A61P 9/12* (2018.01); *A61P 11/08* (2018.01)

(58) Field of Classification Search
CPC .................................................. C07D 215/48
USPC ....................................................... 514/313
See application file for complete search history.

(56) References Cited

U.S. PATENT DOCUMENTS

| | | | |
|---|---|---|---|
| 4,873,262 A | 10/1989 | Junge et al. | |
| 4,880,802 A | 11/1989 | Schohe et al. | |
| 5,047,422 A | 9/1991 | Junge et al. | |
| 6,693,102 B2 | 2/2004 | Stasch et al. | |
| 6,743,798 B1 | 6/2004 | Straub et al. | |
| 6,833,364 B1 | 12/2004 | Straub et al. | |
| 6,939,989 B2 | 9/2005 | Härter et al. | |
| 6,939,990 B2 | 9/2005 | Härter et al. | |
| 7,087,644 B1 | 8/2006 | Alonso-Alija et al. | |
| 7,173,037 B2 | 2/2007 | Alonso-Alija et al. | |
| 7,705,043 B2 | 4/2010 | Alonso-Alija et al. | |
| 8,420,656 B2 | 4/2013 | Follmann et al. | |
| 8,653,099 B2 | 2/2014 | Colburn et al. | |
| 8,673,903 B2 | 3/2014 | Hübsch et al. | |
| 8,921,377 B2 | 12/2014 | Follmann et al. | |
| 8,981,104 B2 * | 3/2015 | Hahn ....................... | A61P 9/12 546/170 |
| 9,096,592 B2 | 8/2015 | Follmann et al. | |
| 9,688,636 B2 | 6/2017 | Hahn et al. | |
| 10,053,428 B2 | 8/2018 | Hahn et al. | |
| 10,729,647 B2 | 8/2020 | Green | |
| 2004/0082658 A1 | 4/2004 | Harter et al. | |
| 2004/0082798 A1 | 4/2004 | Alonso-Alija et al. | |

(Continued)

FOREIGN PATENT DOCUMENTS

| | | |
|---|---|---|
| CA | 2804470 A1 | 1/2012 |
| CA | 2809911 A1 | 3/2012 |

(Continued)

OTHER PUBLICATIONS

Artursson et al., "Correlation between oral drug absorption in humans and apparent drug permeability coefficients in human intestinal epithelial (Caco-2) cells", Biochem. Biophys, 1991, 175 (3), 880-885.

(Continued)

*Primary Examiner* — Taofiq A Solola
(74) *Attorney, Agent, or Firm* — COOLEY LLP; Heidi A. Erlacher; Christine E. Dunne

(57) ABSTRACT

The present invention relates to a novel and improved process for preparing (5S)-{[2-(4-carboxyphenyl)ethyl][2-(2-{[3-chloro-4'-(trifluo-romethyl)biphenyl-4-yl] methoxy}phenyl)ethyl]amino}-5,6,7,8-tetrahydroquinoline-2-carboxylic acid of the formula (I) and to novel crystalline forms of it, which is i.a. the pseudopolymorphic form monohydrate I (I-M-I) or the pseudopolymorphic form monohydrate II (I-M-II), furthermore the present invention relates to a novel and selective crystallization process for preparation of the pseudopolymorphic form monohydrate I (I-M-I) or the pseudopolymorphic form monohydrate II (I-M-II), preferably monohydrate I of formula (I-M-I) and to pharmaceutical compositions comprising monohydrate I of formula (I-M-I) and to its use for the treatment and/or prevention of diseases, in particular for the treatment and/or prevention of pulmonary and cardiopulmonary and cardiovascular diseases.

27 Claims, 45 Drawing Sheets

(56) References Cited

U.S. PATENT DOCUMENTS

| | | |
|---|---|---|
| 2004/0092593 A1 | 5/2004 | Harter et al. |
| 2004/0110840 A1 | 6/2004 | Harter et al. |
| 2004/0176446 A1 | 9/2004 | Alonso-Alija et al. |
| 2006/0052397 A1 | 3/2006 | Alonso-Alija et al. |
| 2009/0227640 A1 | 9/2009 | Bartel et al. |
| 2011/0141409 A1 | 6/2011 | Ashida |
| 2013/0237551 A1 | 9/2013 | Follmann et al. |
| 2013/0267548 A1 | 10/2013 | Follmann et al. |
| 2014/0031391 A1 | 1/2014 | Hahn et al. |
| 2014/0350020 A1 | 11/2014 | Follmann et al. |
| 2015/0080414 A1 | 3/2015 | Follmann et al. |
| 2015/0148376 A1 | 5/2015 | Hahn et al. |
| 2015/0174113 A1 | 6/2015 | Hübsch et al. |
| 2017/0260139 A1 | 9/2017 | Hahn et al. |
| 2023/0183181 A1 | 6/2023 | Fey et al. |

FOREIGN PATENT DOCUMENTS

| | | |
|---|---|---|
| CA | 2816671 A1 | 5/2012 |
| EP | 0041488 A1 | 12/1981 |
| EP | 0064964 B1 | 8/1984 |
| EP | 0270947 B1 | 5/1993 |
| EP | 1617820 B1 | 3/2018 |
| FR | 2659853 A1 | 9/1991 |
| WO | WO-9015047 A1 | 12/1990 |
| WO | WO-9518617 A1 | 7/1995 |
| WO | WO-9962505 A2 | 12/1999 |
| WO | WO-0006568 A1 | 2/2000 |
| WO | WO-0006569 A1 | 2/2000 |
| WO | WO-0035882 A1 | 6/2000 |
| WO | WO-0119780 A2 | 3/2001 |
| WO | WO-0242301 A1 | 5/2002 |
| WO | WO-02070459 A1 | 9/2002 |
| WO | WO-02070460 A1 | 9/2002 |
| WO | WO-02070461 A1 | 9/2002 |
| WO | WO-02070462 A1 | 9/2002 |
| WO | WO-02070510 A2 | 9/2002 |
| WO | WO-03095451 A1 | 11/2003 |
| WO | WO-2005012291 A1 | 2/2005 |
| WO | WO-2006104826 A2 | 10/2006 |
| WO | WO-2009023669 A1 | 2/2009 |
| WO | WO-2009032249 A1 | 3/2009 |
| WO | WO-2011147809 A1 | 12/2011 |
| WO | WO-2011161099 A1 | 12/2011 |
| WO | WO-2012004258 A1 | 1/2012 |
| WO | WO-2012028647 A1 | 3/2012 |
| WO | WO-2012059549 A1 | 5/2012 |
| WO | WO-2012122340 A1 | 9/2012 |
| WO | WO-2013024895 A1 | 2/2013 |
| WO | WO-2013157528 A1 | 10/2013 |
| WO | WO-2014012934 A1 | 1/2014 |
| WO | WO-2014068099 A1 | 5/2014 |
| WO | WO-2019081456 A1 | 5/2019 |
| WO | WO-2021233783 A1 | 11/2021 |
| WO | WO-2023126436 A1 | 7/2023 |
| WO | WO-2023126437 A1 | 7/2023 |
| WO | WO-2023126438 A1 | 7/2023 |

OTHER PUBLICATIONS

Becker et al., "Effects of different pulmonary vasodilators on arterial saturation in a model of pulmonary hypertension," PLoS One 2013, 8: 1-8.

Becker et al., "V/Q mismatch" in secondary pulmonary hypertension— riociguat in comparison, Pulmonology 65, Suppl. 2, 2011, S122-S123.

Becker-Pelster et al., "Inhaled mosliciguat (BAY 1237592): targeting pulmonary vasculature via activating apo-sGC", Respiratory Research, vol. 23, No. 1, Oct. 1, 2022, 15 pages.

Begg et al., "Translation of Inhaled Drug Optimization Strategies into Clinical Pharmacokinetics and Pharmacodynamics Using GSK2292767A, a Novel Inhaled Phosphoinositide 3-Kinase d Inhibitor," J. Pharmacol. Exp. Ther. 2019; 369: 443-453.

Beyer et al., "Stimulation of soluble guanylate cyclase reduces experimental dermal fibrosis," Ann Rheum Dis, Jun. 2012; 71: 1019-1026.

Bice et al., "NO-independent stimulation or activation of soluble guanylyl cyclase during early reperfusion limits infarct size," Cardiovascular Research, Oxford Journal of Medicine, 2014, 101: 220-228.

Bitler, "The Preparation and Properties of Crystalline Firefly Luciferin," Arch Biochem Biophys., Dec. 1957; 72(2): 358-68.

Blanco, et al. "Hemodynamic and Gas Exchange Effects of Sildenafil in Patients with Chronic Obstructive Pulmonary Disease and Pulmonary Hypertension," Am. J. Respir. Crit. Care Med., Feb. 2010; 181(3): 270-278.

CAS-Registry No. 1000533-03-8, "2-(5-fluoro-2-Methoxyphenyl) ethanamine", Jan. 23, 2008, 2 pages.

CAS-Registry No. 192139-92-7, Aug. 5, 1997, 2 pages.

CAS-Registry No. 56985-32-1, "9,11-dideoxy-9a,11a-epoxymethano-prosta-5E,13E-dien-1-oic acid," Cayman Chemical: Product Information 5-trans U-44069; Item No. 16442; 2020, 1 page.

CAS-Registry No. 885050-65-7, May 21, 2006, 1 page.

ClinicalTrials.gov Identifier: NCT04609943; Oct. 30, 2020, 7 pages.

"DAS-1802HC Keithley 12-Bit Multifunctional I/O Board", Artisan Technology Group, Stock # 66977-9; 1999. 3 pages.

Dasgupta et al., "Soluble Guanylate Cyclase: A New Therapeutic Target for Pulmonary Arterial Hypertension and Chronic Thromboembolic Pulmonary Hypertension," Clinical Pharmacology and Therapeutics, vol. 97, No. 1, Nov. 28, 2014, pp. 88-102.

De Boer et al., "A critical view on lactose-based drug formulation and device studies for dry powder inhalation: Which are relevant and what interactions to expect?" Advanced Drug Delivery Reviews 64 (2012) 257-274.

De Boer et al., "Dry powder inhalation: past, present and future," Expert Opinion on Drug Delivery, 2017, vol. 14(4), pp. 499-512.

Durgin et al., "Loss of smooth muscle CYB5R3 amplifies angiotensin II-induced hypertension by increasing sGC heme oxidation" JCI Insight 2019; 4(19): e129183, 16 pages.

Elkins et al., "Inspiratory Flows and Volumes in Subjects with Cystic Fibrosis Using a New Dry Powder Inhaler Device," The Open Respiratory Medicine Journal, 2014, 8, pp. 1-7.

Elkins et al., "Inspiratory Flows and Volumes in Subjects with Non-CF Bronchiectasis Using a New Dry Powder Inhaler Device," The Open Respiratory Medicine Journal, 2014, 8, pp. 8-13.

Erlanson et al., "Fragment-Based Drug Discovery," J. Med. Chem.; Jun. 2004; 47(14): 3463-3482.

Evgenov et al., "Inhaled Agonists of Soluble Guanylate Cyclase Induce Selective Pulmonary Vasodilation," AM. J. Resplr. Crit. Care Med., 2007, 176: 1138-1145.

Evgenov et al., "NO-Independent Stimulators and Activators of Soluble Guanylate Cyclase: Discovery and Therapeutic Potential," Nature Reviews: Drug Discovery, Sep. 2006, 5(9): 755-768.

FDA World Health Organization, "FDA Approves Bayer's New Class of Drug Adempas® (riociguat) tablets to Treat Adults with PAH and Persistent, Recurrent or Inoperable CTEPH," PR Newswire; Oct. 8, 2013, 7 pages.

Gerlach et al., "Synthesis of Benzoic and Tetralone Carboxylic Acid Esters from Phenols by Palladium Catalyzed Alkoxy/Aryloxy Carbonylation," Tetrahedron Letters; 1992. 33(38): 5499-5502.

Ghofrani et al., "Acute effects of riociguat in borderline or manifest pulmonary hypertension associated with chronic obstructive pulmonary disease," Pulm Gire. Jun. 2015;5{2}: 296-304.

Ghofrani et al., "Interventional and pharmacological management of chronic thromboembolic pulmonary hypertension," Respiratory Medicine, Elsevier, Amsterdam, NL, vol. 177, Jan. 6, 2021,12 pages.

Ghofrani et al., "New therapeutic options in the treatment of pulmonary arterial hypertension," Herz, 2005, 30(4): 296-302.

Ghosh et al., "An inherent dysfunction in soluble guanylyl cyclase is present in the airway of severe asthmatics and is associated with aberrant redox enzyme expression and compromised NO-cGMP signaling," in Redox Biology 39 (2021) 101832, pp. 1-13.

Ghosh, "Studies on oxygen heterocycles: Part-1: Acid catalysed and photochemical reactions of some aryldiazoketones," Tetrahedron, 1989, 45(5): 1441-1446.

(56) References Cited

OTHER PUBLICATIONS

Glaab et al., "Repetitive measurements of pulmonary mechanics to inhaled cholinergic challenge in spontaneously breathing mice,". J Appl Physiol 2004; 97: 1104-1111.

Grasmeijer et al. "Recent advances in the fundamental understanding of adhesive mixtures for inhalation," Curr Pharm Des. 2015; 21(40): 5900-14.

Greene, "The Role of Protective Groups In Organic Synthesis," Fifth Edition, Wiley, New York, 2014, 17 pages.

Gur, S. et al., "Exploring the Potential of NO-Independent Stimulators and Activators of Soluble Guanylate Cyclase for the Medical Treatment of Erectile Dysfunction", Current Pharmaceutical Design, 2010, vol. 16, No. 14, 1619-1633.

Healy et al., "Dry powders for oral inhalation free of lactose carrier particles," Advance Drug Delivery reviews 75, (2014), pp. 32-52.

Hoenicka, "Purified soluble guanylyl cyclase expressed in a baculovirus/Sf9 system: stimulation by YC-1, nitric oxide, and carbon monoxide," J Mol Med (Berl); Jan. 1999; 77(1): 14-23.

Hoeper et al., "Diagnosis, Assessment, and Treatment of Non-Pulmonary Arterial Hypertension Pulmonary Hypertension," Journal of the Am. College of Cardiology, 2009, 54(1): S85-S96.

Horig et al., "From bench to clinic and back: Perspective on the 1st IQPC Translational Research conference," Dec. 2004, Journal of Translational Medicine, 2(1): 44, 8 pages.

Hoymann et al., "Measurement of lung function in rodents in vivo," Methods in Pulmonary Research: Birkhäuser Basel; 1998:1-28.

Hoymann et al., "New developments in lung function measurements in rodents," Exp 5 Toxicol Pathol 2006; 57 Suppl 2: 5-11.

Hoymann, "Lung function measurements in rodents in safety pharmacology studies," Front Pharmacol. Aug. 28, 2012 (3), 156: 1-11.

Humbert et al., "Cellular and Molecular Pathobiology of Pulmonary Arterial Hypertension," Journal of The Am. College of Cardiology, 2004, 43(12): S13-S24.

Humbert et al., "The 4th World Symposium on Pulmonary Hypertension," Journal of the Am. College of Cardiology, 2009, 54(1): S1-S2.

Ito et al., "Current Drug Targets and Future Therapy of Pulmonary Arterial Hypertension," Current Med. Chemistry, 2007, 14: 719-733.

Jindal N. et al., "Inhalation of nitric oxide in acute respiratory distress syndrome," J Lab Clin Med Jul. 2000; 136: 21-28.

Johnson E. et al., "Acute lung injury: epidemiology, pathogenesis, and treatment," J Aerosol Med Pulm Drug Deliv. Aug. 2010; 23(4): 243-252.

Kinnunen et al., "An Investigation into the Effect of Fine Lactose Particles on the Fluidization Behaviour and Aerosolization Performance of Carrier-Based Dry Powder Inhaler Formulations", AAPS Pharmscitech, vol. 15, No. 4, Apr. 23, 2014, 12 pages.

Kou et al., "Physico-chemical aspects of lactose for inhalation," Adv. Drug Del. Reviews 64 (2012), 220-232.

Liu et al., "(R )- and (S)-5,6, 7,8-Tetrahydro-1-hydroxy-N,N-dipropyl-9H-benzocyclohepten-8-ylaminen. Stereoselective Interactions with 5-HT1A Receptors in the Brain," J. Med. Chem., 1989, 32: 2311-2318.

Maggie et al., "A New Pathway to Airway Relaxation: Targeting the "Other" Cyclase in Asthma" American Journal of Respiratory Cell and Molecular Biology vol. 62, No. 1, Jan. 2020, 2 pages.

Martin, "Structure of Cinaclguat (BAY 58-2667) Bound to Nostoc H-NOX Domain Reveals Insights into Heme-mimetic Activation of the Soluble Guanylyl Cyclase," Journal of Biol. Chem., Jul. 16, 2010, 285(29): 22651-22657.

Montani et al., "Updated clinical classification of pulmonary hypertension," Pulmonary Circulation, Disease and their treatment, Third Edition, Hodder Arnold Pub., Peacock et al (Eds.), 2011, 197-206.

Moon et al., "Delivery Technologies for Orally Inhaled Products: an Update", AAPS PharmSciTech., Feb. 19, 2019; 20(3):117, pp. 1-17.

Munzel et al., "Targeting heme-oxidized soluble guanylate cyclase: solution for all cardiorenal problems in heart failure?" Hypertension 2007; 49: 974-976.

Nossaman et al., "Stimulators and Activators of Soluble Guanylate Cyclase: Review and Potential Therapeutic Indications," Critical Care Research and Practice, 2012, 290805: 1-12.

Pettit et al., "Synthesis of the 6- and 7-Hydroxy-5,8-dioxocarbostyrils," Journal of Organic Chemistry, Mar. 1968, 33(3): 1089-1092.

Pilcer et al., "Lactose characteristics and the generation of the aerosol," Adv Drug Del Reviews 64 (2012), 233-256.

Raabe et al., "Regional Deposition of Inhaled Monodisperse Coarse and Fine Aerosol Particles in Small Laboratory Animals," The Annals of Occupational Hygiene 1988; 32: 53-63.

Rahaman et al., "Cytochrome b5 Reductase 3 Modulates Soluble Guanylate Cyclase Redox State and cGMP Signaling," Circ Res 2017; 121: 137-148.

Rosenzweig et al., "Emerging treatments for pulmonary arterial hypertension," Expert Opinion Emerging Drugs, 2006, 11(4): 609-619.

Sandner et al., "Discovery and development of sGC stimulators for the treatment of pulmonary hypertension and rare diseases," Nitric Oxide 2018; 77: 88-95.

Sandner et al., "Soluble guanylate cyclase stimulators and activators," Handbook Exp Pharmacol., 264, 2018, pp. 355-394.

Sandner P. et al., "Anti-fibrotic effects of soluble guanylate cyclase stimulators and activators: A review of the preclinical evidence," Respir Med. Jan. 2017: 122 Suppl 1:S1-S9.

Schafer, et al., "Failure is an option: learning from unsuccessful proof-of-concept trials," Drug Discov. Today. Nov. 2008; 13(21-22): 913-916.

Schmidt et al., "NO- and Haem-Independent Soluble Guanylate cyclase Activators," Handbook of Experimental Pharmacology, 2009; 191: 309-339.

Schuhmacher et al., "High-throughput determination of the free fraction of drugs strongly bound to plasma proteins," J Pharm Sci., Apr. 2004; 93(4): 816-30.

Shekunov et al., "Particle size analysis in pharmaceutics: Principles, Methods and Applications," Pharm. Res. 2007, 24 (2), S203-S227.

Simonneau et al., "Haemodynamic definitions and updated clinical classification of pulmonary hypertension", European Respiratory Journal, 2019; 53: 1801913, pp. 1-13.

Singh et al., "Plethysmography and impulse oscillometry assessment of tiotropium and ipratropium bromide; a randomized, double-blind, placebo controlled, cross-over study in healthy subjects," Br. Journal Clin Pharmacol, 2006, 61:4, 398-404.

Stachel et al., "Discovery of pyrrolidine-based b-secretase inhibitors: Lead advancement through conformational design for maintenance of ligand binding efficiency," Bioorganic Med. Chem. Letters, 2012, 22: 240-244.

Stasch et al., "NO-and Haem-Independent Activation of Soluble Guanylyl Cyclase: Molecular Basis and Cardiovascular Implications of a New Pharmacological Principle," British Journal of Pharmacology, 2002, Bd. 136 (5): 773-783.

Stasch et al., "Renal effects of soluble guanylate cyclase stimulators and activators: a review of the preclinical evidence," Current Opinions in Pharmacology (2015) 21: 95-104.

Stasch et al., "Targeting the Heme-Oxidized Nitric Oxide Receptor for Selective Vasodilation of Diseased Blood Vessels," J. Clin. Invest., Sep. 2006, 116(9): 2552-2561.

Stasch J et al., "Soluble guanylate cyclase as an emerging therapeutic target in cardiopulmonary disease," Circulation, May 24, 2011; 123(20): 2263-73.

Stolz et al., "A randomised, controlled trial of bosentan in severe COPD," European Resp. Journal, 2008 32: 619-628.

Takeuchi et al., "Rhodium Complex-Catalyzed Desilylative Cyclocarbonylation of 1-Aryl-2-(trimethylsilyl)acetylenes: A New Route to 2,3,-Dihydro-1H-inden-1-ones," J. Org. Chem. 1993; 58(20): 5386-5392.

Vanejevs et al., "Positive and Negative Modulation of Group I Metabotropic Glutamate Receptors," Journal Med. Chem., 2008, 51: 634-647.

Voswinckel et al., Favorable effects of inhaled Treprostinil in severe pulmonary hypertension, Journal of American College of Cardiology vol. 48, No. 8, Oct. 17, 2006: 1672-81.

(56) References Cited

OTHER PUBLICATIONS

White et al., "Soluble Guanylate Cyclase Agonists Induce Bronchodilation in Human Small Airways," Am J Respir Cell Mol Biol vol. 62, Issue 1, Jan. 2020, pp. 43-48.
Witte et al., "Experimental heart failure in rats: effects on cardiovascular circadian rhythms and on myocardial 13-adrenergic signaling," 2000, 47: 350-358.
Wood et al., "Smooth muscle cytochrome b5 reductase 3 deficiency accelerates pulmonary hypertension development in sickle cell mice," Blood Adv 2019; 3: 4104-4116.
Wunder et al., "A cell-based cGMP assay useful for ultra-high-throughput screening and identification of modulators of the nitric oxide/cGMP pathway," Anal Biochem. Apr. 2005; 339(1): 104-12.
Zhang et al., "Compilation of 222 drugs' plasma protein binding data and guidance for study designs," Drug Discovery Today 2012; 9-10(17): 475-485.

\* cited by examiner

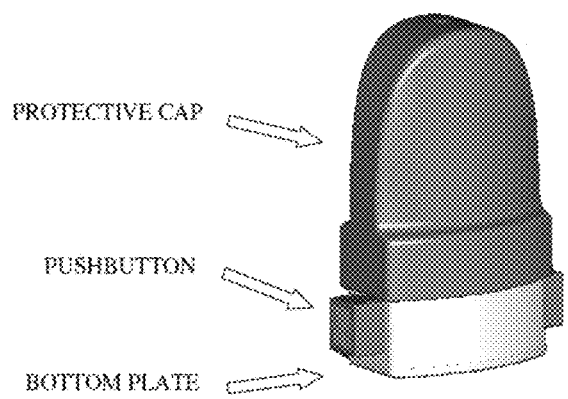
Fig. 1a: capsule based single-unit dose inhaler
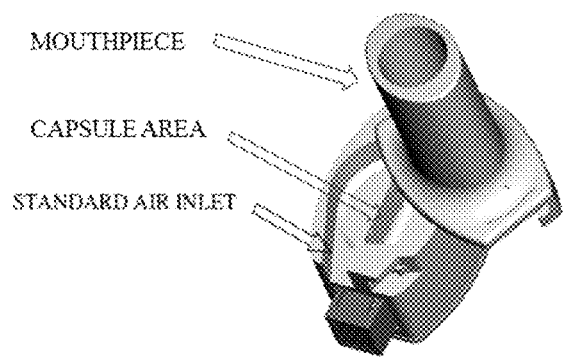
Fig. 1b: capsule based single-unit dose inhaler

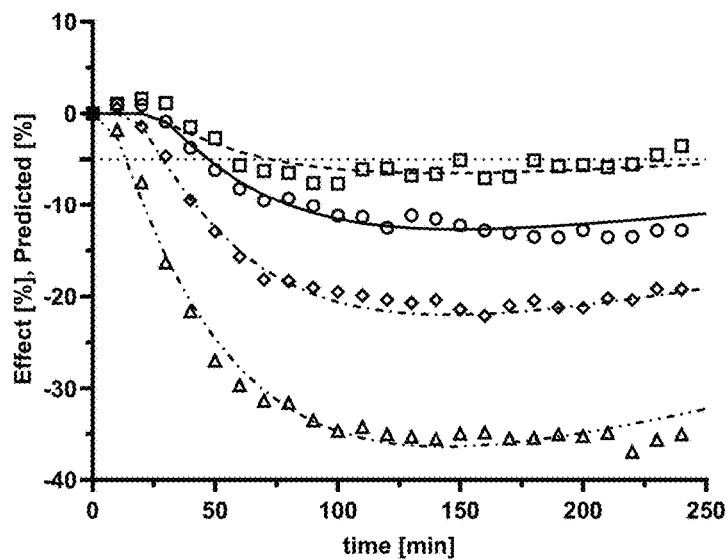
Fig. 2: Observed (symbols) and fitted (solid lines) PAP es after administration of 0.15, 0.5, 1.5 and 5 µg/kg Example 1 (doses expressed as lung deposited doses) to minipigs (7 min inhalation as liquid aerosol). Relevant PAP reduction of 5% indicated as dotted line

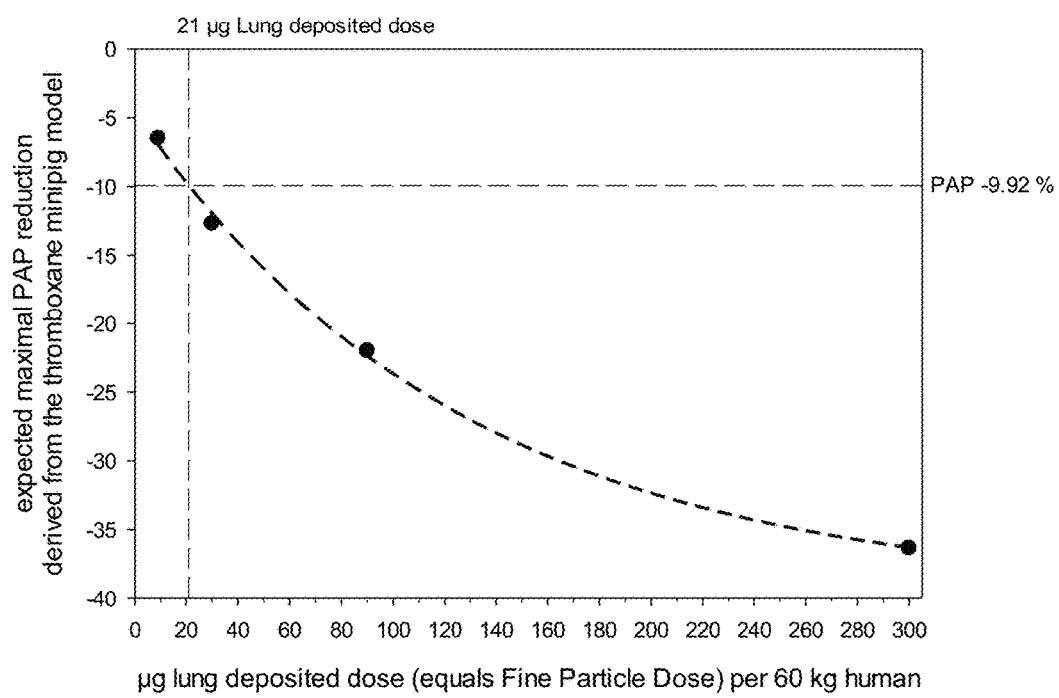
Fig. 3: Maximal expected PAP reduction for a 60 kg human at the corresponding lung deposited doses (FPD) based on the results of the anaesthetized thromboxane minipig model without considering interspecies differences in protein binding.

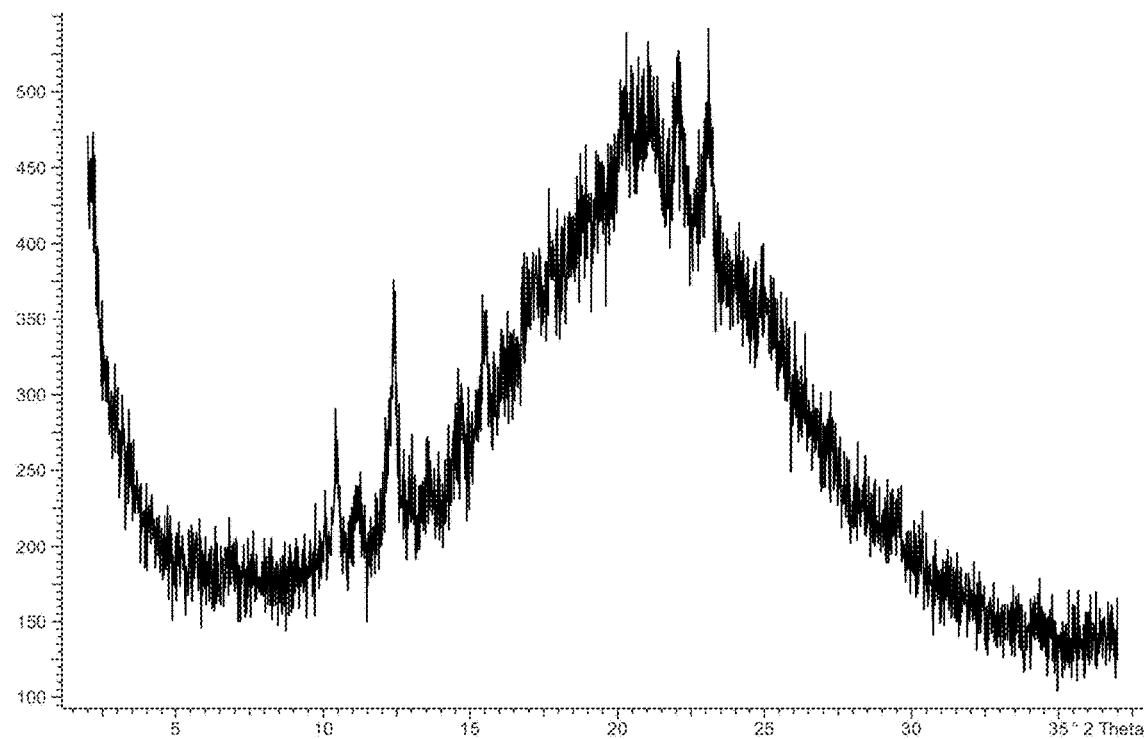
Fig. 4: X-Ray powder diffractogram of the amorphous residue build on salt screening experiments with L-arginine

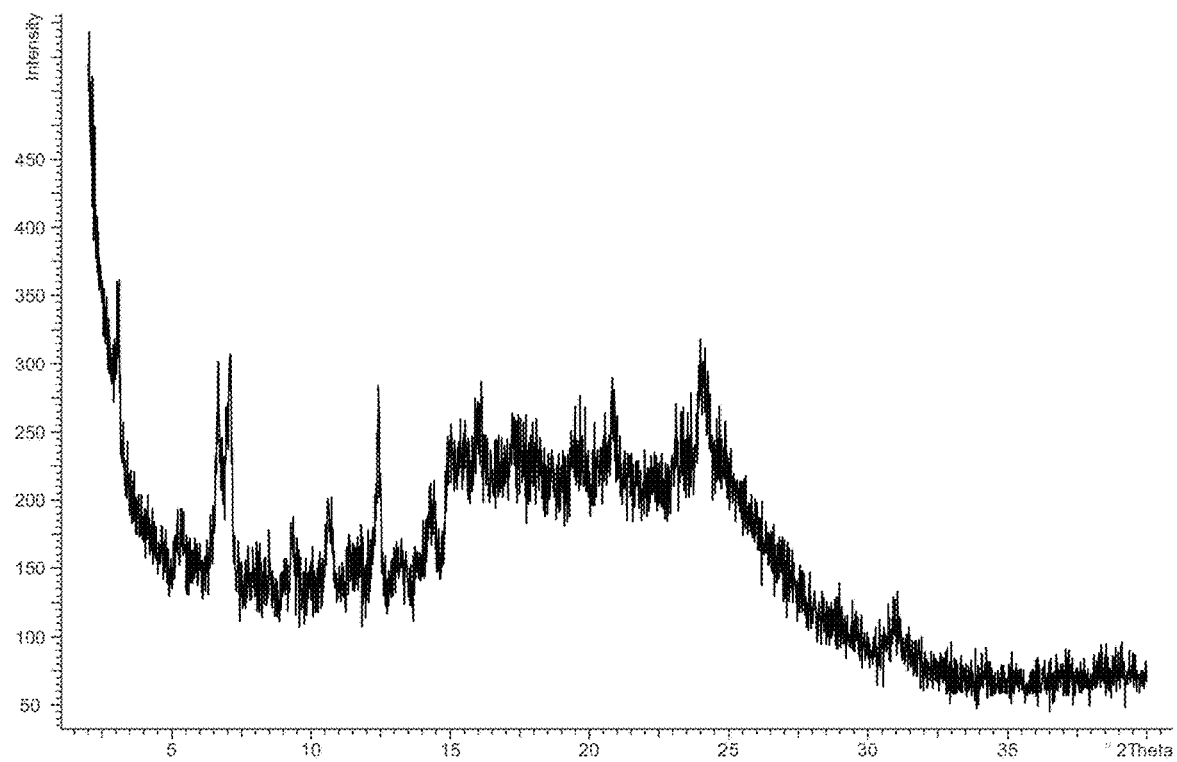
Fig. 5: X-Ray powder diffractogram of the Semihydrate, example 6a
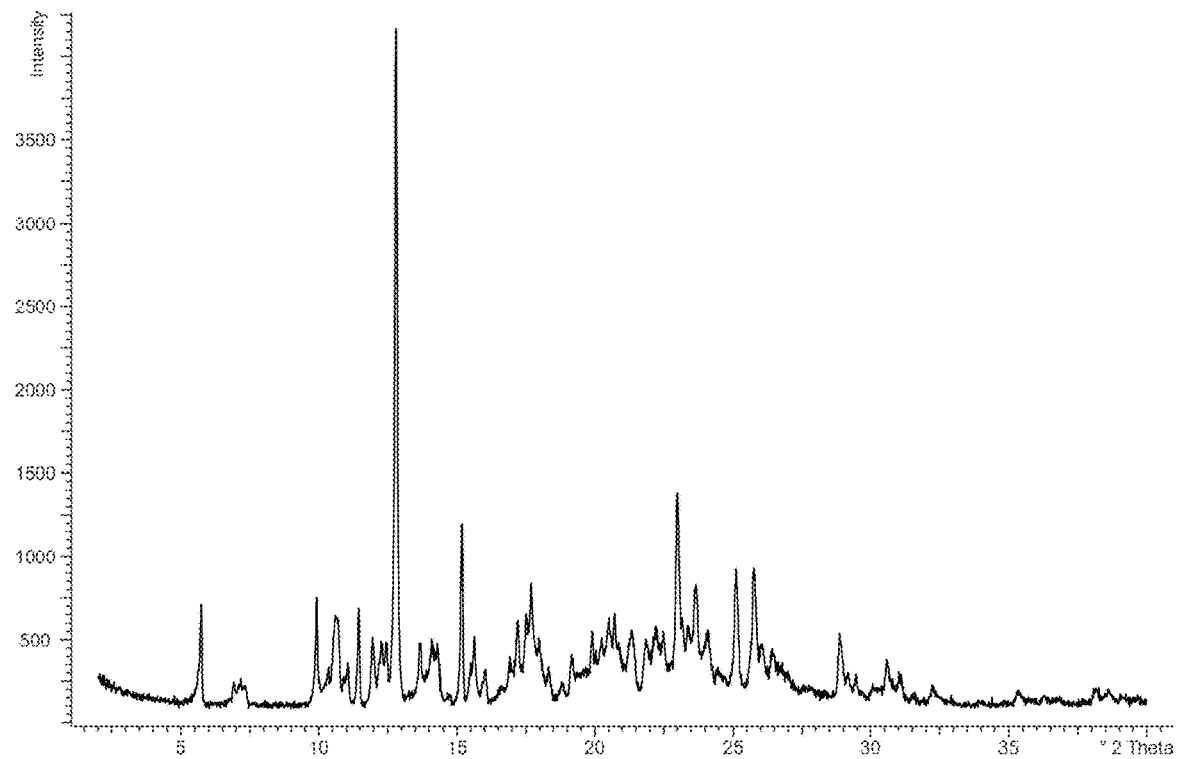
Fig. 6: X-Ray powder diffractogram of the Monohydrate 1, example 6b

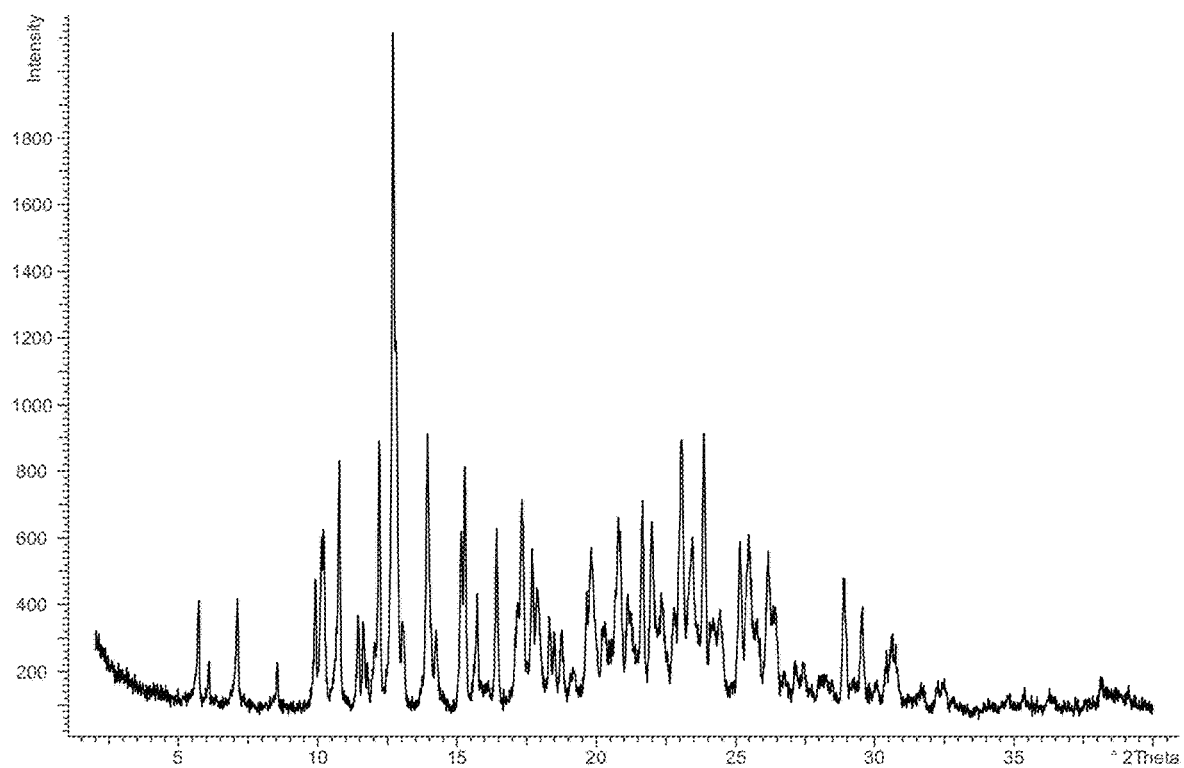
Fig. 7: X-Ray powder diffractogram of the Monohydrate II, example 6c
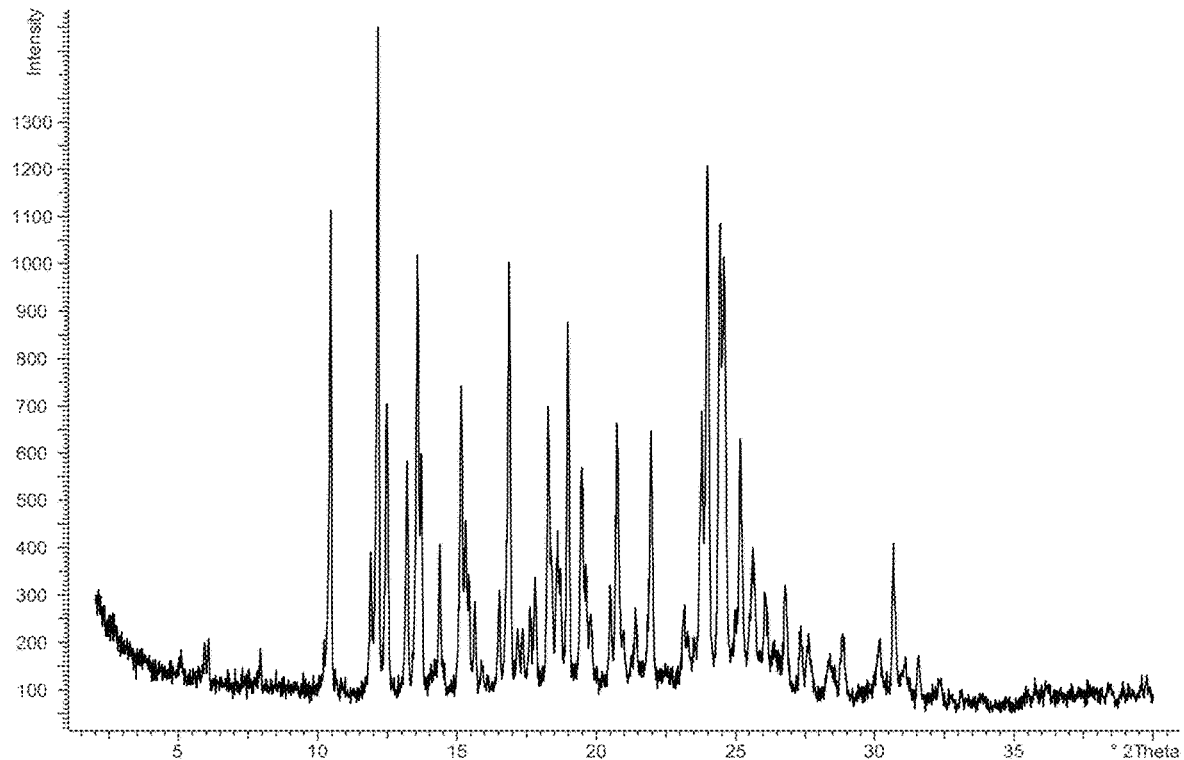
Fig. 8: X-Ray powder diffractogram of the 1,25-Hydrate, example 6d

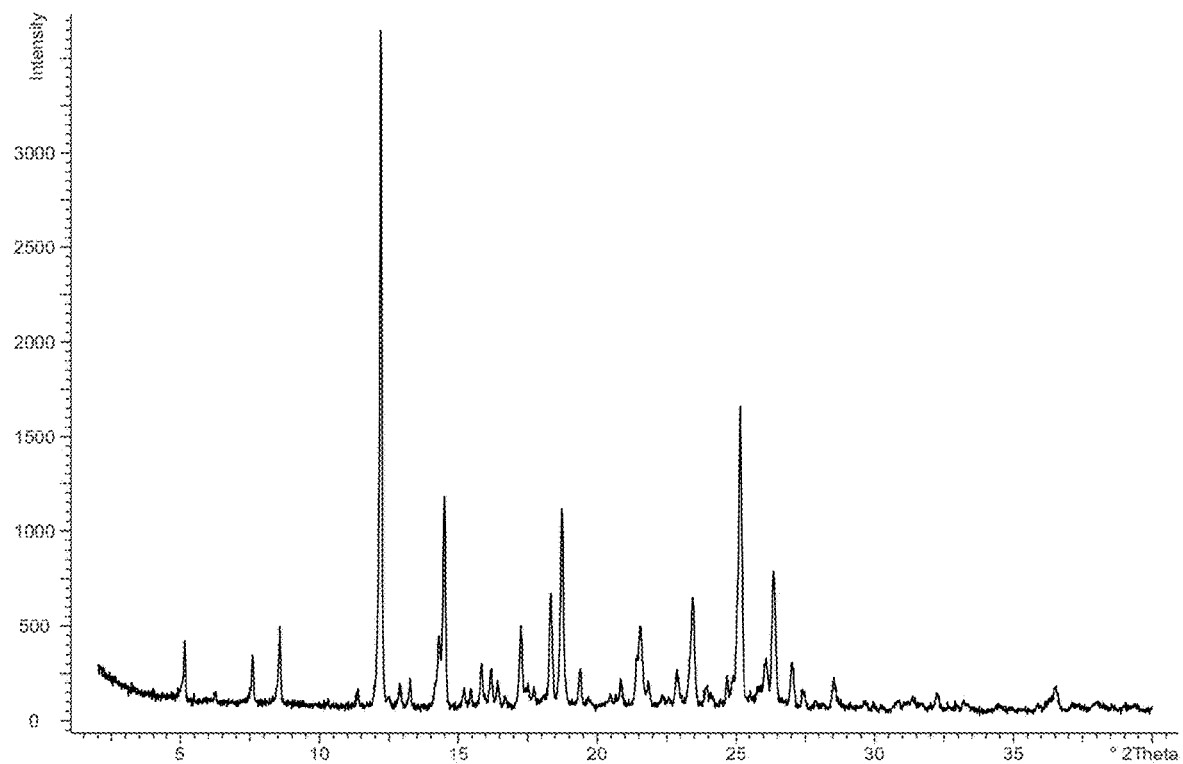
Fig. 9: X-Ray powder diffractogram of the Sesquihydrate, example 6e
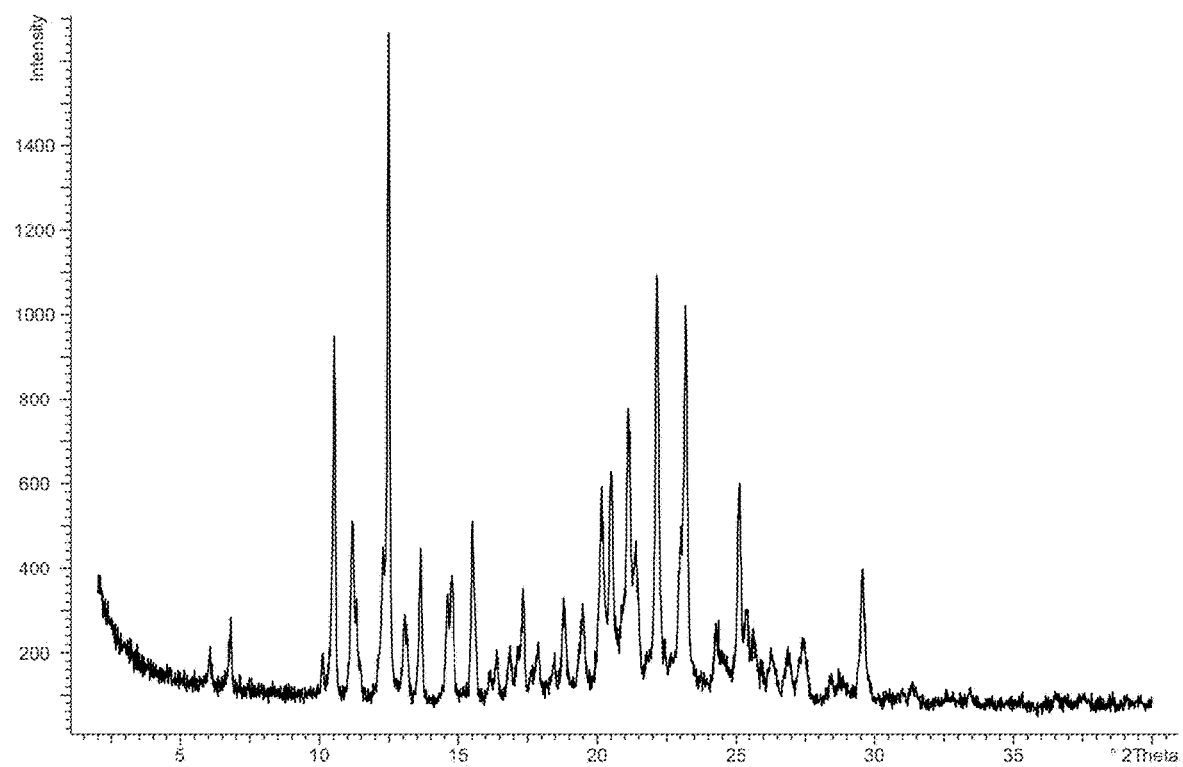
Fig. 10: X-Ray powder diffractogram of the Dihydrate, example 6f

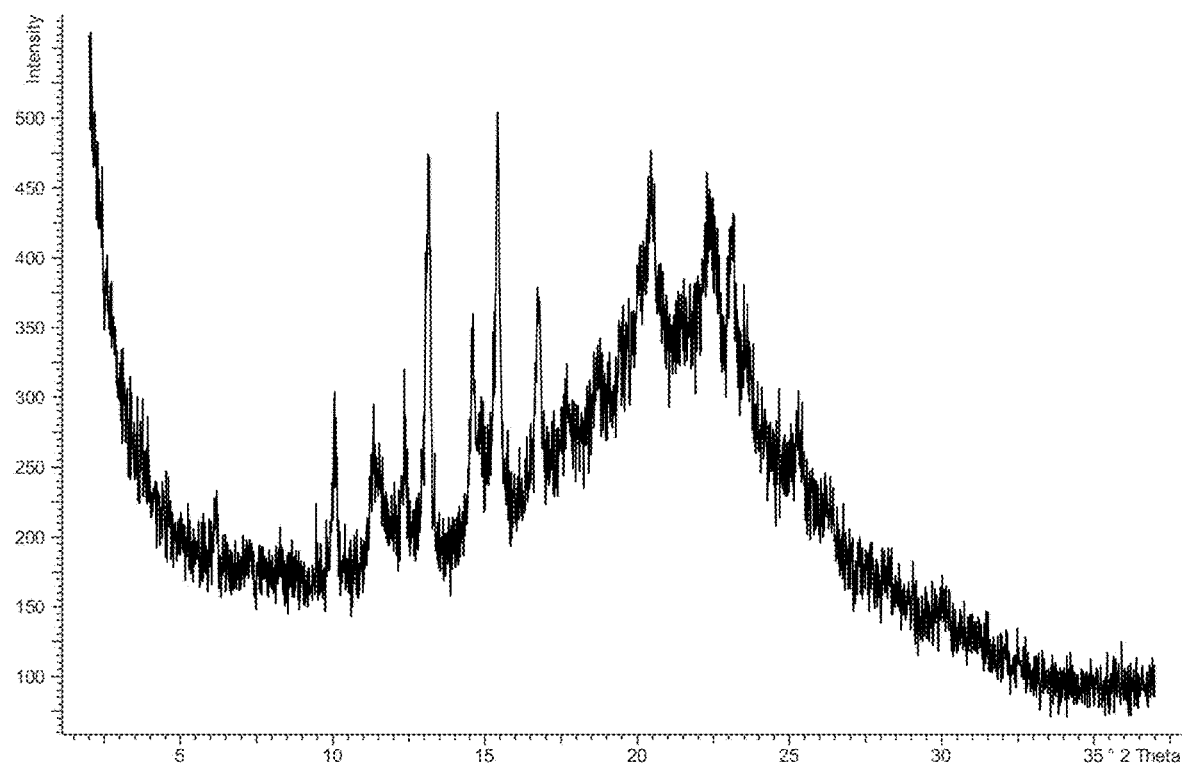
Fig. 10a: X-ray powder diffractogram of example 6f after drying
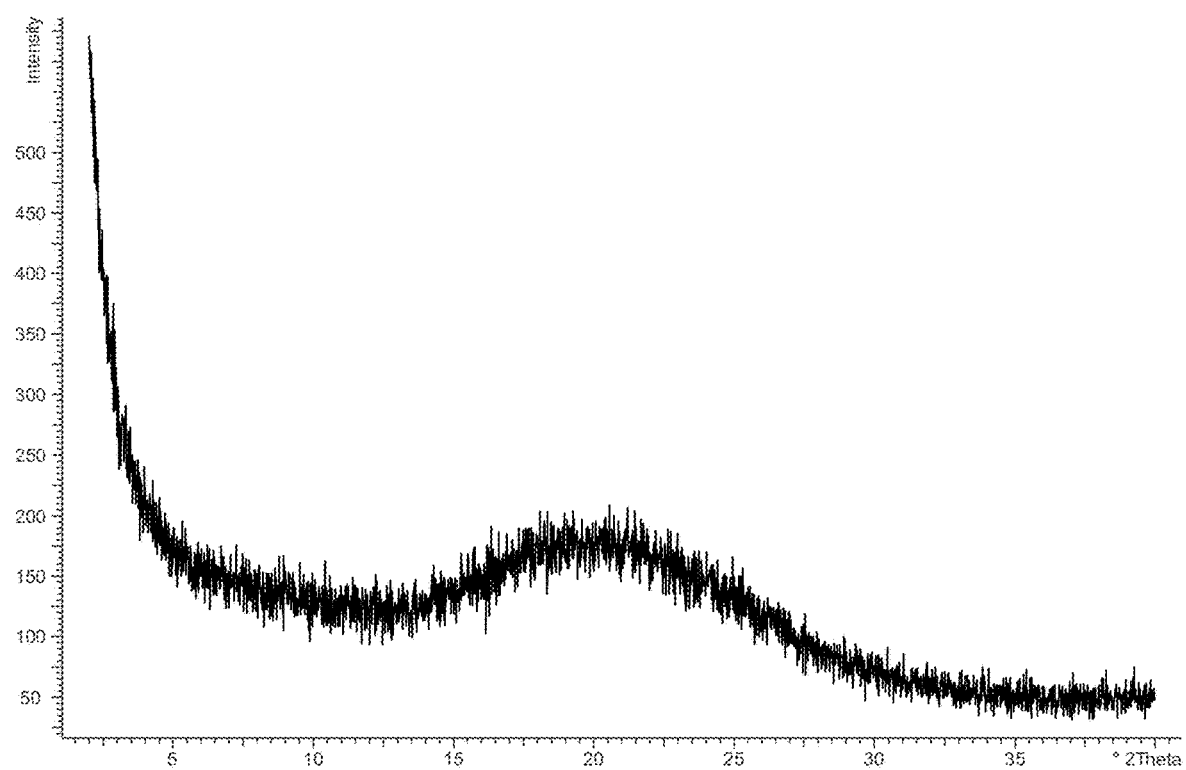
Fig. 11: X-Ray powder diffractogram of the amorphous form, example 6g

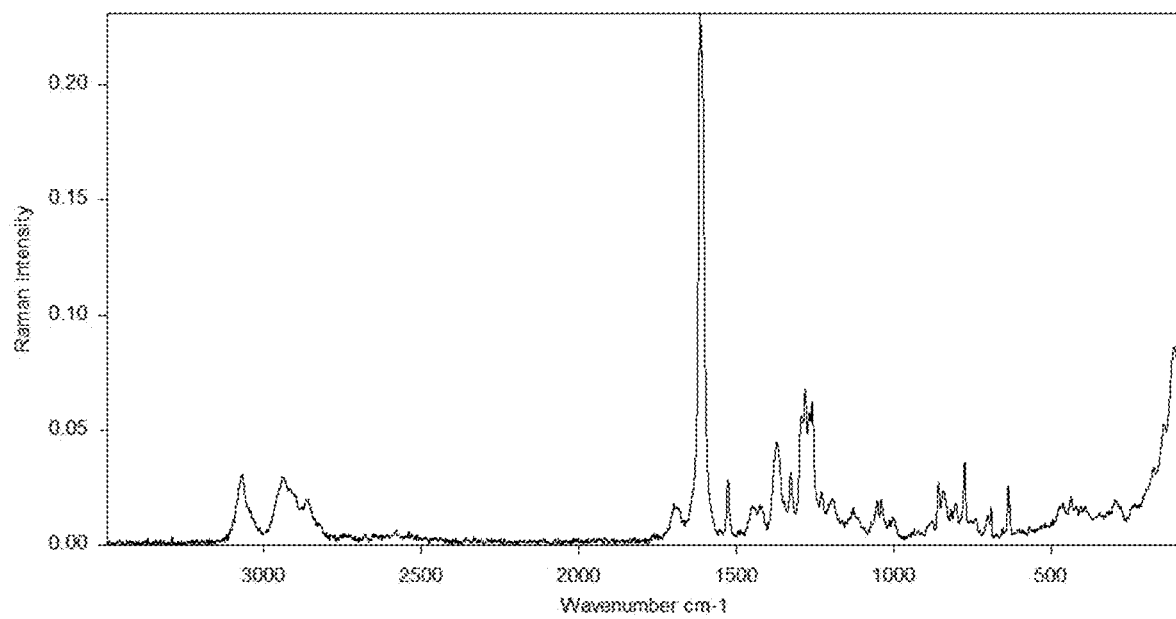
Fig. 12: Raman spectrum of the Semihydrate, example 6a
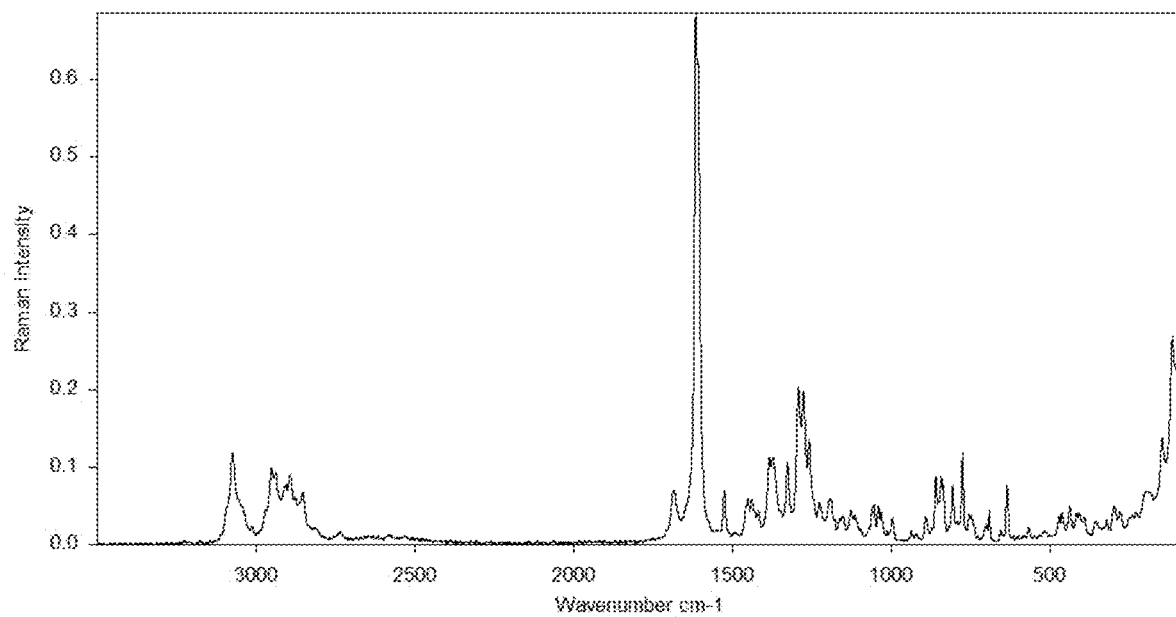
Fig. 13: Raman spectrum of the Monohydrate I, example 6b

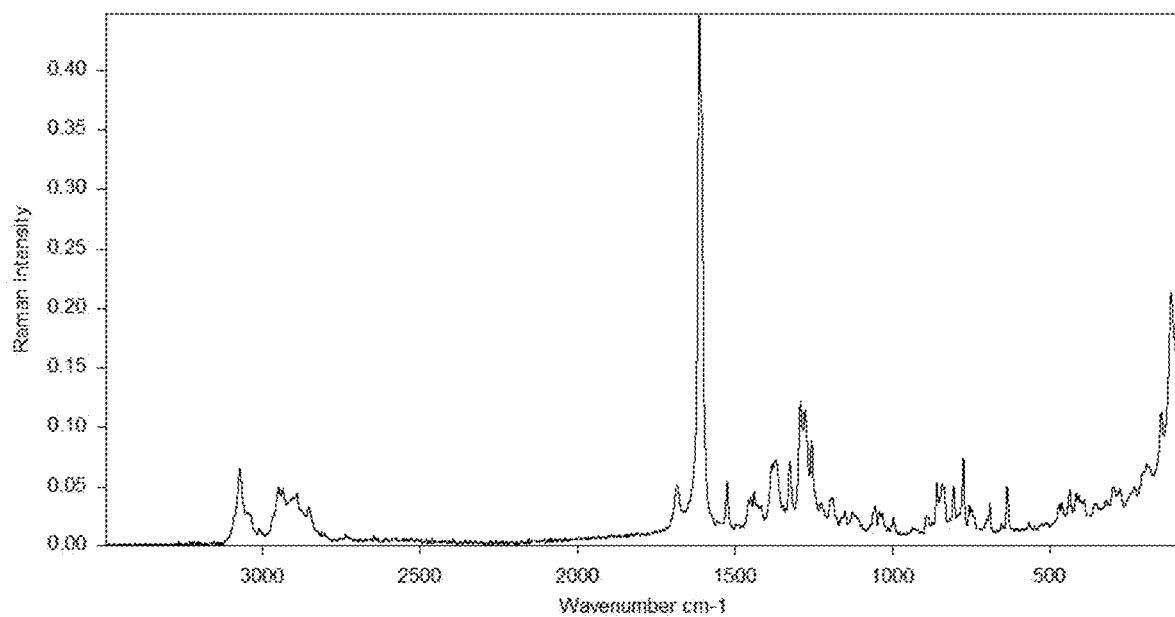
Fig. 14: Raman spectrum of the Monohydrate II, example 6c
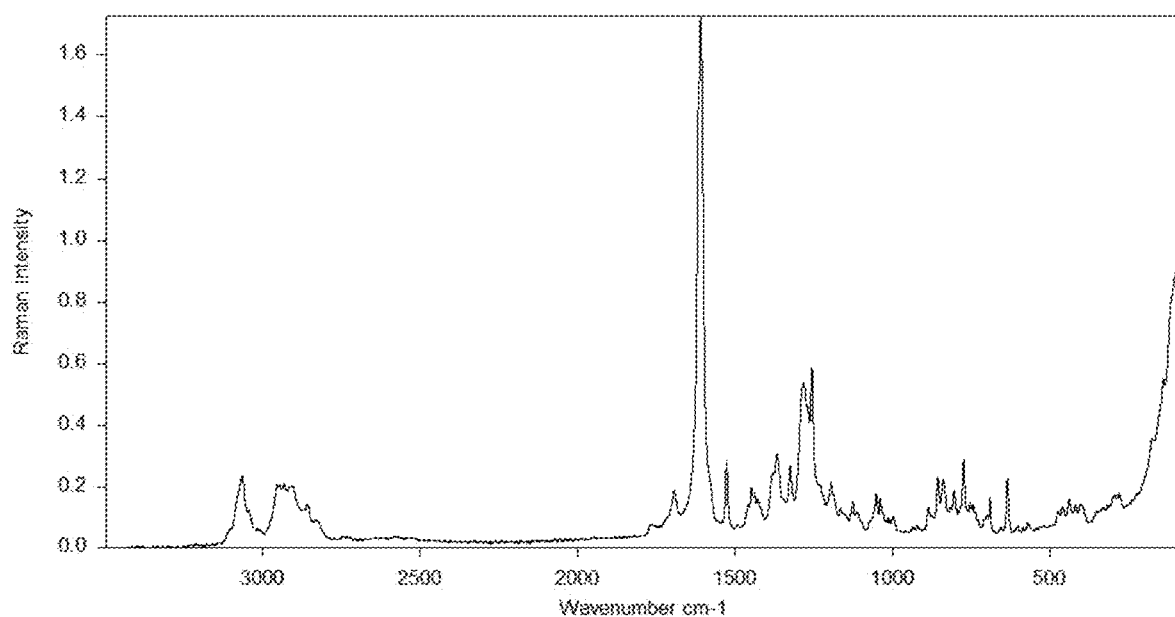
Fig. 15: Raman spectrum of the 1,25-Hydrate, example 6d

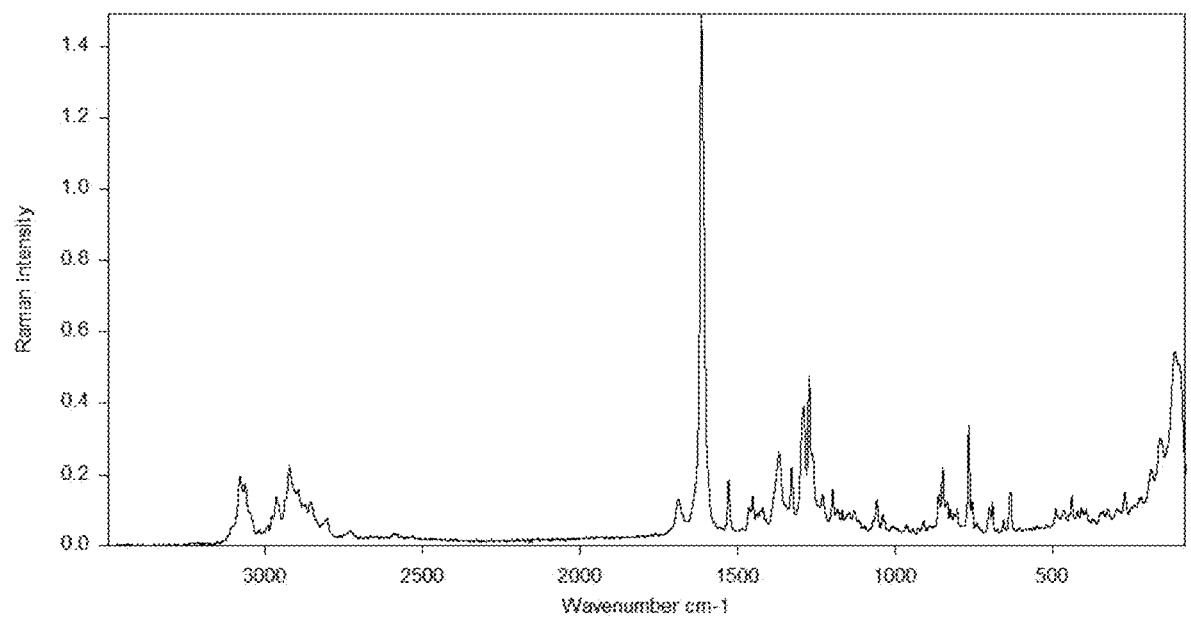
Fig. 16: Raman spectrum of the Sesquihydrate, example 6e
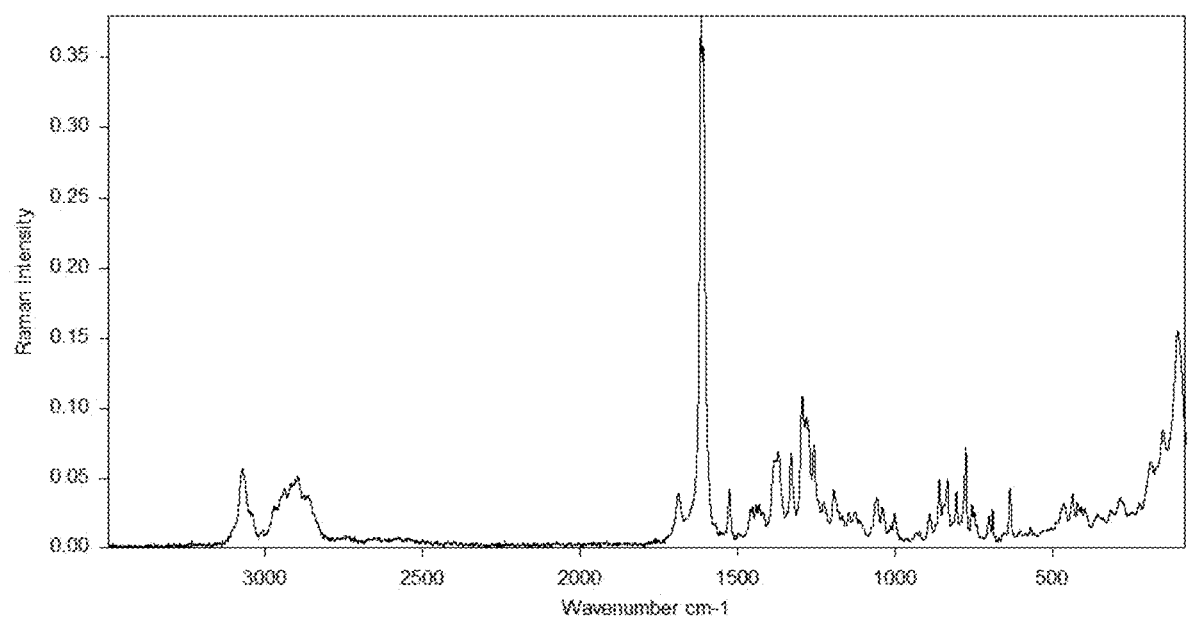
Fig. 17: Raman spectrum of the Dihydrate, example 6f

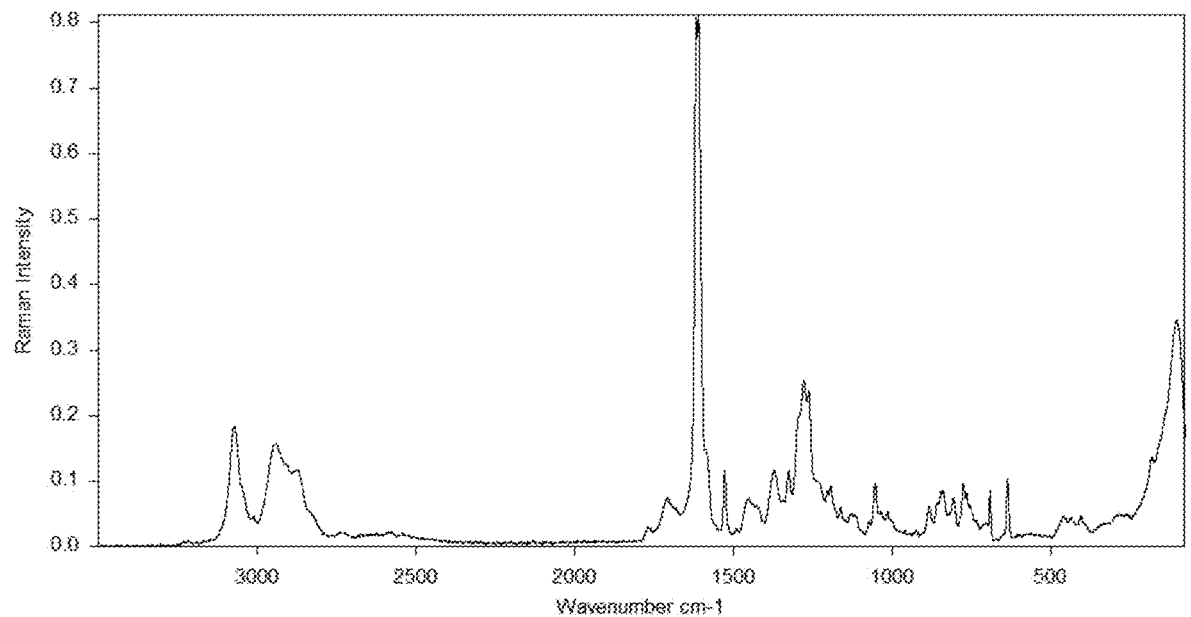
Fig. 18: Raman spectrum of the amorphous form, example 6g
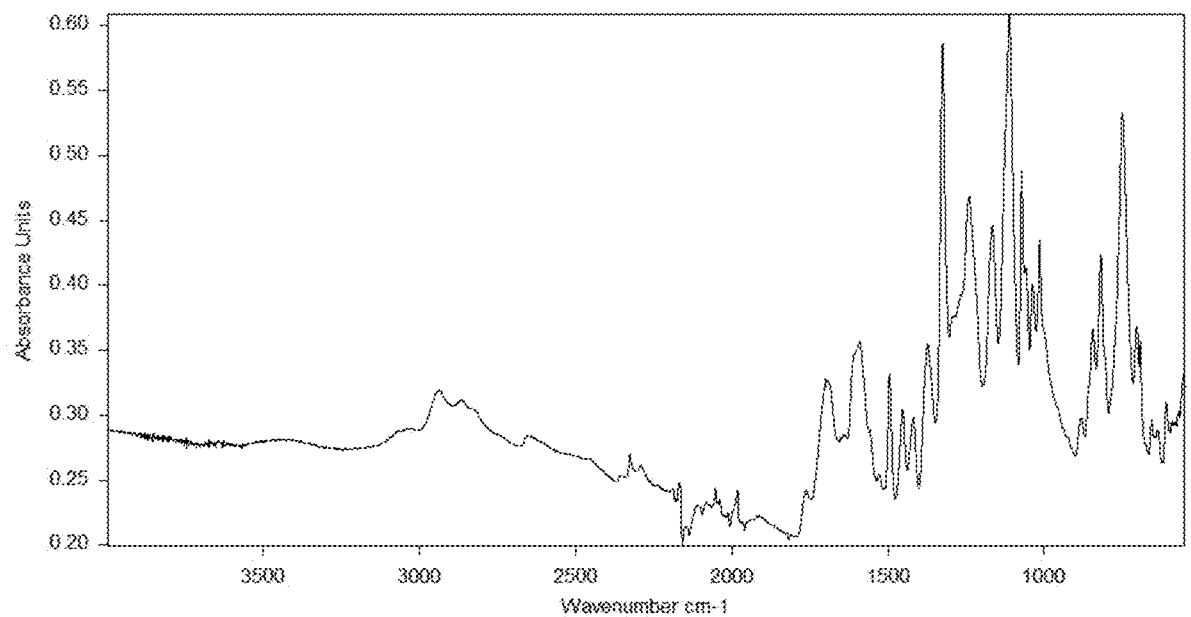
Fig. 19: IR spectrum of the Semihydrate, example 6a

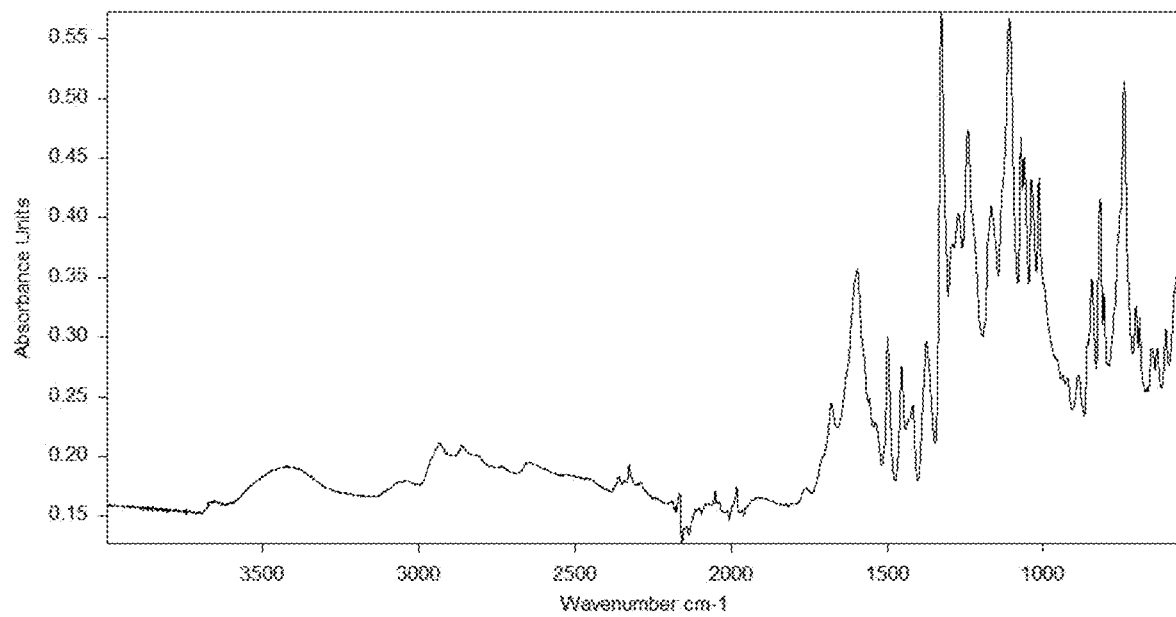
Fig. 20: IR spectrum of the Monohydrate I, example 6b
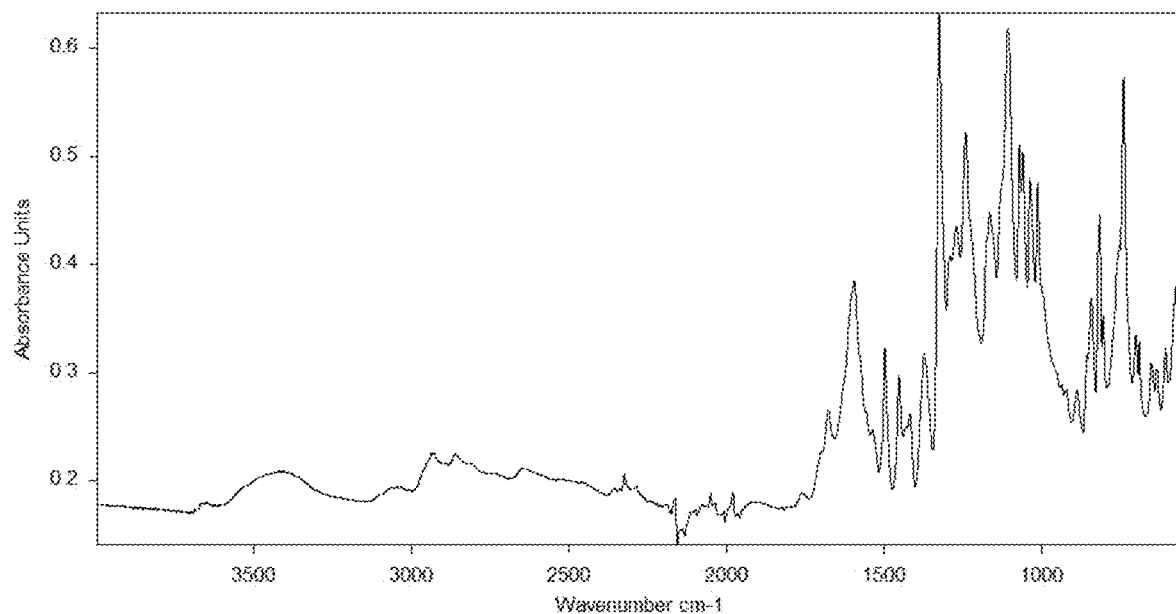
Fig. 21: IR spectrum of the Monohydrate II, example 6c

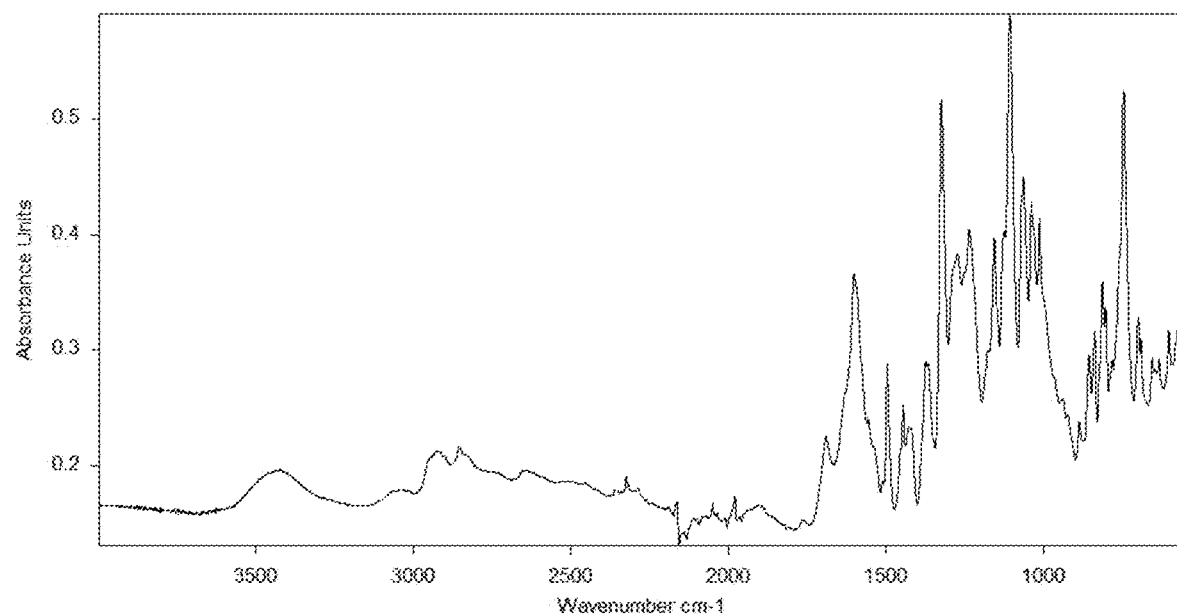
Fig. 22: IR spectrum of the 1,25-Hydrate, example 6d
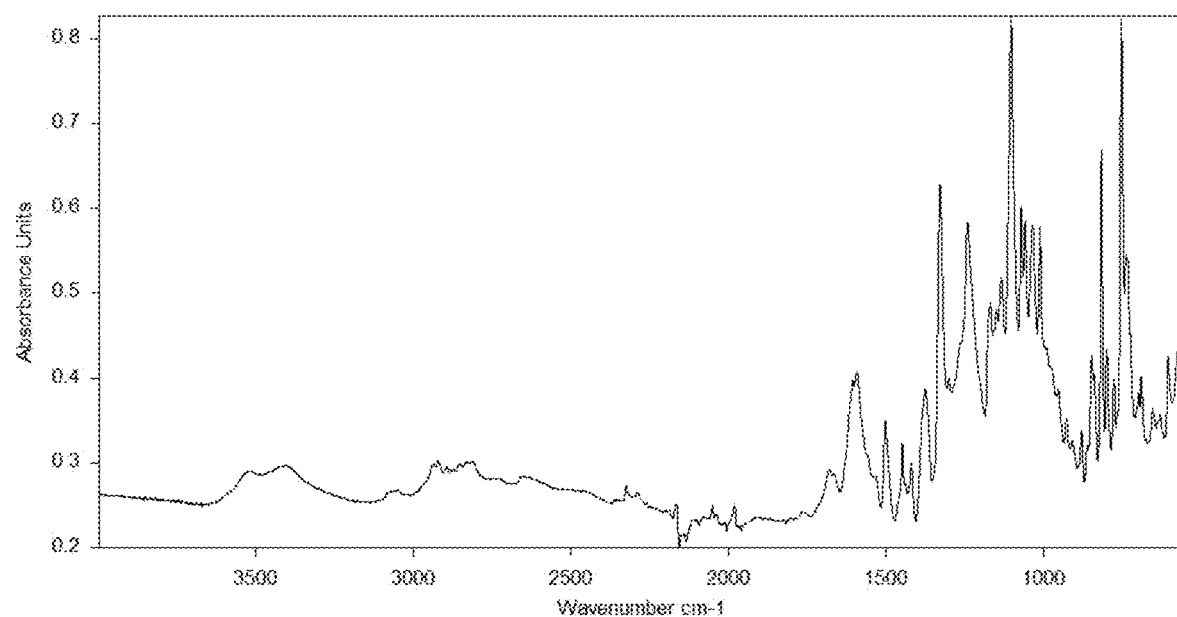
Fig. 23: IR spectrum of the Sesquihydrate, example 6e

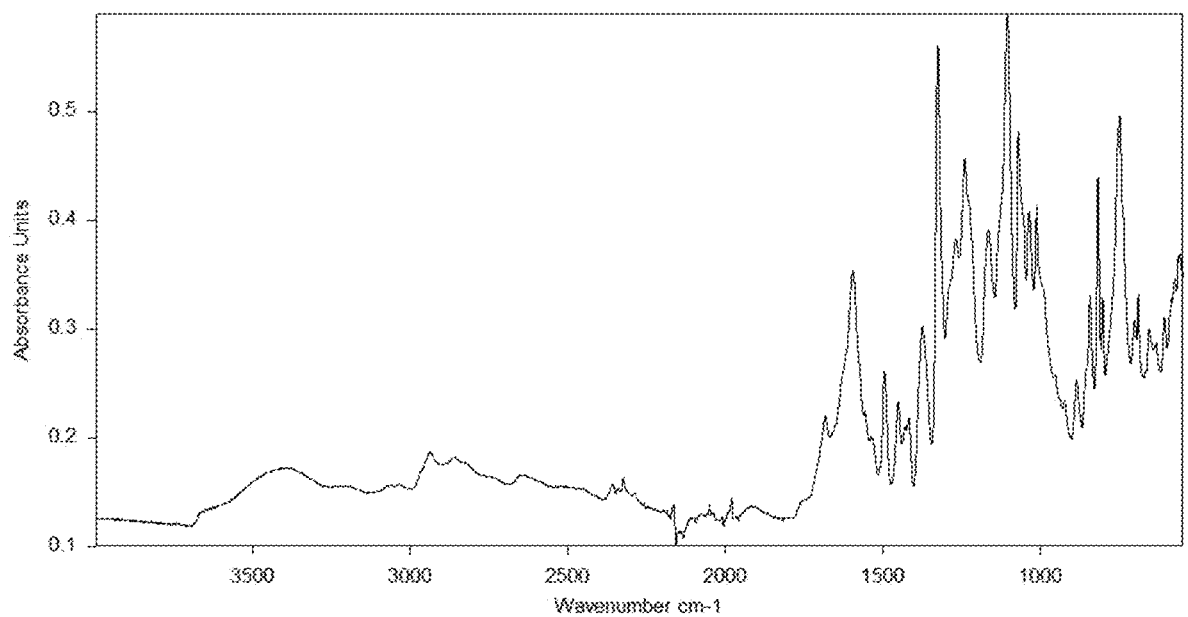
Fig. 24: IR spectrum of the Dihydrate, example 6f
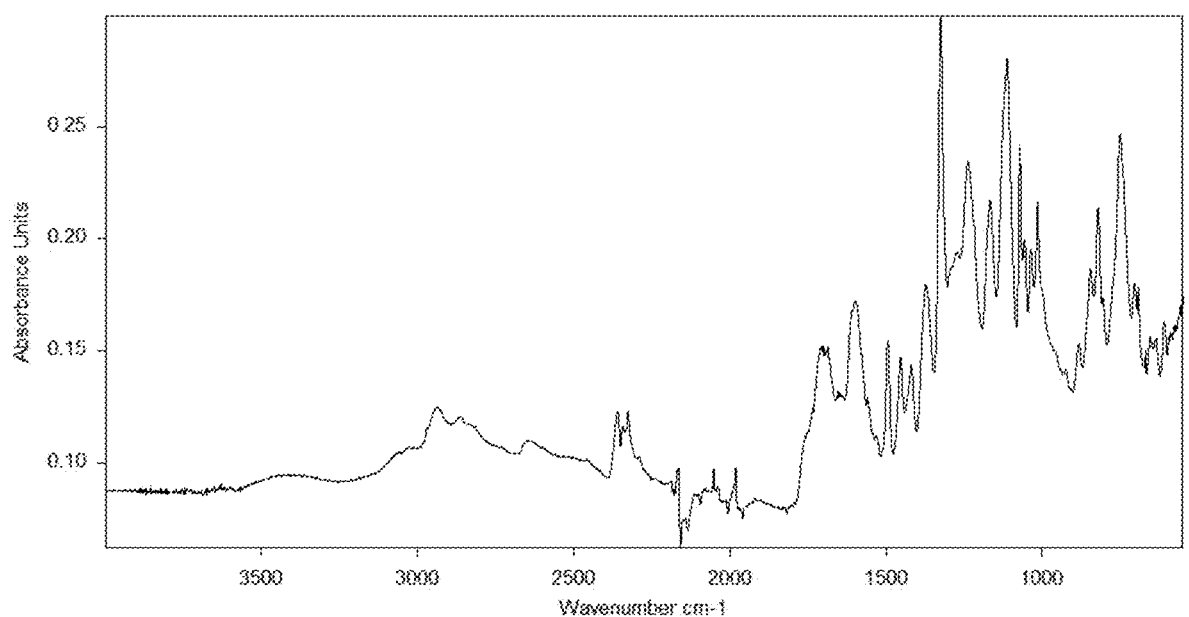
Fig. 25: IR spectrum of the amorphous form, example 6g

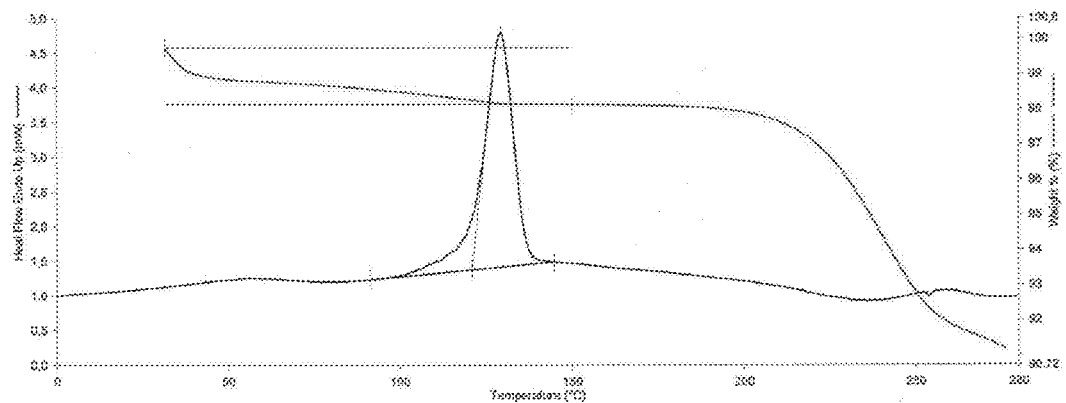
Fig. 26: DSC- and TGA-thermogram of the Semihydrate, example 6a
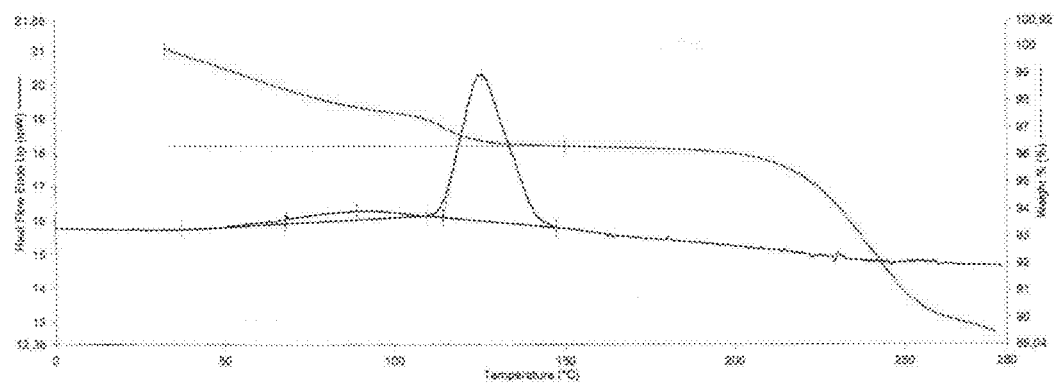
Fig. 27: DSC- and TGA-thermogram of the Monohydrate I, example 6b

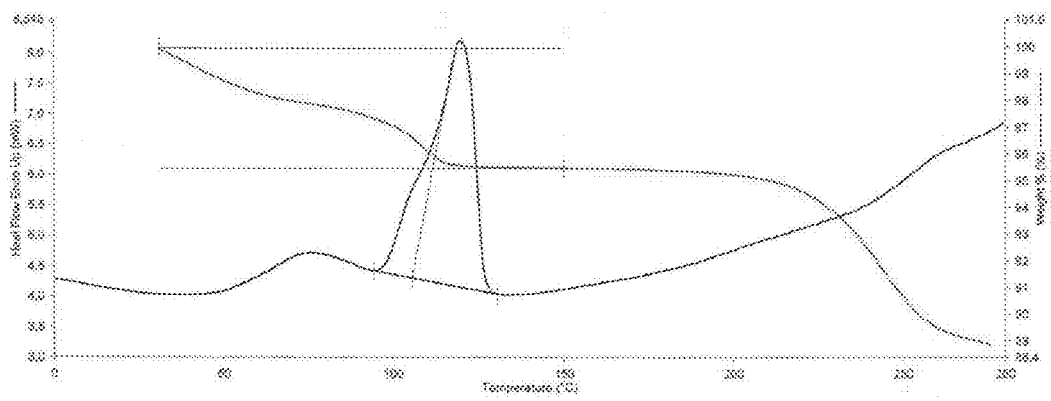
Fig. 28: DSC- and TGA-thermogram of the Monohydrate II, example 6c
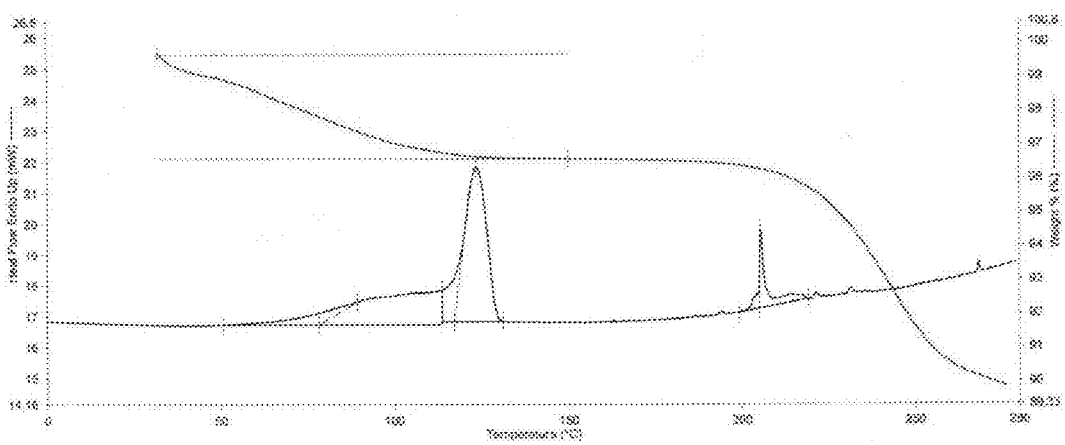
Fig. 29: DSC- and TGA-thermogram of the 1,25-Hydrate, example 6d

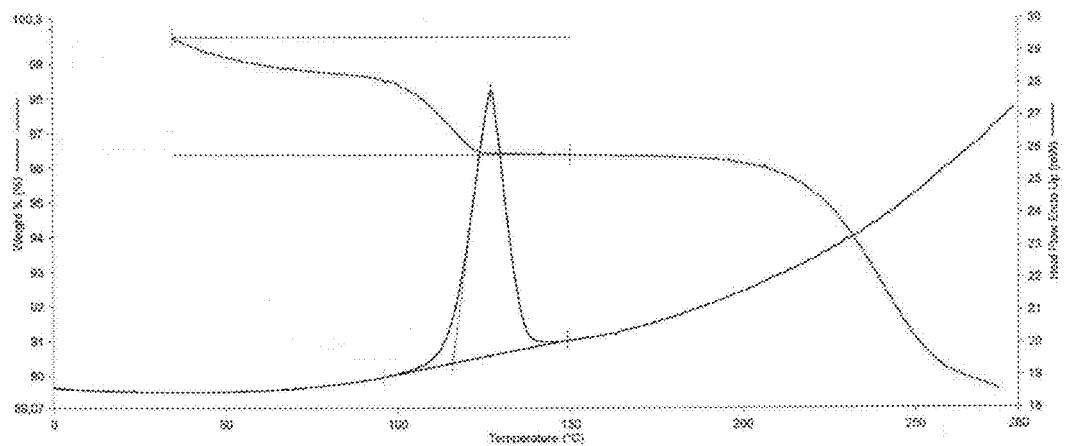
Fig. 30: DSC- and TGA-thermogram of the Sesquihydrate, example 6e
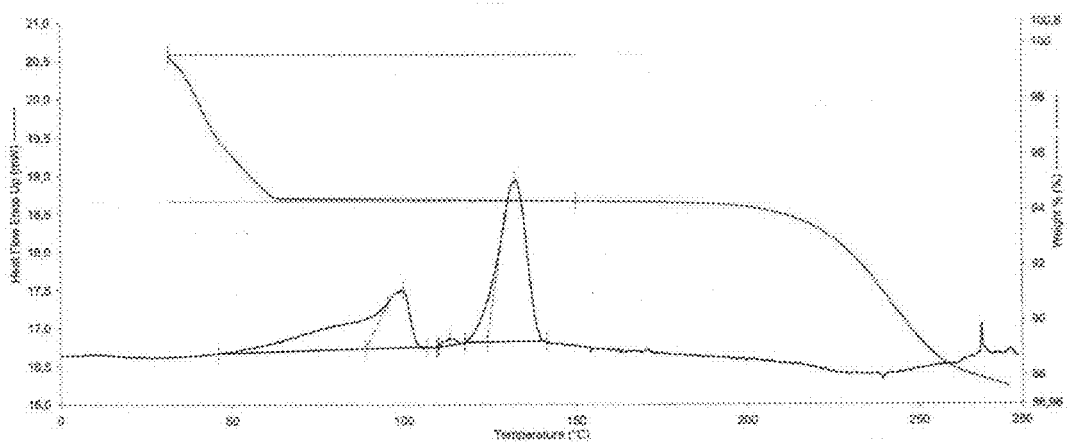
Fig. 31: DSC- and TGA-thermogram of the Dihydrate, example 6f

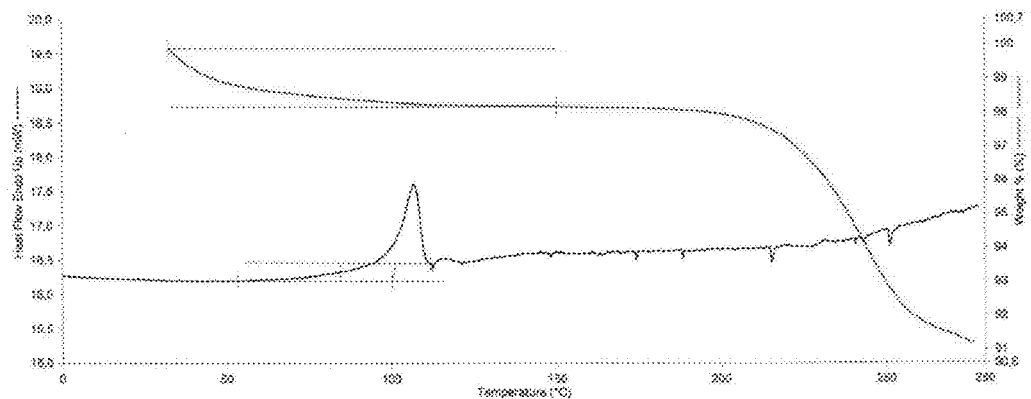
Fig. 32: DSC- and TGA-thermogram of the amorphous form, example 6g
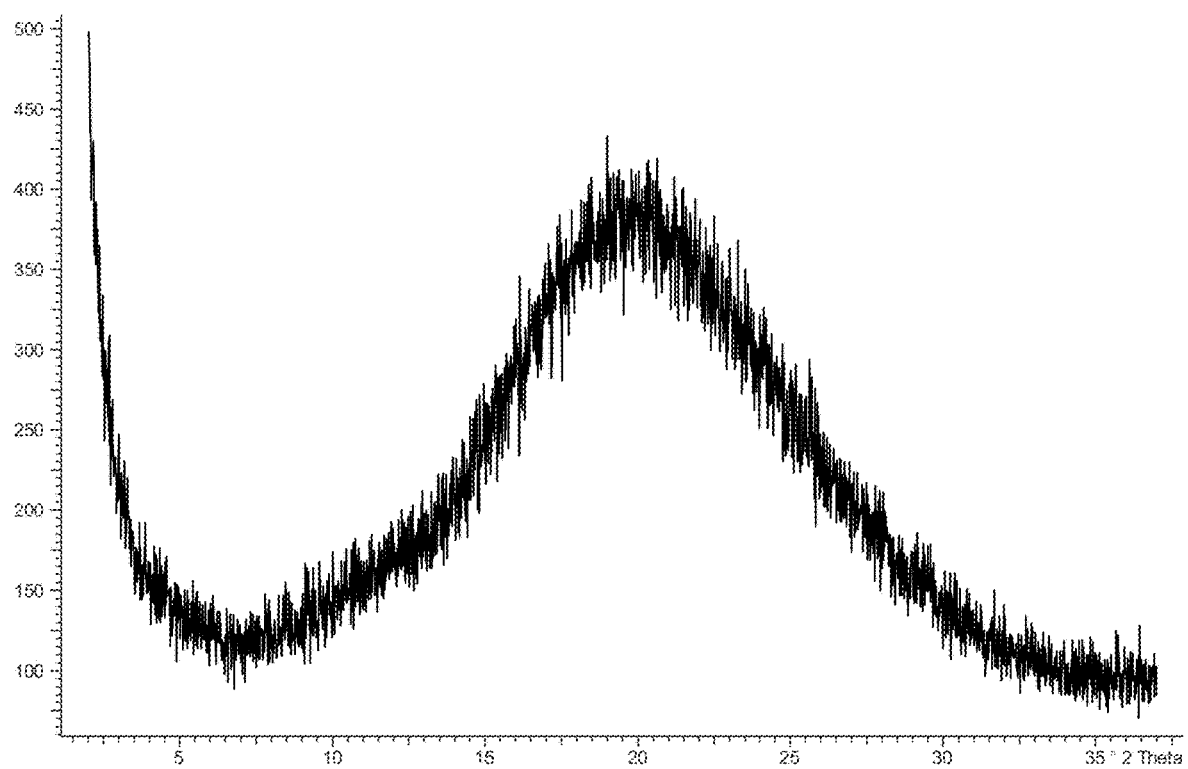
Fig. 33: X-Ray powder diffractogram of comparative example 11, amorphous form

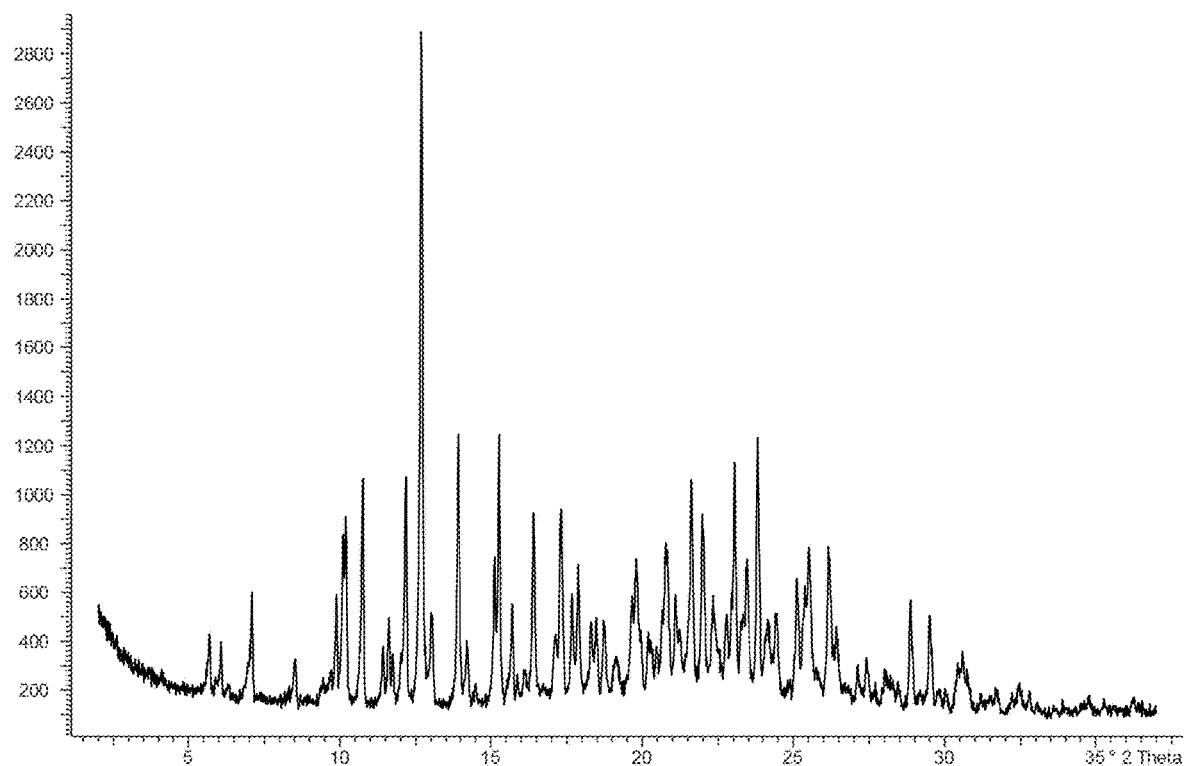
Fig. 34: X-Ray powder diffractogram of example 1, monohydrate II
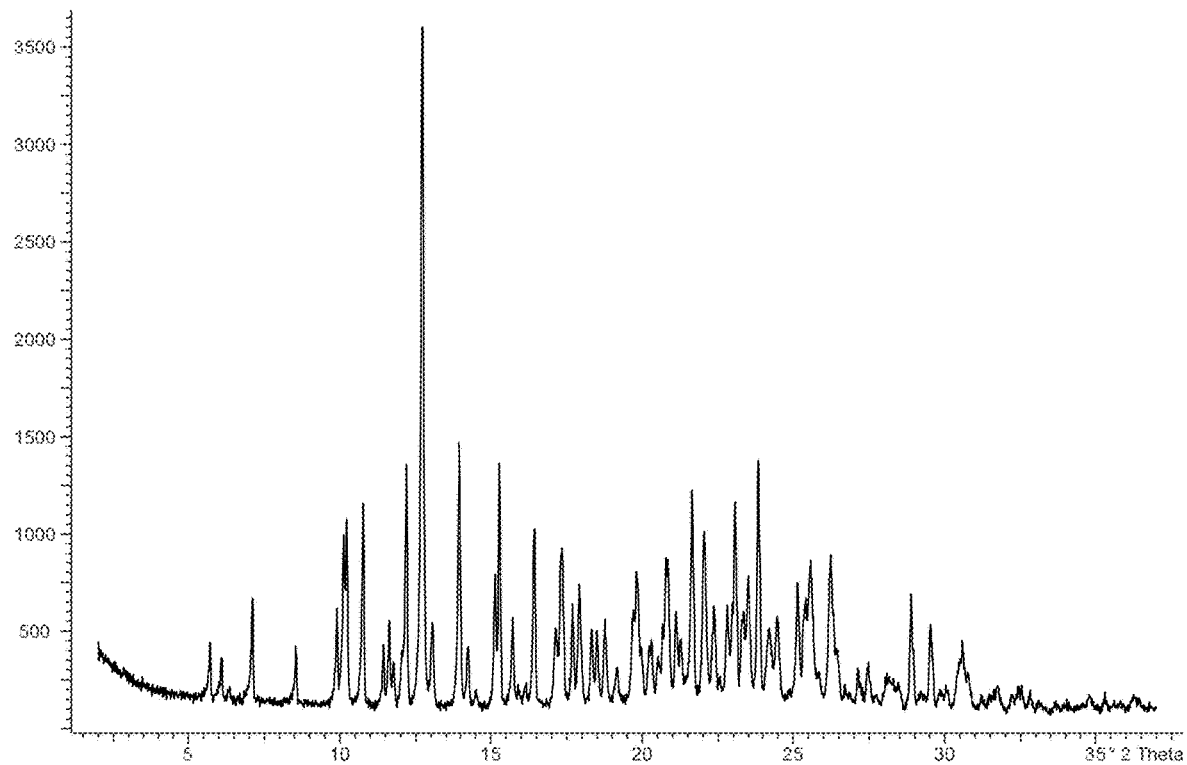
Fig. 35: X-Ray powder diffractogram of example 2 before micronization, monohydrate II

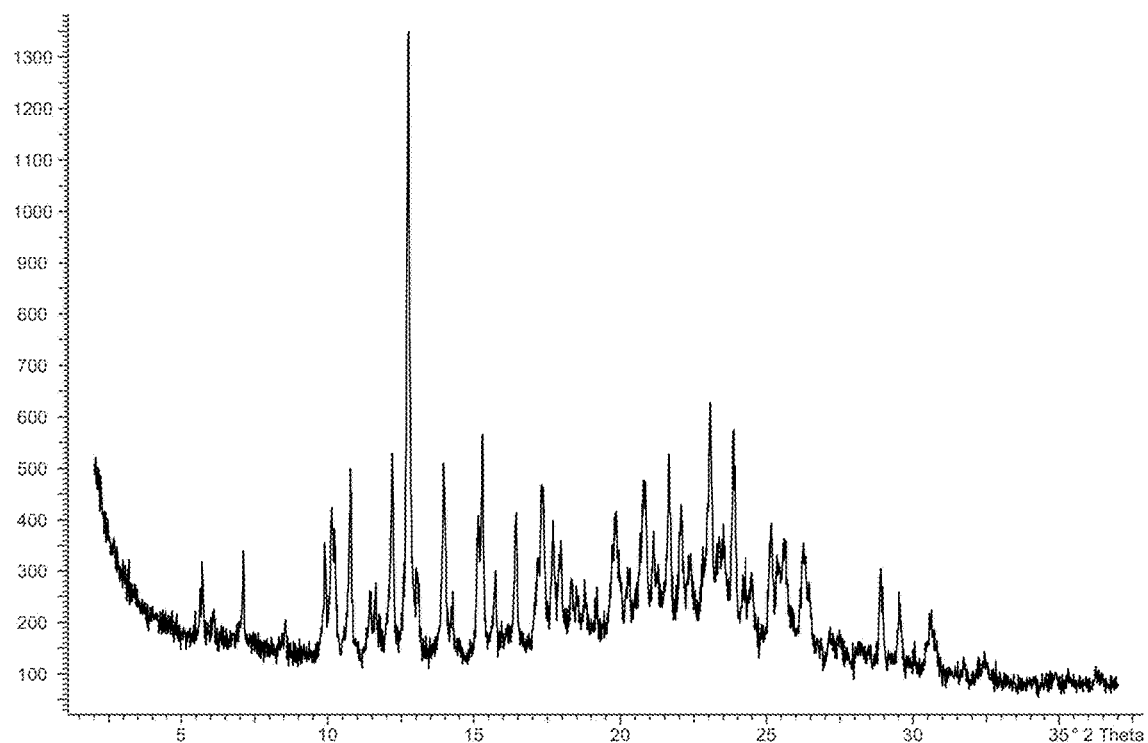
Fig. 36: X-Ray powder diffractogram of example 2 after micronization, monohydrate II, partial amorphization
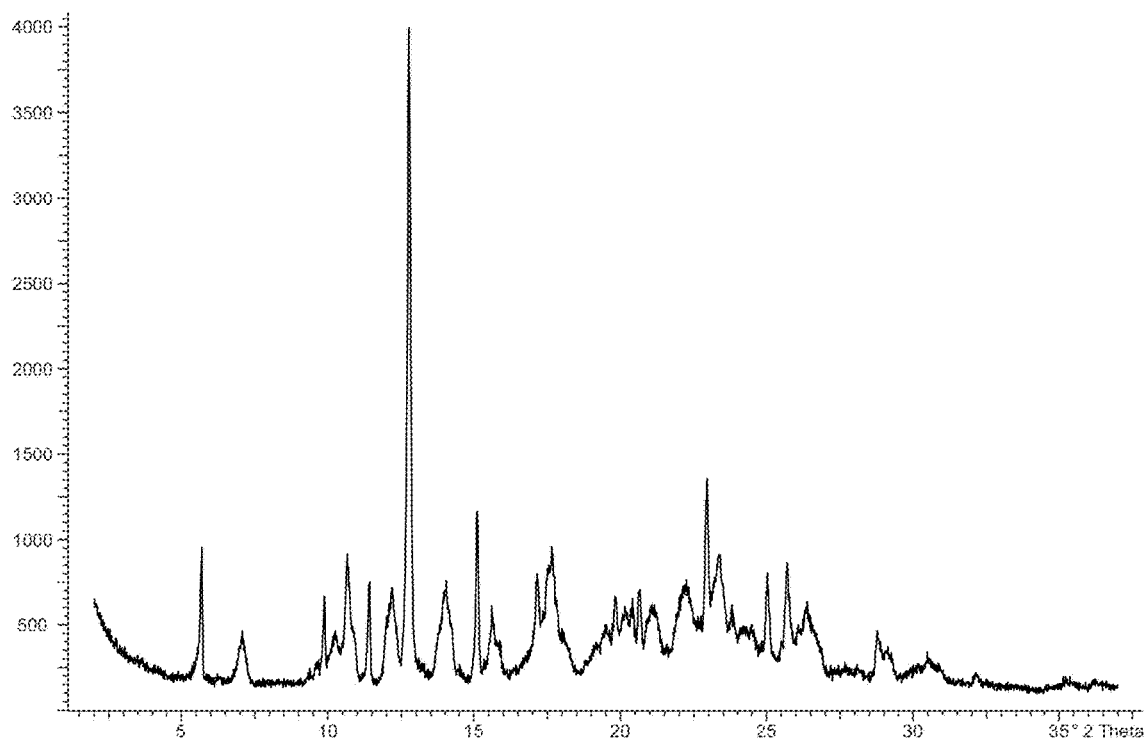
Fig. 37: X-Ray powder diffractogram of example 3, monohydrate I

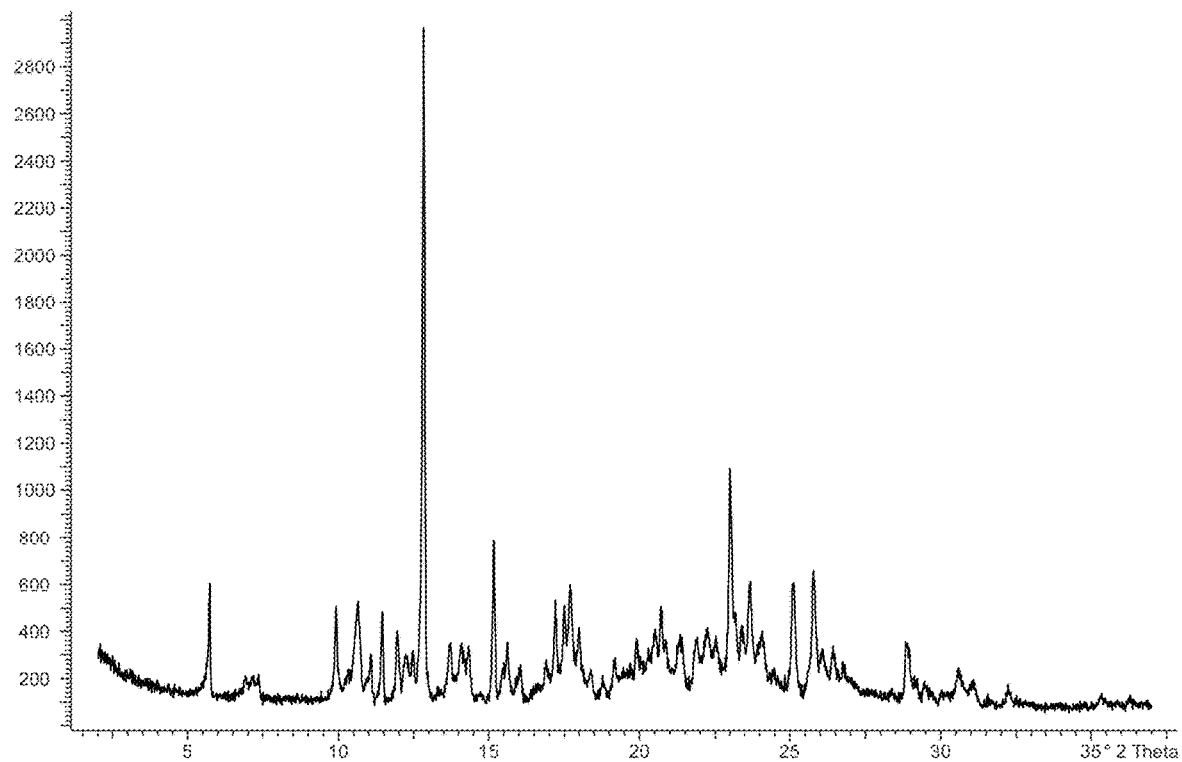
Fig. 38: X-Ray powder diffractogram of Example 4, monohydrate I
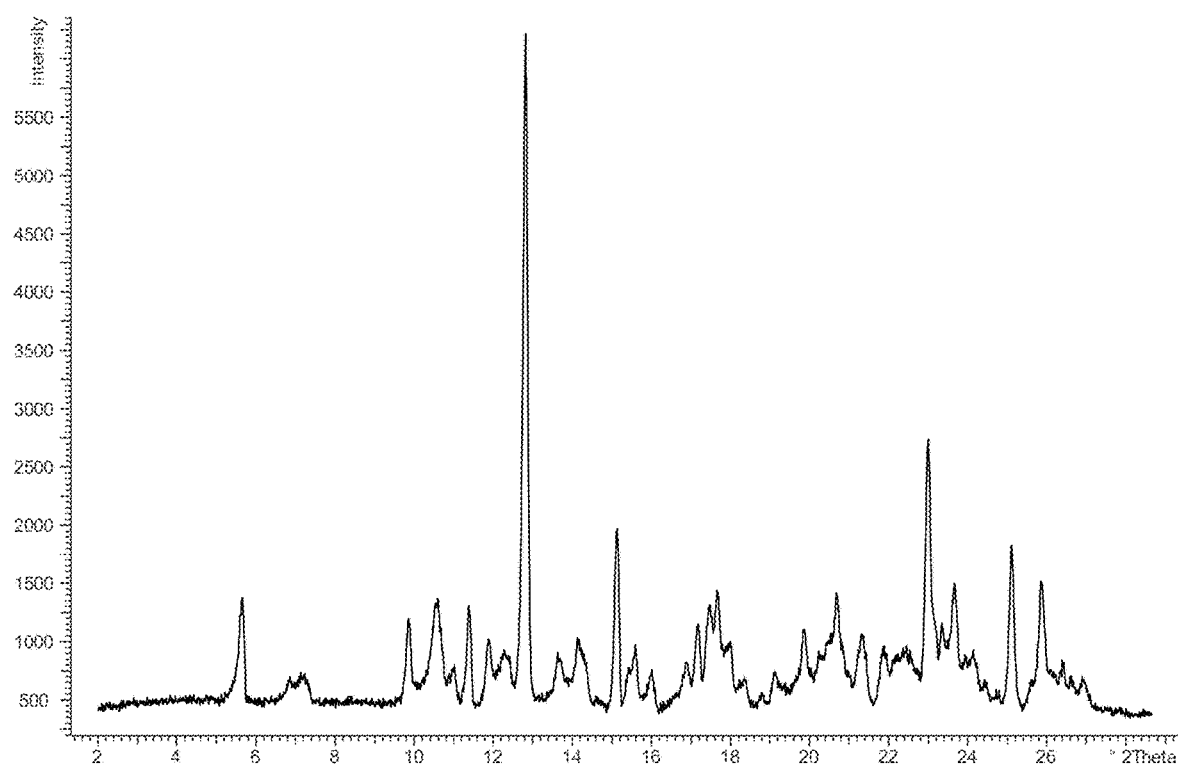
Fig. 39: X-Ray powder diffractogram of example 5, monohydrate I

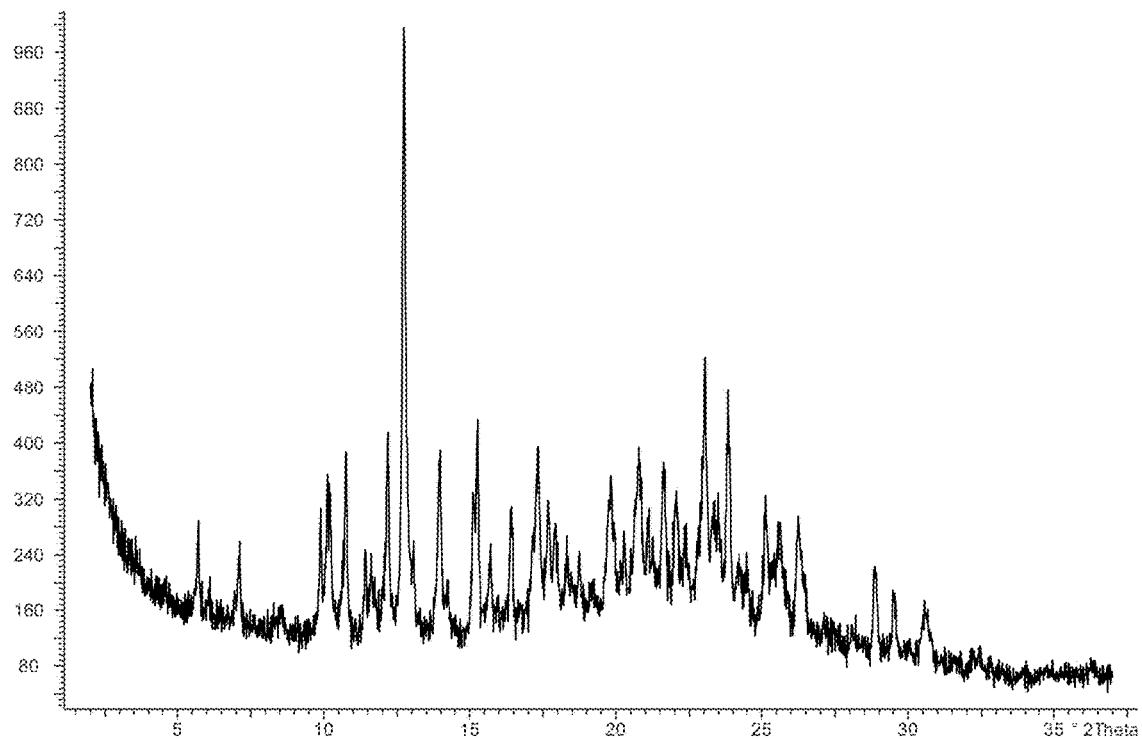
Fig. 40: X-Ray powder diffractogram of example 7 (storage stability): starting material for storage stability, monohydrate II
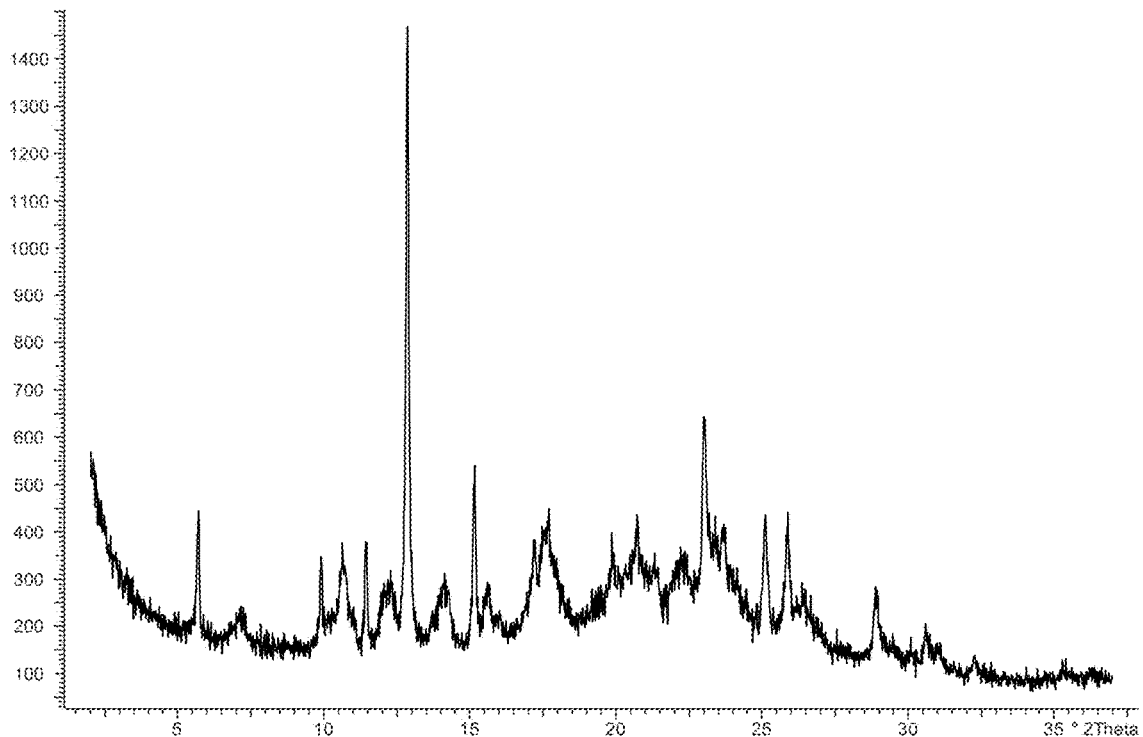
Fig. 41: X-Ray powder diffractogram of example 7b (storage stability): material after one month storage stability testing at 25°C and 60 % relative humidity in polyethylene, monohydrate I

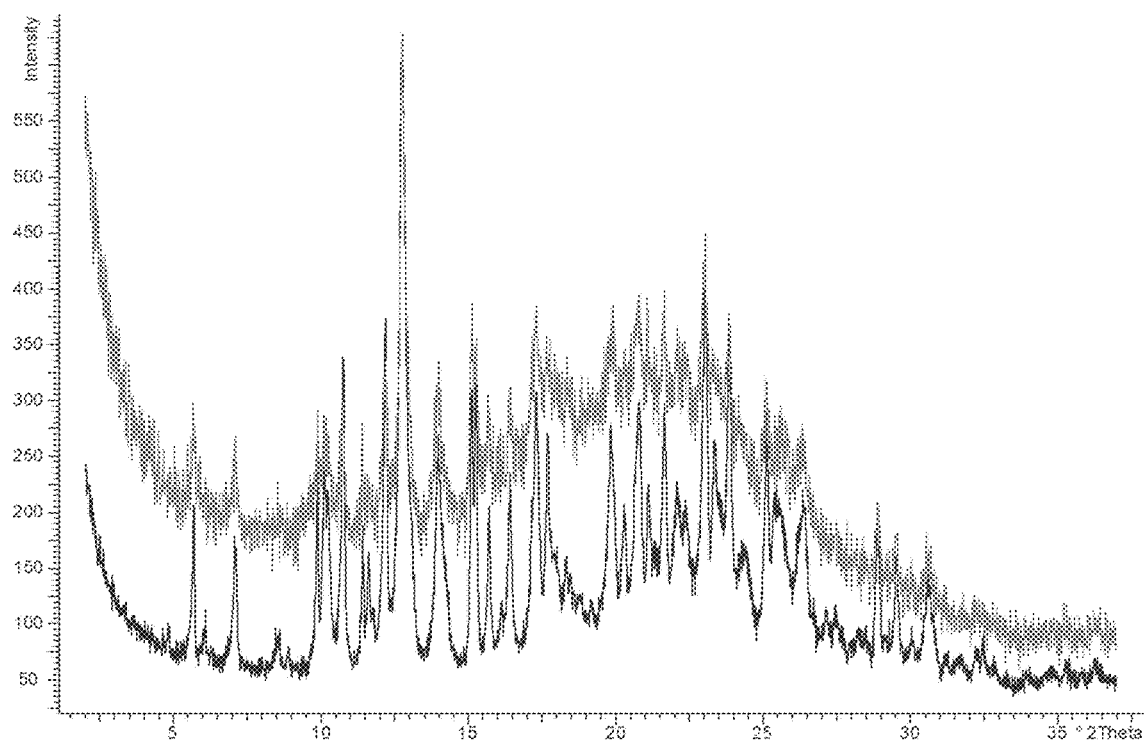
Fig. 42: Overlay of X-ray powder diffractograms of example 8b (micronization): starting material (monohydrate II) (bottom line) and material after micronization (monohydrate II with amorphous amounts, PTFE coated jet mill, 25°C) (top line)

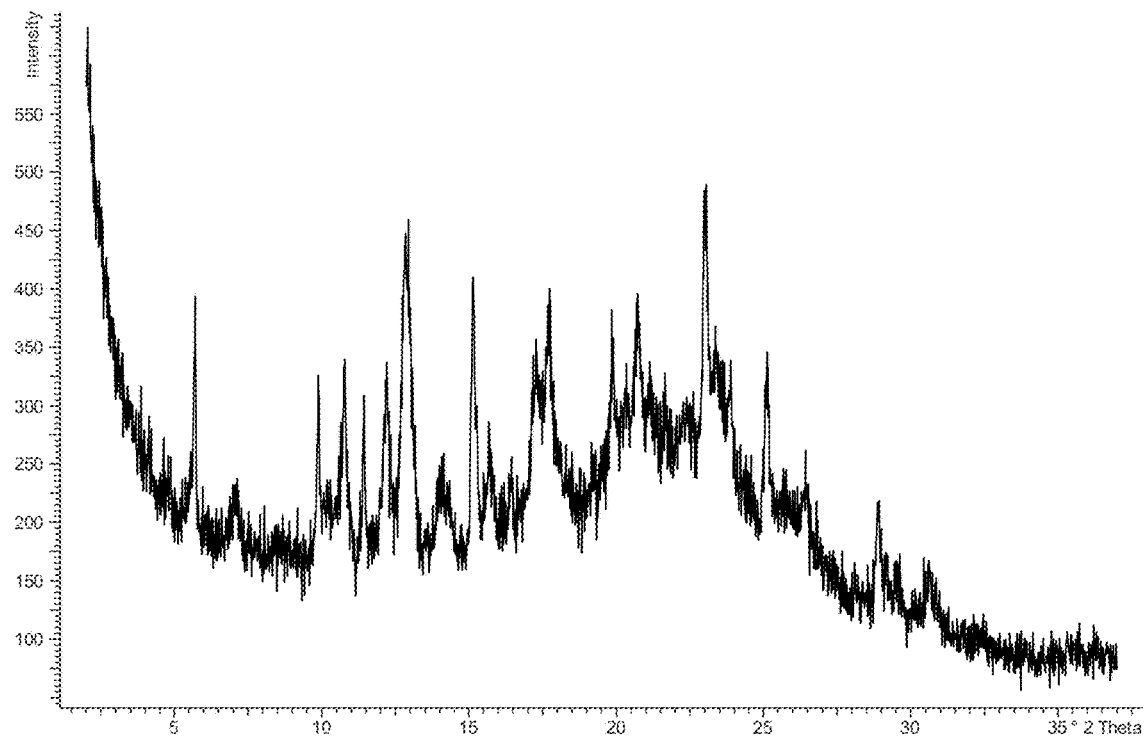
Fig. 43: X-ray powder diffractogram of example 8a: material after micronization (monohydrate I with amorphous amounts, VA jet mill, 25°C)
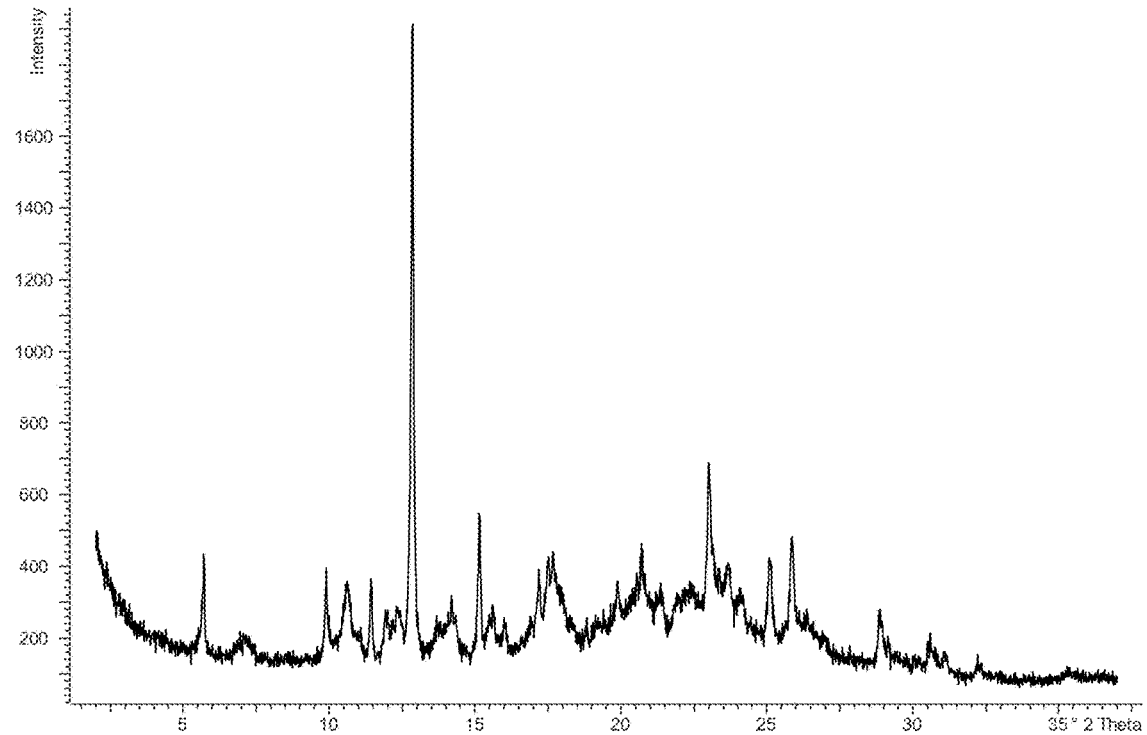
Fig. 44: X-ray powder diffractogram (example 8e): after micronization (monohydrate I)

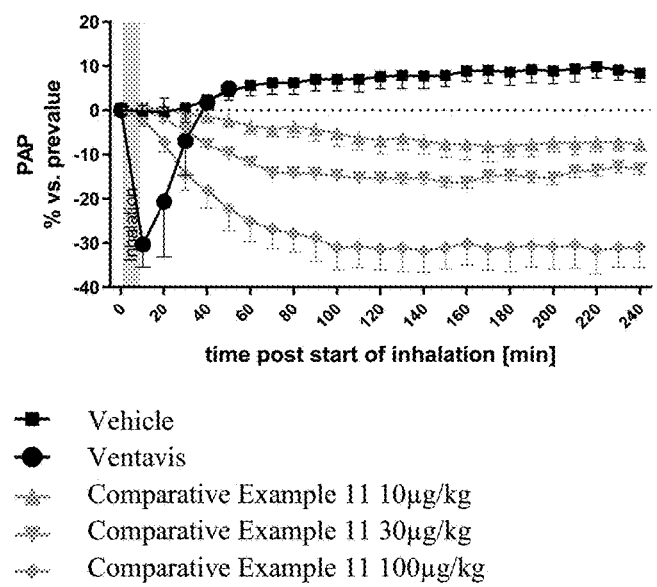

- Vehicle
- Ventavis
- Comparative Example 11 10µg/kg
- Comparative Example 11 30µg/kg
- Comparative Example 11 100µg/kg Fig. 45: Effects of vehicle solution, comparative example 11 (10, 30 and 100 µg/kg nominal dose) and Ventavis (10 µg/kg nominal dose) after inhaled application in the PAH minipigs model. Data are expressed as % changes in PAP and BP vs baseline (10 min interval prior to start of nebulization). Data are mean ± SEM. Nebulizsation interval took 5-7 min for all compounds (grey bar).

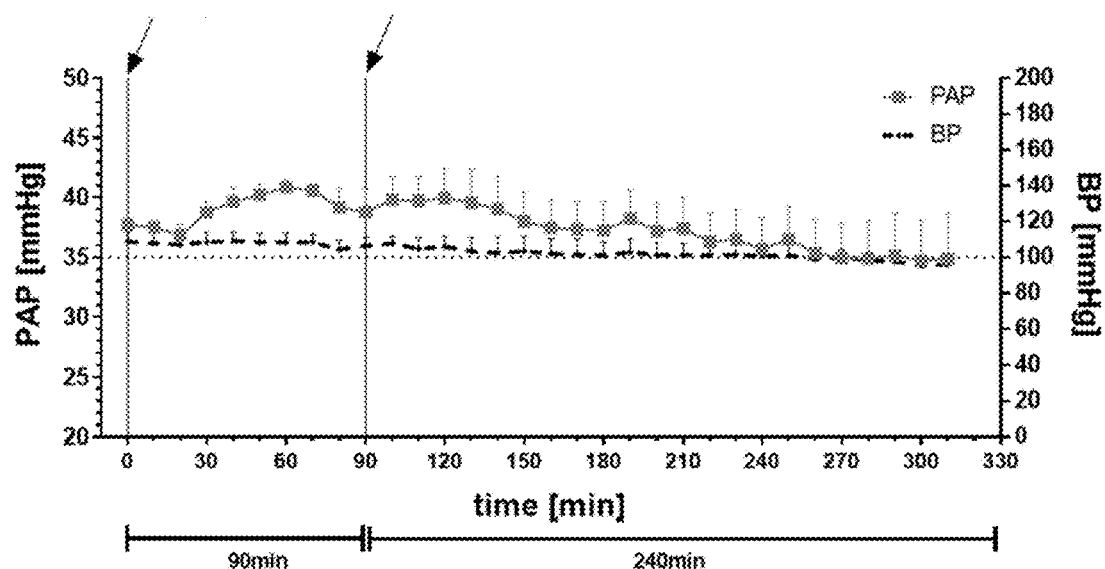
↙ @0 min: Lactose 1.5mg/4kg; @90 min: Lactose formulation I (2%) 1.5mg/4kg
Fig. 46: Effects of lactose as well as lactose formulation I (7.5 µg/kg) after intratracheal application. Data are mean ± SEM (n=3); Intratracheal application was conducted with PennCentury dry powder insufflator and Air Pump; BP: arterial blood pressure; PAP: pulmonary artery pressure; SEM: standard error of the mean

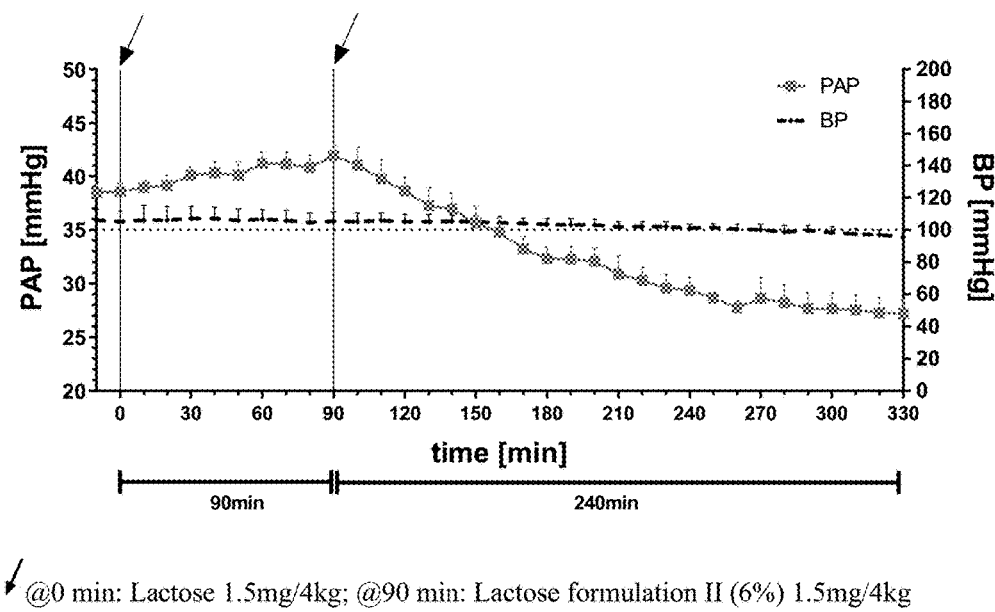

↙ @0 min: Lactose 1.5mg/4kg; @90 min: Lactose formulation II (6%) 1.5mg/4kg

Fig. 47: Effects of lactose as well as lactose formulation II (22.5 µg/kg) after intratracheal application. Data are mean ± SEM (n=3); Intratracheal application was conducted with PennCentury dry powder insufflator and Air Pump; BP: arterial blood pressure; PAP: pulmonary artery pressure; SEM: standard error of the mean

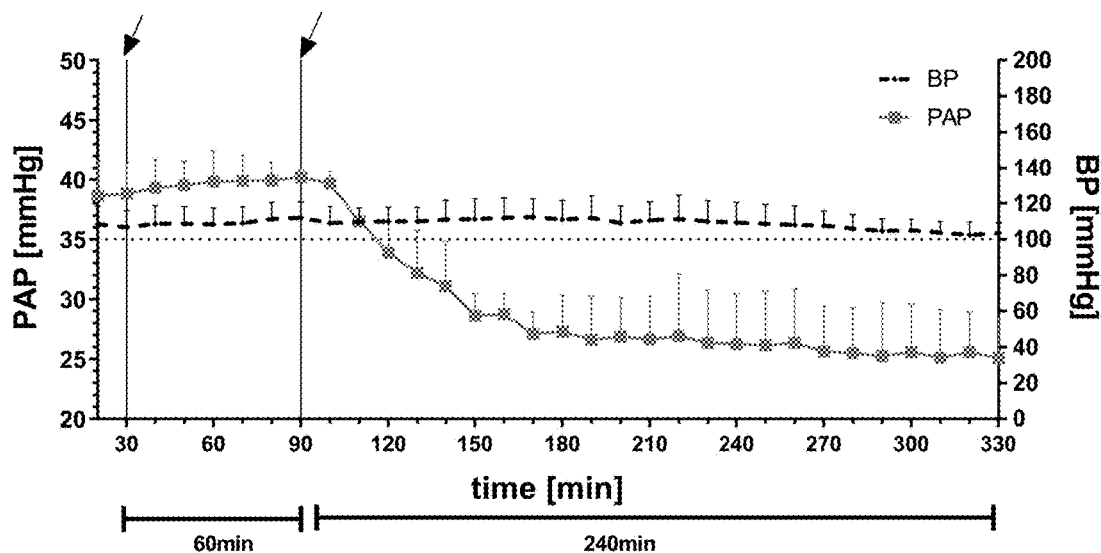

↓ @30 min: Lactose 1.5mg/4kg; @90 min: micronized example 6e 1.5mg/4kg

Fig. 48: Effects of lactose and micronized sesquihydrate, e.g. ex.. 6e (375 µg/kg) after intratracheal application. Data are mean ± SEM (n=3) Intratracheal application was conducted with PennCentury dry powder insufflator and Air Pump; BP: arterial blood pressure; PAP: pulmonary artery pressure; SEM: standard error of the mean

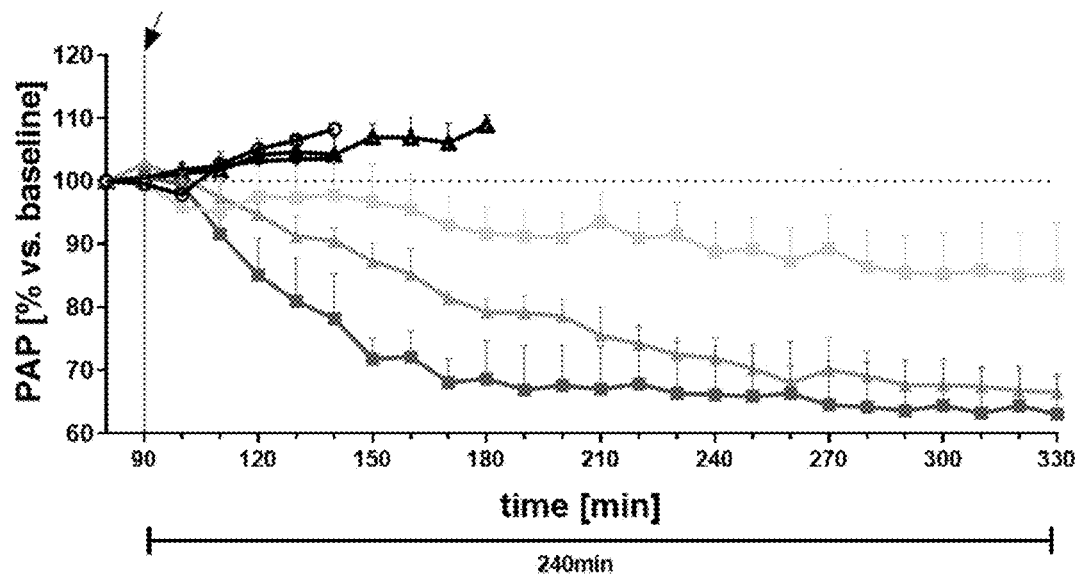

↯ @90 min: Example 6e (mikro.) or lactose formulation I or II (2 or 6%) or Lactose 1.5mg/4kg

- ⊖ PAP Lactose LH300/LH200 20:78m/m
- ▲ PAP Lactose LH300/LH200 20:80m/m
- ＋ PAP Lactose LH300/LH200 20:80m/m
- PAP Lactose formulation I (2%)
- PAP Lactose formulation II (6%)
- PAP Micronized example 6e Fig. 49: Effects of intratracheal application of different lactose vehicles, lactose formulation I (7.5 µg/kg), lactose formulation II (22.5 µg/kg) and micronized sesquihydrate example 6e (375 µg/kg). Data are shown as %changes vs. prevalues as mean ± SEM (n=3)

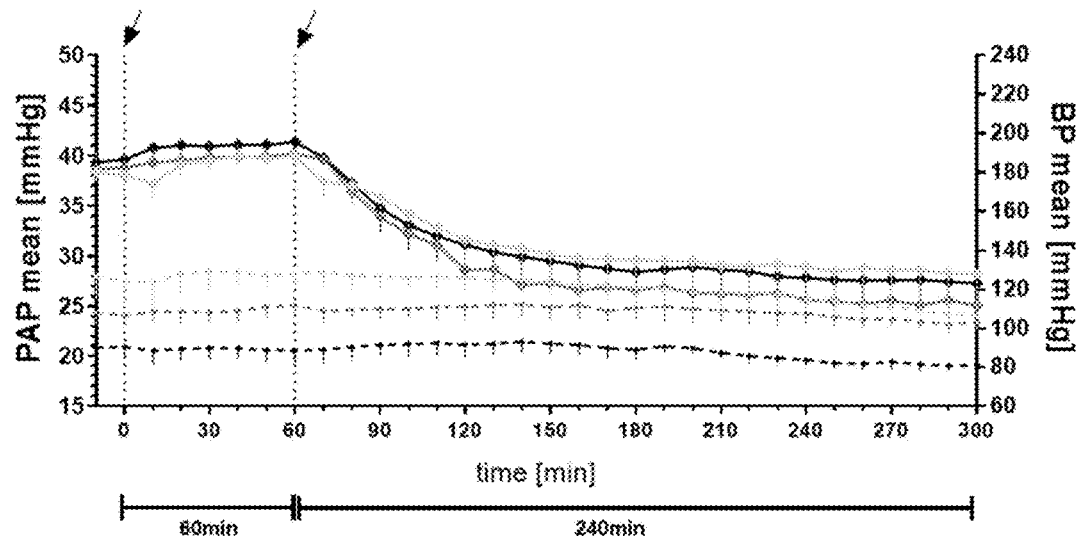

↙ @0 min: Lactose LH300/LH200 1.5mg/4kg @60min: Hydrates of comparative example 11 micronized 1.5mg/4kg

- PAP mean Monohydrate II, example 2 (n=3)
- BP mean Monohydrate II, example 2 (n=3)
- ♦ PAP mean Semihydrate in analogy to example 6a (n=3)
- BP mean Semihydrate in analogy to example 6a (n=3)
- PAP mean Sesquihydrate in analogy to example 6e (n=3)
- BP mean Sesquihydrate in analogy to example 6e (n=3)

Fig. 50: Effects of comparative example 11 after intratracheal application of different hydrates micronized monohydrate II (example 2), micronized semihydrate (example 6a) and micronized sesquihydrate (example 6e), on BP and PAP. Data are shown as absolute values [mmHg] as mean ± SEM (n=3)

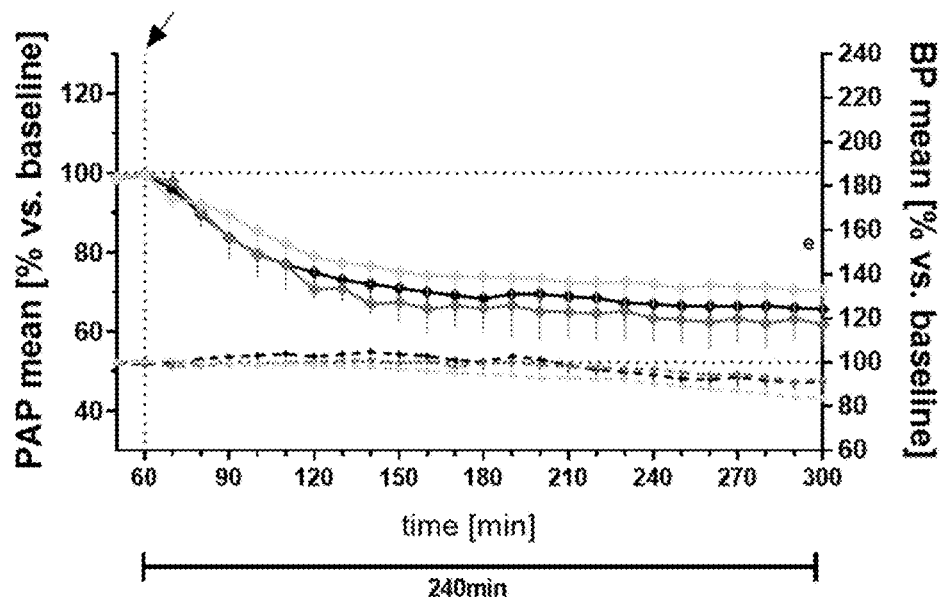

↙ @60 min: Hydrates of comparative example 11 micronized 1.5mg/4kg

- PAP mean Monohydrate II, example 2 (n=3)
- BP mean Monohydrate II, example 2 (n=3)
- PAP mean Semihydrate in analogy to example 6a (n=3)
- BP mean Semihydrate in analogy to example 6a (n=3)
- PAP mean Sesquihydrate in analogy to example 6e (n=3)
- BP mean Sesquihydrate in analogy to example 6e (n=3)

Fig. 51: Effects of comparative example 11 after intratracheal application of different hydrates micronized monohydrate II (example 2), micronized semihydrate (example 6a) and micronized sesquihydrate (example 6e), on BP and PAP. Data are shown as absolute values [mmHg] as mean ± SEM (n=3)

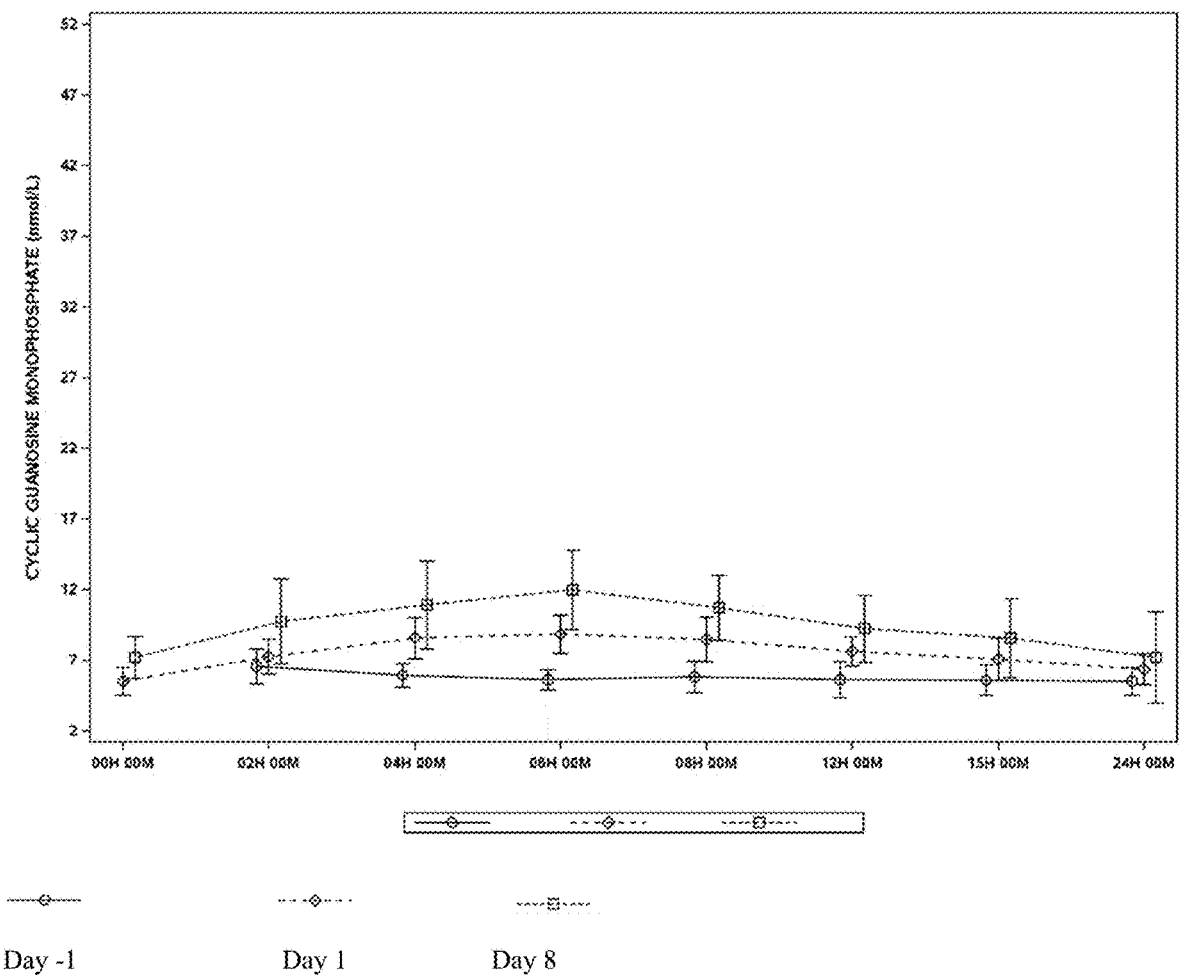
Fig. 52: Means ± SDs for cGMP (nmol/L) – comparison of pretreatment (day -1), first (day 1) and last (day 8) treatment days for the 480 µg (example 2) dose group (SAF, N = 9)

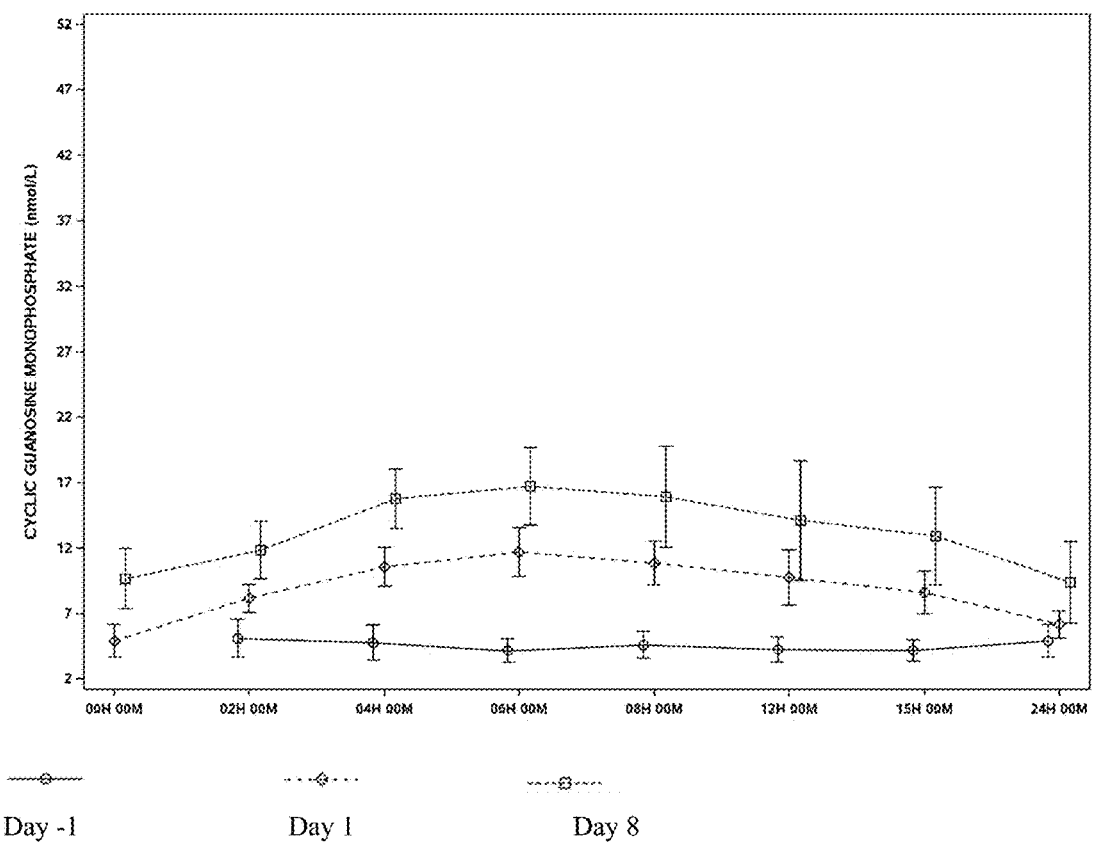
Fig. 53: Means ± SDs for cGMP (nmol/L) – comparison of pretreatment (day-1), first (day 1) and last (day 8) treatment days for the 1000 µg (example 2) dose group (SAF, N = 9)

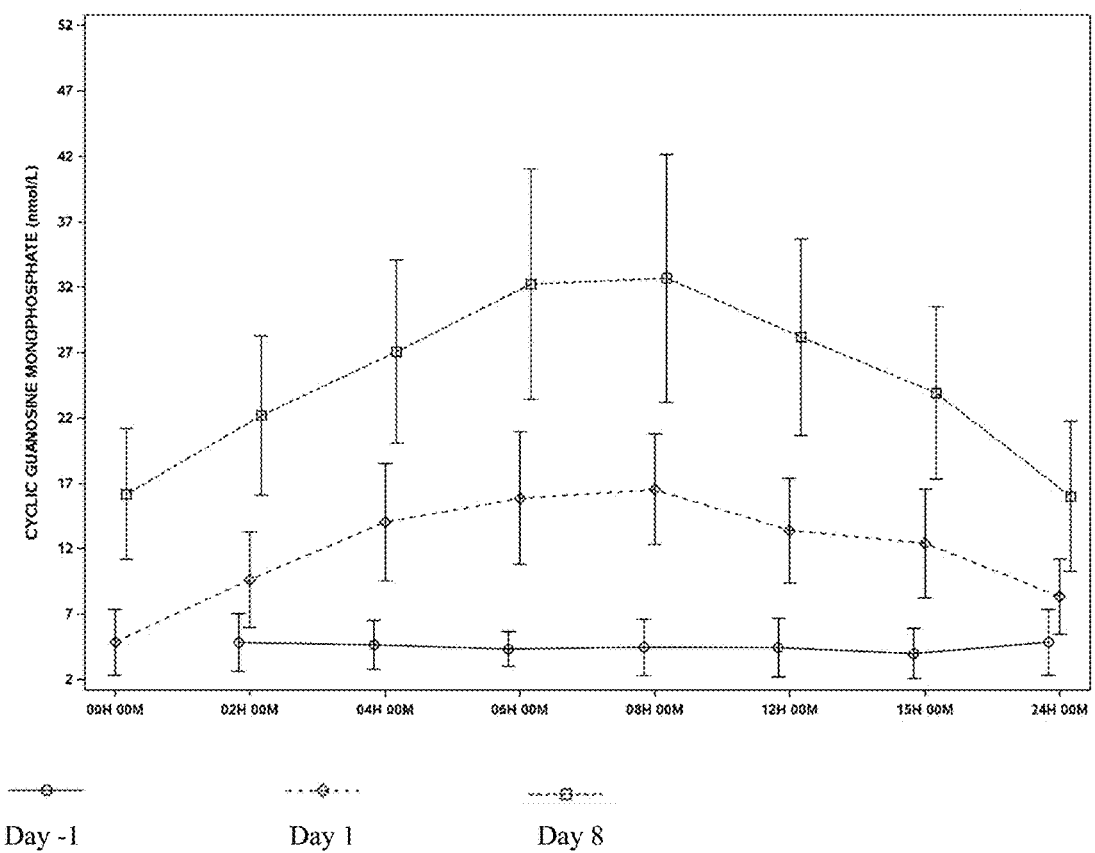
Day -1       Day 1       Day 8
Fig. 54: Means ± SDs for cGMP (nmol/L) – comparison of pretreatment (day-1), first (day 1) and last (day 8) treatment days for the 2000 μg (example 2) dose group (SAF, N = 9)

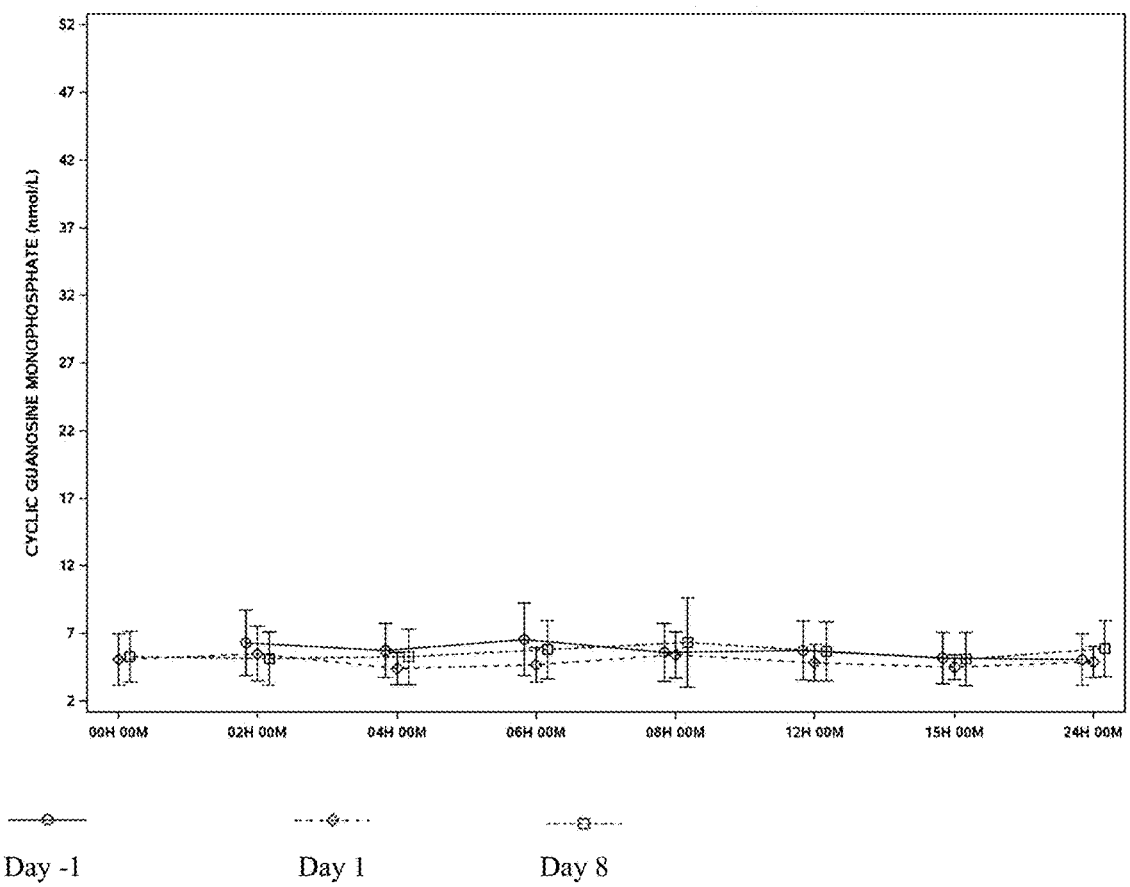
Fig. 55: Means ± SDs for cGMP (nmol/L) – comparison of treatment days for the placebo group (SAF, N = 9)

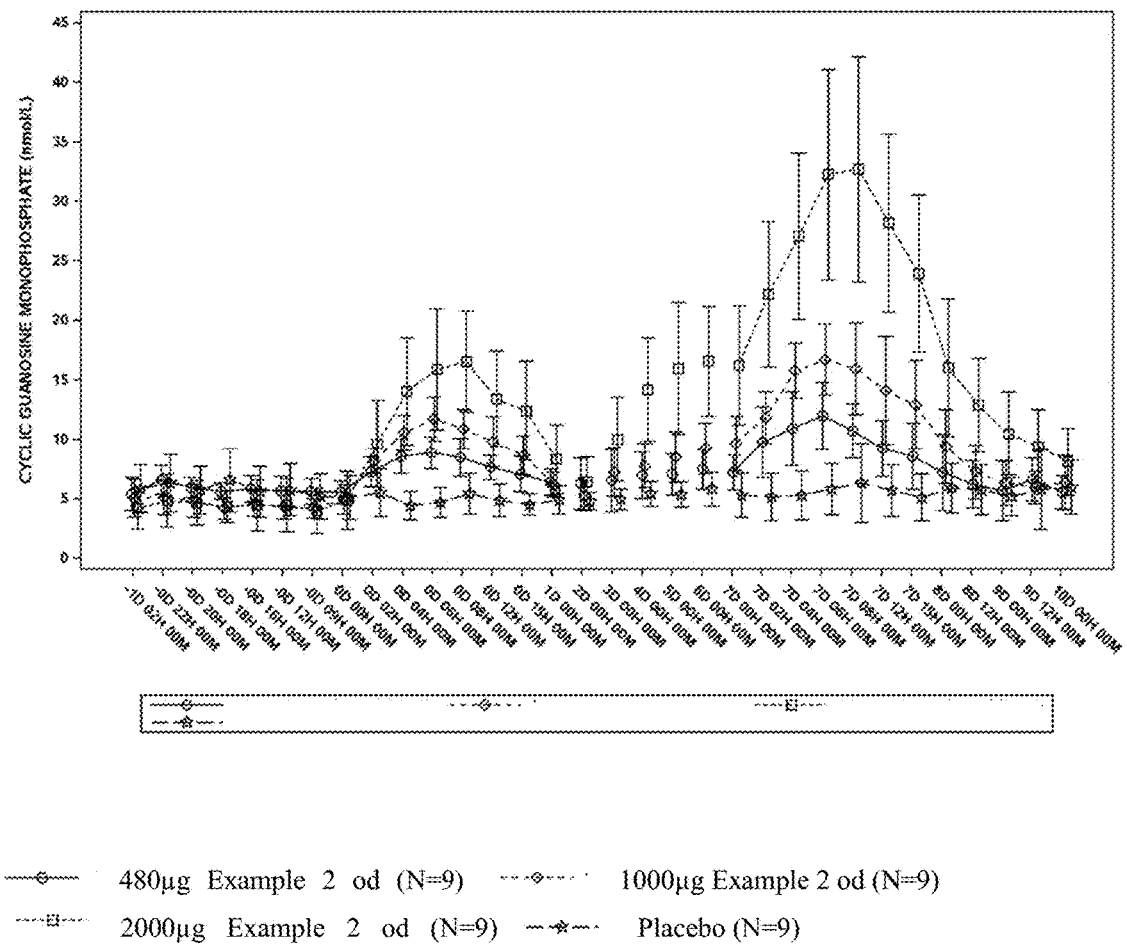
Fig. 56: Means (N = 9) ± SDs for cGMP in body liquids over time (nmol/L) on baseline day (-1d02h – 0d00h) first inhalation day (0d00h -2d00h), trough measurements 2d00h- 7d00h) and after 7 days inhalation (7d00h- 10d00h).

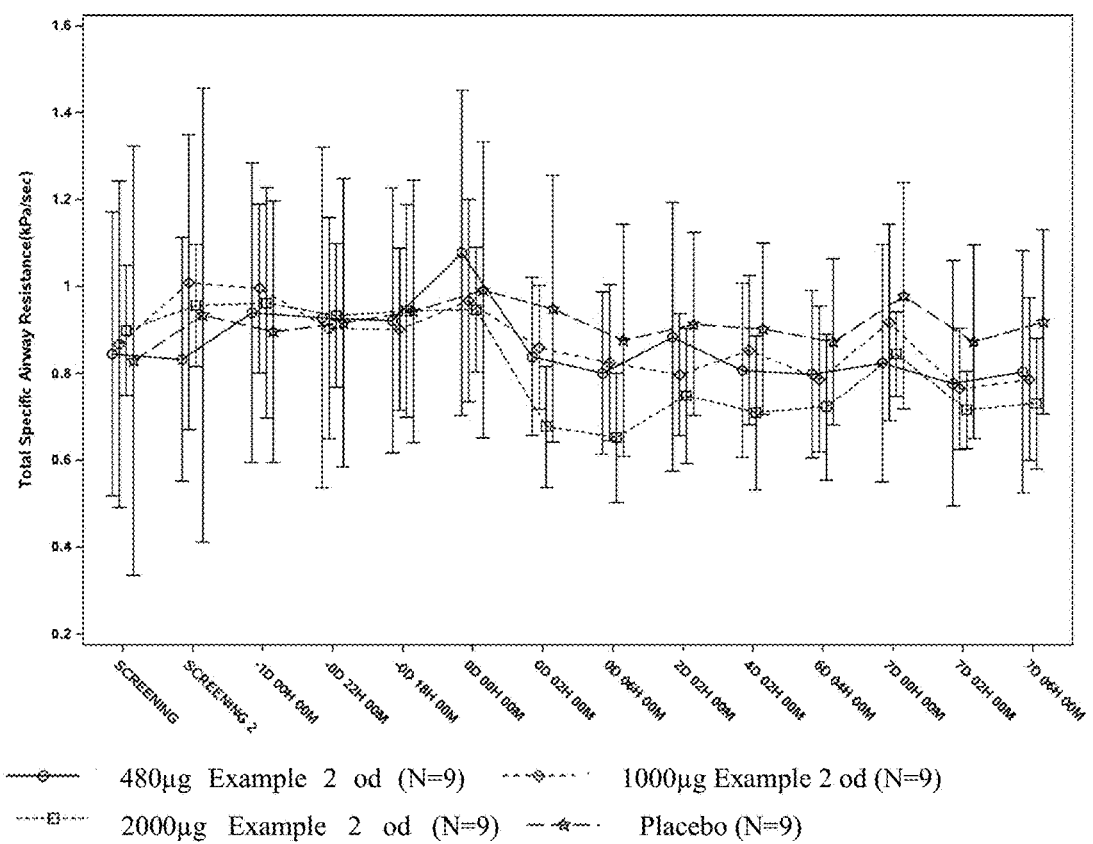
Fig. 57: Means (N = 36, 12 each for 480, 1000 and 2000 µg, example 2) and SDs for total specific airway resistance (kPa/sec) over time: screening 1/2, baseline day (-1d00h – 0d00h) first inhalation day (0d00h - 0d06h), measurements after inhalations 2d02h- 6d04h) and after 7 days inhalation (7d00h- 7d06h).

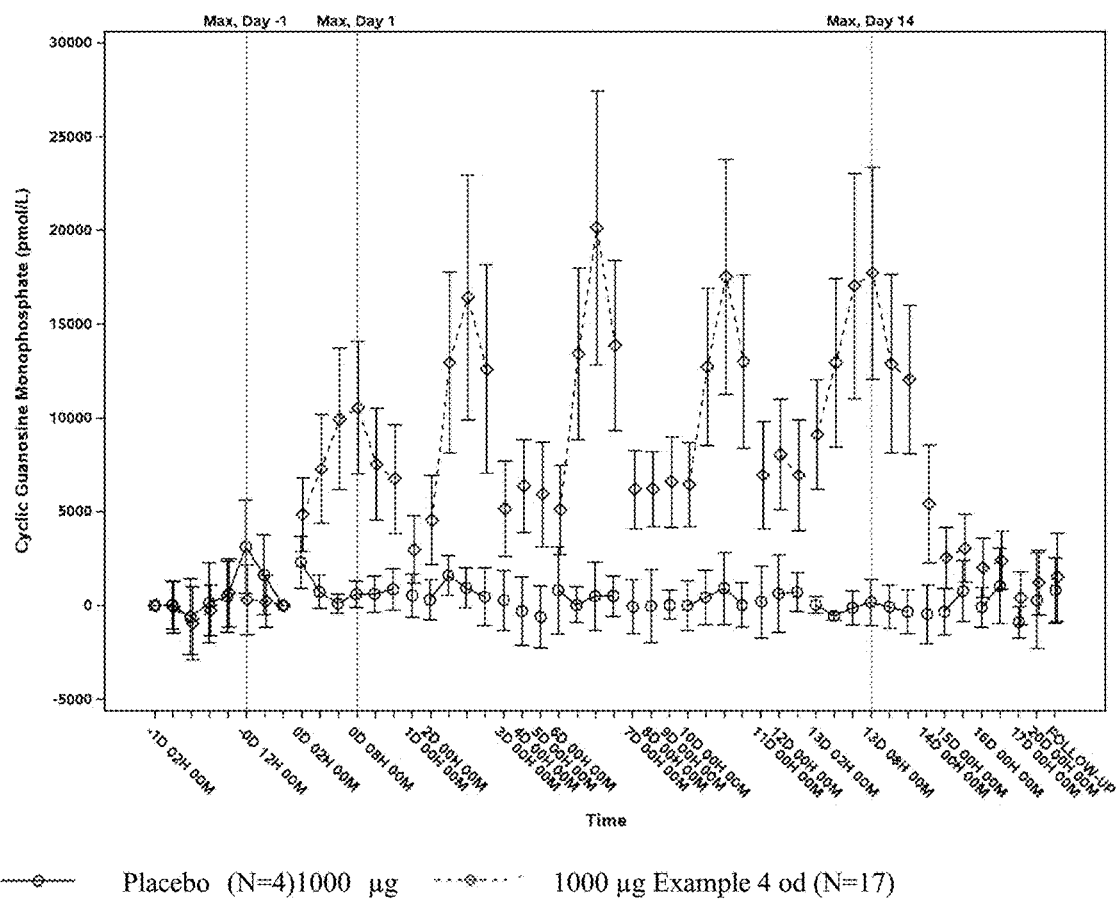
Fig. 58: Means for cGMP difference to baseline for Placebo (N = 4) and 1000 µg, (N = 17) example 4) over time (nmol/L) on pretreatment day (-1d00h – -0d09h) first inhalation day (-0d02h - 1d00h;), measurements prior and after inhalations 2d00h- 2d12h, 6d00h- 6d12h, 10d00h- 10d12h) (profile days), at trough prior inhalation on days 3d – 5d, 7d-9d, 11d-12d) and for last of 14 days inhalation (12d22h-20d00h).

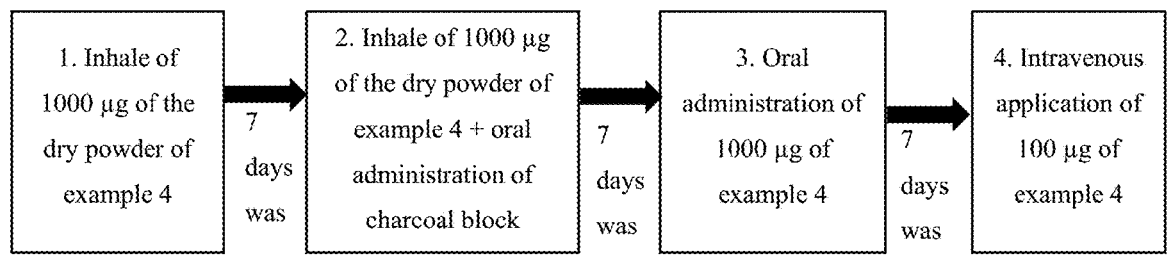
Figure 59: scheme of the treatments conducted to investigate lung deposition
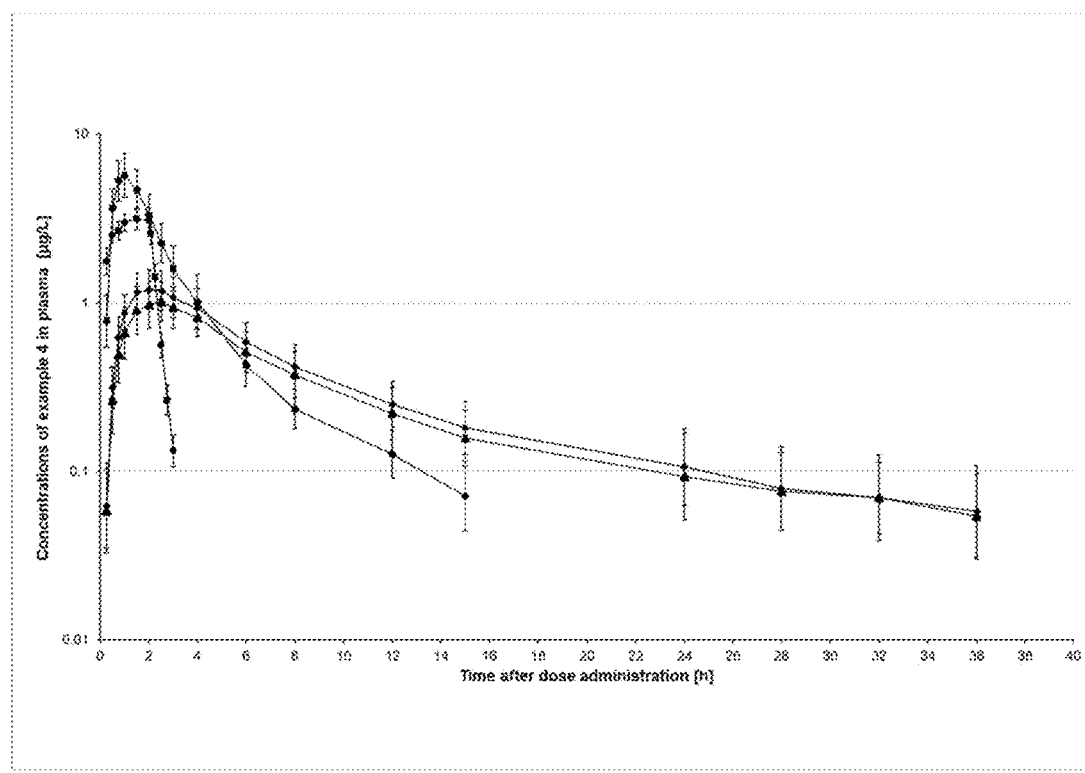
→ 100 μg Example 4 intrevenous, n= 15,   → 1000 μg inhale of example 4, n= 16
→ 1000 μg inhale of example 4 + charcoal, n=16,   → 1000 μg oral dose of example 4, n= 16
Figure 60: Geometric means and standard deviations for concentrations of example 4 (μg/L) in plasma, on semilogarithmic scale.

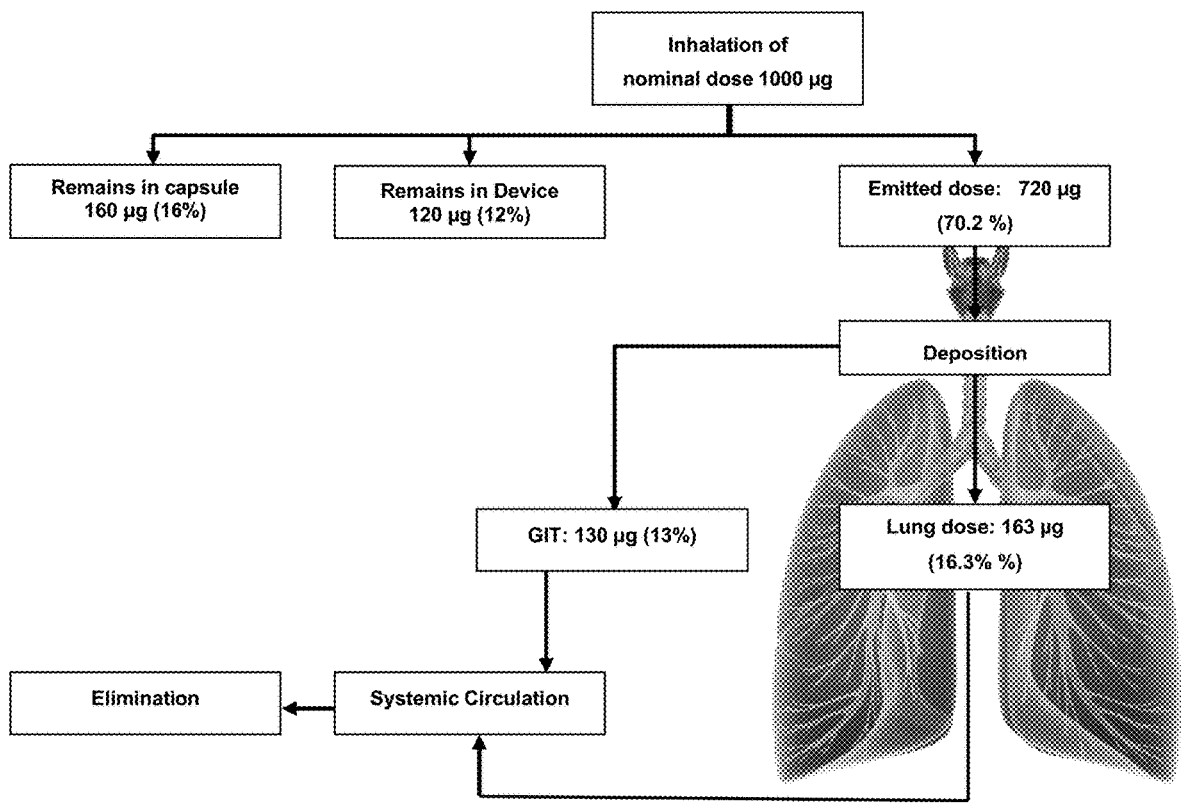
Figure 61: Part of the dose reached the mouthpiece (emitted dose) and parts of the dose remains in the capsule, in the device, the deposited lung dose and part of the dose reached the GIT tract

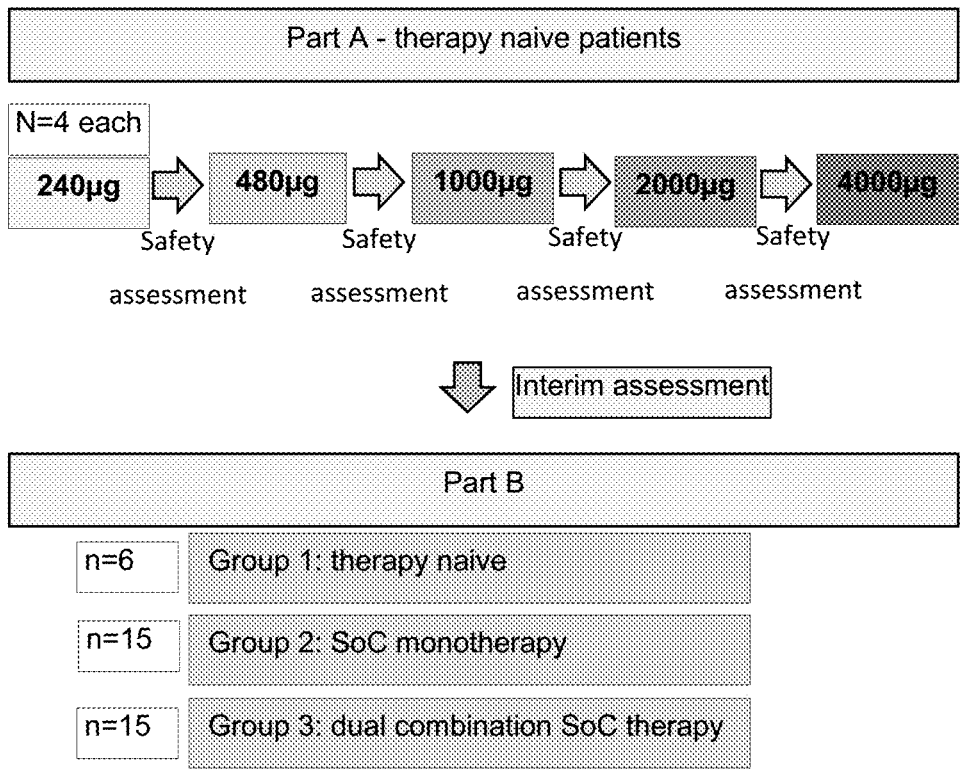

Figure 62: study design of clinical study in patients with PAH or CTEPH

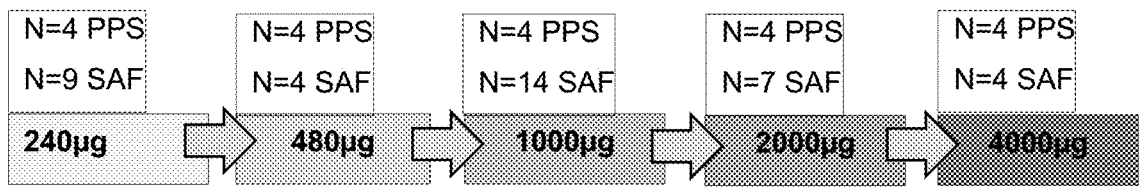

*SAF: safety analysis set: all patients matching in- and exclusion criteria (IC/EC)

*PPS: per protocol set: IC/EC met + PVR > 400 dyn + PAP decrease during inhaled nitric oxide (NO) challenge < 10 mmHG (exclusion of vasoresponsivness)

Figure 63: summary of conducted Part A of clinical study in patients with PAH or CTEPH

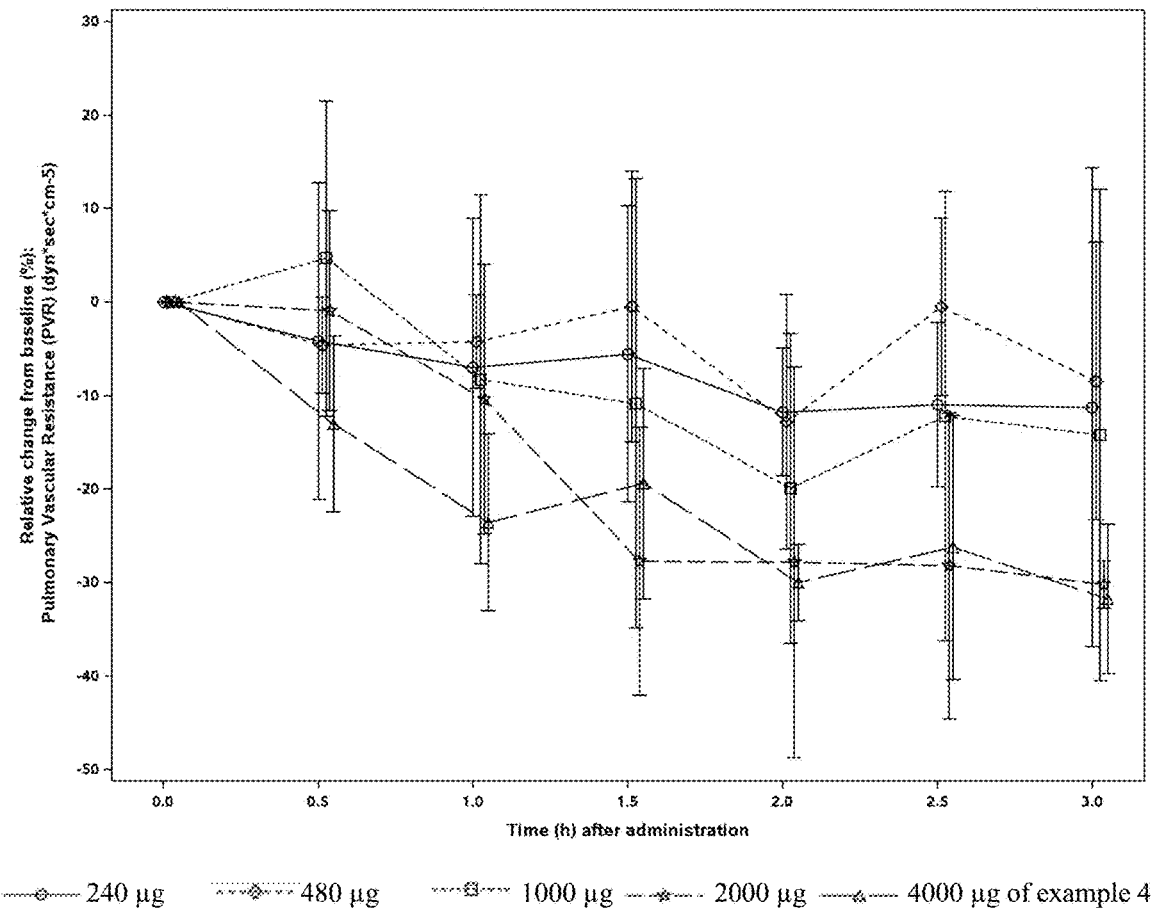
Figure 64: Means and SDs for relative changes (%) from baseline (0D00H00M) of pulmonary vascular resistance (PVR) over time after inhalation (0D00H30M until 0D03H00M) of example 4 in patients with PAH or CTEPH (N=4 each for 240, 480, 1000, 2000 and 4000 µg group, per protocol set)

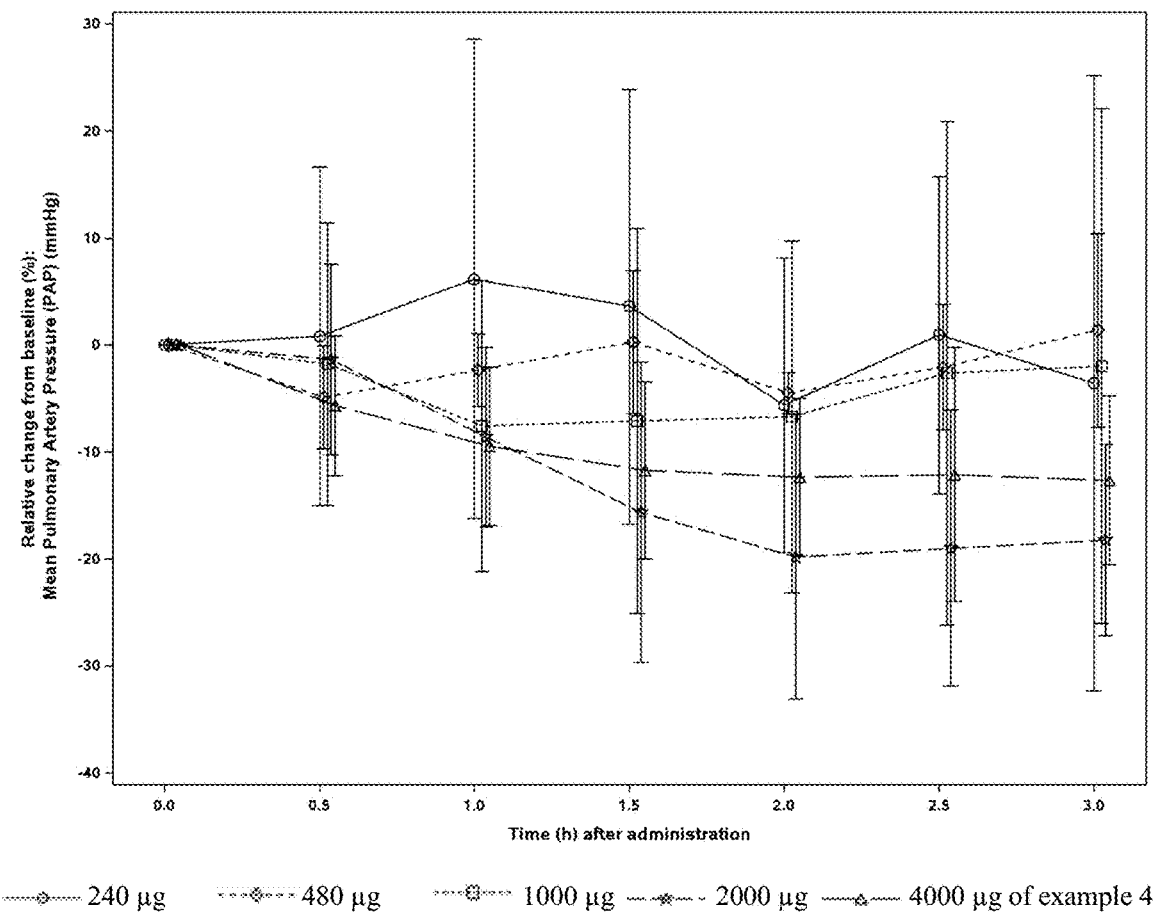
Figure 65: Means and SDs for relative changes (%) from baseline (0D00H00M) of mean pulmonary arterial pressure (mPAP) over time after inhalation (0D00H30M until 0D03H00M) of example 4 in patients with PAH or CTEPH (N=4 each for 240, 480, 1000, 2000 and 4000 μg group, per protocol set).

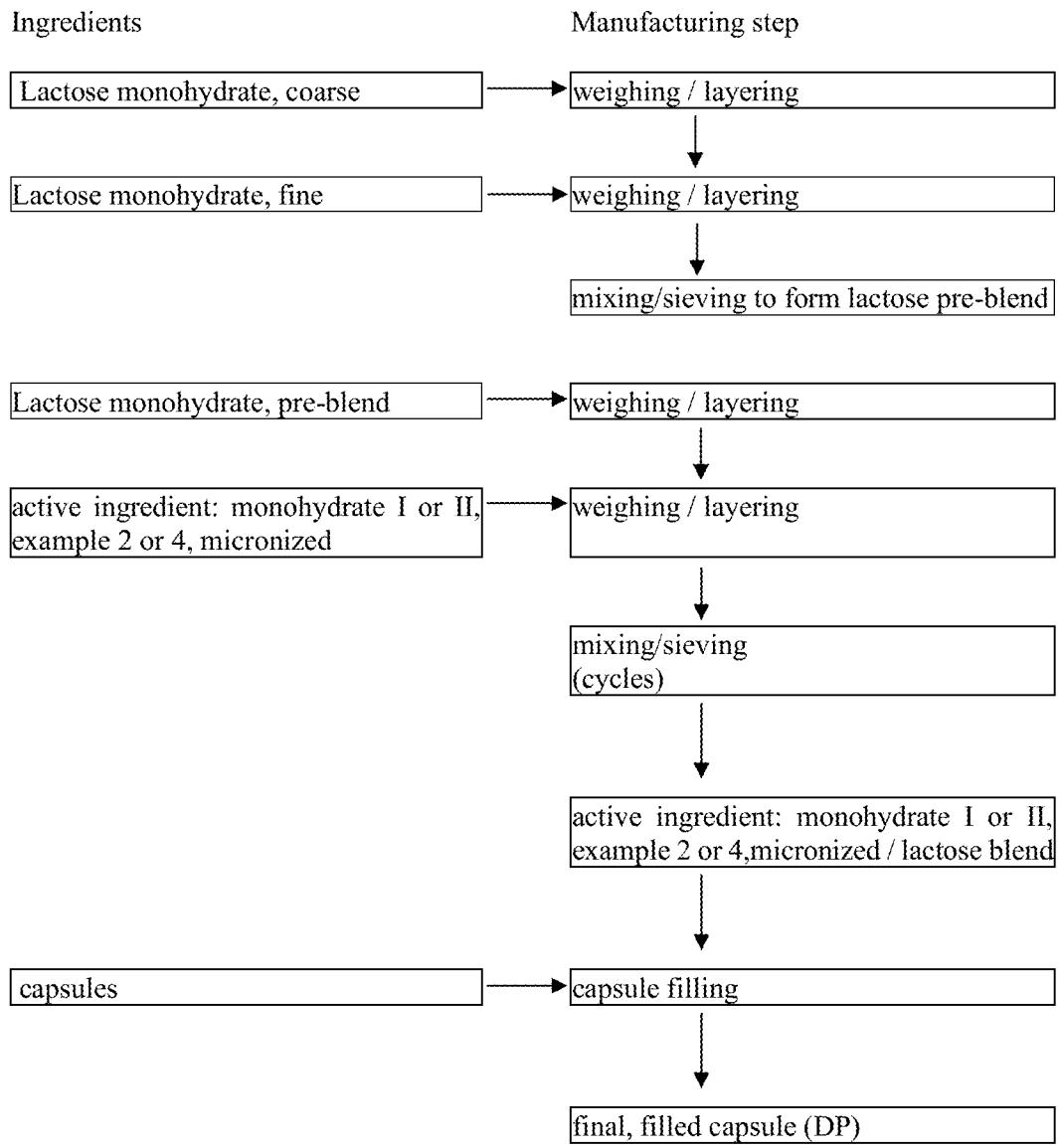
Figure 66. Manufacture flow chart for compounds of the present disclosure

PROCESS FOR PREPARING (5S)-{[2-(4-CARBOXYPHENYL)ETHYL] [2-(2-{[3-CHLORO-4'-(TRIFLUOROMETHYL) BIPHENYL-4-YL]METHOXY}PHENYL) ETHYL]AMINO}-5,6,7,8-TETRAHYDROQUINOLINE-2-CARBOXYLIC ACID AND ITS CRYSTALLINE FORMS FOR USE AS PHARMACEUTICALLY ACTIVE COMPOUND

CROSS-RELATED APPLICATIONS

This application is a continuation of International Application No. PCT/EP2022/087952, filed Dec. 28, 2022, which claims the benefit of Provisional European Patent Application No. 21218163.0, filed Dec. 29, 2021, each of which are hereby incorporated by reference in their entirety.

The present invention relates to a novel and improved process for preparing (5S)—{[2-(4-carboxyphenyl)ethyl][2-(2-{[3-chloro-4'-(trifluoromethyl)biphenyl-4-yl] methoxy}phenyl)ethyl]ami-no}-5,6,7,8-tetrahydroquinoline-2-carboxylic acid of the formula (I)

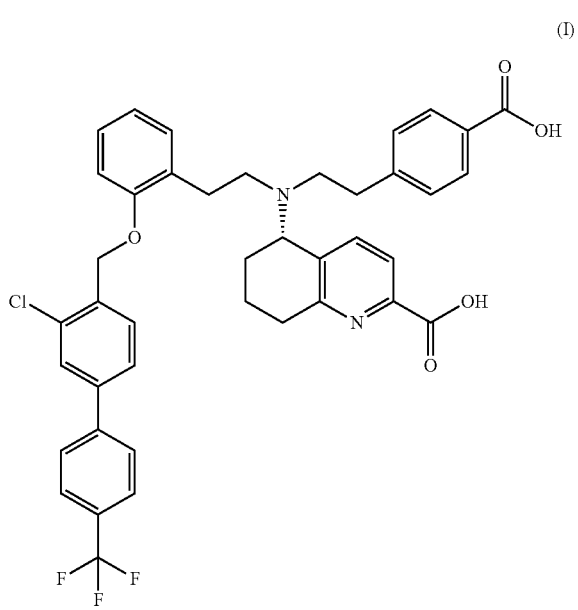 [SMILES: O=C(O)c1ccc(CCN(CCc2ccccc2OCc2ccc(-c3ccc(C(F)(F)F)cc3)cc2Cl)[C@H]2CCCc3nc(C(=O)O)ccc32)cc1]

(I)

and to novel crystalline forms of it, which is i.a. the pseudopolymorphic forms monohydrate I (I-M-I) or monohydrate II (I-M-II),

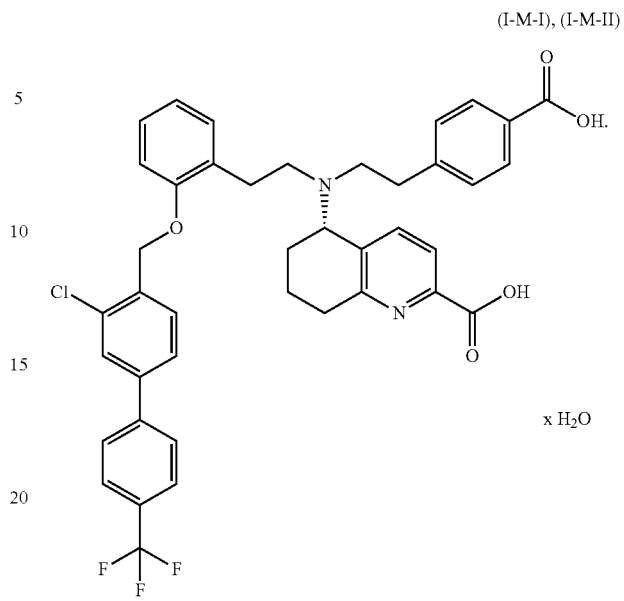

(I-M-I), (I-M-II)

x H₂O

Furthermore the present invention relates to a novel and selective crystallization process for preparation of the pseudopolymorphic form monohydrate I (I-M-I) or the pseudopolymorphic form monohydrate II (I-M-II), preferably monohydrate I of formula (I-M-I) and to pharmaceutical compositions comprising monohydrate I of formula (I-M-I) or the pseudopolymorphic form monohydrate II (I-M-II), preferably monohydrate I of formula (I-M-I) and to its use for the treatment and/or prevention of diseases, in particular for the treatment and/or prevention of pulmonary, cardiopulmonary and cardiovascular diseases such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

In the context of this invention, (I-A) refers to the compound of the formula (I) in amorphous form; the crystalline modification I, monohydrate I is referred to as (I-M-I) and the crystalline modification II, monohydrate II is referred to as (I-M-II). Without further differentiation, the compound of the formula (I) is present in one or more modifications or as a solvate, especially as hydrate.

Unpublished pharmacological studies surprisingly revealed that example 23 of WO 2014/012934, namely (5S)—{[2-(4-carboxyphenyl)ethyl][2-(2-{[3-chloro-4'-(trifluoromethyl)biphenyl-4-yl]methoxy}phenyl)-ethyl] amino}-5,6,7,8-tetrahydroquinoline-2-carboxylic acid of the formula (I) compared to similar 5,6,7,8-tetrahydroquinoline-2-carboxylic acids disclosed in WO 2014/012934 has improved pharmacological properties, like e.g. a longer duration of action. Therefore acid of formula I is suitable for use in the treatment of cardiopulmonary diseases and use in the production of inhalative medicaments for these diseases.

As preferred medicament form dry powder inhale dosage forms were chosen due to their suitability, convenience and patient compliance and adherence in the targeted pulmonary diseases.

However as disclosed in example 23 of WO 14/012934-A1, (5S)—{[2-(4-Carboxyphenyl)ethyl][2-(2-{[3-chloro-4'-(trifluoromethyl)biphenyl-4-yl]methoxy}phenyl)ethyl]

amino}-5,6,7,8-tetrahydroquino-line-2-carboxylic acid of formula (I) is only obtainable in amorphous form (see comparative example 11), which is unsuitable for use in inhalative dosage forms administered by dry powder inhalers.

For the development of a medicinal form, especially in form of a dry powder inhalation form comprising (5S)—{[2-(4-carboxyphenyl)ethyl][2-(2-{[3-chloro-4'-(trifluoromethyl)biphenyl-4-yl]methoxy}phenyl)-ethyl]amino}-5,6,7,8-tetrahydroquinoline-2-carboxylic acid of the formula (I) in solid form, there is a high demand for the reproducible manufacturing and isolation of the compound of the formula (I) in one defined crystalline form.

Many efforts were needed to crystallize compound of formula I finally into a defined solid form.

Usually (5S)—{[2-(4-Carboxyphenyl)ethyl][2-(2-{[3-chloro-4'-(trifluoromethyl)biphenyl-4-yl]methoxy}-phenyl)ethyl]amino}-5,6,7,8-tetrahydroquinoline-2-carboxylic acid of formula I tends to solidify in the amorphous state. To overcome this property a salt selection screening was performed in an attempt to find a new crystalline material with beneficial properties. All trials led to amorphous or highly disordered material and a salt formation was not observed. As example the XRPD patterns of the resulting residue of the experiment with L-arginine are presented (see FIG. 4).

Surprisingly compound of formula I was obtained in several pseudopolymorphic forms, no anhydrous crystalline form was found.

The following crystalline forms of the compound of formula (I) have been identified which are the pseudopolymorphic forms Monohydrate I and II ((I-M-I) and (I-M-II)), Semihydrate, Sesquihydrate, Dihydrate and the 1.25 Hydrate (see example 6, FIGS. 5-32). In this context modifications, polymorphic forms and polymorphs have the same meaning. In addition the amorphous form exists. All together—the pseudopolymorphic forms and the amorphous form—are different solid forms of the compound of formula (I).

Compound stability and uniformity is a key requirement for a pharmaceutical and a prerequisite for an approval by health authorities. It increases the safety and quality of preparations and formulations comprising of the compound of the formula (I) and thus reduces the risk to the patient.

However out of the several identified pseudopolymorphic forms the most suitable and stable form had to be identified during several stages.

It was found that the dihydrate underwent amorphization during drying processes (see FIG. 10a). The crystalline lattice of the semihydrate exhibits disorder (see FIG. 5), which can support phase transitions and/or amorphization in mechanical processing, like e. g. formulation processes. The crystallization of the sesquihydrate was not feasible for scale up, because of very long stirring procedures.

Both monohydrates were found to overcome these unwanted properties of the different pseudopolymorphic forms. However finally it turned out that only one of these monohydrate forms is stable during micronization and therefore the most suitable form e.g. for use in the production of an inhalative medicament, especially as a dry powder based inhalative medicament. Surprisingly during micronization it was found that monohydrate II showed depending on the micronization conditions either partial amorphization (see example 8b, FIG. 42) or in addition to that a transformation to monohydrate I (see example 8a, FIG. 43). Furthermore it was observed that monohydrate II showed transformation to monohydrate I also during storage (see example 7b, FIGS. 40 and 41). Pseudopolymorphic form monohydrate I is therefore suitable and preferred over the other solid forms of the compound of formula I for use in the pharmaceutical field, in particular suitable for pharmaceutical compositions, especially for dry powder inhalative dosage forms.

In particular the monohydrate I form of the compound of the formula (I) ensures that an undesired conversion into another form of the compound of formula (I) and an associated change in the properties as described above is prevented.

The compounds of formulae (I), (I-M-I) and (I-M-II) act as activators of soluble guanylate cyclase and can be employed as agents for the prophylaxis and/or the treatment of pulmonary, cardiopulmonary and cardiovascular diseases, such as for example for the treatment of pulmonary arterial hypertension (PAH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP), more specifically it relates to a method of treating a cardiopulmonary disorder, such as pulmonary arterial hypertension (PAH) and pulmonary hypertension (PH) associated with chronic lung disease (PH group 3) such as PH-COPD and PH-IIP.

BACKGROUND OF THE INVENTION

Pulmonary hypertension (PH) is a progressive lung disorder which, untreated, leads to death within a few years after diagnosis. Pulmonary hypertension is defined by an elevation of the mean pulmonary arterial pressure (mPAP) (normal value<20 mmHg at rest). The pathophysiology of pulmonary hypertension is characterized by vasoconstriction and remodeling of the pulmonary vessels. In chronic PH there is neomuscularization primarily of unmuscularized pulmonary vessels, and the vascular muscles of the already muscularized vessels increase in circumference. This increasing obliteration of the pulmonary circulation results in progressive stress on the right heart, which leads to a reduced output from the right heart and eventually ends in right heart failure [M. Humbert et al., J. Am. Coll. Cardiol. 2004, 43, 13S-24S]. Idiopathic (or primary) pulmonary arterial hypertension (IPAH) is a very rare disorder, whereas secondary pulmonary hypertension (non-PAH PH) is very common, and it is thought that the latter is currently the third most common group of cardiovascular disorders after coronary heart disease and systemic hypertension. Since 2008, pulmonary hypertension is classified in accordance with the Dana Point classification into various sub-groups according to the respective etiology [M. Humbert and V. V. McLaughlin, J. Am. Coll. Cardiol. 2009, 54 (1), S1-S2; D. Montana and G. Simonneau, in: A. J. Peacock et al. (Eds.), Pulmonary Circulation. Diseases and their treatment, 3rd edition, Hodder Arnold Publ., 2011, pp. 197-206; updated Nizza classification Gérald Simonneau, David Montani, David S. Celermajer, Christopher P. Denton, Michael A. Gatzoulis, Michael Krowka, Paul G. Williams, Rogerio Souza: Haemodynamic definitions and updated clinical classification of pulmonary hypertension, in: European Respiratory Journal, 2018; DOI: 10.1183/13993003.01913-2018].

Despite all the advances in the therapy of PH there is as yet no prospect of cure of this serious disorder. Standard therapies available on the market (for example prostacyclin analogs, endothelin receptor antagonists, phosphodiesterase inhibitors) are able to improve the quality of life, the exercise tolerance and the prognosis of the patients. These are therapeutic principles which are mainly administered systemically (beside inhaled Treprostinil and inhaled Iloprost or NO) and act primarily haemodynamically by modulating vessel tone. The applicability of these medicaments is limited owing to side effects, some of which are serious, and/or complicated administration forms. The period over which the clinical situation of the patients can be improved or stabilized by specific monotherapy is limited (for example owing to the development of tolerance). Eventually the therapy escalates and thus a combination therapy is applied, where a plurality of medicaments must be given concurrently. Currently, these standard therapeutics are approved only for the treatment of pulmonary arterial hypertension (PAH) and chronic thromboembolic pulmonary hypertension (CTEPH). In the case of secondary forms of PH related to lung diseases (PH group 3) such as PH-COPD or PH-IIP, these therapeutic principles (for example sildenafil, bosentan) have failed in clinical studies since, as a result of non-selective vasodilatation, they lead to a reduction (desaturation) of the arterial oxygen content in the patients. The probable reason for this is an unfavourable effect on the ventilations-perfusion adaptation in the lung in heterogenous lung disorders owing to the systemic administration of non-selective vasodilators [I. Blanco et al., Am. J. Respir. Crit. Care Med. 2010, 181, 270-278; D. Stolz et al., Eur. Respir. J. 2008, 32, 619-628].

Novel combination therapies are one of the most promising future therapeutic options for the treatment of pulmonary hypertension. In this connection, the finding of novel pharmacological mechanisms for the treatment of PH is of particular interest [Ghofrani et al., Herz 2005, 30, 296-302; E. B. Rosenzweig, Expert Opin. Emerging Drugs 2006, 11, 609-619; T. Ito et al., Curr. Med. Chem. 2007, 14, 719-733]. In particular novel therapeutic approaches which can be combined with the therapy concepts already on the market may form the basis of a more efficient treatment and thus be of great advantage for the patients. In addition, selective pulmonary applicability of such a novel principle of action could offer the option of not only using it for PAH, but especially also provide a first therapy option for patients suffering from secondary forms of PH (PH group 3)) because they avoid unselective systemic vasodilation by targeted application to ventilated areas of the lung via inhaled application.

In an animal model of pulmonary hypertension, it was demonstrated that inhalative administration of the sGC activator BAY 58-2667 (cinaciguat) in the form of microparticles leads to a dose-dependent selective reduction of the pulmonary arterial pressure. In this model, intravenous administration of 1H-1,2,4-oxadiazolo[4,3-a]quinoxalin-1-one (ODQ), which oxidizes the prosthetic haem group of the sGC, reduced the vasodilative effect of inhaled NO (iNO), whereas this was increased by BAY 58-2267. These results led to the hypothesis that inhalative administration of an sGC activator might represent a novel effective treatment method for patients suffering from pulmonary hypertension, in particular if the response of these patients to iNO and/or to PDE5 inhibitors is reduced as a consequence of a lack of NO or an oxidation of sGC [O. V. Evgenov et al., Am. J. Respir. Crit. Care Med. 2007, 176, 1138-1145]. However, in this model cinaciguat for its part did not have a sufficient duration of action, and in addition higher dosages led to unwanted systemic side effects.

Merck Sharp Dohme is developing a sGC stimulator inhaled application as dry powder (MK5475; NCT04609943) for PAH. However as in PH and other lung diseases, the responsiveness to inhaled nitric oxide (iNO) and sGC stimulators could be impaired by the oxidation of sGC. An inhaled sGC activator targeted to the lungs may overcome this limitation.

To this end, it should be possible to combine (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid with approved, established standard therapy of pulmonary hypertension, but also with the basic therapeutics for chronic lung diseases e.g. COPD and IIP in secondary PH forms.

Oral application is often a preferable route of administration for an active drug. With respect to cardiopulmonary indications a local application of the drug to the target organ lung is preferred to improve efficacy by increase of local drug concentration and avoid systemic side effects of a drug caused by systemic availability. In general less frequent dose regimen is desirable e.g. to improve patient's adherence (patient's compliance) to therapy, but 24 h coverage has to be ascertained for sustained efficacy of haemodynamically active drugs during the dosing interval. A lot of lung targeted, inhaled drugs require frequent application schemes (e.g. Iloprost/Ventavis)) due to their e.g. short half-lives and/or lung retention time, which require multiple daily applications for a 24 hours coverage. In particular, once daily application is preferred due to favourable convenience for the patient and for compliance reasons. However, this goal is sometimes difficult to achieve depending on the specific behaviour and properties of the drug substance, especially its lung selectivity and lung retention time.

A further way of systemic administration, injection, is even more associated with many drawbacks (e.g. inconvenience of clinical visit required, discomfort, patient aversion to needle-based delivery methods, drug reactions at the administration side), all the more requiring alternative administration routes.

Pulmonary delivery by inhalation is one such alternative administration route which can offer several advantages over oral and injection administration. These advantages are especially the higher efficacy by increased local concentration and the potential for reduced systemic drug side effects but include also the convenience of patient self-administration, ease of delivery by inhalation, the elimination of needles, and the like.

For the pharmaceutical preparation for inhalation, where no adjuvants are necessary, especially in the case of solid preparations for suspension inhalation, preparations may consist of active ingredient alone. However, for practical reasons, e.g. to facilitate drug delivery of very low doses of active ingredients, the preparations are often medicaments which, besides the active ingredient, contain one or more pharmacologically inactive and physiologically acceptable excipients or carrier. A review of various suitable preparations and corresponding administration aids is to be found for example in R. Stangl, "An Overview of Innovative Inhalation Devices", European Pharmaceutical Review, pages 50-55, (2002) and the literature cited therein. In 2019, Moon et al published an updated review on delivery technologies for orally inhaled products (Moon et al., AAPS PharmSciTech 20, 2019 117 pp 1-17).

PRIOR ART

The compound of the formula (I) in amorphous form (see comparative example 11) and its preparation process are described in the patent application WO 2014/012934 (see example 23), starting from the precursor ethyl-5-([2-(2-{[3-chlor-4'-(trifluormethyl)biphenyl-4-yl]methoxy}phenyl)

ethyl]{2-[4-(methoxycarbonyl)-phenyl] ethyl-}amino)-5,6,7,8-tetrahydro-chinolin-2-carboxylate (example 92A in WO 2014/012934) and outlined in scheme 1 below.

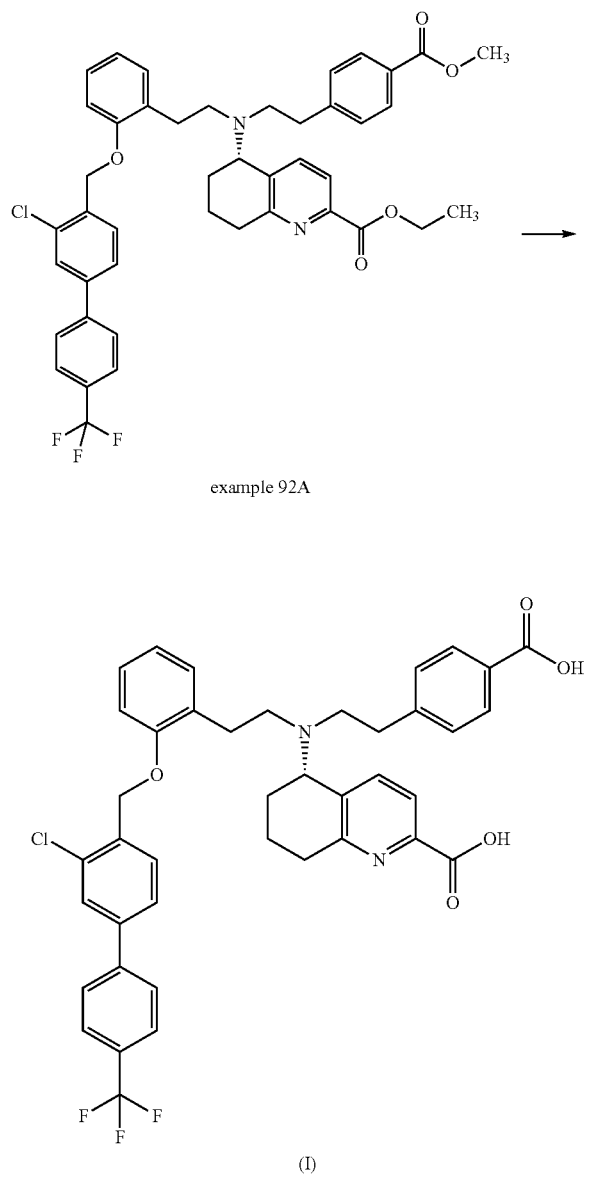

Scheme 1: preparation of compound of formula (I) according to WO 2014/012934 example 92A (I)

The compound of the formula (I) (mosliciguat) was obtained as an amorphous solid by concentration of chromatography fractions. A defined process for the crystallization of the final stage for adjusting polymorphism has hitherto not been described.

A further disadvantage of this manufacturing method is that it leads to an increased formation of the monosodium salt which is of low solubility (see e.g. comparative example 12). It is not possible to convert this monosodium salt into the free acid by adding further acid. This leads to a large amount of unused monosodium salt which is not acceptable with respect to the quality requirements of the drug substance and has to be filtered off and thus reduces the yield of compound of the formula I.

Furthermore in the process disclosed in WO 2014/012934 dioxane is used as a solvent, which is not according to ICH Guidelines. Contrary to this in the present process dioxane is replaced by THF.

An improved synthesis of another precursor of the compound of formula (I), namely butyl-(5S)-5-({2-[4-(butoxycarbonyl)phenyl]ethyl}[2-(2-{[3-chloro-4'-(trifluoromethyl)[biphenyl]-4-yl]methoxy}phenyl)ethyl]amino)-5,6,7,8-tetrahydrochinoline-2-carboxylate (compound XII)

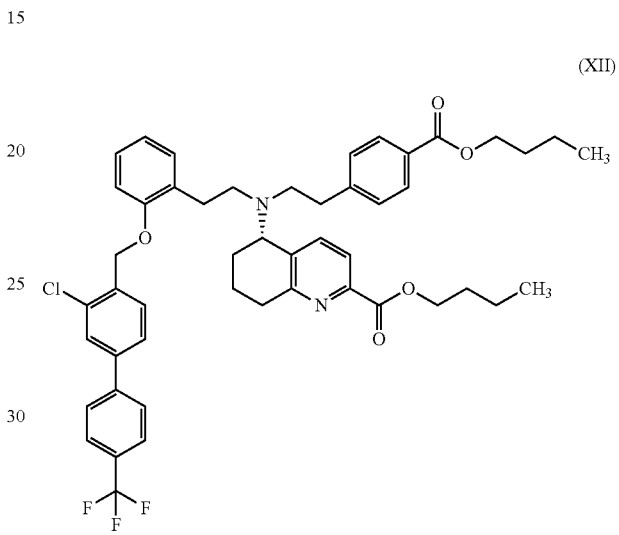

(XII)

has been disclosed in WO2021/233783. However a synthetic approach to compound of formula (I) itself has not been disclosed in this reference.

Therefore there was a need for an improved synthesis practicable on a large industrial scale that affords the compound of formula (I) and especially the crystalline monohydrates I (I-M-1) and/or II (I-M-II), preferably the monohydrate I of formula (I-M-I) reproducibly in a high overall yield, with low production costs and high purity that meets all regulatory requirements.

DETAILED DESCRIPTION OF THE INVENTION

Process

The process according to the present invention, as shown in scheme 2, is characterized in, that purification steps of the intermediates are done via salt formation/extraction/clarification filtration and thereby chromatographic purification steps are avoided. Additionally the process according to the present invention offers high flexibility as the target compound of formula (I) can be made by three routes:

A) route 1 starts with the ester of formula (XII) (process steps [A] and [B]=route 1), B) route 2 starts with an intermediate of formula (X) (WO2021/233783) of a telescope process (process steps [C], [A] and [B]=route 2), C) route 3 starts with the solid NSA salt of formula (XII-NSA) (process steps [D], [A] and [B]=route 3).

Scheme 2: process of making compound formula (I) according to the present invention, including process routes 1, 2 and 3
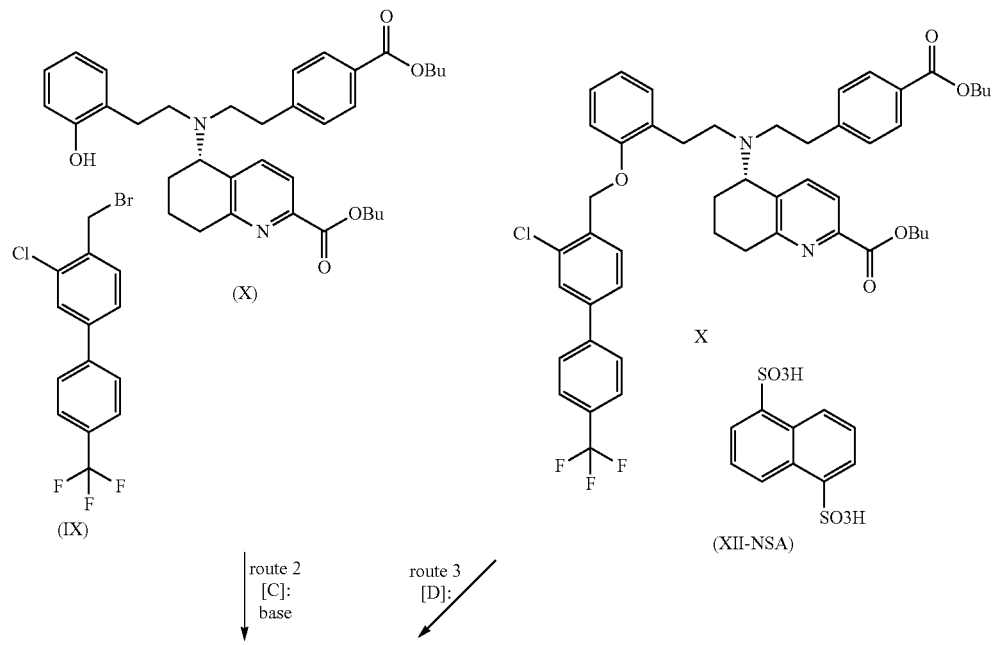
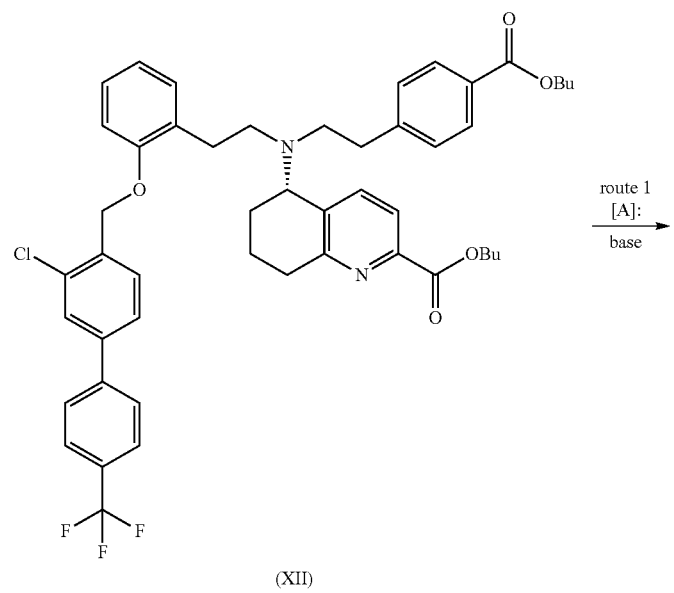

-continued

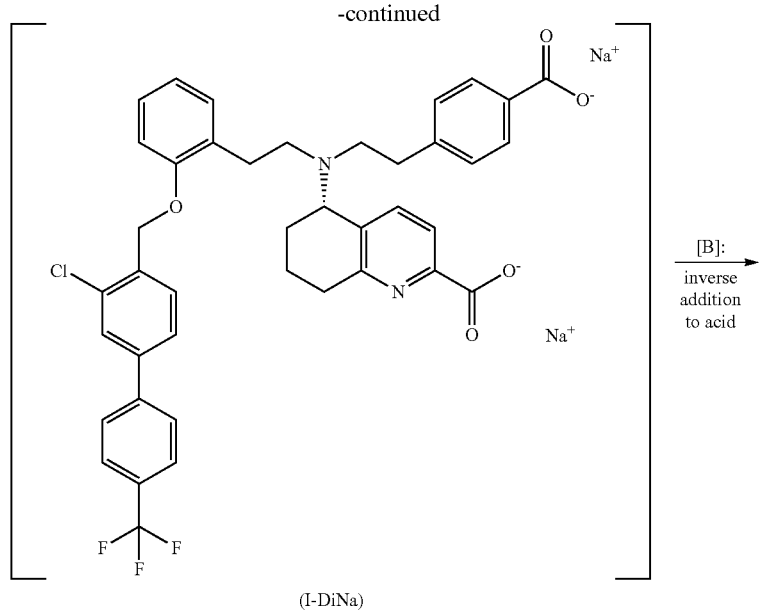

(I-DiNa)

[B]:
inverse addition to acid

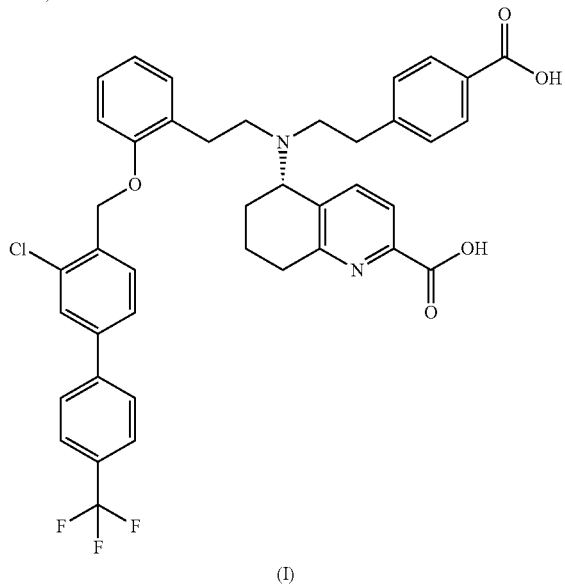

(I)

The core process (route 1) comprising the steps [A] and [B] is utilized in all three alternative routes. This process according to the present invention has several advantages over the prior art process disclosed in WO 2014/012934. Several byproducts which inevitably were included in the product of formula I if made according to the prior art procedure can be avoided or at least easier be separated. The present inventors identified the formation of the target acid of formula (I) from the disodium salt of formula (I-diNa) in step [B] as a major issue. It is crucial to run this step in an inverse manner controlling the pH of the reaction mixture. Therefore process step [B] requires the inverse addition of the disodium salt intermediate of formula (I-DiNa) to an equimolar amount of acid equivalents. By this inverse addition the formation of the sparingly soluble mono sodium salt of compound of formula (I) is significantly reduced in comparison to the prior art process (see comparative example 11). However principally formed low amounts of the mono sodium salt as well as other sparingly soluble impurities can be separated by clarification filtration of the disodium salt solution. Additionally further byproducts like hydrochlorides are avoided by the inverse addition.

Alternatively, the compound of the formula (I) can be prepared without isolating intermediates starting from compounds (X) and (XI) by coupling, subsequent cleavage of the diester and acidic release (shown by way of example in process step [C], [A] and [B], see scheme 2 (route 2).

In an alternative route 3) the compound of the formula (I) can be prepared via its NSA salt, characterized in that in a first step [D] the dibutylester has to be released from the NSA salt of formula (XII-NSA) which is than further transformed into the free acid via two steps (basic saponification of the dibutylester (step [A]) and thereafter inverse addition to acid to release the free acid of formula (I) (step [B]).

Therefore the process according to the present invention provides (5S)—{[2-(4-Carboxyphenyl)ethyl][2-(2-{[3-chloro-4'-(trifluoromethyl)biphenyl-4-yl]methoxy}phenyl)

ethyl]amino}-5,6,7,8-tetrahydro-quinoline-2-carboxylic acid of formula (I) in increased yield and high purity in contrast to the process disclosed in WO 2014/012934.

In order to provide the desired crystalline form monohydrate I of formula (I-M-I) in high purity a selective crystallization method was needed.

A selective crystallization process according to the present invention, as shown in scheme 3, is characterized in that (5S)—{[2-(4-Carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid of formula (I) is obtained in crystalline, pure form, especially in form of monohydrate, modification I, (I-M-I) or monohydrate, modification II (I-M-II), preferably monohydrate, modification I, (I-M-I).

Scheme 3: selective crystallization of the acid of formula (I) to yield monohydrate forms thereof

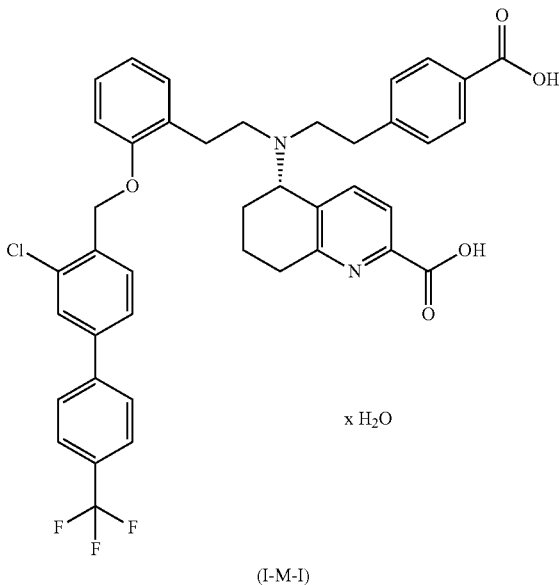

(I-M-I)

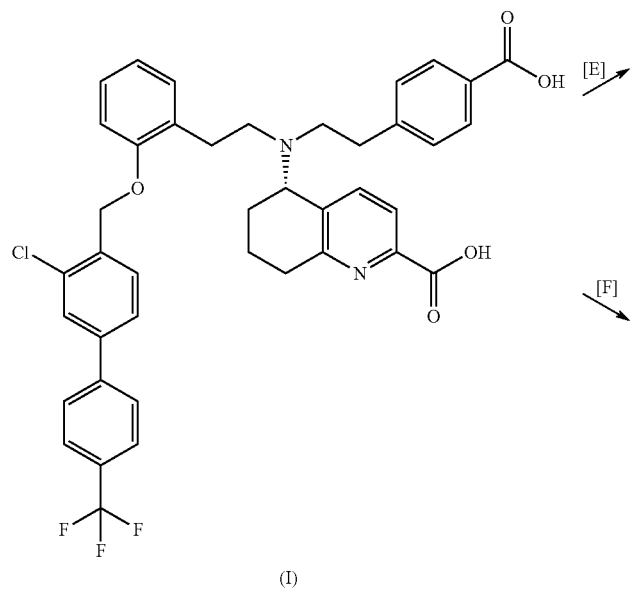

(I)

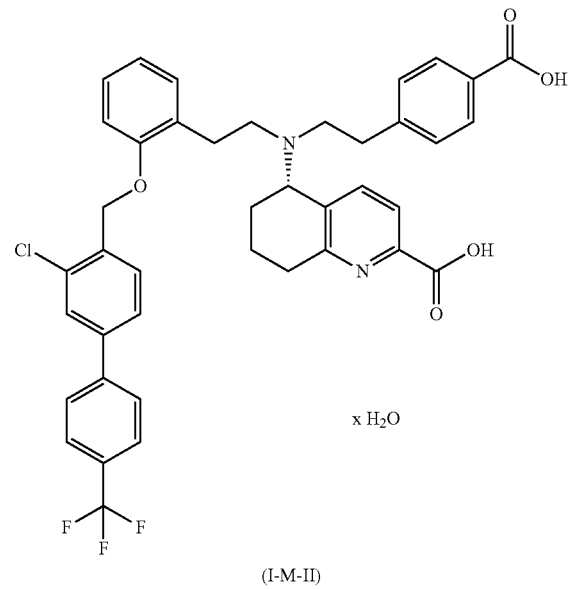

(I-M-II)

Depending on the used solvent either the monohydrate (I-M-I) is formed or the monohydrate (I-M-II). Surprisingly crystallization from a mixture of acetone, methanol and water or methanol and water (process [E]) selectively yields the monohydrate I, compound of formula (I-M-I) whereas crystallization from a mixture of acetone and water (process [F]) selectively yields the monohydrate II, compound of formula (I-M-II).

The described manufacturing process, including all three process routes 1, 2 and 3 according to the present invention (see scheme 2) can be advantageously combined with the described crystallization process (see scheme 3) in order to obtain selectively and in high yield and purity the crystalline forms of the acid of formula (I), preferably monohydrate I of formula (I-M-I) by using crystallization from a mixture of methanol and water (process [E]).

The processes according to the present invention thereby are suitable, to manufacture the acid of formula (I), especially in the form of monohydrate modification I (I-M-I) or monohydrate, modification II (I-M-II), preferably monohydrate, modification I, (I-M-I) reproducibly, in high yield and purity in an industrial scale synthesis.

Schemes 4, 5 and 6 below illustrate the process according to the present invention: (route 1), (route 2) and route 3 in an exemplary manner.

Scheme 4: process for perparing compound of formula (I)
via inverse acidic titration of di sodium salt (I-DiNa) (route 1)

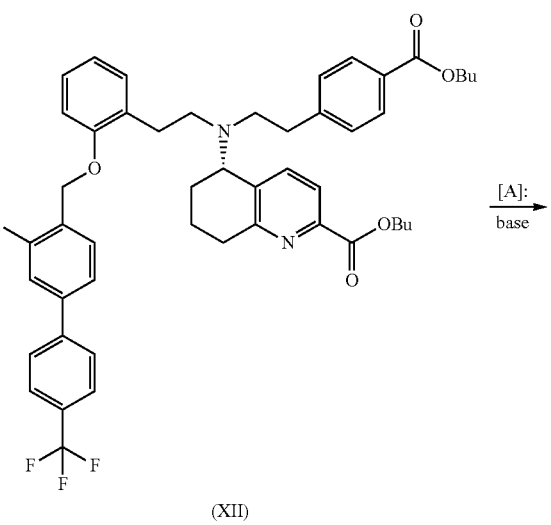

(XII)

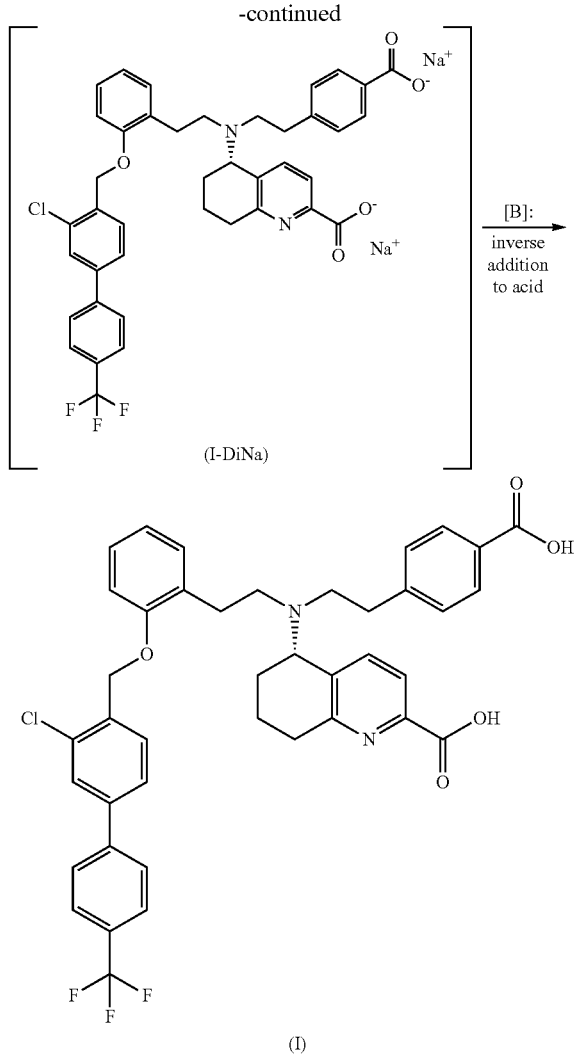

(I-DiNa)

[B]: inverse addition to acid (I)

The process comprises the following steps: basic cleavage of a diester of the compound of the formula (XII) (step [A]), for example the dibutyl ester of the formula (XII), and subsequent acidic release of the final acid of formula (I) in process step [B], scheme 4). This process is characterized in, that the di sodium salt (I-DiNa) is portionwise added to a solution of a mineral acid in a suitable solvent, e.g. THF, wherein the endpoint of the pH of the solution is carefully monitored to stay within a window of between pH values of 3.8 and 4.2.

Process Step [A]

To prepare the target acid of formula (I) from the diester (XII), the diester (XII) is first cleaved.

Compound of formula (XII) is available via e.g. a coupling reaction of its precursor (X) with 4-(bromomethyl)-3-chloro-4'-(trifluoromethyl)[biphenyl] (XI) in an inert polar solvent (disclosed in WO2021/233783, example 11).

For the ester cleavage (XII)→(I-DiNa) (step [A]), the compound of the formula (XII) is dissolved in THF or dioxane, preferably THF, and a suitable base, e.g. sodium hydroxide, potassium hydroxide or lithium hydroxide solution, preferably sodium hydroxide solution, particularly preferred 4% sodium hydroxide solution (1 N), is added in excess, preferably in a 4 fold molar excess and stirred at a temperature of 20° C. to 70° C., preferably 60° C., until complete conversion to the disodium salt, dilithium salt or dipotassium salt of the compound of the formula (I). To purify the reaction mixture, a suitable ester as solvent, preferably ethyl acetate, and optionally deionized water is added, preferably at a temperature of 10° C. to 40° C., preferably 23° C., and the aqueous phase containing the di-alkali metal salt (I-DiM), e.g. (I-DiNa), (I-DiK) or (I-DiLi), preferably (I-DiNa), is separated. Extraction is preferably carried out again with the suitable ester, preferably ethyl acetate. Residual ester solvent in the aqueous phase is distilled off under reduced pressure at a temperature of not more than 40° C., preferably 36° C. Optionally, the reaction mixture can be filtered, the filter residue is disposed of. The filtrate is used in the next step.

Process Step [B]

The release of the dicarboxylic acid of the formula (I) from the di-alkali metal salt (I-DiM), e.g. (I-DiNa), (I-DiK) or (I-DiLi), preferably the disodium salt of the compound of the formula (I) (I-DiNa) surprisingly cannot be achieved quantitatively by adding a mineral acid to a solution of the disodium salt of the compound of the formula (I). This leads to incomplete conversion and formation of substantial amounts of the monosodium salt of the compound of the formula (I), which precipitates and cannot be converted to the compound of the formula (I) even by further addition of mineral acids.

Surprisingly, it has been found that the preparation of the compound of the formula (I) is possible by adding a solution of the disodium salt of the compound of the formula (I) (I-DiNa) to a defined amount of acid until a narrowly defined pH Value adjusts. With the method described below ("inverse process"), the reaction of (I-DiNa)→(I) is possible with a high degree of efficiency.

A mixture of THF and a mineral acid, preferably hydrochloric acid, is presented.

As the reaction with an excess of hydrochloric acid results in formation of the unwanted hydrochloride of compound of formula (I) and a shortage of hydrochloric acid results in residual amounts of sodium salts it is crucial to adjust the acid to equimolar amounts. Consequently as compound of formula I contains two basic carboxylate functions it needs to be reacted with 2 equivalents of acid, e.g. preferably 2 equivalents of hydrochloric acid. According to the process of the present invention the main precursor dibutyl ester of the formula (XII) can be presented in several forms: a) in defined content (e.g. by release from NSA salt) or b) as an intermediate solution obtained from telescoped process. Therefore optionally in order to determine the content of disodium salt solution and to calculate the corresponding necessary amounts of acid a small amount of disodium salt solution can be triturated with a defined amount of acid solution, preferably hydrochloric acid.

The consumption of disodium salt solution is than set in relation to the amount of hydrochloric acid submitted and the amount of hydrochloric acid for the conversion of the further partial amounts is calculated accordingly.

The pH of the initially charged hydrochloric acid/THF mixture is less than 3.8. The solution of the compound of the formula (I-DiNa) obtained in step [A] is added in several partial amounts to this mixture, wherein the endpoint of the pH of the solution is carefully monitored to stay within a window of between pH values of 3.8 and 4.2. The organic phase of the reaction mixture is then separated off.

The separation is preferably carried out after the addition of sodium chloride and THF to the reaction mixture and subsequent stirring.

For isolation/purification and/or crystallization of the target compound of formula (I) the organic phase is concentrated. The concentration of the organic phase is done preferably at reduced atmospheric pressure, very preferably at 200 mbar and preferably at a temperature of between 2° and 50° C., very preferably at 40° C.

Optionally the target compound of formula I can be isolated as solid, e.g. by drying at elevated temperatures, e.g. at 60° C. in a stream of nitrogen under vacuum, at reduced atmospheric pressure, very preferably at 200 mbar.

The present invention also provides combinations of the partial reactions introduced above for preparing the compound of the formula (I) in crystalline modification I, monohydrate I of formula (I-M-I) or modification II, monohydrate II of formula (I-M-II), preferably monohydrate I of formula (I-M-I).

Instead of the dibutyl ester derivative, in the aforementioned "inverse" process, also other ester derivatives can be used as the starting material in the alkaline hydrolysis step with sodium hydroxide solution.

Compared to the prior art process (WO 2014/012934, example 23), the novel process has the advantage that formation of the sparingly soluble monosodium salt is decreased (see e.g. comparative example 12). As it is not possible to convert this monosodium salt into the free acid by adding further acid, this leads to a large amount of unused monosodium salt which has to be filtered off and thus reduces the yield of compound of the formula I. This surprising result is obtained by the inverse addition of the disodium salt solution to 2 equivalents of mineral acid.

Furthermore the compound of formula I is obtained in high purity. Thus, in contrast to the prior art (WO 2014/012934) complex chromatography can be dispensed. Additionally in the present process residual sodium salts are separable by filtration prior to crystallization.

Furthermore in the process disclosed in WO 2014/012934 dioxane is used as a solvent, which is not according to ICH Guidelines. Contrary to this in the present process dioxane is replaced by THF.

Surprisingly (5S)—{[2-(4-Carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid of formula I is obtained in defined crystalline forms: a) monohydrate I of formula (I-M-1) b) monohydrate II of formula (I-M-II), depending on the choice of solvent. Whereas by the prior art synthesis compound of formula I is only obtainable in amorphous form.

Surprisingly (5S)—{[2-(4-Carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid of formula I is obtained in one defined crystalline form as monohydrate I of formula (I-M-1) when crystallized from a solvent mixture comprising methanol, acetone and water or methanol and water.

Surprisingly (5S)—{[2-(4-Carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid of formula I is obtained in one defined crystalline form as monohydrate II of formula (I-M-II) when crystallized from a solvent mixture comprising acetone and water.

It has been found that (5S)—{[2-(4-Carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid obtained by the crystallization process described above crystallizes in high yield and purity selectively in form of monohydrate I of formula (I-M-1).

(5S)—{[2-(4-Carboxyphenyl)ethyl][2-(2-{[3-chloro-4'-(trifluoromethyl)biphenyl-4-yl]methoxy}phenyl)-ethyl]amino}-5,6,7,8-tetrahydroquinoline-2-carboxylic acid is not formed in amorphous form but in the crystalline form of monohydrate I of formula (I-M-1) in a high overall yield, including the steps of saponification, disodium salt formation and further conversion to the free acid of formula I and finally purification and crystallization, e.g. of 71% of theory, especially in large scale. Starting from biarylbenzylbromide of formula XI an overall yield of 67% o. theory was achieved. Furthermore the compound is obtained in high purity, e.g. sodium salts are separable by filtration prior to crystallization, hydrochlorides and further impurities are separated off by the crystallization process according to the present invention.

Thus, in contrast to the prior art (WO 2014/012934) complex chromatography can be dispensed and the target compound acid of formula I is finally obtained in high purity and yield in form of e.g. the crystalline monohydrate I of formula (I-M-I).

Embodiment 1 (Route 1)

The present invention provides a process for preparing the compound of the formula (I), characterized in that in a first step [A] the compound of the formula (XII-1),

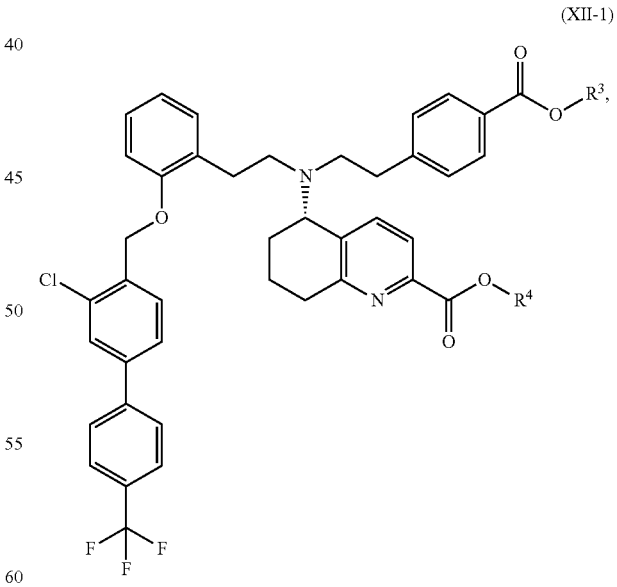

(XII-1)

wherein

R$_3$ and R$_4$ are independently C$_1$-C$_4$-alkyl, solubilized in a suitable solvent is reacted with a base selected from sodium, lithium or potassium hydroxide solution to yield the dialkalimetal salt (I-DiM), wherein M=Na, Li or K

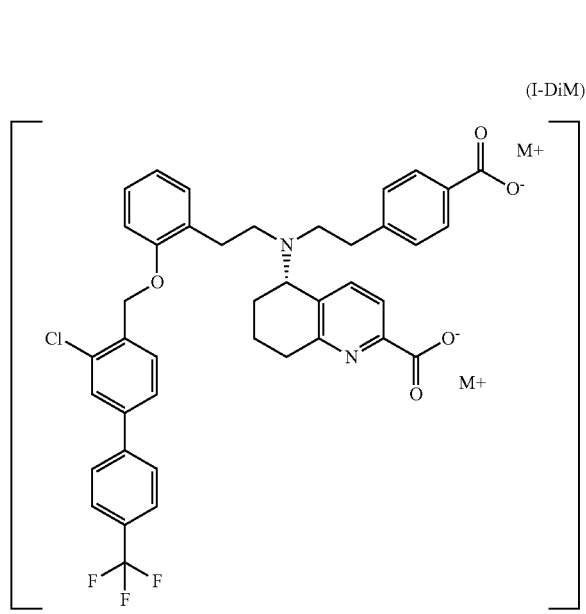

(I-DiM)

which is after extractive purification but without further isolation reacted in a second step [1B]
by adding the reaction solution portionwise to a mixture of a mineral acid in a suitable solvent until a pH value of 3.8 to 4.2 is reached, wherein the pH value of the initially charged mineral acid mixture has a value of less than 3.8 and comprises at maximum two acid equivalents related to the disodium salt
to finally yield compound of the formula (I)

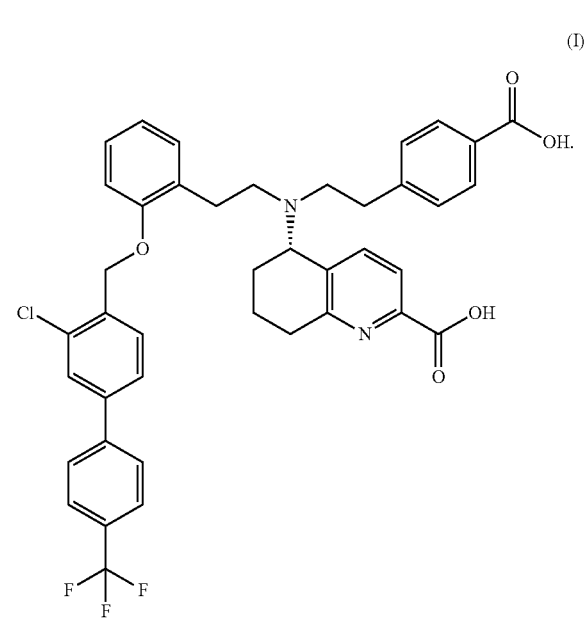 [SMILES: O=C(O)c1ccc(CCN(CCc2ccccc2OCc2ccc(-c3ccc(C(F)(F)F)cc3)cc2Cl)[C@H]2CCCc3nc(C(=O)O)ccc32)cc1]

(I)

The present invention further provides a process for preparing the compound of the formula (I),
characterized in that in a first step [A] the compound of the formula (XII-1) according to embodiment 1,

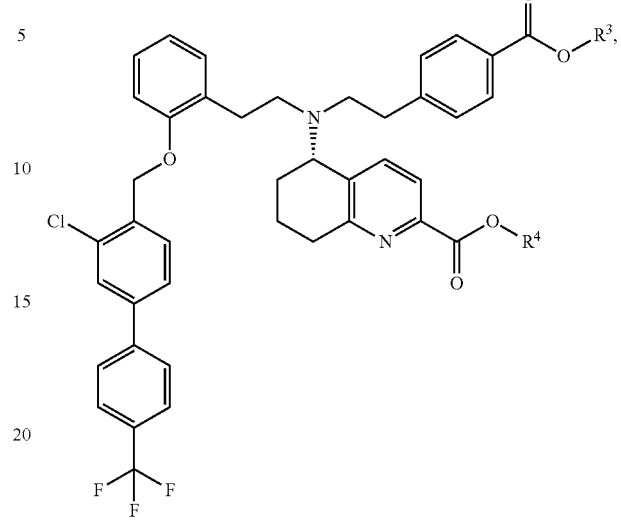

(XII-1)

wherein
R$_3$ and R$_4$ are independently C$_1$-C$_4$-alkyl,
solubilized in a suitable solvent is reacted with sodium hydroxide solution to yield the disodium salt (I-DiNa)

(I-DiNa)

which is after extractive purification but without further isolation reacted in a second step [B]
by adding the reaction solution portionwise to a mixture of a mineral acid in a suitable solvent until a pH value of 3.8 to 4.2 is reached, wherein the pH value of the initially charged mineral acid mixture has a value of less than 3.8 and comprises at maximum two acid equivalents related to the disodium salt

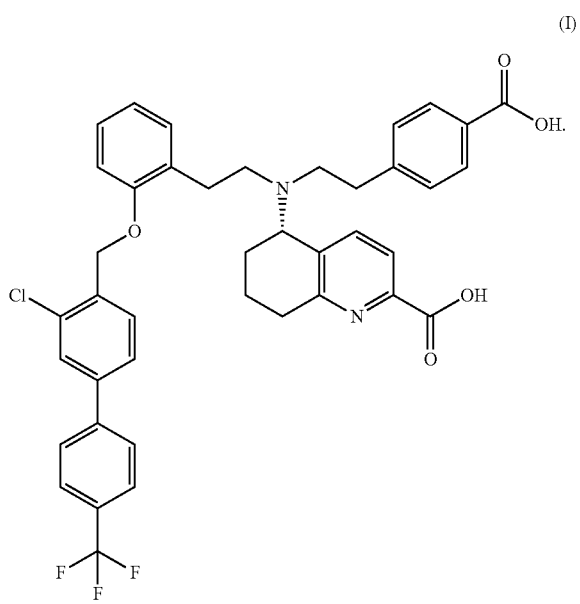 [SMILES: O=C(O)c1ccc(CCN(CCc2ccccc2OCc2ccc(-c3ccc(C(F)(F)F)cc3)cc2Cl)[C@H]2CCCc3nc(C(=O)O)ccc32)cc1]

(I)

to finally yield compound of the formula (I)

The present invention further provides a process for the preparation of the compound of the formula (I) as described above according to embodiment 1 and one or more further embodiments above, characterized in that sodium hydroxide solution is used as base in step [A] to obtain the disodium salt

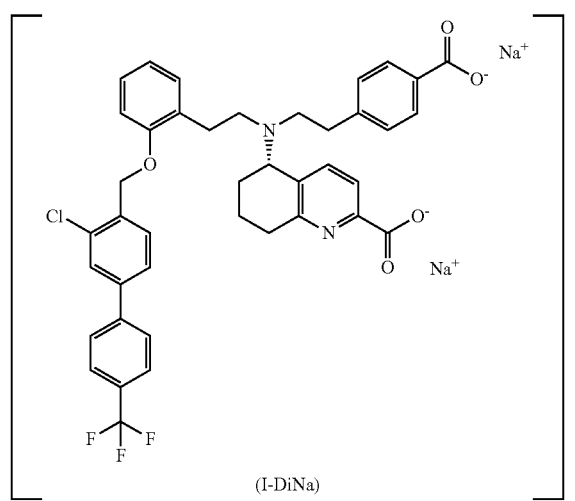

(I-DiNa)

s intermediate.

The present invention further provides a process for the preparation of the compound of the formula (I) as described above according to embodiment 1 and one or more further embodiments above, wherein in formula (XII-1) the residues R3 and R4 are identical, in particular preferred is when R3=R4=Butyl.

The present invention further provides a process for the preparation of the compound of the formula (I) as described above according to embodiment 1 and one or more further embodiments above, wherein the solvent in the first step [A] is tetrahydrofuran or dioxane, preferably tetrahydrofuran.

Another object of the present invention is a process for the preparation of the compound of the formula (I) as described above according to embodiment 1 and one or more further embodiments above, wherein in the first step [A] a sodium hydroxide or potassium hydroxide solution, preferably a 4% sodium hydroxide solution (1N) in excess based on the compound of the formula (XII-1), preferably 4 equivalents is used.

The present invention further provides a process for the preparation of the compound of the formula (I) as described above according to embodiment 1 and one or more further embodiments above, wherein the first step [A] is taking place at a temperature of 40° C. to 70° C., preferably 60° C.

The present invention also provides a process for the preparation of the compound of the formula (I) as described above according to embodiment 1 and one or more further embodiments above, wherein the disodium salt solution is purified by extraction with an organic solvent preferably ethyl acetate.

The present invention further provides a process for the preparation of the compound of the formula (I) as described above according to embodiment 1 and one or more further embodiments above, wherein the mineral acid of the second step [B] is hydrochloric acid.

The present invention also provides a process for the preparation of the compound of the formula (I) as described above according to embodiment 1 and one or more further embodiments above, wherein in a second step [B] the organic product layer is separated after the addition of sodium chloride to the mixture.

The present invention further provides a process for the preparation of the compound of the formula (I) as described above according to embodiment 1 and one or more further embodiments above, characterized in that the concentration of the organic product layer is done at reduced atmospheric pressure, preferably at 200 mbar and preferably at a temperature of between 2° and 50° C., very preferably at 40° C.

The present invention further provides a process for the preparation of the compound of the formula (I) as described above according to embodiment 1 and one or more further embodiments above, characterized in that the compound of the formula (I) is isolated as solid alternatively the organic product layer is concentrated to a residual volume.

The present invention further provides a process for the preparation of the compound of the formula (I) as described above according to embodiment 1 and one or more further embodiments above, wherein the target compound of formula I can be isolated as solid, e.g. by drying at elevated temperatures, e.g. at 60° C. in a stream of nitrogen under vacuum, at reduced atmospheric pressure, very preferably at 200 mbar.

The present invention further provides a process for the preparation of the compound of the formula (I) as described above according to embodiment 1 and one or more further embodiments above, characterized in that the compound of the formula (I) is isolated as solid.

The present invention further provides a process for the preparation of the compound of the formula (I) as described above according to embodiment 1 and one or more further embodiments above, characterized in that the compound of the formula (I) is either isolated as solid by filtration or as concentrated residual volume characterized in that
- the organic product layer is separated from the mixture,
- the organic product layer is concentrated, wherein a solid separates,
- the solid is separated by filtration and
- separated solid is dried.
- alternatively the organic product layer is concentrated to a residual volume.

The present invention further provides a process for the preparation of the compound of the formula (I) as described above according to embodiment 1 and one or more further embodiments above, characterized in that the organic solvent is separated after addition of brine.

The present invention further provides a process for the preparation of the compound of the formula (I) as described above according to embodiment 1 and one or more further embodiments above, characterized in that the concentration of the organic solvent is done at reduced atmospheric pressure, preferably at 200 mbar and preferably at a temperature of between 2° and 50° C., very preferably at 40° C.

The present invention further provides a process for the preparation of the compound of the formula (I) as described above according to embodiment 1 and one or more further embodiments above, characterized in that the solids are separated by filtration.

The present invention further provides a process for the preparation of the compound of the formula (I) as described above according to embodiment 1 and one or more further embodiments above, characterized in that the solids are dried at temperatures of between 40° C. o 50° C. and at reduced atmospheric pressure of 40 mbar to 30 mbar.

Alternatively, the compound of the formula (I) can be prepared without isolating intermediates starting from compounds (X) and (XI) by coupling, subsequent cleavage of the diester and acidic release (shown by way of example in route 2, comprising process steps [C], [A] and [B], (see scheme 5).

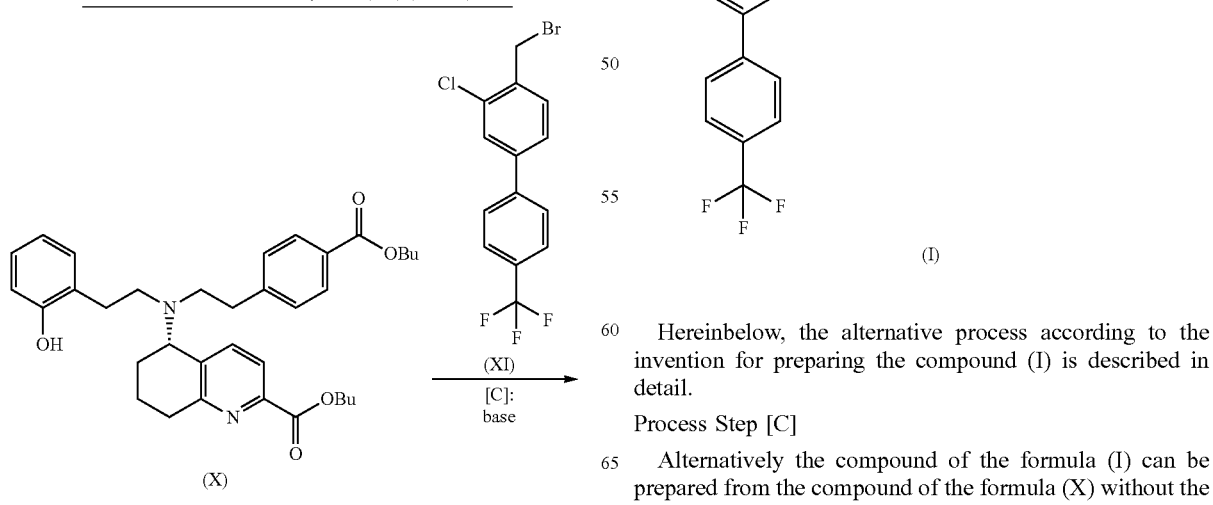

Scheme 5: process for making compound of formula (I) without isolation of dibutylester (XII) (route 2)

Hereinbelow, the alternative process according to the invention for preparing the compound (I) is described in detail.

Process Step [C]

Alternatively the compound of the formula (I) can be prepared from the compound of the formula (X) without the isolation of intermediates (telescoped process). For this purpose, a coupling reaction takes place (Step [C]), analogously to process step 11 in scheme 2 as disclosed in WO2021/233783.

Compound of formula (X) is available via e.g. an acidic esterification reaction of its precursor in n-butanol as solvent (disclosed in WO2021/233783, example 10).

To obtain compound according to formula (XII) butyl-(5S)-5-({2-[4-(butoxycarbonyl)phenyl]ethyl}[2-(2-hydroxyphenyl)ethyl]amino)-5,6,7,8-tetrahydrochinolino-2-carboxylate of formula (X) is solubilized in an inert polar solvent, for example in ether, acetone or acetonitrile, preferably in acetonitrile, at a temperature of between 10° C. and 40° C., preferably at 25° C. Preferably the reaction mixture is distilled at temperatures between 40° C. and 60° C. and reduced pressure, preferably at between 80 mbar and 120 mbar, very preferably at 120 mbar, and further acetonitrile is added. This procedure could be repeated.

4-(Bromomethyl)-3-chlor-4'-(trifluormethyl)[biphenyl] of formula (XI) is added, preferably in an amount of between 1 eq to 2 eq, very preferably in 1.2 eq, in relation to compound (X). To the solution base is added, wherein the base is selected from the group consisting of alkalicarbonates, e.g. sodium carbonate, potassium carbonate or cesiumcarbonate or alkalihydroxides, e.g. sodium hydroxide or potassium hydroxide, or tetraalkylammoniumcarbonate, preferably cesiumcarbonate. The base is added in a molar excess, preferably in an amount of 2 eq to 4 eq, very preferably 2 eq. in relation to compound (X). The reaction mixture is stirred until completion of the reaction to obtain compound (XII). Preferably a further amount of base, preferably cesiumcarbonate could be added to the reaction mixture under continued stirring. The obtained suspension will be filtered. Before discarding the filter residue (cake) it will be preferably washed with acetonitrile. The liquid reaction mixture can be further reacted in a further reaction step without isolation of compound of formula (XII), for example in reaction step [A].

Alternatively compound of formula (XII) can be isolated as an oil and than it can be reacted in a further reaction step, for example reaction step [A]. For isolation of the oil the mixture is concentrated to an oil, preferably after washing with acetonitrile, at temperatures of between 15° C. and 60° C., preferably of between 30° C. and 50° C., especially preferably at 40° C. The concentration is preferably done at reduced atmospheric pressure.

The liquid reaction solution is used as an oil in the next stage without isolating the compound of the formula (XII), by first changing the solvent to THF or dioxane by means of a distillation, whereby THF is preferably used.

The ester cleavage step [A] is then carried out analogously to process step [A] as described above and the release of the dicarboxylic acid of the formula (I) from the disodium salt of the formula (I-DiNa) step [B] analogously to process step [B] as described above.

Embodiment 2 (Route 2)

The present invention provides a process for the preparing the compound of the formula (I), characterized in that in a first step [C] the compound of the formula (X-1),

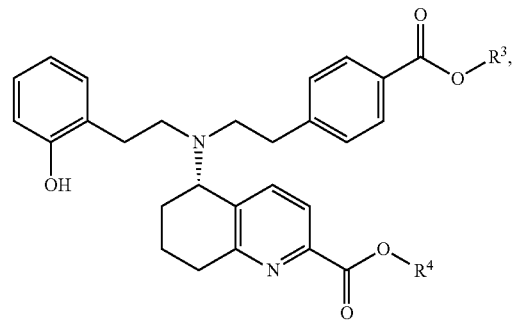

wherein
R$_3$ and R$_4$ are independently C$_1$-C$_4$-alkyl,
is reacted in the presence of a base, selected from the group consisting of alkalicarbonate, alkalihydroxide or tetraalkylammoniumcarbonate with a compound of formula (XI),

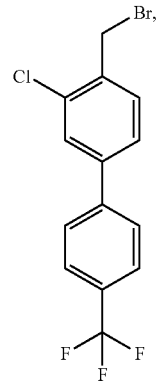

to provide compound of formula (XII-1),

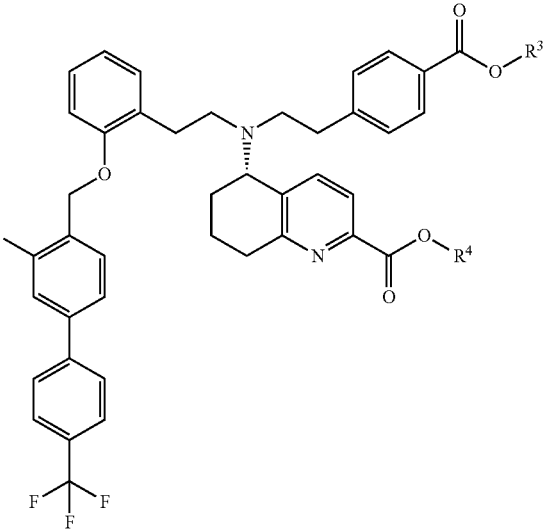

wherein
R$_3$ and R$_4$ are independently C$_1$-C$_4$-alkyl,
further characterized in that compound of formula (XII-1) is reacted without purification in a second step [A] solubilized in a suitable solvent with a base selected from sodium, lithium or potassium hydroxide solution to yield the dialkalimetal salt (I-DiM),
wherein M=Na, Li or K (I-DiM)

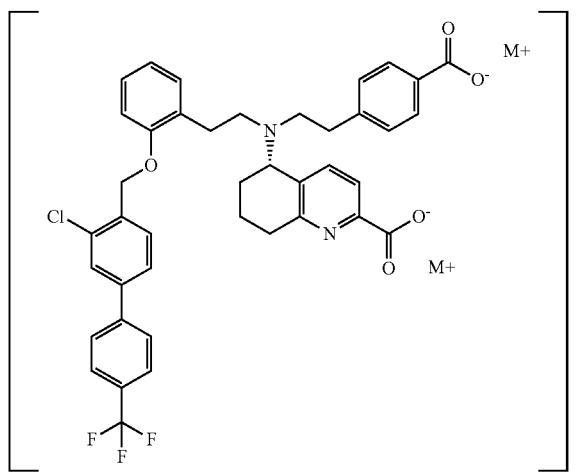

which is after extractive purification but without further isolation reacted in a second step [B]
by adding the reaction solution portionwise to a mixture of a mineral acid in a suitable solvent until a pH value of 3.8 to 4.2 is reached, wherein the pH value of the initially charged mineral acid mixture has a value of less than 3.8 and comprises at maximum two acid equivalents related to the disodium salt to finally yield compound of the formula (I)

(I)

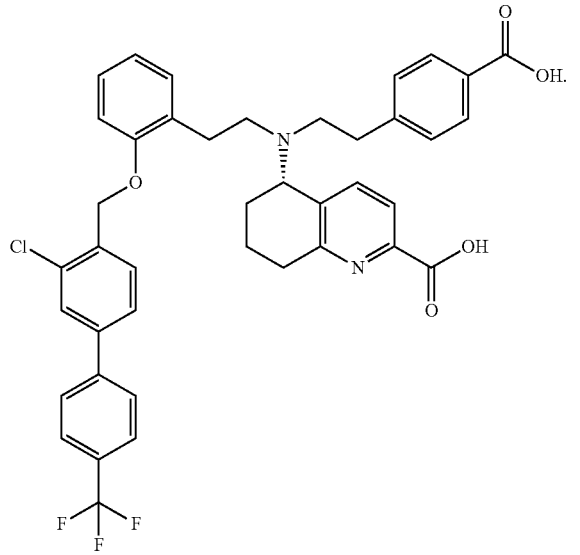

The present invention further provides a process for the preparing the compound of the formula (I) according to embodiment 2, characterized in that in a first step [C] the compound of the formula (X-1), (X-1)

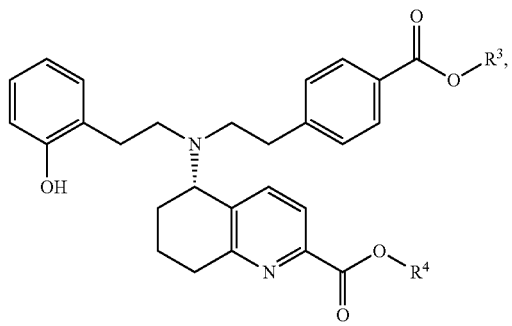

wherein
R$_3$ and R$_4$ are independently C$_1$-C$_4$-alkyl
is reacted in the presence of a base, selected from the group consisting of alkalicarbonate, alkalihydroxide or tetraalkylammoniumcarbonate with a compound of formula (XI), (XI)

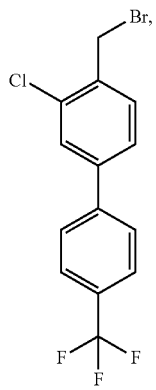

to provide compound of formula (XII-1), (XII-1)

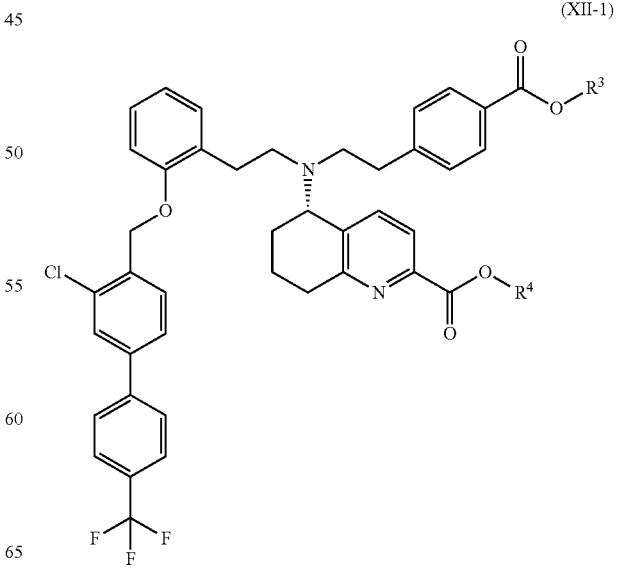

wherein

R$_3$ and R$_4$ are independently C$_1$-C$_4$-alkyl further characterized in that compound of formula (XII-1) is reacted without purification in a second step [A] solubilized in a suitable solvent with a sodium hydroxide solution to yield the disodium salt (I-DiNa)

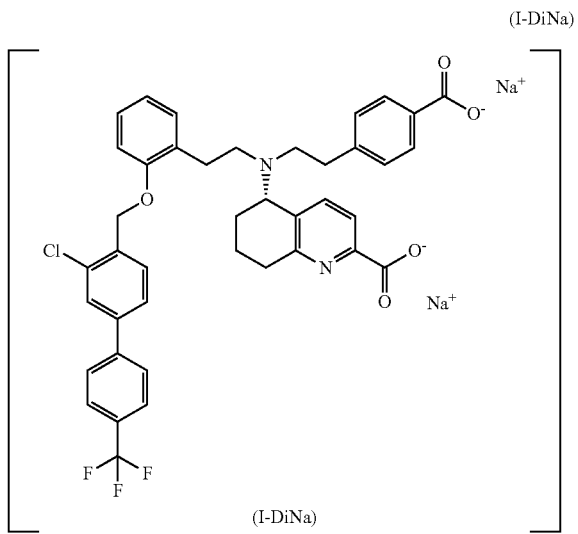

(I-DiNa)

which is after extractive purification but without further isolation reacted in a second step [B]

by adding the reaction solution portionwise to a mixture of a mineral acid in a suitable solvent until a pH value of 3.8 to 4.2 is reached, wherein the pH value of the initially charged mineral acid mixture has a value of less than 3.8 and comprises at maximum two acid equivalents related to the disodium salt to finally yield compound of the formula (I)

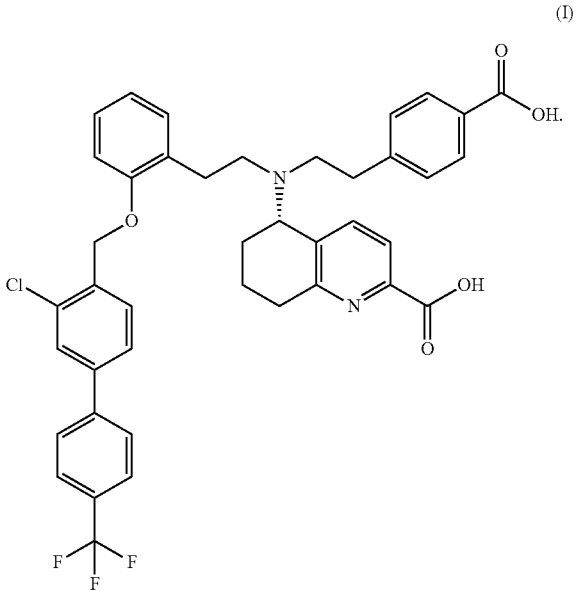 [SMILES: O=C(O)c1ccc(CCN(CCc2ccccc2OCc2ccc(-c3ccc(C(F)(F)F)cc3)cc2Cl)[C@H]2CCCc3nc(C(=O)O)ccc32)cc1]

(I)

The present invention further provides a process for the preparation of the compound of the formula (I) as described above according to embodiment 2 and one or more further embodiments above, wherein in formula (XII-1) the residues R$_3$ and R$_4$ are identical, in particular preferred is when R$_3$=R4=Butyl.

Another object of the present invention is a process for the preparation of the compound of the formula (I) as described above according to embodiment 2 and one or more further embodiments above, characterized in that in a first step [C] a suitable solvent selected from the group consisting of ether, acetone or acetonitril, preferably acetonitrile, is used.

Another object of the present invention is a process for the preparation of the compound of the formula (I) as described above according to embodiment 2 and one or more further embodiments above, characterized in that in a first step [C] a suitable base is used selected from the group consisting of alkalicarbonates, e.g. sodium carbonate, potassium carbonate or cesiumcarbonate, preferably cesiumcarbonate.

Another object of the present invention is a process for the preparation of the compound of the formula (I) as described above according to embodiment 2 and one or more further embodiments above, characterized in that in a first step [C] the base is an alkalihydroxide, selected from the group consisting of sodium hydroxide or potassium hydroxide.

Another object of the present invention is a process for the preparation of the compound of the formula (I) as described above according to embodiment 2 and one or more further embodiments above, characterized in that in a first step [C] tetraalkylammoniumcarbonate is used as base.

Another object of the present invention is a process for the preparation of the compound of the formula (I) as described above according to embodiment 2 and one or more further embodiments above, characterized in that in a first step [C] the base, chosen from the group consisting of alkalicarbonates, alkalihydroxides or tetraalkylammoniumcarbonate is used in a molar excess, preferably in an amount of 2 eq to 4 eq in relation to compound of formula (X), especially preferably 2 eq. in relation to compound (X).

Another object of the present invention is a process for the preparation of the compound of the formula (I) as described above according to embodiment 2 and one or more further embodiments above, characterized in that in a first step [C] the compound of formula (XI) is preferably used in a molar ratio of between 1:1 to 2:1 in relation to compound of formula (X), especially preferably in a molar ratio of 1.2:1 in relation to compound of formula (X).

The present invention further provides a process for the preparation of the compound of the formula (I) as described above according to embodiment 2 and one or more further embodiments above, wherein in a second step [A] the solvent is tetrahydrofuran or dioxane, preferably tetrahydrofuran.

Another object of the present invention is a process for the preparation of the compound of the formula (I) as described above according to embodiment 2 and one or more further embodiments above, wherein in a second step [A] a sodium hydroxide or potassium hydroxide solution, preferably a 4% sodium hydroxide solution (1N) in excess based on the compound of the formula (XII-1), preferably 4 equivalents is used.

The present invention further provides a process for the preparation of the compound of the formula (I) as described above according to embodiment 2 and one or more further embodiments above, wherein in a second step [A] the step is taking place at a temperature of 40° C. to 70° C., preferably 60° C.

The present invention also provides a process for the preparation of the compound of the formula (I) as described above according to embodiment 2 and one or more further embodiments above, wherein the disodium salt solution is purified by extraction with an organic solvent preferably ethyl acetate.

The present invention further provides a process for the preparation of the compound of the formula (I) as described above according to embodiment 2 and one or more further embodiments above, wherein in a third step [B] the mineral acid is hydrochloric acid.

The present invention also provides a process for the preparation of the compound of the formula (I) as described above according to embodiment 2 and one or more further embodiments above, wherein in a third step [B] the organic product layer is separated after the addition of sodium chloride to the mixture.

The present invention further provides a process for the preparation of the compound of the formula (I) as described above according to embodiment 2 and one or more further embodiments above, wherein the target compound of formula I can be isolated as solid, e.g. by drying at elevated temperatures, e.g. at 60° C. in a stream of nitrogen under vacuum, at reduced atmospheric pressure, very preferably at 200 mbar.

The present invention further provides a process for the preparation of the compound of the formula (I) as described above according to embodiment 2 and one or more further embodiments above, characterized in that the compound of the formula (I) is isolated as solid alternatively the organic product layer is concentrated to a residual volume.

The present invention further provides a process for the preparation of the compound of the formula (I) as described above according to embodiment 2 and one or more further embodiments above, characterized in that the compound of the formula (I) is either isolated as solid by filtration or as concentrated residual volume
characterized in that
   the organic product layer is separated from the mixture,
   the organic product layer is concentrated, wherein a solid separates,
   the solid is separated by filtration and
   separated solid is dried.
   alternatively the organic product layer is concentrated to a residual volume.

The present invention further provides a process for the preparation of the compound of the formula (I) as described above according to embodiment 2 and one or more further embodiments above, characterized in that the organic solvent is separated after addition of brine.

The present invention further provides a process for the preparation of the compound of the formula (I) as described above according to embodiment 2 and one or more further embodiments above, characterized in that the concentration of the organic solvent is done at reduced atmospheric pressure, preferably at 200 mbar and preferably at a temperature of between 2° and 50° C., very preferably at 40° C.

The present invention further provides a process for the preparation of the compound of the formula (I) as described above according to embodiment 2 and one or more further embodiments above, characterized in that the solids are separated by filtration.

The present invention further provides a process for the preparation of the compound of the formula (I) as described above according to embodiment 2 and one or more further embodiments above, characterized in that the solids are dried at temperatures of between 40° C. o 50° C. and at reduced atmospheric pressure of 40 mbar to 30 mbar.

Another alternative process route to manufacture the target compound of formula (I) via the NSA salt of formula (XII-NSA) is outlined in scheme 6.

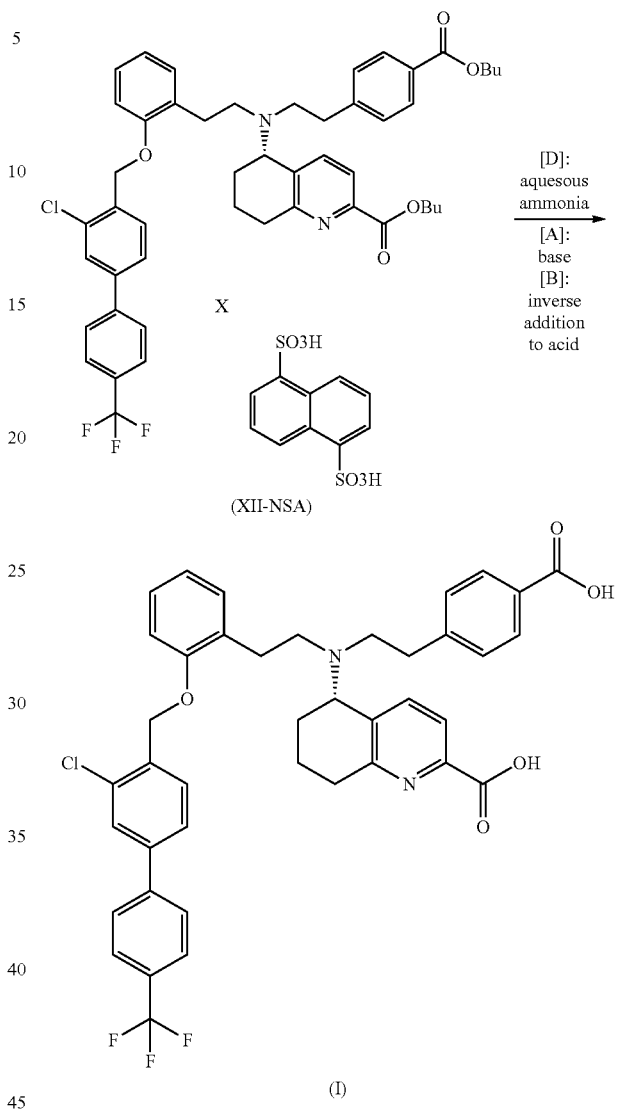

Scheme 6: process for making compound of formula (I) via NSA salt of formula (XII-NSA) (route 3)

This process is characterized in that the solid NSA salt of formula (XII-NSA) (available via a reaction step [G], see scheme 7) is transformed into the free acid via three steps (first: basic release of the dibutylester of formula (XII) (step [D]), secondly: basic cleavage of the dibutylester (step [A]) and thereafter inverse addition of the disodium salt of formula (I-DiNa) to acid (step [B]).

Process Step [D]

To obtain compound of formula (I) starting from compound of formula (XII-NSA), in a first step compound of formula (XII) is released from the salt [step D]. Therefore compound of formula (XII-NSA) is treated with a suitable ether, preferably THF, and stirred with water and aqueous ammonia at temperatures of 10° C. to 25° C., whereby finally a pH-value of 7.8 to 8.2 is reached. By addition of an organic solvent not miscible with water, for example and preferably diisopropylether, a phase separation is achieved.

Surprisingly phase separation is only possible when aqueous ammonia is used as base. Other bases, e.g. potassium carbonate, potassium hydroxide or sodium hydroxide failed due to formation of extensive duff layer.

The aqueous phase is discarded. The organic phase is concentrated to an evaporation residue, preferably after washing with a mixture of water and aqueous ammonia (pH-value of 7.8 to 8.2) and drying over sodium sulfate. The obtained evaporation residue is reacted in the next step. The concentration is done at temperatures of a maximum of 40° C. under reduced atmospheric pressure.

Surprisingly the process via the NSA salt formation and release bears the advantage, that the oily dibutylester can be converted to a solid. This makes overall processability even more convenient. Surprisingly we found, that despite to other common acids, like e.g. toluene sulfonic acid, hydrochloric acid only with NSA a stable solid was formed.

Process Step [A]

For the ester cleavage (XII)→(I-DiNa) (reaction step [A]) the diester of formula (XII) obtained in step [D] is dissolved in THF or dioxane, preferably in THF, and a suitable base, e.g. sodium hydroxide, potassium hydroxide or lithium hydroxide solution is added, preferably sodium hydroxide solution, especially preferably 4% by weight sodium hydroxide solution, is added in excess, preferably 4 equivalents at a temperature of 40° C. to 70° C., preferably at 60° C. The reaction mixture is stirred until complete conversion to disodium salt, dilithium salt or dipotassium salt of compound of formula (I).

For the described reaction also diester of formula (XII-1) can be utilized instead of compound of formula (XII)

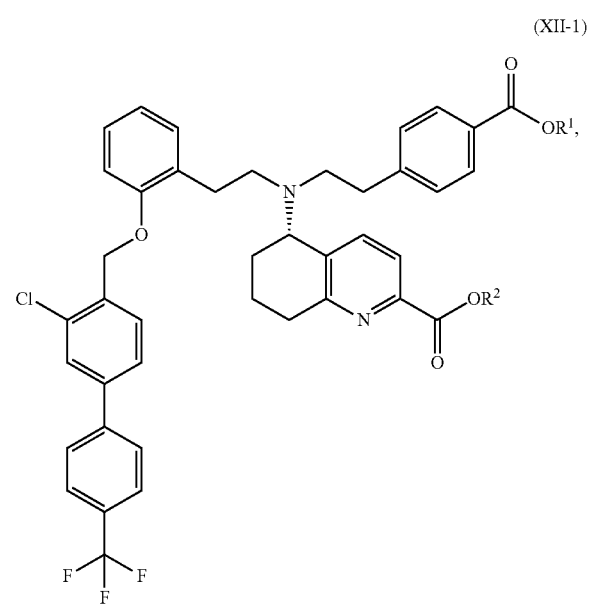

(XII-1)

wherein $R_1$ and $R_2$ are independently $C_1$-$C_4$-alkyl.

To purify the reaction mixture, a suitable ester as solvent, preferably ethyl acetate, and optionally deionized water is added, preferably at a temperature of 10° C. to 40° C., preferably 23° C., and the aqueous phase containing the di-alkali metal salt (I-DiM), e.g. (I-DiNa), (I-DiK) or (I-DiLi), preferably (I-DiNa), is separated. Preferably the extraction with the same ester is repeated. Residual ester solvent in the aqueous phase is distilled off under reduced pressure at temperatures of maximum of 40° C., preferably at 36° C. Optionally the reaction mixture can be filtered, wherein the filter residue will be discarded. The reaction mixture is used in the next reaction step (process step [B]).

Process Step [B]

The release of the dicarboxylic acid of the formula (I) from the di-alkali metal salt (I-DiM), e.g. (I-DiNa), (I-DiK) or (I-DiLi), preferably the disodium salt of the compound of the formula (I) (I-DiNa) surprisingly cannot be achieved quantitatively by adding a mineral acid to a solution of the disodium salt of the compound of the formula (I). This leads to incomplete conversion and formation of substantial amounts of to the monosodium salt of the compound of the formula (I), which precipitates and cannot be converted to the compound of the formula (I) even by further addition of mineral acids.

Surprisingly, it has been found that the preparation of the compound of the formula (I) is possible by adding a solution of the disodium salt of the compound of the formula (I) (I-DiNa) to an excess of acid until a narrowly defined pH Value adjusts. With the method described below ("inverse process"), the reaction of (I-DiNa)→(I) is possible with a high degree of efficiency.

A mixture of THF and a mineral acid, preferably hydrochloric acid, is presented.

As the reaction with an excess of hydrochloric acid results in formation of the unwanted hydrochloride of compound of formula (I) and a shortage of hydrochloric acid results in residual amounts of sodium salts it is crucial to adjust the acid to equimolar amounts. Consequently as compound of formula I contains two basic carboxylate functions it needs to be reacted with 2 equivalents of acid, e.g. preferably 2 equivalents of hydrochloric acid. Therefore optionally in order to determine the content of disodium salt solution and to calculate the corresponding necessary amounts of acid a small amount of disodium salt solution can be triturated with a defined amount of acid solution, preferably hydrochloric acid.

The consumption of disodium salt solution is than set in relation to the amount of hydrochloric acid submitted and the amount of hydrochloric acid for the conversion of the further partial amounts is calculated accordingly.

The pH of the initially charged hydrochloric acid/THF mixture is less than 3.8. The solution of the compound of the formula (I-DiNa) obtained in step [A] is added in several partial amounts to this mixture until a pH of 3.8 to 4.2 is reached. The organic phase of the reaction mixture is then separated off.

The separation is preferably carried out after the addition of sodium chloride and THF to the reaction mixture and subsequent stirring.

For isolation/purification and/or crystallization of the target compound of formula (I) the organic phase is concentrated. The concentration of the organic phase is done preferably at reduced atmospheric pressure, very preferably at 200 mbar and preferably at a temperature of between 2° and 50° C., very preferably at 40° C.

Optionally the target compound of formula I can be isolated as solid, e.g. by drying at elevated temperatures, e.g. at 60° C. in a stream of nitrogen under vacuum, at reduced atmospheric pressure, very preferably at 200 mbar.

Embodiment 3 (NSA Salt)

The NSA salt of formula (XII-NSA) is novel.

A further embodiment of the invention is the NSA salt of formula (XII-NSA)

[Structure of XII-NSA shown]

The synthesis of the NSA salt of formula (XII-NSA) is outlined in scheme 7 below.

Scheme 7: synthesis of NSA salt of formula (XII-NSA)

[Scheme 7 showing conversion of (XII) to (XII-NSA) via step [G] with NSA]

Process Step [G]

To obtain compound according to formula (XII-NSA) in reaction step [G] (scheme 7), compound of formula (XII) is solubilized in THF at a temperature of between 15° C. and 40° C., preferably at 25° C., naphthaline-1,5-disulfonic acid is added and stirred until the reaction is completed. The reaction mixture is concentrated at temperatures of between 15° C. and 60° C., preferably of between 30° C. and 50° C., very preferably at 40° C. and finally the residue is dried at same temperatures until constant weight is reached. The drying process is preferably done under inert gas, preferably under nitrogen, and/or at reduced atmospheric pressure.

Embodiment 4 (Route 3)

The present invention provides a process for preparing the compound of the formula (I), characterized in that in a first step [D] the NSA salt of formula (XII-NSA-1)

(XII-NSA-1)

[Structure of XII-NSA-1 shown]

wherein $R_1$ and $R_2$ are independently $C_1$-$C_4$-alkyl.

is treated with a suitable ether and stirred with water and aqueous ammonia at temperatures of 10° C. to 25° C., whereby finally a pH-value of between 7.8 and 8.2 is reached, afterwards the reaction mixture is treated with an organic solvent not miscible with water, the phases are separated and finally organic phase is concentrated further characterized in that in a second step [A] the compound of the formula (XII-1),

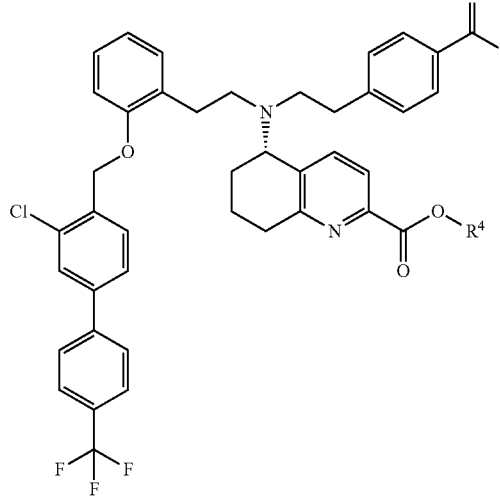

(XII-1)

wherein R₁ and R₂ are independently $C_1$-$C_4$-alkyl.

solubilized in a suitable solvent is reacted with a base selected from sodium, lithium or potassium hydroxide solution to yield the dialkalimetal salt (I-DiM), wherein M=Na, Li or K (I-DiM)

which is after extractive purification but without further isolation reacted in a third step [B]

by adding the reaction solution portionwise to a mixture of a mineral acid in a suitable solvent until a pH value of 3.8 to 4.2 is reached, wherein the pH value of the initially charged mineral acid mixture has a value of less than 3.8 and comprises at maximum two acid equivalents related to the disodium salt to finally yield compound of the formula (I)

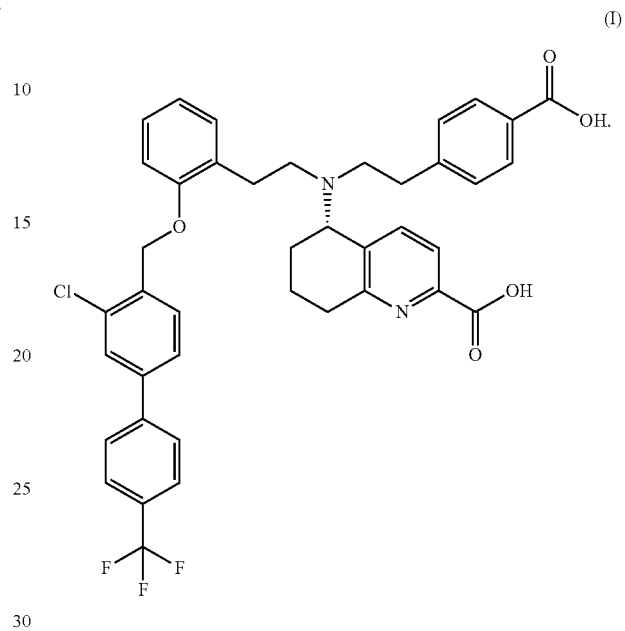

(I)

The present invention further provides a process for preparing the compound of the formula (I) according to embodiment 4, characterized in that in a first step [D] the NSA salt of formula (XII-NSA-1)

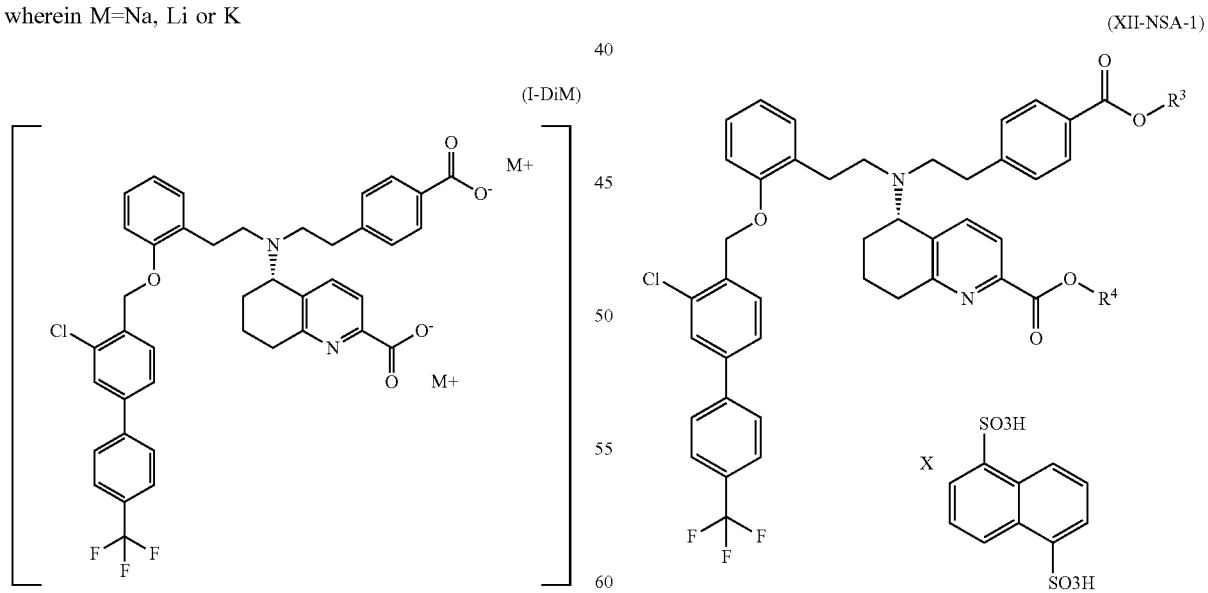

(XII-NSA-1)

wherein R₁ and R₂ are independently $C_1$-$C_4$-alkyl, is treated with a suitable ether and stirred with water and aqueous ammonia at temperatures of 10° C. to 25° C., whereby finally a pH-value of between 7.8 and 8.2 is reached, afterwards the reaction mixture is treated with an organic solvent not miscible with water, the phases are separated and finally organic phase is concentrated further characterized in that in a second step [A] the compound of the formula (XII-1),

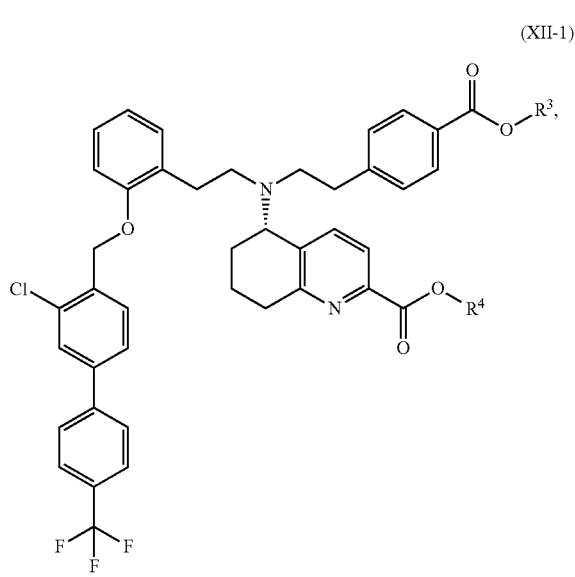

(XII-1)

wherein $R_1$ and $R_2$ are independently $C_1$-$C_4$-alkyl, solubilized in a suitable solvent is reacted with a sodium hydroxide solution to yield the disodium salt (I-DiNa)

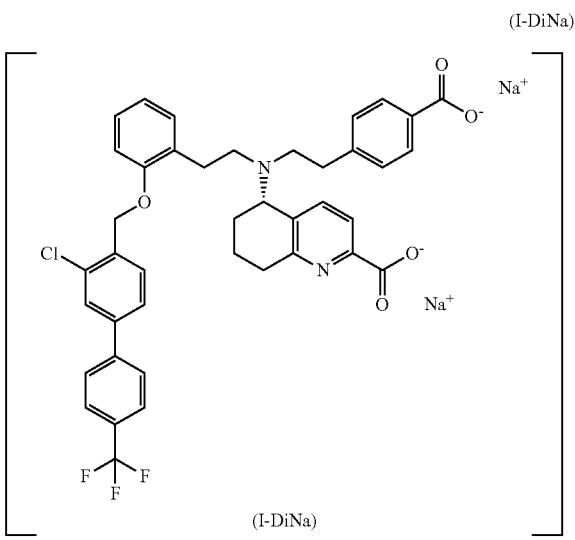

(I-DiNa)

which is after extractive purification but without further isolation reacted in a third step [B] by adding the reaction solution portionwise to a mixture of a mineral acid in a suitable solvent until a pH value of 3.8 to 4.2 is reached, wherein the pH value of the initially charged mineral acid mixture has a value of less than 3.8 and comprises at maximum two acid equivalents related to the disodium salt to finally yield compound of the formula (I)

(I)

The present invention further provides a process for the preparation of the compound of the formula (I) as described above according to embodiment 4 and one or more further embodiments above, wherein in formula (XII-1) the residues R3 and R4 are identical, in particular preferred is when R3=R4=Butyl.

The present invention further provides a process for the preparation of the compound of the formula (I) as described above according to embodiment 4 and one or more further embodiments above, wherein in a first step [D] the ether is tetrahydrofuran.

The present invention further provides a process for the preparation of the compound of the formula (I) as described above according to embodiment 4 and one or more further embodiments above, wherein in a first step [D] the added solvent is diisopropylether.

The present invention further provides a process for the preparation of the compound of the formula (I) as described above according to embodiment 4 and one or more further embodiments above, wherein in a first step [D] after phase separation the aqueous phase is discarded and the organic phase is concentrated to a solid, preferably after washing with a mixture of water sand ammonia water, aqueous ammonia (pH-value of 7.8 to 8.2) and drying over sodium sulfate.

The present invention further provides a process for the preparation of the compound of the formula (I) as described above according to embodiment 4 and one or more further embodiments above, wherein in a second step [A] the solvent is tetrahydrofuran or dioxane, preferably tetrahydrofuran.

Another object of the present invention is a process for the preparation of the compound of the formula (I) as described above according to embodiment 4 and one or more further embodiments above, wherein in a second step [A] a sodium hydroxide or potassium hydroxide solution, preferably a 4% sodium hydroxide solution (1N) in excess based on the compound of the formula (XII-1), preferably 4 equivalents is used.

The present invention further provides a process for the preparation of the compound of the formula (I) as described above according to embodiment 4 and one or more further embodiments above, wherein in a second step [A] the step is taking place at a temperature of 40° C. to 70° C., preferably 60° C.

The present invention also provides a process for the preparation of the compound of the formula (I) as described above according to embodiment 4 and one or more further embodiments above, wherein the disodium salt solution is purified by extraction with an organic solvent preferably ethyl acetate.

The present invention further provides a process for the preparation of the compound of the formula (I) as described above according to embodiment 4 and one or more further embodiments above, wherein in a third step [B] the mineral acid is hydrochloric acid.

The present invention also provides a process for the preparation of the compound of the formula (I) as described above according to embodiment 4 and one or more further embodiments above, wherein in a third step [B] the organic product layer is separated after the addition of sodium chloride to the mixture.

The present invention further provides a process for the preparation of the compound of the formula (I) as described above according to embodiment 4 and one or more further embodiments above, characterized in that the concentration of the organic product layer is done at reduced atmospheric pressure, preferably at 200 mbar and preferably at a temperature of between 2° and 50° C., very preferably at 40° C.

The present invention further provides a process for the preparation of the compound of the formula (I) as described above according to embodiment 4 and one or more further embodiments above, characterized in that the compound of the formula (I) is isolated as solid alternatively the organic product layer is concentrated to a residual volume.

The present invention further provides a process for the preparation of the compound of the formula (I) as described above according to embodiment 4 and one or more further embodiments above, characterized in that the compound of the formula (I) is either isolated as solid by filtration or as concentrated residual volume
characterized in that
the organic product layer is separated from the mixture,
the organic product layer is concentrated, wherein a solid separates,
the solid is separated by filtration and
separated solid is dried.
alternatively the organic product layer is concentrated to a residual volume.

The present invention further provides a process for the preparation of the compound of the formula (I) as described above according to embodiment 4 and one or more further embodiments above, characterized in that the solids are dried at temperatures of up to 60° C. in a stream of nitrogen and at reduced atmospheric pressure, e.g. of 40 mbar to 30 mbar.

The present invention also provides combinations of the partial reactions introduced above for preparing the compound of the formula (I) in crystalline modification I, monohydrate I of formula (I-M-I) or modification II, monohydrate II of formula (I-M-II), preferably monohydrate I of formula (I-M-I).

In an exemplary manner the further purification of (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid of the formula (I)

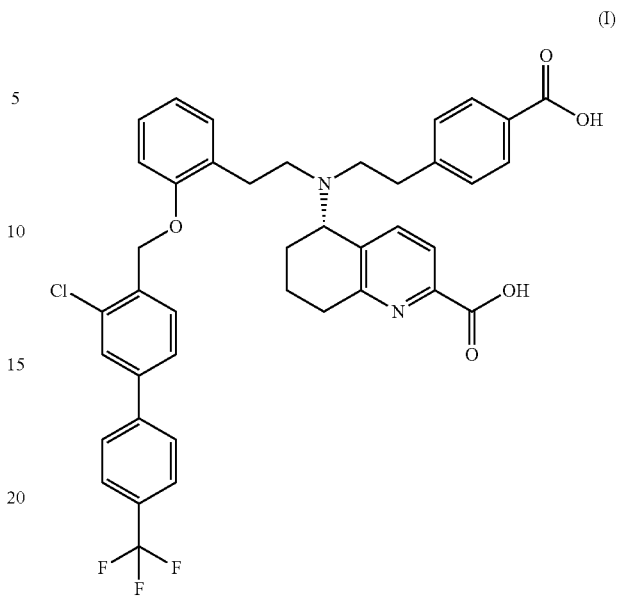

obtainable via one of the above described process routes 1, 2 or 3 (see scheme 2) to finally yield the monohydrate I of formula (I-M-I) is described.

Depending on the scale and on the process route it might be preferable to purify the compound of formula I before the final crystallization. Therefore the crystallization may comprise process steps [H] and [E] in combination. It is also possible just to crystallize compound of formula (I) according to the step [E]. This is described in an exemplary manner.
Process Step [H]:
Purification of target compound I (1. Crystallization):

The crude organic phase containing the free acid of formula I for e.g. obtained via one of the above described process routes 1, 2 or 3 (see scheme 2) was concentrated in vacuum, dissolved in tetrahydrofuran, preferably in a 0.8-1.1 fold g amount related to evaporation residue of tetrahydrofuran, and then a 2.2:1 mixture of methanol and water was added, preferably in a ca. 5 fold amount of the 2.2:1 methanol water mixture in relation to butylester, preferably dropwise at 20° C. with stirring. Seed crystals of (5S)-5-{[2-(4-carboxyphenyl) ethyl] [2-(2-{[3-chloro-4'-(trifluoromethyl) [biphenyl]-4-yl] methoxy} phenyl) ethyl]amino}-5,6,7,8-tetrahydroquinoline-2-carboxylic acid monohydrate I were added and it was stirred for a period of time, preferably 12 h. The solid was separated and washed with a 1:1 mixture of methanol and water. The solid was then dried in vacuo at 20° C.

The drying happens at temperatures of preferably 40° C. and 50° C. and 40 mbar to 30 mbar.
Process Step [E]:
crystallization/formation of monohydrate form I, (I-M-I): methanol, acetone water crystallization The compound of formula I, (either in solid form, in form of an evaporation residue or also as a concentrate in THF) as obtained via one of the process routes 1, 2 or 3 as described above), e.g via route 3 is heated to elevated temperatures, preferably to 50° C. with a 1:1 mixture of acetone and methanol, preferably 4-8 fold amount, preferably ca. 4 fold amount of each solvent in relation to amount of solid compound of formula I, and cooled to 20° C. The solution obtained is filtered, e.g. through a Seitz filter plate, heated to 50° C. and finally water, preferably a 1.8 fold amount of water in relation to amount of solid compound of formula I is added dropwise over a period of time, preferably over a period of 30 minutes. Consequently the compound is finally stirred in a 2.2:2.2:1 mixture of acetone, methanol and water, wherein the g amount of solvent in relation to g of solid acid of formula (I) is ca 10:1. The solution is inoculated with a small amount of seed crystals of monohydrate I of formula (I-M-I), depending on the scale with a small amount of up to a few g, stirred for 30 min, cooled to 20° C. in at least 30 min and the solid is filtered off with suction. The moist product is preferably stirred with water, preferably a 10 fold amount of water in relation to amount of solid compound of formula I, for a period of time, preferably for 12 hours. Finally the solids are filtered off with suction and washed twice with water, preferably a 2 fold amount of water in relation to amount of solid compound of formula I. The moist product is dried to constant weight at 20° C. in a stream of nitrogen under vacuum to obtain the compound of formula I in the crystalline modification I, monohydrate I of formula (I-M-I).

Alternatively the crude organic phase containing the free acid of formula I for e.g. obtained via one of the above described process routes 1, 2 or 3 (see scheme 2), e.g via route 2 was concentrated in vacuum, dissolved in tetrahydrofuran, preferably in a 0.8-1.1 fold g amount related to evaporation residue of tetrahydrofuran, and then a 2.3:1 mixture of methanol and water was added, preferably in a ca. 7 fold amount of the 2.3:1 methanol water mixture in relation to butylester, preferably at 20° C. with stirring. Seed crystals of (5S)-5-{[2-(4-carboxyphenyl) ethyl] [2-(2-{[3-chloro-4'-(trifluoromethyl) [biphenyl]-4-yl] methoxy} phenyl) ethyl] amino}-5,6,7,8-tetrahydroquinoline-2-carboxylic acid monohydrate I were added. Then a further ca 17.3 fold amount of a 2.3:1 methanol water mixture was metered in. Consequently the compound was finally stirred in an 24.3 fold amount in g in relation to solid compound of a 2.3:1 methanol water mixture. and it was stirred for a period of time, preferably overnight. The solid was separated and washed with a 1:1 mixture of methanol and water. The solid was then dried in vacuo, preferably at 40-50° C. and 40-30 mbar.

Alternatively solid compound of formula I was dissolved in a 4:1 mixture of methanol and water, wherein the ratio of solvent to solid is as follows: 4 fold amounts in g in correlation to g amount of compound of formula (I) of methanol and ca 1 fold amounts in g in correlation to g amount of compound of formula (I) of water. Afterwards a 4:1 mixture of acetone and water is added, wherein the ratio of solvent to solid is as follows: 4 fold amounts of acetone and ca 1 fold amounts of water were added. Consequently the compound is finally stirred in 4:4:2 mixture of acetone, methanol and water, wherein the g amount of solvent in relation to g of solid acid of formula (I) is ca 10:1. It was stirred overnight. The solid was filtered off with suction, washed with 1 fold amount of a mixture of acetone/water (8:2) and dried overnight at 60° C. in vacuo with nitrogen air.

Embodiment 5 (Crystallization Process [E] for Monohydrate I)

The present invention provides a process for preparing (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid (I) in crystalline modification monohydrate I (I-M-I), characterized in that the compound of formula (I)

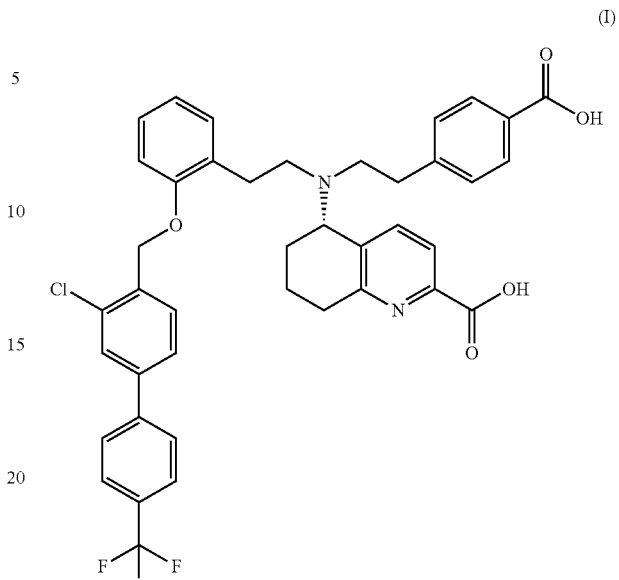

(I)

is crystallized from a mixture of polar solvents wherein the polar solvent is selected from a list consisting of methanol, acetone, water, wherein at least a mixture of methanol and water is necessary at a temperature of from 20° C. to 100° C. and the compound of formula (I-M-I)

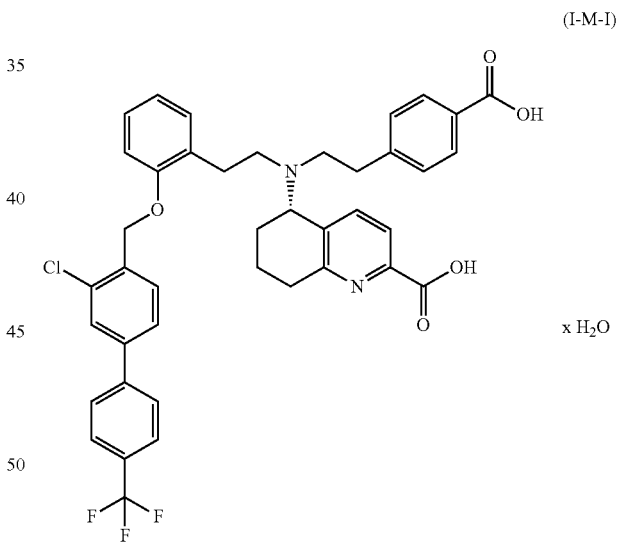

(I-M-I)

x H$_2$O is isolated, optionally after cooling.

The present invention also provides a process for preparing (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid (I) in crystalline modification monohydrate I (I-M-I) according to embodiment 5 above, characterized in that the crude organic phase containing the free acid of formula I for e.g. obtained via one of the above described process routes 1, 2 or 3 (see scheme 2) was concentrated in vacuum, dissolved in tetrahydrofuran, preferably in a 0.8-1.1 fold g amount related to evaporation residue of tetrahydrofuran, and then a 2.2:1 mixture of methanol and water was added, preferably in a ca. 5 fold amount of the 2.2:1 methanol water mixture in relation to butylester, preferably dropwise at 20° C. with stirring.

The present invention also provides a process for preparing (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid (I) in crystalline modification monohydrate I (I-M-I) according to embodiment 5 and one or more further embodiments above, characterized in that the compound of formula (I) is stirred in a 2.2:1 or 2.3:1 mixture of methanol and water at a temperature of between about 20° C. to about 50° C.

The present invention also provides a process for preparing (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid (I) in crystalline modification monohydrate I (I-M-I) according to embodiment 5 and one or more further embodiments above, characterized in that the compound of formula (I) is stirred in a 2.2:1 or 2.3:1 mixture of methanol and water at a temperature of between about 20° C. to about 50° C. and the amount of the mixture of methanol and water is ca 5 to 24, preferably ca 10 fold amount in g in relation to amount of solid compound of formula I in g.

The present invention also provides a process for preparing (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid (I) in crystalline modification monohydrate I (I-M-I) according to embodiment 5 and one or more further embodiments above, characterized in that the compound of formula (I) is firstly dissolved in a 1:1 mixture of methanol and acetone at a temperature of about 50° C. cooled down to room temperature and filtered for clarification of the solution.

The present invention also provides a process for preparing (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid (I) in crystalline modification monohydrate I (I-M-I) according to embodiment 5 and one or more further embodiments above, characterized in that the acid of formula I is firstly dissolved in a 1:1 mixture of acetone and methanol, wherein each solvent is provided in a 4 to 8 fold amount in g in relation to amount of solid compound of formula I in g.

The present invention also provides a process for preparing (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid (I) in crystalline modification monohydrate I (I-M-I) according to embodiment 5 and one or more further embodiments above, characterized in that the acid of formula I is firstly dissolved in a 1:1 mixture of methanol and acetone, preferably in a 4 fold amount of each solvent (8 fold amount in relation to the 1:1 mixture) in g in relation to amount of solid compound of formula I in g, at a temperature of 50° C. and cooled to room temperature, preferably 20° C. the solution is clarified by filtration, heated to 50° C. and water is added dropwise over a period of time.

The present invention also provides a process for preparing (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid (I) in crystalline modification monohydrate I (I-M-I) according to embodiment 5 and one or more further embodiments above, characterized in that water is added dropwise over a period of 30 minutes.

The present invention also provides a process for preparing (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid (I) in crystalline modification monohydrate I (I-M-I) according to embodiment 5 and one or more further embodiments above, characterized in that water is added dropwise over a period of 30 minutes in a 1.8 fold amount in g in relation to amount of solid compound of formula I in g.

The present invention also provides a process for preparing (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid (I) in crystalline modification monohydrate I (I-M-I) according to embodiment 5 and one or more further embodiments above, characterized in that after water addition, preferably in a 1.8 fold amount in g in relation to amount of solid compound of formula I in g, seed crystals of compound of formula (I-M-I) are added to the stirred mixture.

The present invention also provides a process for preparing (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid (I) in crystalline modification monohydrate I (I-M-I) according to embodiment 5 and one or more further embodiments above, characterized in that after water addition, preferably in a 1.8 fold amount in g in relation to amount of solid compound of formula I in g, seed crystals of compound of formula (I-M-I) are added to the stirred mixture, stirring is continued for a period of time, preferably 30 minutes and the mixture is cooled to 20° C. and finally the solid is filtered off.

The present invention also provides a process for preparing (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid (I) in crystalline modification monohydrate I (I-M-I) according to embodiment 5 and one or more further embodiments above, characterized in that after water addition, preferably in a 1.8 fold amount in g in relation to amount of solid compound of formula I in g, inoculation with seed crystals of compound of formula (I-M-I), continued stirring for a period of time, preferably 30 minutes and filtration the moist product is stirred with water, preferably a 10 fold amount of water in relation to amount of solid compound of formula I, for a period of time, preferably for 12 hours.

The present invention also provides a process for preparing (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid (I) in crystalline modification monohydrate I (I-M-I) according to embodiment 5 and one or more further embodiments above, characterized in that finally the solids are filtered off with suction and washed twice with water, preferably a 2 fold amount of water in relation to amount of solid compound of formula I.

The present invention also provides a process for preparing (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid (I) in crystalline modification monohydrate I (I-M-I) according to embodiment 5 and one or more further embodiments above, characterized in that after filtration of the solid the moist product is dried to constant weight at 20° C. in a stream of nitrogen under vacuum, e.g. 40 to 30 mbar.

The present invention also provides a process for preparing (5S)—{[2-(4-carboxyphenyl)ethyl][2-(2-{[3-chloro-4'-(trifluoromethyl)biphenyl-4-yl]methoxy}phenyl)ethyl]

amino}-5,6,7,8-tetrahydroquinoline-2-carboxylic acid (I) in crystalline modification monohydrate I (I-M-I) according to embodiment 5 and one or more further embodiments above, characterized in that after filtration of the solid the moist product is dried to constant weight at elevated temperatures, e.g. between 40° C. and 50° C. under vacuum of e.g. 40 to 30 mbar.

In an exemplary manner the further purification of (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid of the formula (I)

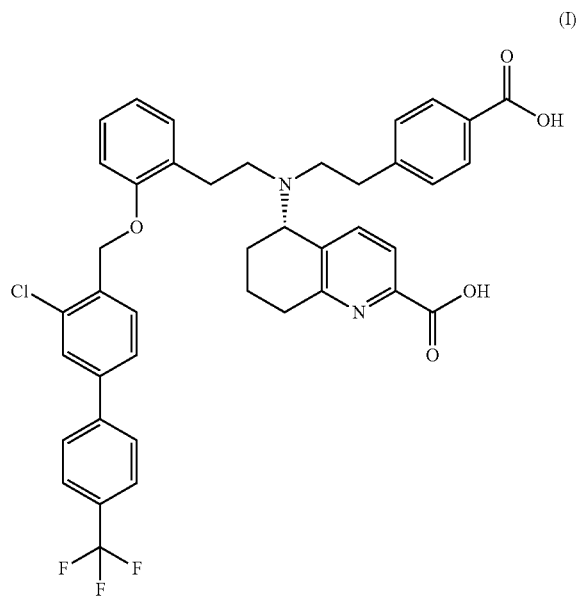 [SMILES: O=C(O)c1ccc(CCN(CCc2ccccc2OCc2ccc(-c3ccc(C(F)(F)F)cc3)cc2Cl)[C@H]2CCCc3nc(C(=O)O)ccc32)cc1]

(I)

obtainable via one of the above described process routes 1, 2 or 3 (see scheme 2) to finally yield the monohydrate II of formula (I-M-II) is described.

This is described in an exemplary manner.
Process Step [F]
crystallization/formation of monohydrate form II, (I-M-II): acetone water crystallization (see scheme 3 above)

The compound of formula I, (either in solid form, in form of an evaporation residue or also as a concentrate in THF) as obtained via one of the process routes 1, 2 or 3 as described above), e.g via route 3 is heated to elevated temperatures, preferably to 50° C. with a mixture of acetone and water, wherein the ratio of acetone to water varies between 7.8:1, 9:1 and 22.2.:1, characterized in that the total amount of solvent in relation to solid compound of formula I is ca 2 to 3 fold amount in g. The solution obtained is cooled to 20° C. and filtered, e.g. through a Seitz filter plate, heated to 50° C. It was cooled to 45° C., inoculated with (5S)-5-{[2-(4-carboxyphenyl) ethyl] [2-(2-{[3-chloro-4'-(trifluoromethyl) [biphenyl]-4-yl] methoxy} phenyl) ethyl] amino}-5,6,7,8-tetrahydroquinoline-2-carboxylic acid in form of the monohydrate II, cooled to 20° C. for a period of time, preferably ca 3 hours, stirred and heated to 40° C. (crystallisation I and 2 heated to 50° C.). The suspension was stirred, cooled to 20° C. and stirred, and the solid was filtered off with suction. The moist product was dried to constant weight at 25° C. in a stream of nitrogen under vacuum to obtain the compound of formula I in the crystalline modification II, monohydrate II of formula (I-M-II).

Alternatively solid compound of formula I was dissolved in a 8:1 mixture of acetone and water, wherein the ratio of solvent to solid is as follows: 8 fold amounts in g in correlation to g amount of compound of formula (I) of acetone and ca 1 fold amounts in g in correlation to g amount of compound of formula (I) of water. Consequently the compound is finally stirred in 8:1 mixture of acetone and water, wherein the g amount of solvent in relation to g of solid acid of formula (I) is ca 9:1. It was stirred overnight. The solid was filtered off with suction, washed with 1 fold amount of a mixture of acetone/water (8:2) and dried overnight at 60° C. in vacuo with nitrogen air.

Embodiment 6 (Crystallization Process [F] for Monohydrate II)

The present invention provides a process for preparing (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid (I) in crystalline modification monohydrate II (I-M-II), characterized in that the compound of formula (I)

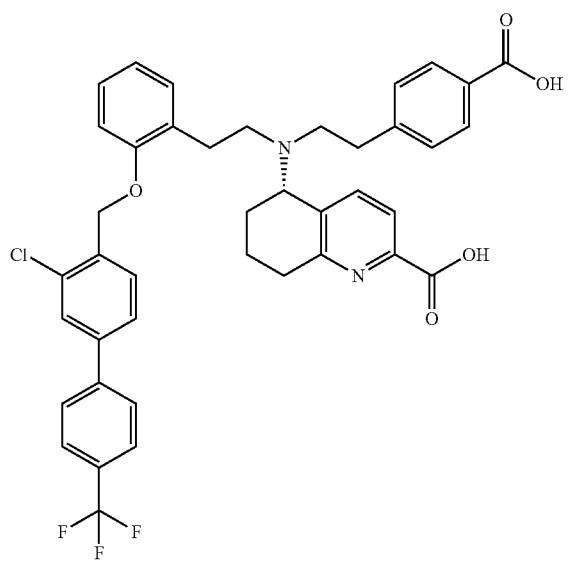

(I)

is crystallized from a mixture of acetone and water at a temperature of from 20° C. to 100° C. and the compound of formula (I-M-II)

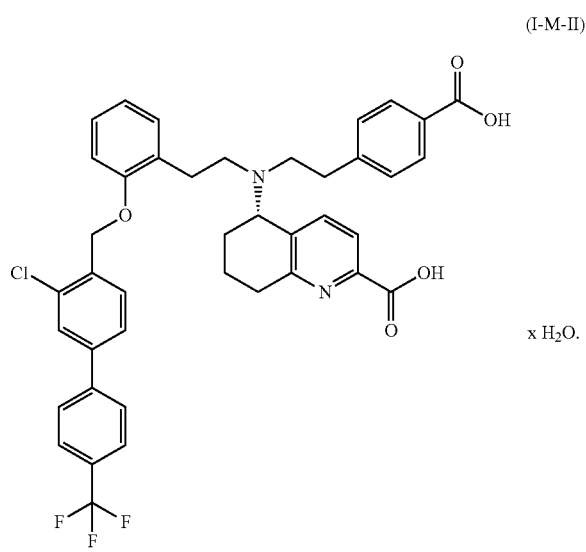 [SMILES: O=C(O)c1ccc(CCN(CCc2ccccc2OCc2ccc(-c3ccc(C(F)(F)F)cc3)cc2Cl)[C@H]2CCCc3nc(C(=O)O)ccc32)cc1]

(I-M-II)

is isolated, optionally after cooling.

The present invention also provides a process for preparing (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid (I) in crystalline modification monohydrate II (I-M-II) according to embodiment 6, characterized in that the compound of formula (I) is stirred in a mixture of acetone and water at a temperature of 50° C., wherein the ratio of acetone to water is between 23:1 and 4:1, preferably 23:1 and 7:1.

The present invention also provides a process for preparing (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid (I) in crystalline modification monohydrate II (I-M-II) according to embodiment 6 and one or more further embodiments above, characterized in that the acid of formula I is stirred in a mixture of acetone and water, wherein the ratio of acetone to water is between 23:1 and 7:1 and further wherein acetone is provided in a 4 to 8 fold amount and wherein the water is provided in 0.2 to 0.8 fold amount in g in relation to amount of solid compound of formula I in g.

The present invention also provides a process for preparing (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid (I) in crystalline modification monohydrate II (I-M-II) according to embodiment 6 and one or more further embodiments above, characterized in that the acid of formula I is stirred in a mixture of acetone and water, wherein the ratio of acetone to water is between 23:1 and 7:1 and further wherein acetone is provided in a 4 to 8 fold amount and wherein the water is provided in 0.2 to 0.8 fold amount in g in relation to amount of solid compound of formula I in g, the mixture is heated to 50° C. and filtered for clarification of the solution.

The present invention also provides a process for preparing (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid (I) in crystalline modification monohydrate II (I-M-II) according to embodiment 6 and one or more further embodiments above, characterized in that the acid of formula I is stirred in a mixture of acetone and water, wherein the ratio of acetone to water is between 23:1 and 7:1 and further wherein acetone is provided in a 4 to 8 fold amount and wherein the water is provided in 0.2 to 0.8 fold amount in g in relation to amount of solid compound of formula I in g, the mixture is heated to 50° C. and filtered for clarification of the solution and then at a temperature of between 45 to 50° C. seed crystals of compound of formula (I-M-II) are added to the stirred mixture.

The present invention also provides a process for preparing (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid (I) in crystalline modification monohydrate II (I-M-II) according to embodiment 6 and one or more further embodiments above, characterized in that the acid of formula I is stirred in a mixture of acetone and water, wherein the ratio of acetone to water is between 23:1 and 7:1 and further wherein acetone is provided in a 4 to 8 fold amount and wherein the water is provided in 0.2 to 0.8 fold amount in g in relation to amount of solid compound of formula I in g, the mixture is heated to 50° C. and filtered for clarification of the solution and then at a temperature of between 45 to 50° C. seed crystals of compound of formula (I-M-II) are added to the stirred mixture, stirring is continued for a period of time, preferably 30 minutes and the mixture is cooled to 20° C. and finally the solid is filtered off.

The present invention also provides a process for preparing (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid (I) in crystalline modification monohydrate I (I-M-II) according to embodiment 6 and one or more further embodiments above, characterized in that after filtration of the solid the moist product is dried to constant weight at 25° C. in a stream of nitrogen under vacuum, e.g. 40 to 30 mbar.

(Pseudo-)Polymorphic Forms

WO 2014/012934 discloses (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid of the formula (I) as an amorphous solid only. The corresponding X-ray diffractogram of the compound of the formula (I) prepared according to the synthesis described in example 23 of WO 2014/012934 is shown in FIG. 33 (see comparative example 11), which is unsuitable for use in inhalative dosage forms administered by dry powder inhalers.

For the development of a medicinal form, especially in form of a dry powder inhalation form comprising (5S)—{[2-(4-carboxyphenyl)ethyl][2-(2-{[3-chloro-4'-(trifluoromethyl)biphenyl-4-yl]methoxy}phenyl)-ethyl]amino}-5,6,7,8-tetrahydroquinoline-2-carboxylic acid of the formula (I) in solid form, there is a high demand for the reproducible manufacturing and isolation of the compound of the formula (I) in one defined crystalline form.

Many efforts were needed to crystallize compound of formula I finally into a defined solid form.

First attempts to convert (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid into a crystalline form failed and only resulted in the undesired amorphous form exhibiting uncontrolled phase changes.

To overcome this property a salt selection screening was performed in an attempt to find a new crystalline material with beneficial properties. However all trials led to amorphous or highly disordered material and a salt formation was not observed (see FIG. 4: salt screening experiment with L-arginine).

Surprisingly compound of formula I was obtained in several pseudopolymorphic forms, no anhydrous crystalline form was found.

The following crystalline forms of the compound of formula (I) have been identified which are the pseudopolymorphic forms Monohydrate I and II ((I-M-I) and (I-M-II)), Semihydrate, Sesquihydrate, Dihydrate and the 1.25 Hydrate (see example 6 and FIGS. 5-32). In this context modifications, polymorphic forms and polymorphs have the same meaning. In addition the amorphous form exists. All together—the pseudopolymorphic forms and the amorphous form—are different solid forms of the compound of formula (I).

Compound stability and uniformity is a key requirement for a pharmaceutical and a prerequisite for an approval by health authorities. It increases the safety and quality of preparations and formulations comprising of the compound of the formula (I) and thus reduces the risk to the patient.

However out of the several identified pseudopolymorphic forms the most suitable and stable form had to be identified during several stages.

It was found that the dihydrate underwent amorphization during drying processes (see FIG. 10a). The crystalline lattice of the semihydrate exhibits disorder (see FIG. 5), which can support phase transitions and/or amorphization in mechanical processing, like e. g. formulation processes. The crystallization of the sesquihydrate was not feasible for scale up, because of very long stirring procedures.

Both monohydrates were found to overcome these unwanted properties of the different pseudopolymorphic forms. However finally it turned out that only one of these monohydrate forms is stable during micronization and therefore the most suitable form e.g. for use in the production of an inhalative medicament, especially as a dry powder based inhalative medicament. Surprisingly during micronization it was found that monohydrate II showed depending on the micronization conditions either partial amorphization (see example 8b, FIG. 42) or in addition to that a transformation to monohydrate I (see example 8a, FIG. 43). Furthermore it was observed that monohydrate II showed transformation to monohydrate I also during storage (see example 7b, FIGS. 40 and 41). Pseudopolymorphic form monohydrate I is therefore suitable and preferred over the other solid forms of the compound of formula I for use in the pharmaceutical field, in particular suitable for pharmaceutical compositions, especially for dry powder inhalative dosage forms.

In particular the monohydrate I form of the compound of the formula (I) ensures that an undesired conversion into another form of the compound of formula (I) and an associated change in the properties as described above is prevented.

Object of the present invention is therefore the provision of a pseudopolymorph having superior application properties such as mechanical stability during micronization processes and storage stability in relation to solid state conversions.

It has now surprisingly been found the monohydrate I, which is obtained by applying specific crystallisation conditions, has such superior properties. In particular, monohydrate I displays improved properties as mechanically stability in micronization processes, enhanced storage stability and better processability if compared with the amorphous form known from the prior art or all other pseudopolymorphic forms described here. In particular, monohydrate I displays an increased stability and thereby ensures that an undesired conversion into another pseudopolymorphic form of the compound of formula (I) and thereby associated changes in the properties as described above are prevented. The increase in stability enhances the safety and quality of formulations comprising the compound of formula (I).

Therefore the pseudopolymorphic form monohydrate I of the compound of the formula (I) (I-M-I) is the most preferred form of compound of formula I for industrial application.

Using the processes according to the present invention (see schemes 2 and 3 above), it was possible to isolate selectively and in high yield and purity the compound of the formula (I) in crystalline form of monohydrate I of formula (I-M-I).

The polymorphic forms, especially the hydrates, preferably the monohydrate in forms I and II can be made by crystallization of the acid of formula (I) (see scheme 3).

Depending on the used solvent either the monohydrate (I-M-I) is formed or the monohydrate (I-M-II). Crystallization from a mixture of methanol and water or a mixture of acetone, methanol and water selectively yields (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid of formula I in form of its monohydrate I of formula (I-M-I) whereas crystallization from a mixture acetone and water yields selectively the monohydrate in form II (I-M-II).

The monohydrate I of (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid can be characterized by X-ray powder diffractometry on the basis of the respective diffraction diagrams, which are recorded at 25° C. and with Cu—K alpha 1 radiation (1.5406 Å). The monohydrate I according to the present invention displays at least 2, often at least 3, often at least 5, in particular at least 7, more particularly at least 10, and especially all of the reflections quoted in the following as values:

The pseudopolymorphic form of compound of formula (I), the monohydrate I of formula (I-M-I) can be characterized by a X-Ray powder diffractogram (at 25° C. and with Cu—K alpha 1 as radiation source) which displays at least the following reflections: 12.8 and 29.2 or at least 6.9, 7.2 and 7.3 or at least 6.9, 7.2, 7.3, 12.8 and 29.2 or at least 6.9, 7.2, 7.3, 12.8, 29.2, 23.0 and 15.2, or at least the following reflections: 6.9, 7.2, 7.3, 12.8, 29.2, 23.0, 15.2, 25.8 and 25.1 or at least the following reflections: 6.9, 7.2, 7.3 12.8, 29.2, 23.0, 15.2, 25.8, 25.1, 17.7 and 23.7, or at least the following reflections: 6.9, 7.2, 7.3, 12.8, 29.2, 23.0, 15.2, 25.8, 25.1, 17.7, 23.7, 9.9, 5.7 and 11.5, each quoted as 2Θ value±0.2°.

In another embodiment the pseudopolymorphic form of compound of formula (I), the monohydrate I of formula (I-M-I) can be characterized by a X-Ray powder diffractogram (at 25° C. and with Cu—K alpha 1 as radiation source) which displays at least the following reflections: 12.8, 16.0 and 25.8 or at least 6.9, 7.2 and 7.3, or at least 6.9, 7.2, 7.3, 12.8, 16.0 and 25.8 or at least 6.9, 7.2, 7.3, 12.8, 16.0, 25.8, 15.2 and 25.1 or at least 6.9, 7.2, 7.3, 12.8, 16.0, 25.8, 15.2, 25.1 and 23.7 or at least 6.9, 7.2, 7.3, 12.8, 16.0, 25.8, 15.2, 25.1, 23.7, 9.9, 5.7 and 11.5, each quoted as 2Θ value±0.2°.

In another embodiment the pseudopolymorphic form of compound of formula (I), the monohydrate I of formula (I-M-I) can be characterized by a X-Ray powder diffractogram (at 25° C. and with Cu—K alpha 1 as radiation source) which displays at least the following reflections: 12.8, 20.5 and 25.8 or at least 6.9, 7.2 and 7.3 or at least 6.9, 7.2, 7.3, 12.8, 20.5, 25.8, 15.2 and 25.1 or at least 6.9, 7.2, 7.3, 12.8, 20.5, 25.8, 15.2, 25.1 and 23.7 or at least 6.9, 7.2, 7.3, 12.8, 20.5, 25.8, 15.2, 25.1, 23.7, 9.9, 5.7 and 11.5, each quoted as 2Θ value±0.2°.

The pseudopolymorphic form of compound of formula (I), the monohydrate I of formula (I-M-I) can additionally be characterized by a X-Ray powder diffractogram (at 25° C. and with Cu—K alpha 1 as radiation source) which displays the following reflections: 5.7, 6.9, 7.2, 7.3, 9.9, 10.4, 10.6, 11.1, 11.5, 12.0, 12.3, 12.4, 12.8, 13.7, 14.1, 14.3, 15.2, 15.6, 16.0, 16.9, 17.2, 17.5, 17.7, 18.0, 18.4, 18.8, 19.2, 19.9, 20.2, 20.5, 20.7, 21.3, 21.9, 22.2, 22.5, 23.0, 23.4, 23.7, 24.1, 25.1, 25.8, 26.0, 26.4, 28.9, 29.2, 29.4, 30.6, 31.1, 32.2, 35.3 each quoted as 2Θ value±0.2°.

The pseudopolymorphic form of compound of formula (I), the monohydrate I of formula (I-M-I) can additionally be characterized by a X-Ray powder diffractogram (at 25° C. and with Cu—K alpha 1 as radiation source) which does not display at least the following reflections 3.1 and 9.3 each quoted as 2Θ value±0.2°.

The pseudopolymorphic form of compound of formula (I), the monohydrate I of formula (I-M-I) can additionally be characterized by a X-Ray powder diffractogram (at 25° C. and with Cu—K alpha 1 as radiation source) which does not display at least the following reflections: 6.1 and 8.5 each quoted as 2Θ value±0.2°.

The pseudopolymorphic form of compound of formula (I), the monohydrate I of formula (I-M-I) can additionally be characterized by a X-Ray powder diffractogram (at 25° C. and with Cu—K alpha 1 as radiation source) which does not display at least the following reflections: 8.5 and/or 30 each quoted as 2Θ value±0.2°.

The pseudopolymorphic form of compound of formula (I), the monohydrate I of formula (I-M-I) can additionally be characterized by a X-Ray powder diffractogram (at 25° C. and with Cu—K alpha 1 as radiation source) which does not display at least the following reflections: 7.9 and/or 31.6 each quoted as 2Θ value±0.2°.

The pseudopolymorphic form of compound of formula (I), the monohydrate I of formula (I-M-I) can additionally be characterized by a X-Ray powder diffractogram (at 25° C. and with Cu—K alpha 1 as radiation source) which does not display at least the following reflections: 7.6 each quoted as 2Θ value±0.2°.

The pseudopolymorphic form of compound of formula (I), the monohydrate I of formula (I-M-I) can additionally be characterized by a X-Ray powder diffractogram (at 25° C. and with Cu—K alpha 1 as radiation source) which does not display at least the following reflections: 14.8 each quoted as 2Θ value±0.2°.

The pseudopolymorphic form of compound of formula (I), the monohydrate I of formula (I-M-I) can additionally be characterized by a X-Ray powder diffractogram (at 25° C. and with Cu—K alpha 1 as radiation source) which displays at least the following reflections: 12.8 and 29.2 or at least 6.9, 7.2 and 7.3 or at least 6.9, 7.2, 7.3, 12.8 and 29.2 or at least 6.9, 7.2, 7.3 12.8, 29.2, 23.0 and 15.2, or at least the following reflections: 6.9, 7.2, 7.3, 12.8, 29.2, 23.0, 15.2, 25.8 and 25.1 or at least the following reflections: 6.9, 7.2, 7.3 12.8, 29.2, 23.0, 15.2, 25.8, 25.1, 17.7 and 23.7, or at least the following reflections: 6.9, 7.2, 7.3, 12.8, 29.2, 23.0, 15.2, 25.8, 25.1, 17.7, 23.7, 9.9, 5.7 and 11.5 and at the same does not display at least the following reflections: 6.1 and 8.5 each quoted as 2Θ value±0.2°.

The pseudopolymorphic form of compound of formula (I), the monohydrate I of formula (I-M-I) can additionally be characterized by a X-Ray powder diffractogram (at 25° C. and with Cu—K alpha 1 as radiation source) which displays at least the following reflections: 12.8, 16.0 and 25.8 or at least 6.9, 7.2 and 7.3, or at least 6.9, 7.2, 7.3, 12.8, 16.0 and 25.8 or at least 6.9, 7.2, 7.3, 12.8, 16.0, 25.8, 15.2 and 25.1 or at least 6.9, 7.2, 7.3, 12.8, 16.0, 25.8, 15.2, 25.1 and 23.7 or at least 6.9, 7.2, 7.3, 12.8, 16.0, 25.8, 15.2, 25.1, 23.7, 9.9, 5.7 and 11.5 and at the same does not display at least the following reflections: 6.1 and 8.5 each quoted as 2Θ value±0.2°.

The pseudopolymorphic form of compound of formula (I), the monohydrate I of formula (I-M-I) can additionally be characterized by a X-Ray powder diffractogram (at 25° C. and with Cu—K alpha 1 as radiation source) which displays at least the following reflections: 12.8, 20.5 and 25.8 or at least 6.9, 7.2 and 7.3 or at least 6.9, 7.2, 7.3, 12.8, 20.5, 25.8, 15.2 and 25.1 or at least 6.9, 7.2, 7.3, 12.8, 20.5, 25.8, 15.2, 25.1 and 23.7 or at least 6.9, 7.2, 7.3, 12.8, 20.5, 25.8, 15.2, 25.1, 23.7, 9.9, 5.7 and 11.5 and at the same does not display at least the following reflections: 6.1 and 8.5 each quoted as 2Θ value±0.2°.

The compound of formula (I) in the polymorphic form Monohydrate I can also be characterized unambiguously by the X-Ray powder diffractogram (at 25° C. and with Cu—K alpha 1 as radiation source) as shown in FIG. 6.

The pseudopolymorphic form of the compound of formula (I), the monohydrate I of formula (I-M-I) can be characterized by a Raman spectroscopy which exhibits at least the following band maxima at: 3073, 2950, 2937, 1685, 1616, 1527, 1293, 1278, 1259 cm-1.

The pseudopolymorphic form monohydrate I of the compound of formula (I) can be characterized by a IR spectroscopy which exhibits at least the following band maxima at: 2933, 1595, 1375, 1327, 1272, 1242, 1167, 1110 cm-1.

Embodiment 7 (Monohydrate I of Formula (I-M-I))

The present invention provides the compound of the formula (I) in crystalline form monohydrate I of formula (I-M-I)

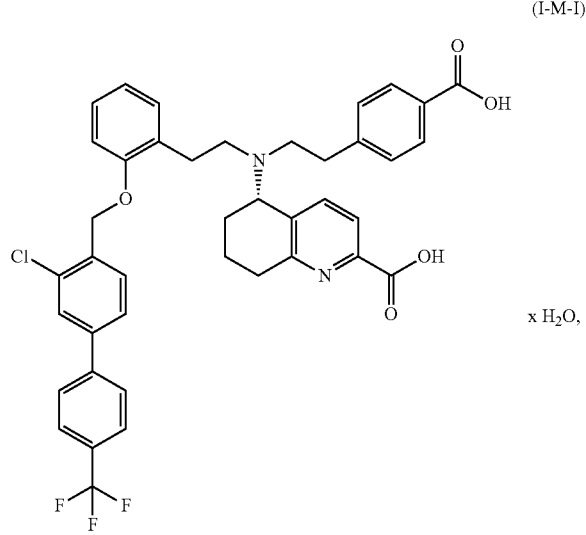 [SMILES: O=C(O)c1ccc(CCN(CCc2ccccc2OCc2ccc(-c3ccc(C(F)(F)F)cc3)cc2Cl)[C@H]2CCCc3nc(C(=O)O)ccc32)cc1]

characterized in that the x-ray diffractogram (at 25° C. and with Cu—K alpha 1 as radiation source) of the compound displaying at least the following reflections, quoted as 2Θ value±0.2°:12.8 and 29.2.

The present invention further provides the compound of the formula (I) in crystalline form of monohydrate I of formula (I-M-I) according to embodiment 7, characterized in that the x-ray diffractogram (at 25° C. and with Cu—K alpha 1 as radiation source) of the compound displaying at least the following reflections, quoted as 2Θ value±0.2°: 6.9, 7.2 and 7.3.

The present invention further provides the compound of the formula (I) in crystalline form of monohydrate I of formula (I-M-I) according to embodiment 7, characterized in that the x-ray diffractogram (at 25° C. and with Cu—K alpha 1 as radiation source) of the compound displaying at least the following reflections, quoted as 2Θ value±0.2°: 6.9, 7.2, 7.3, 12.8, 29.2, 23.0 and 15.2.

The present invention further provides the compound of the formula (I) in crystalline form of monohydrate I of formula (I-M-I) according to embodiment 7 and one or more further embodiments above,
characterized in that the x-ray diffractogram (at 25° C. and with Cu—K alpha 1 as radiation source) of the compound displaying at least the following reflections, quoted as 2Θ value±0.2°: 6.9, 7.2, 7.3, 12.8, 29.2, 23.0, 15.2, 25.8, 25.1, 17.7 and 23.7.

The present invention further provides the compound of the formula (I) in crystalline form monohydrate I of formula (I-M-I) according to embodiment 7 and one or more further embodiments above,
characterized in that the x-ray diffractogram (at 25° C. and with Cu—K alpha 1 as radiation source) of the compound displaying at least the following reflections, quoted as 2Θ value±0.2°: 6.9, 7.2 and 7.3, 12.8, 29.2, 23.0, 15.2, 25.8, 25.1, 17.7, 23.7, 9.9, 5.7 and 11.5.

Alternatively the present invention provides the compound of the formula (I) in crystalline form monohydrate I of formula (I-M-I)

characterized in that the x-ray diffractogram (at 25° C. and with Cu—K alpha 1 as radiation source) of the compound displaying at least the following reflections, quoted as 2Θ value±0.2°:12.8, 16.0 and 25.8.

The present invention further provides the compound of the formula (I) in crystalline form of monohydrate I of formula (I-M-I) according to embodiment 7, characterized in that the x-ray diffractogram (at 25° C. and with Cu—K alpha 1 as radiation source) of the compound displaying at least the following reflections, quoted as 2Θ value±0.2°: 12.8, 16.0, 25.8, 6.9, 7.2 and 7.3.

The present invention further provides the compound of the formula (I) in crystalline form of monohydrate I of formula (I-M-I) according to embodiment 7, characterized in that the x-ray diffractogram (at 25° C. and with Cu—K alpha 1 as radiation source) of the compound displaying at least the following reflections, quoted as 2Θ value±0.2°: 6.9, 7.2 and 7.3, 12.8, 29.2, 23.0 and 15.2.

The present invention further provides the compound of the formula (I) in crystalline form of monohydrate I of formula (I-M-I) according to embodiment 7 and one or more further embodiments above,
characterized in that the x-ray diffractogram (at 25° C. and with Cu—K alpha 1 as radiation source) of the compound displaying at least the following reflections, quoted as 2Θ value±0.2°: 6.9, 7.2, 7.3, 12.8, 29.2, 23.0, 15.2, 25.8 and 25.1.

The present invention further provides the compound of the formula (I) in crystalline form monohydrate I of formula (I-M-I) according to embodiment 7 and one or more further embodiments above,
characterized in that the x-ray diffractogram (at 25° C. and with Cu—K alpha 1 as radiation source) of the compound displaying at least the following reflections, quoted as 2Θ value±0.2°: 6.9, 7.2 and 7.3, 12.8, 29.2, 23.0, 15.2, 25.8, 25.1, 17.7, 23.7, 9.9, 5.7 and 11.5.

The present invention further provides the compound of the formula (I) in crystalline form monohydrate I of formula (I-M-I)

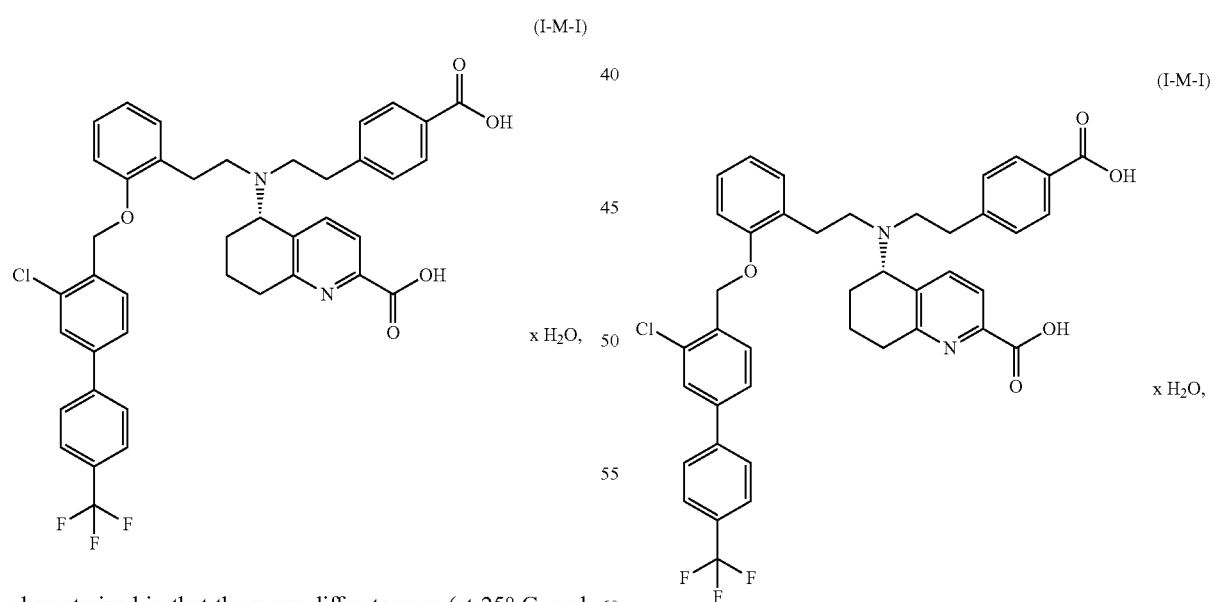

characterized in that the IR spectrum of the compound exhibits band maxima at 2933, 1595, 1375, 1327, 1272, 1242, 1167, 1110 cm-1 cm-1.

The present invention further provides the compound of the formula (I) in crystalline form monohydrate I of formula (I-M-I)

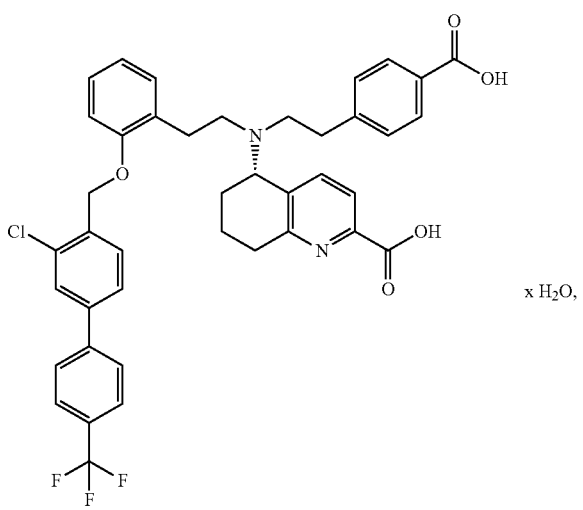

(I-M-I)

characterized in that the Raman spectrum of the compound exhibits band maxima at 3073, 2950, 2937, 1685, 1616, 1527, 1293, 1278, 1259 cm-1.

The other different forms of the compound of formula (I) can be distinguished by X-ray powder diffraction, differential scanning calorimetry (DSC), IR- and Raman-spectroscopy.

In addition to the monohydrate I, further pseudopolymorphic forms monohydrate II, semihydrate, 1,25-hydrate, sesquihydrate as well as dihydrate (see example 6, FIGS. 2-29) have been identified, which are further characterized in the following.

The pseudopolymorphic forms monohydrate II, semihydrate, 1,25-hydrate, sesquihydrate as well as dihydrate of (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid can be characterized by X-ray powder diffractometry on the basis of the respective diffraction diagrams, which are recorded at 25° C. and with Cu-Kalpha 1 radiation (1.5406 Å). The pseudopolymorphic forms monohydrate II, semihydrate, 1,25-hydrate, sesquihydrate as well as dihydrate display at least 3, often at least 5, in particular at least 7, more particularly at least 10, and especially all of the reflections quoted in the following as values:

The pseudopolymorphic form monohydrate II of the compound of formula (I) can be characterized unambiguously by a X-Ray powder diffractogram (at 25° C. and with Cu—K alpha 1 as radiation source) which displays at least the following reflections: 6.1 and 8.5, also at least 6.1, 8.5, 12.7, 23.9 and 13.9, preferably at least the following reflections: 6.1, 8.5, 12.7, 23.9, 13.9, 23.0 and 12.2, more preferably at least the following reflections: 6.1, 8.5, 12.7, 23.9, 13.9, 23.0, 12.2, 10.8 and 15.3, most preferably at least the following reflections: 6.1, 8.5, 12.7, 23.9, 13.9, 23.0, 12.2, 10.8, 15.3, 17.3, 21.7 and 22, also most preferably at least the following reflections: 6.1, 8.5, 12.7, 23.9, 13.9, 23.0, 12.2, 10.8, 15.3, 17.3, 21.7 and 22, each quoted as 2Θ value±0.2°.

The pseudopolymorphic form of compound of formula (I), the monohydrate II of formula (I-M-II) can additionally be characterized by a X-Ray powder diffractogram (at 25° C. and with Cu—K alpha 1 as radiation source) which displays the following reflections: 5.7, 6.1, 7.1, 8.5, 9.9, 10.2, 10.8, 11.4, 11.6, 11.8, 12.0, 12.2, 12.7, 13.0, 13.9, 14.2, 15.2, 15.3, 15.7, 16.4, 17.3, 17.7, 17.9, 18.3, 18.5, 18.8, 19.2, 19.8, 20.2, 20.8, 21.1, 21.7, 22.0, 22.4, 22.8, 23.1, 23.4, 23.9, 24.2, 24.4, 25.1, 25.5, 25.7, 26.2, 26.4, 26.8, 27.2, 27.5, 28.9, 30.0, 30.1, 30.6, 32.2, 32.4, each quoted as 2Θ value±0.2°.

The pseudopolymorphic form of compound of formula (I), the monohydrate II of formula (I-M-II) can additionally be characterized by a X-Ray powder diffractogram (at 25° C. and with Cu—K alpha 1 as radiation source) which does not display at least the following reflections: 3.1 and 9.3 each quoted as 2Θ value±0.2°.

The pseudopolymorphic form of compound of formula (I), the monohydrate II of formula (I-M-II) can additionally be characterized by a X-Ray powder diffractogram (at 25° C. and with Cu—K alpha 1 as radiation source) which does not display at least the following reflections: 6.9, 7.2 and 7.3 each quoted as 2Θ value f 0.2°.

The pseudopolymorphic form of compound of formula (I), the monohydrate II of formula (I-M-II) can additionally be characterized by a X-Ray powder diffractogram (at 25° C. and with Cu—K alpha 1 as radiation source) which does not display at least the following reflections: 29.2 each quoted as 2Θ value±0.2°.

The pseudopolymorphic form of compound of formula (I), the monohydrate II of formula (I-M-II) can additionally be characterized by a X-Ray powder diffractogram (at 25° C. and with Cu—K alpha 1 as radiation source) which does not display at least the following reflections: 7.9 and/or 31.6 each quoted as 2Θ value±0.2°.

The pseudopolymorphic form of compound of formula (I), the monohydrate II of formula (I-M-II) can additionally be characterized by a X-Ray powder diffractogram (at 25° C. and with Cu—K alpha 1 as radiation source) which does not display at least the following reflections: 7.6 each quoted as 2Θ value±0.2°.

The pseudopolymorphic form of compound of formula (I), the monohydrate II of formula (I-M-II) can additionally be characterized by a X-Ray powder diffractogram (at 25° C. and with Cu—K alpha 1 as radiation source) which does not display at least the following reflections: 14.8 each quoted as 2Θ value±0.2°.

The pseudopolymorphic form of compound of formula (I), the monohydrate II of formula (I-M-II) can additionally be characterized by a X-Ray powder diffractogram (at 25° C. and with Cu—K alpha 1 as radiation source) which displays at least the following reflections: 6.1 and 8.5, also at least 6.1, 8.5, 12.8, 23.0, and 15.2, preferably at least the following reflections: 6.1, 8.5, 12.8, 23.0, 15.2, 25.8 and 25.1, more preferably at least the following reflections: 6.1, 8.5, 12.8, 23.0, 15.2, 25.8, 25.1, 17.7 and 23.7, most preferably at least the following reflections: 6.1, 8.5, 12.8, 23.0, 15.2, 25.8, 25.1, 17.7, 23.7, 9.9, 5.7 and 11.5, also most preferably at least the following reflections: 12.8, 23.0, 15.2, 25.8, 25.1, 17.7, 23.7, 9.9, 5.7, 6.1, 8.5 and 11.5 and at the same time does not display at least the following reflections: 6.9, 7.2 and 7.3 each quoted as 2Θ value±0.2°.

The compound of formula (I) in the pseudopolymorphic form monohydrate II can also be characterized unambiguously by the X-Ray powder diffractogram (at 25° C. and with Cu—K alpha 1 as radiation source) as shown in FIG. 7.

The pseudopolymorphic form monohydrate II of the compound of formula (I-M-II) can be characterized by a Raman spectroscopy which exhibits at least the following band maxima at: 3073, 2950, 2936, 1685, 1615, 1526, 1294, 1279, 1259 cm-1.

The pseudopolymorphic form monohydrate I of the compound of formula (I) can be characterized by a IR spectroscopy which exhibits at least the following band maxima at: 2934, 1595, 1375, 1327, 1272, 1242, 1167, 1110 cm-1.

Embodiment 8 (Monohydrate II of Formula (I-M-II))

The present invention further provides the compound of the formula (I) in crystalline form monohydrate II of formula (I-M-II)

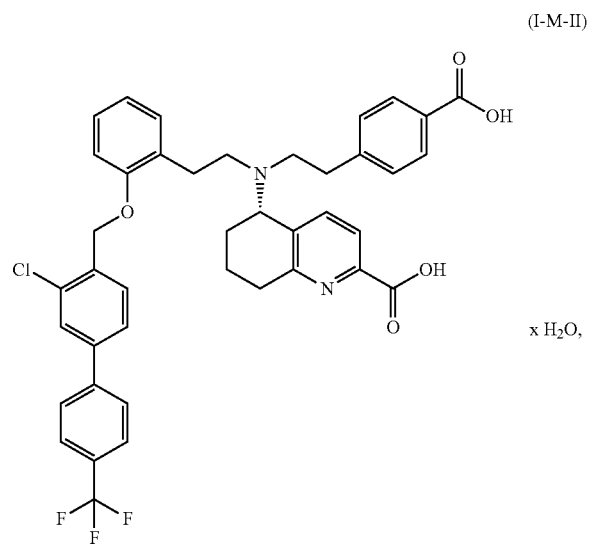 [SMILES: O=C(O)c1ccc(CCN(CCc2ccccc2OCc2ccc(-c3ccc(C(F)(F)F)cc3)cc2Cl)[C@H]2CCCc3nc(C(=O)O)ccc32)cc1]

(I-M-II)

characterized in that that the x-ray diffractogram (at 25° C. and with Cu—K alpha 1 as radiation source) of the compound displaying at least the following reflections, quoted as 2Θ value±0.2°: 6.1 and 8.1, preferably 6.1, 8.1, 12.7, 23.9 and 13.9, preferably at least the following reflections: 6.1, 8.1, 12.7, 23.9, 13.9, 23.1 and 12.2, more preferably at least the following reflections: 6.1, 8.1, 12.7, 23.9, 13.9, 23.1, 12.2, 10.8 and 15.3, most preferably at least the following reflections: 6.1, 8.1, 12.7, 23.9, 13.9, 23.1, 12.2, 10.8, 15.3, 17.3, 21.7 and 22.0.

The compound of formula (I) in the pseudopolymorphic form monohydrate II can also be characterized unambiguously by the X-Ray powder diffractogram (at 25° C. and with Cu—K alpha 1 as radiation source) as shown in FIG. 7.

The pseudopolymorphic form of compound of formula (I), the monohydrate II of formula (I-M-II) can additionally be characterized by a X-Ray powder diffractogram (at 25° C. and with Cu—K alpha 1 as radiation source) which does not display at least the following reflections: 3.1 and 9.3 each quoted as 2Θ value±0.2°.

The pseudopolymorphic form of compound of formula (I), the monohydrate II of formula (I-M-II) can additionally be characterized by a X-Ray powder diffractogram (at 25° C. and with Cu—K alpha 1 as radiation source) which does not display at least the following reflections: 6.9, 7.2 and 7.3 each quoted as 2Θ value±0.2°.

The pseudopolymorphic form of compound of formula (I), the monohydrate II of formula (I-M-II) can additionally be characterized by a X-Ray powder diffractogram (at 25° C. and with Cu—K alpha 1 as radiation source) which does not display at least the following reflections: 29.2 each quoted as 2Θ value±0.2°.

The pseudopolymorphic form of compound of formula (I), the monohydrate II of formula (I-M-II) can additionally be characterized by a X-Ray powder diffractogram (at 25° C. and with Cu—K alpha 1 as radiation source) which does not display at least the following reflections: 7.9 and/or 31.6 each quoted as 2Θ value±0.2°.

The pseudopolymorphic form of compound of formula (I), the monohydrate II of formula (I-M-II) can additionally be characterized by a X-Ray powder diffractogram (at 25° C. and with Cu—K alpha 1 as radiation source) which does not display at least the following reflections: 7.6 each quoted as 2Θ value±0.2°.

The pseudopolymorphic form of compound of formula (I), the monohydrate II of formula (I-M-II) can additionally be characterized by a X-Ray powder diffractogram (at 25° C. and with Cu—K alpha 1 as radiation source) which does not display at least the following reflections: 14.8 each quoted as 2Θ value±0.2°.

Embodiment 9 (Semihydrate of Compound of Formula (I))

The pseudopolymorphic form of compound of formula (I), the semihydrate can unambiguously be characterized by a X-Ray powder diffractogram (at 25° C. and with Cu—K alpha 1 as radiation source) which displays the following reflections: 3.1, 5.3, 6.7, 7.1, 9.3, 10.6, 12.4, 14.3, 16.1, 19.7, 20.8, 24.0, 31.1 each quoted as 2Θ value±0.2°.

The pseudopolymorphic form of compound of formula (I), the semihydrate can unambiguously be characterized by a X-Ray powder diffractogram (at 25° C. and with Cu—K alpha 1 as radiation source) which displays at least the following reflections: 3.1, 5.3, 6.7, 7.1, 9.3 and 31.1 each quoted as 2Θ value±0.2°.

The compound of formula (I) in the pseudopolymorphic form semihydrate can also be characterized unambiguously by the X-Ray powder diffractogram (at 25° C. and with Cu—K alpha 1 as radiation source) as shown in FIG. 5.

The pseudopolymorphic form of compound of formula (I), the semihydrate can additionally be characterized by a X-Ray powder diffractogram (at 25° C. and with Cu—K alpha 1 as radiation source) which does not display at least the following reflections: 6.9, 7.2 and 7.3 each quoted as 2Θ value±0.2°.

The pseudopolymorphic form of compound of formula (I), the semihydrate can additionally be characterized by a X-Ray powder diffractogram (at 25° C. and with Cu—K alpha 1 as radiation source) which does not display at least the following reflections: 29.2 each quoted as 2Θ value±0.2°.

The pseudopolymorphic form of compound of formula (I), the semihydrate can additionally be characterized by a X-Ray powder diffractogram (at 25° C. and with Cu—K alpha 1 as radiation source) which does not display at least the following reflections: 8.5 and/or 30.0 each quoted as 2Θ value±0.2°.

The pseudopolymorphic form of compound of formula (I), the semihydrate can additionally be characterized by a X-Ray powder diffractogram (at 25° C. and with Cu—K alpha 1 as radiation source) which does not display at least the following reflections: 7.9 and/or 31.6 each quoted as 2Θ value±0.2°.

The pseudopolymorphic form of compound of formula (I), the semihydrate can additionally be characterized by a X-Ray powder diffractogram (at 25° C. and with Cu—K alpha 1 as radiation source) which does not display at least the following reflections: 7.6 each quoted as 2Θ value±0.2°.

The pseudopolymorphic form of compound of formula (I), the semihydrate can additionally be characterized by a X-Ray powder diffractogram (at 25° C. and with Cu—K alpha 1 as radiation source) which does not display at least the following reflections: 14.8 each quoted as 2Θ value±0.2°.

Embodiment 10 (1.25 Hydrate of Compound of Formula (I))

The pseudopolymorphic form of compound of formula (I), the 1.25 hydrate can unambiguously be characterized by a X-Ray powder diffractogram (at 25° C. and with Cu—K alpha 1 as radiation source) which displays the following reflections: 5.9, 6.1, 7.9, 10.5, 11.9, 12.2, 12.5, 13.2, 13.6, 13.7, 14.4, 15.2, 15.3, 15.4, 15.7, 15.9, 16.5, 16.9, 17.2, 17.4, 17.6, 17.8, 18.3, 18.6, 18.7, 19.0, 19.5, 19.6, 19.8, 20.5, 20.7, 21.0, 21.4, 22.0, 23.2, 23.8, 24.0, 24.4, 24.6, 25.0, 25.2, 25.6, 26.1, 26.8, 27.4, 27.6, 28.4, 28.8, 30.2, 30.7, 31.1, 31.6, 32.3 each quoted as 2Θ value±0.2°.

The pseudopolymorphic form of compound of formula (I), the 1.25 hydrate can unambiguously be characterized by a X-Ray powder diffractogram (at 25° C. and with Cu—K alpha 1 as radiation source) which displays at least the following reflections: 7.9, 10.5, 12.2, 12.5, 13.6, 15.2, 16.9, 19.0, 24.0, 24.4, 24.6, 31.6 each quoted as 2Θ value±0.2°.

The compound of formula (I) in the pseudopolymorphic form 1.25 hydrate can also be characterized unambiguously by the X-Ray powder diffractogram (at 25° C. and with Cu—K alpha 1 as radiation source) as shown in FIG. 8.

The pseudopolymorphic form of compound of formula (I), the 1.25 hydrate can additionally be characterized by a X-Ray powder diffractogram (at 25° C. and with Cu—K alpha 1 as radiation source) which does not display at least the following reflections: 3.1 and 9.3 each quoted as 2Θ value±0.2°.

The pseudopolymorphic form of compound of formula (I), the 1.25 hydrate can additionally be characterized by a X-Ray powder diffractogram (at 25° C. and with Cu—K alpha 1 as radiation source) which does not display at least the following reflections: 6.9, 7.2 and 7.3 each quoted as 2Θ value±0.2°.

The pseudopolymorphic form of compound of formula (I), the 1.25 hydrate can additionally be characterized by a X-Ray powder diffractogram (at 25° C. and with Cu—K alpha 1 as radiation source) which does not display at least the following reflections: 29.2 each quoted as 2Θ value±0.2°.

The pseudopolymorphic form of compound of formula (I), the 1.25 hydrate can additionally be characterized by a X-Ray powder diffractogram (at 25° C. and with Cu—K alpha 1 as radiation source) which does not display at least the following reflections: 8.5 and/or 30.0 each quoted as 2Θ value±0.2°.

The pseudopolymorphic form of compound of formula (I), the 1.25 hydrate can additionally be characterized by a X-Ray powder diffractogram (at 25° C. and with Cu—K alpha 1 as radiation source) which does not display at least the following reflections: 7.9 and/or 31.6 each quoted as 2Θ value±0.2°.

The pseudopolymorphic form of compound of formula (I), the 1.25 hydrate can additionally be characterized by a X-Ray powder diffractogram (at 25° C. and with Cu—K alpha 1 as radiation source) which does not display at least the following reflections: 7.6 each quoted as 2Θ value±0.2°.

The pseudopolymorphic form of compound of formula (I), the 1.25 hydrate can additionally be characterized by a X-Ray powder diffractogram (at 25° C. and with Cu—K alpha 1 as radiation source) which does not display at least the following reflections: 14.8 each quoted as 2Θ value±0.2°.

Embodiment 11 (Sesquihydrate of Compound of Formula (I))

The pseudopolymorphic form sesquihydrate of the compound of formula (I) can be characterized unambiguously by a X-Ray powder diffractogram (at 25° C. and with Cu—K alpha 1 as radiation source) which displays at least the following reflections: 12.2, 25.1 and 14.5, preferably at least 12.2, 25.1, 14.5, 18.7 and 26.4 preferably at least the following reflections: 12.2, 25.1, 14.5, 18.7, 26.4, 18.3 and 23.4 more preferably at least the following reflections: most preferably at least the following reflections: 12.2, 25.1, 14.5, 18.7, 26.4, 18.3, 23.4, 21.5, 8.6 and 5.1, and 7.6 each quoted as 2Θ value±0.2°.

The pseudopolymorphic form of compound of formula (I), the sesquihydrate can also unambiguously be characterized by a X-Ray powder diffractogram (at 25° C. and with Cu—K alpha 1 as radiation source) which displays at least the following reflections: 5.1, 7.6, 8.6, 12.2, 14.5, 18.3, 18.7, 21.5, 23.4, 24.7, 25.1, 26.4, each quoted as 2Θ value±0.2°.

The pseudopolymorphic form of compound of formula (I), the sesquihydrate can unambiguously be characterized by a X-Ray powder diffractogram (at 25° C. and with Cu—K alpha 1 as radiation source) which displays the following reflections: 5.1, 6.3, 7.6, 8.6, 11.4, 12.2, 12.5, 12.9, 13.3, 14.3, 14.5, 15.2, 15.5, 15.8, 16.2, 16.4, 16.7, 17.3, 17.5, 17.7, 18.3, 18.7, 19.4, 20.5, 20.7, 20.8, 21.4, 21.5, 21.8, 22.4, 22.9, 23.4, 24.0, 24.7, 25.1, 26.1, 26.4, 27.0, 27.4, 28.5, 32.2, 36.5 each quoted as 2Θ value±0.2°.

The compound of formula (I) in the pseudopolymorphic form sesquihydrate can also be characterized unambiguously by the X-Ray powder diffractogram (at 25° C. and with Cu—K alpha 1 as radiation source) as shown in FIG. 9.

The pseudopolymorphic form of compound of formula (I), the sesquihydrate can additionally be characterized by a X-Ray powder diffractogram (at 25° C. and with Cu—K alpha 1 as radiation source) which does not display at least the following reflections: 3.1 and 9.3 each quoted as 2Θ value±0.2°.

The pseudopolymorphic form of compound of formula (I), the sesquihydrate can additionally be characterized by a X-Ray powder diffractogram (at 25° C. and with Cu—K alpha 1 as radiation source) which does not display at least the following reflections: 6.9, 7.2 and 7.3 each quoted as 2Θ value±0.2°.

The pseudopolymorphic form of compound of formula (I), the sesquihydrate can additionally be characterized by a X-Ray powder diffractogram (at 25° C. and with Cu—K alpha 1 as radiation source) which does not display at least the following reflections: 29.2 each quoted as 2Θ value±0.2°.

The pseudopolymorphic form of compound of formula (I), the sesquihydrate can additionally be characterized by a X-Ray powder diffractogram (at 25° C. and with Cu—K alpha 1 as radiation source) which does not display at least the following reflections: 8.5 and/or 30.0 each quoted as 2Θ value±0.2°.

The pseudopolymorphic form of compound of formula (I), the sesquihydrate can additionally be characterized by a X-Ray powder diffractogram (at 25° C. and with Cu—K alpha 1 as radiation source) which does not display at least the following reflections: 7.9 and/or 31.6 each quoted as 2Θ value±0.2°.

The pseudopolymorphic form of compound of formula (I), the sesquihydrate can additionally be characterized by a X-Ray powder diffractogram (at 25° C. and with Cu—K alpha 1 as radiation source) which does not display at least the following reflections: 14.8 each quoted as 2Θ value±0.2°.

Embodiment 12 (Dihydrate of Compound of Formula (I))

The pseudopolymorphic form of compound of formula (I), the dihydrate can be characterized unambiguously by a X-Ray powder diffractogram (at 25° C. and with Cu—K alpha 1 as radiation source) which displays at least the following reflections: 10.1, 10.5, 11.2, 12.5, 13.6, 14.8, 15.5, 20.2, 20.5, 21.1, 22.2, 23.2, 25.1, 29.6 each quoted as 2Θ value±0.2°.

The pseudopolymorphic form of compound of formula (I), the dihydrate can be characterized unambiguously by a X-Ray powder diffractogram (at 25° C. and with Cu—K alpha 1 as radiation source) which displays the following reflections: 6.1, 6.8, 10.1, 10.5, 11.2, 11.3, 12.3, 12.5, 13.1, 13.6, 14.6, 14.8, 15.5, 16.2, 16.4, 16.8, 17.1, 17.3, 17.9, 18.5, 18.8, 19.5, 20.2, 20.5, 21.1, 21.4, 22.2, 23.2, 24.3, 25.1, 25.4, 25.6, 26.3, 26.9, 27.4, 28.5, 28.7, 29.6 each quoted as 2Θ value±0.2°.

The compound of formula (I) in the pseudopolymorphic form dihydrate can also be characterized unambiguously by the X-Ray powder diffractogram (at 25° C. and with Cu—K alpha 1 as radiation source) as shown in FIG. 10.

The pseudopolymorphic form of compound of formula (I), the dihydrate can additionally be characterized by a X-Ray powder diffractogram (at 25° C. and with Cu—K alpha 1 as radiation source) which does not display at least the following reflections: 3.1 and 9.3 each quoted as 2Θ value±0.2°.

The pseudopolymorphic form of compound of formula (I), the dihydrate can additionally be characterized by a X-Ray powder diffractogram (at 25° C. and with Cu—K alpha 1 as radiation source) which does not display at least the following reflections: 6.9, 7.2 and 7.3 each quoted as 2Θ value±0.2°.

The pseudopolymorphic form of compound of formula (I), the dihydrate can additionally be characterized by a X-Ray powder diffractogram (at 25° C. and with Cu—K alpha 1 as radiation source) which does not display at least the following reflections: 29.2 each quoted as 2Θ value±0.2°.

The pseudopolymorphic form of compound of formula (I), the dihydrate can additionally be characterized by a X-Ray powder diffractogram (at 25° C. and with Cu—K alpha 1 as radiation source) which does not display at least the following reflections: 8.5 and/or 30.0 each quoted as 2Θ value±0.2°.

The pseudopolymorphic form of compound of formula (I), the dihydrate can additionally be characterized by a X-Ray powder diffractogram (at 25° C. and with Cu—K alpha 1 as radiation source) which does not display at least the following reflections: 7.9 and/or 31.6 each quoted as 2Θ value±0.2°.

The pseudopolymorphic form of compound of formula (I), the dihydrate can additionally be characterized by a X-Ray powder diffractogram (at 25° C. and with Cu—K alpha 1 as radiation source) which does not display at least the following reflections: 7.6 each quoted as 2Θ value 10.2°.

Method for Treatment:

The crystalline forms of the compound of formula (I), preferably the monohydrate I (I-M-I) or the monohydrate II (I-M-II), more preferably the monohydrate I (I-M-I) according to the invention have useful pharmacological properties and can be employed for the prevention and treatment of disorders in humans and animals. The forms of the compound of formula (I) according to the invention can open up a further treatment alternative and may therefore be an enrichment of pharmacy.

In the context of the present invention, the term "treatment" or "treat" includes the inhibition, delay, arrest, amelioration, attenuation, limitation, reduction, suppression, reversal or cure of a disease, a condition, a disorder, an injury or a health impairment, of the development, course or the progression of such states and/or the symptoms of such states. Here, the term "therapy" is understood to be synonymous with the term "treatment".

In the context of the present invention, the terms "prevention", "prophylaxis" or "precaution" are used synonymously and refer to the avoidance or reduction of the risk to get, to contract, to suffer from or to have a disease, a condition, a disorder, an injury or a health impairment, a development or a progression of such states and/or the symptoms of such states.

The treatment or the prevention of a disease, a condition, a disorder, an injury or a health impairment may take place partially or completely.

The term "therapeutic efficacy" within the context of the present invention is defined as a reduction of the mean pulmonary artery pressure with simultaneously clinically not relevantly changed systemic blood pressure of the patient by administering the pharmaceutical dry powder formulation comprising a therapeutically effective amount of compound of formula (I), especially of comparative example 11 or a salt, a solvate or a polymorphic form or a solvate or a crystal modification of a salt of the compound of formula (I) or a metabolite of compound of formula (I), especially its pseudopolymorphic forms, like e.g. (I-M-I) and (I-M-II).

The term "pulmonary vascular resistance (PVR)" within the context of the present invention is defined as the parameter 1) to characterize the severity of pulmonary hypertension as wall tension in the main pulmonary blood vessels, analysed by an invasive method of measuring the blood pressure in the pulmonary artery and 2) to evaluate the effect of a new drug by substantially lowering this parameter directly related to the blood pressure in the pulmonary artery (see D. Singh, R. Tal-Singer, I. Faiferman, S. Lasenby, A. Henderson, D. Wessels, A. Goosen, N. Dallow, R. Vessey & M. Goldman, Plethysmography and impulse oscillometry assessment of tiotropium and ipratropium bromide; a randomized, double-blind, placebo-controlled, cross-over study in healthy subjects, Br. Journal Clin Pharmacol, 2006, 61, 398-404).

An improved 6 minutes walking test result within the context of the present invention is defined as an improvement in the distance patients are able to walk within a time window of 6 minutes, which corresponds to the increased physical ability of the patients with severe disease under treatment.

A shift in "NYHA class" within the context of the present invention is defined as the improvement to a lower class number of the NYHA classification from a higher class, corresponding to an improved heart function with better cardial capability.

The physiological function of the lung is evaluated in lung function tests like spirometry or bodyplethysmography under standardized conditions to get standardized and validated measurements for parameters like e.g. forced expiratory volume in 1 second (FEV1) that allow a direct assessment of drug effects like bronchodilation, an effect that is therapeutically used by different drugs for improvement of lung function in pulmonary diseases with bronchoconstriction like COPD or asthma.

The terms "improved haemodynamic effect" within the context of the present invention is defined as the drug's vasodilative effect to decrease pulmonary artery pressure, to improve the circulation of blood in ventilated areas of the lung as well as to improve lung function without systemic side effects and thereby causing a clinical relevant improvement of physical capability and general situation for the individual patient.

The term "Intrapulmonary selectivity" in the context of this invention means the property of the inhaled active ingredient to unfold its pharmacodynamic property of vasodilation only in the ventilated areas of the lung and not in the unventilated areas. This is to prevent a worsening of the mismatch between ventilation and perfusion (by increase of perfusion in the unventilated areas) which could happen if the active ingredient also reached the unventilated areas. Intrapulmonary selectivity is ensured in particular by the inhaled route of application which is carried out by active inhalation of the patient.

The term "bronchodilatory effect" within the context of the present invention is defined as improvement in parameters such as e.g. relaxation of carbachol preconstricted guinea pig trachea, lung resistance (RL) and dynamic compliance (Cdyn), specific airway resistance in humans (E-2.1), FEV1 in humans or other parameters indicating improvement in ventilation.

The term "chronic treatment/use" within the context of the present invention is defined as once or twice daily inhalative treatment of patients for a period of at least two consecutive days, preferably at least 2 to 7 consecutive days, preferably for a period of at least 14 consecutive days, in particular from after onset of treatment for the whole course of the disease, optionally also in combination with standard of care (SoC e.g. endothelin antagonists such as bosentan, PDE5 inhibitors e.g. sildenafil, IP agonists e.g. Ilomedin or treprostinil, calcium channel blockers, sotatercept and sGC stimulators e.g. riociguat).

The term "once daily" is well known by those skilled in the art and means administration of the drug once a day and includes the administration of one dosage form as well as administration of two or more dosage forms simultaneously or consecutively within a short time period.

The term "once or twice daily" is well known by those skilled in the art and means administration of the drug once a day or twice a day whereas the administration of the drug at each corresponding time point of the day includes the administration of one dosage form as well as administration of two or more dosage forms simultaneously or consecutively within a short time period.

The term "consecutive days" means a period of days occurring one after the other with no intervening days and does not mean sequential days or cyclical days.

The term "inhalative dosage form" means the combination of the drug substance, i.e. the active ingredient, preferably in one crystalline form, e.g. in form of the monohydrate I or the monohydrate II or the sesquihydrate, preferably in form of the monohydrate I or the monohydrate II, more preferably in form of the monohydrate I of formula (I-M-I), in combination with a pharmaceutically suitable carrier for inhalation. The combination of the drug substance and the pharmaceutically suitable carrier for inhalation are in the form of a dry powder. Preferably the dry powder is filled in a cavity, more preferably filled in a capsule. Preferably the pharmaceutically suitable carrier is lactose for inhalation.

The terms "reflection(s)" or "peak(s)" are synonyms and have the same meaning in connection with X-ray values and diffractograms. Crystalline forms are most commonly characterized by X-ray powder diffraction (XRPD). An XRPD pattern of reflections (peaks, typically expressed in degrees 2-theta) is commonly considered a fingerprint of a particular crystalline form.

The term "respiratory organs" (or respiratory system) refers for the purposes of the invention to the airways—including nose, oral cavity and pharynx, larynx, trachea, bronchi and the lung—as functional organ system.

The terms "Local administration" or "local control" in connection with cardiopulmonary disorders, means for the purposes of the invention—in contrast to oral administration of dosage forms intended for absorption via the gastrointestinal tract, and in contrast to intravenous administration, both leading to systemic drug distribution via bloodstream—administration of the active ingredient by inhalation in inhalable dosage form to primarily cover the lung as target organ, which requires a lower dose and causes a lower general drug exposure. The preparation in powder form or powder-containing suspensions to be used according to the invention are preparations which are inhaled.

The term "inhalation" or "administration by inhalation" refers in this connection to the introduction into the respiratory organs, especially into and/or via the airways, preferably into and/or via the nasal cavity or oral cavity, particularly preferable via oral cavity in order to achieve a deposition of the active ingredient to the bronchi and lung as the sites of action.

The term "intratracheal" or "intratracheal administration" refers for the purposes of the invention to introduce the compound into the trachea not by inhalation, in particular for pulmonary disease control in experimental animals such as rats or piglets and dogs as a model of administration (e.g. intratracheal application via PennCentury Device, applicable for dry powder as well as drug solutions and suspensions).

The compounds according to the invention, like (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydro-quino-line-2-carboxylic acid of formula I as well as its pseudopolymorphic forms, like e.g. (I-M-I) and (I-M-II) are potent activators of soluble guanylate cyclase. They lead to vasorelaxation, inhibition of platelet aggregation and a lowering of the blood pressure, as well as an increased coronary blood flow and microcirculation. Furthermore they have a bronchodilatory effect. These activities are mediated via direct haem-independent activation of soluble guanylate cyclase and an increase in intracellular cGMP levels.

In addition, the compounds according to the invention, especially (5S)—{[2-(4-carboxyphenyl)ethyl][2-(2-{[3-chloro-4'-(trifluoromethyl)biphenyl-4-yl]methoxy}phenyl) ethyl]amino}-5,6,7,8-tetrahydro-quino-line-2-carboxylic acid of formula I as well as its pseudopolymorphic forms, like e.g. (I-M-I) and (I-M-II) have further advantageous pharmacological properties, in particular with respect to their pulmoselective action (in contrast to a systemic action), their lung retention time and/or their duration of action following intrapulmonary administration (E-1).

Also a good therapeutical efficacy and target engagement of the compounds according to the invention, especially (5S)—{[2-(4-carboxyphenyl)ethyl][2-(2-{[3-chloro-4'-(trifluoromethyl)biphenyl-4-yl]methoxy}-phenyl)ethyl]amino}-5,6,7,8-tetrahydro-quino-line-2-carboxylic acid of formula I as well as its pseudopolymorphic forms, like e.g. (I-M-I) and (I-M-II) could be shown clinically: after inhaled application a reduced total specific airway resistance (E-2.1), an increase in plasma cGMP concentrations as surrogate for drug concentration in the lung (indicative of target engagement) (E-2.1, E-2.2) and a selective decrease in pulmonary artery pressure and pulmonary vascular resistance (E-2.4) was observed.

Furthermore suitable pharmacokinetic properties of the drug substance for inhaled applications could be shown. The analysis of plasma concentrations after oral, intravenous and inhalative administration of the drug substance showed the longest half-life after inhaled application (E-2.3). The emitted dose has been determined to be 720 µg after inhalation of 1000 µg in humans. The outcome from this investigation confirms the deposited lung dose and that the half-life is adequate for an inhaled dry powder administration enabling a once daily treatment for a sufficient 24 h drug coverage of the drug substance (as shown for example 4) in the lung.

In conclusion all results show that (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I as well as its pseudopolymorphic forms, like e.g. (I-M-I) and (I-M-II), especially the monohydrate I of formula (I-M-I) are suitable in particular for the treatment of pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP) and are adequate for an inhaled dry powder administration enabling a once daily treatment for a sufficient 24 h drug coverage of example 4 in the lung.

The compounds according to the invention, (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydro-quino-line-2-carboxylic acid of formula I as well as its pseudopolymorphic forms, like e.g. (I-M-I) and (I-M-II) are particularly suitable for the treatment and/or prevention of cardiovascular, cardiopulmonary and pulmonary disorders, preferably for cardiopulmonary disorders.

Accordingly, the compounds according to the invention, especially (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydro-quino-line-2-carboxylic acid as well as its pseudopolymorphic forms, like e.g. (I-M-I) and (I-M-II) can be used in medicaments for the treatment and/or prevention of cardiovascular and cardiopulmonary disorders such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP), as well as pulmonary disorders such as asthma, chronic obstructive pulmonary disease (COPD) or pulmonary fibrosis.

In the context of the present invention, the term "sGC modulators" encompasses two distinct compound classes capable of modulating sGC, the sGC stimulators and sGC activators (Sandner P, Becker-Pelster E M, Stasch J P. Discovery and development of sGC stimulators for the treatment of pulmonary hypertension and rare diseases. Nitric Oxide 2018; 77:88-95.; Hoenicka M, Becker E M, Apeler H, Sirichoke T, Schröder H, Gerzer R, Stasch J P. Purified soluble guanylyl cyclase expressed in a baculovirus/Sf9 system: stimulation by YC-1, nitric oxide, and carbon monoxide. J Mol Med (Berl) 1999; 77:14-23; Evgenov O V, Kohane D S, Bloch K D, Stasch J P, Volpato G P, Bellas E, Evgenov N V, Buys E S, Gnoth M J, Graveline A R, Liu R, Hess D R, Langer R, Zapol W M. Inhaled agonists of soluble guanylate cyclase induce selective pulmonary vasodilation. Am J Respir Crit Care Med 2007; 176:1138-1145). Both classes of compounds directly bind to sGC as allosteric modulators. sGC stimulators have a dual mode of action, directly stimulating the native sGC independently of NO and also sensitizing sGC to low levels of NO by stabilizing NO-sGC binding. In contrast, sGC activators bind to the unoccupied heme-binding domain, thereby mimicking NO-bound heme, and activate the pathologically changed, NO-unresponsive apo-sGC. Recent evidence has shown that oxidative stress associated with many cardiopulmonary diseases shifts intracellular levels of native sGC toward the apo-sGC form (Evgenov O V, Pacher P, Schmidt P M, Hasko G, Schmidt H H, Stasch J P. NO-independent stimulators and activators of soluble guanylate cyclase: discovery and therapeutic potential. Nat Rev Drug Discov 2006; 5:755-768; Minzel T, Genth-Zotz S, Hink U. Targeting heme-oxidized soluble guanylate cyclase: solution for all cardio-renal problems in heart failure?Hypertension 2007; 49:974-976), providing the rationale for sGC activators (Wood K C, Durgin B G, Schmidt H M, Hahn S A, Baust J J, Bachman T, Vitturi D A, Ghosh S, Ofori-Acquah S F, Mora A L, Gladwin M T, Straub A C. Smooth muscle cytochrome b5 reductase 3 deficiency accelerates pulmonary hypertension development in sickle cell mice. Blood Adv 2019; 3:4104-4116.; Rahaman M M, Nguyen A T, Miller M P, Hahn S A, Sparacino-Watkins C, Jobbagy S, Carew N T, Cantu-Medellin N, Wood K C, Baty C J, Schopfer F J, Kelley E E, Gladwin M T, Martin E, Straub A C. Cytochrome b5 Reductase 3 Modulates Soluble Guanylate Cyclase Redox State and cGMP Signaling. Circ Res 2017; 121:137-148.; Durgin B G, Hahn S A, Schmidt H M, Miller M P, Hafeez N, Mathar I, Freitag D, Sandner P, Straub A C. Loss of smooth muscle CYB5R3 amplifies angiotensin II-induced hypertension by increasing sGC heme oxidation. JCI Insight 2019; 4:e129183.; Sandner P, Zimmer D P, Milne G T, Follmann M, Hobbs A, Stasch J P. Soluble guanylate cyclase stimulators and activators. Handb Exp Pharmacol 2019; doi:10.1007/164_2018_197) in various cardiovascular pathophysiological conditions such as PH.

In the context of the present invention, the term "pulmonary hypertension" encompasses both primary and secondary subforms thereof, as defined below by the Dana Point/Nizza classification according to their respective aetiology [see D. Montana and G. Simonneau, in: A. J. Peacock et al. (Eds.), Pulmonary Circulation. Diseases and their treatment, 3rd edition, Hodder Arnold Publ., 2011, pp. 197-206; M. M. Hoeper et al., J. Am. Coll. Cardiol. 2009, 54 (1), S85-S96] updated Nizza classification Gérald Simonneau, David Montani, David S. Celermajer, Christopher P. Denton, Michael A. Gatzoulis, Michael Krowka, Paul G. Williams, Rogerio Souza: Haemodynamic definitions and updated clinical classification of pulmonary hypertension, in: European Respiratory Journal, 2018; DOI: 10.1183/13993003.01913-2018]. These include in particular in group 1 pulmonary arterial hypertension (PAH), which, among others, embraces the idiopathic and the familial forms (IPAH and FPAH, respectively). Furthermore, PAH also embraces persistent pulmonary hypertension of the newborn and pulmonary arterial hypertension associated with collagenoses (APAH), congenital systemic pulmonary shunt lesions, portal hypertension, HIV infections, the intake of certain drugs and medicaments (for example of appetite supressants), with disorders having a significant venous/capillary component such as pulmonary venoocclusive disorder and pulmonary capillary haemangiomatosis, or with other disorders such as disorders of the thyroid, glycogen storage diseases, Gaucher disease, hereditary teleangiectasia, haemoglobinopathies, myeloproliferative disorders and splenectomy. Group 2 comprises PH patients having a causative left heart disorder, such as ventricular, atrial or valvular disorders. Group 3 comprises forms of pulmonary hypertension associated with a lung disorder, for example with chronic obstructive lung disease (COPD), interstitial lung disease (ILD), pulmonary fibrosis (IPF), and/or hypoxaemia (e.g. sleep apnoe syndrome, alveolar hypoventilation, chronic high-altitude sickness, hereditary deformities). Group 4 includes PH patients having chronic thrombotic and/or embolic disorders, for example in the case of thromboembolic obstruction of proximal and/or distal pulmonary arteries (CTEPH) or non-thrombotic embolisms (e.g. as a result of tumour disorders, parasites, foreign bodies). Less common forms of pulmonary hypertension, such as in patients suffering from sarcoidosis, histiocytosis X or lymphangiomatosis, are summarized in group 5.

The compounds according to the invention, especially (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydro-quino-line-2-carboxylic acid of formula I as well as its pseudopolymorphic forms, like e.g. (I-M-I) and (I-M-II) are also suitable for treatment and/or prevention of pulmonary disorders such as asthma, chronic-obstructive pulmonary disease (COPD) and pulmonary fibrosis.

In the context of the present invention, the term "Asthma" encompasses a heterogenous chronic inflammatory disease of the airways of the lungs. It is characterized by variable and recurring symptoms, from reversible airflow obstruction, often caused by a hyperreagibility of the bronchi up to bronchospasms. Symptoms include episodes of wheezing, coughing, chest tightness, and shortness of breath. These may occur a few times a day or a few times per week. Depending on the person, asthma symptoms may become worse at night or with exercise. Asthma is thought to be caused by a combination of genetic and environmental factors. Environmental factors include exposure to air pollution and allergens. Other potential triggers include medications such as aspirin and beta blockers. Diagnosis is usually based on the pattern of symptoms, response to therapy over time, and spirometry lung function testing. Asthma is classified according to the frequency of symptoms, forced expiratory volume in one second (FEV1), and peak expiratory flow rate. It may also be classified as atopic or non-atopic, where atopy refers to a predisposition toward developing a type 1 hypersensitivity reaction. There is no known cure for asthma, but it is well treatable systematically. Symptoms can be prevented by avoiding triggers, such as allergens and respiratory irritants, and suppressed with the use of inhaled corticosteroids. Long-acting beta agonists (LABA), and other substances, e.g. antileukotriene agents may be used in addition to inhaled corticosteroids if asthma symptoms remain uncontrolled. Treatment of acute worsening symptoms is usually performed with an inhaled short-acting beta-2 agonist such as salbutamol and corticosteroids. In severe cases, systemic corticosteroids, magnesium sulfate, and hospitalization may be required. A subset of asthmatics develop a severe form of the disease whose etiology involves airway inflammation along with inherent drivers that remain ill-defined. To address this, we studied human airway smooth muscle cells (HASMC), whose relaxation drives airway bronchodilation and whose dysfunction contributes to airway obstruction and hypersensitivity in severe asthma. Because HASMC relaxation can be driven by the NO-soluble guanylyl cyclase (sGC)-cGMP signaling pathway, HASMC from severe asthma donors might possess inherent defects in their sGC or in redox enzymes that support sGC function. A majority of the severe asthma donor HASMC (12/17) and lung samples primarily expressed a dysfunctional sGC that was NO-unresponsive and had low heterodimer content and high Hsp90 association. This sGC phenotype correlated with lower expression levels of the supporting redox enzymes cytochrome b5 reductase, catalase, and thioredoxin-1, and higher expression of heme oxygenases 1 and 2 hinting towards a hypothesis that severe asthmatics are predisposed toward defective NO-sGC-cGMP signaling in their airway smooth muscle due to an inherent sGC dysfunction, which in turn is associated with inherent changes in the cell redox enzymes that impact sGC maturation and function. Therefore sGC activators might be a new target option for these patients with respect to optimized bronchodilation under these pathophysiologic conditions (see for example the following references: Arnab Ghosh, Cynthia J. Koziol-White, William F. Jester Jr., Serpil C. Erzurum, Kewal Asosingh, Reynold A. Panettieri Jr. see, Dennis J. Stuehr: An inherent dysfunction in soluble guanylyl cyclase is present in the airway of severe asthmatics and is associated with aberrant redox enzyme expression and compromised NO-cGMP signaling in Redox Biology 39 (2021) 101832; Maggie Lam, Jane E. Bourke, Ph.D., A New Pathway to Airway Relaxation: Targeting the "Other" Cyclase in Asthma American Journal of Respiratory Cell and Molecular Biology Volume 62 Number 1|January 2020; Cynthia J. Koziol-White, Arnab Ghosh, Peter Sandner, Serpil E. Erzurum, Dennis J. Stuehr, and Reynold A. Panettieri, Jr.: Soluble Guanylate Cyclase Agonists Induce Bronchodilation in Human Small Airways, Am J Respir Cell Mol Biol Vol 62, Iss 1, pp 43-48, January 2020.).

By virtue of their activity profile, the compounds according to the invention, especially (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydro-quino-line-2-carboxylic acid of formula I as well as its pseudopolymorphic forms, like e.g. (I-M-I) and (I-M-II) are particularly suitable for the treatment and/or prevention of cardiovascular and cardiopulmonary disorders such as primary and secondary forms of pulmonary hypertension.

The present invention furthermore provides the use of the compounds according to the invention, especially (5S)—{[2-(4-carboxyphenyl)ethyl][2-(2-{[3-chloro-4'-(trifluoromethyl)biphenyl-4-yl]methoxy}phenyl)-ethyl]amino]-5,6,7,8-tetrahydro-quino-line-2-carboxylic acid of formula I as well as its pseudopolymorphic forms, like e.g. (I-M-I) and (I-M-II) for the treatment and/or prevention of disorders, in particular cardiopulmonary disorders, such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

The present invention furthermore provides the use of the compounds according to the invention especially (5S)—{[2-(4-carboxyphenyl)ethyl][2-(2-{[3-chloro-4'-(trifluoromethyl)biphenyl-4-yl]methoxy}phenyl)-ethyl]amino}-5,6,7,8-tetrahydro-quino-line-2-carboxylic acid of formula I as well as its pseudopolymorphic forms, like e.g. (I-M-I) and (I-M-II) for preparing a medicament for the treatment and/or prevention of disorders, in particular cardiopulmonary disorders, such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

The present invention furthermore provides a medicament comprising at least one of the compounds according to the invention, especially (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydro-quino-line-2-carboxylic acid of formula I as well as its pseudopolymorphic forms, like e.g. (I-M-I) and (I-M-II) for use in the treatment and/or prevention of disorders, in particular cardiopulmonary disorders, such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

The present invention furthermore provides the use of the compounds according to the invention, especially (5S)—{[2-(4-carboxyphenyl)ethyl][2-(2-{[3-chloro-4'-(trifluoromethyl)biphenyl-4-yl]methoxy}phenyl)-ethyl]amino}-5,6,7,8-tetrahydro-quino-line-2-carboxylic acid of formula I as well as its pseudopolymorphic forms, like e.g. (I-M-I) and (I-M-II) in a method for the treatment and/or prevention of disorders, in particular cardiopulmonary disorders, such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

The present invention furthermore provides a method for the treatment and/or prevention of disorders, in particular cardiopulmonary disorders, such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP), comprising administering (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydro-quino-line-2-carboxylic acid of formula I, especially comparative example 11 as well as its pseudopolymorphic forms, like e.g. (I-M-I) and (I-M-II) once or twice daily for a period of equal or more than two days, preferably at least 2 to 7 consecutive days, preferably for a period of at least 14 consecutive days, in particular from after onset of treatment for the whole course of the disease in an inhalative dosage form, e.g. a dry powder inhaler in form of a dry powder formulation to a patient in need thereof, wherein said sGC activator has a sustained efficacy over a period of 24 hours, when inhalatively administered to a patient in need thereof.

The present invention further relates to the use of an inhalative dosage form of a sGC activator of formula I, especially comparative example 11, (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I as well as its pseudopolymorphic forms, like e.g. (I-M-I) and (I-M-II) for the manufacture of a medicament for the treatment of a cardiopulmonary disorders, such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP), administered once or twice daily for a period of equal or more than two days, preferably at least 2 to 7 consecutive days, preferably for a period of at least 14 consecutive days, in particular from after onset of treatment for the whole course of the disease, wherein said sGC activator has a sustained efficacy over a period of 24 hours when inhalatively administered to a patient in need thereof.

The present invention further relates to a packaged pharmaceutical composition comprising a container containing a dry powder inhaler (=DPI) and a pharmaceutical formulation comprising (5S)—{[2-(4-Carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid of formula I as well as its pseudopolymorphic forms, like e.g. (I-M-I) and (I-M-II), said container furthermore containing instructions for using said dry powder, e.g. that after one deep inhalative breath the subjects have to hold breath for about 2 seconds, so that the dry powder drug condenses from the airstream onto the surface of the deeper lung areas where it is deposited close to its site of intended pharmacological action, to treat a cardiopulmonary disorder, preferably pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

In a preferred embodiment the present invention further relates to a packaged pharmaceutical composition comprising a container containing a dry powder inhaler (=DPI) and a pharmaceutical formulation comprising (5S)—{[2-(4-Carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid of formula I as well as its pseudopolymorphic forms, like e.g. (I-M-I) and (I-M-II), said packaged pharmaceutical composition, comprising a container containing dry powder comprising (5S)—{[2-(4-Carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid, said container furthermore containing instructions for administering said dry powder at a frequency of once or twice daily to treat a cardiopulmonary disorder, preferably pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP), furthermore a pulmonary disorder.

The present invention further relates to medicaments that contain at least one compound according to the invention, usually together with one or more inert, non-toxic, pharmaceutically suitable excipients, and use thereof for the aforementioned purposes.

The compounds according to the invention especially (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydro-quino-line-2-carboxylic acid of formula I as well as its pseudopolymorphic forms, like e.g. (I-M-I) and (I-M-II) can be used alone or in combination with other active compounds if necessary. The present invention further relates to medicaments containing at least one of the compounds according to the invention, especially (5S)—{[2-(4-carboxyphenyl)ethyl][2-(2-{[3-chloro-4'-(trifluoromethyl)biphenyl-4-yl]methoxy}phenyl)-ethyl]amino}-5,6,7,8-tetrahydro-quino-line-2-carboxylic acid of formula I as well as its pseudopolymorphic forms, like e.g. (I-M-I) and (I-M-II) and one or more further active compounds, in particular for the treatment and/or prophylaxis of the aforementioned diseases. As suitable combination active compounds, we may mention for example and preferably:

organic nitrates and NO-donors, for example sodium nitroprusside, nitroglycerin, isosorbide mononitrate, isosorbide dinitrate, molsidomine or SIN-1, and inhalational NO Ca-channel blockers used for PAH patients with preserved vasoresponsiveness compounds that inhibit the degradation of cyclic guanosine monophosphate (cGMP) and/or cyclic adenosine monophosphate (cAMP), for example inhibitors of phosphodiesterases (PDE) 1, 2, 3, 4 and/or 5, in particular PDE 3 inhibitors as ensifentrine, PDE 4 inhibitors such as roflumilast, tanimilast or revamilast and PDE 5 inhibitors such as sildenafil, vardenafil, tadalafil, udenafil, dasantafil, avanafil, mirodenafil or lodenafil;

NO-independent but haem-dependent stimulators of guanylate cyclase, in particular riociguat and the compounds described in WO 00/06568, WO 00/06569, WO 02/42301, WO 03/095451, WO 2011/147809, WO 2012/004258, WO 2012/028647, WO 2012/059549 and WO2014/068099;

prostacyclin analogs and IP receptor agonists, for example and preferably iloprost, beraprost, treprostinil, epoprostenol or NS-304;

endothelin receptor antagonists, for example and preferably bosentan, darusentan, ambrisentan or sitaxsentan;

human neutrophile elastase (HNE) inhibitors, for example and preferably sivelestat or DX-890 (Reltran);

compounds which inhibit the signal transduction cascade, in particular from the group of the tyrosine kinase inhibitors, for example and preferably dasatinib, nilotinib, bosutinib, regorafenib, sorafenib, sunitinib, cediranib, axitinib, telatinib, imatinib, brivanib, pazopanib, vatalanib, gefitinib, erlotinib, lapatinib, canertinib, lestaurtinib, pelitinib, semaxanib, masitinib or tandutinib;

compounds which act as ligand trap with high selectivity for multiple proteins within the TGF-beta superfamily, including activins, GDFs, and others with its believed ability to block the TGF-beta superfamily signaling pathway, and thereby could promote a rebalancing of bone morphogenetic protein receptor type II (BMPR-II) signaling and, potentially, restore vascular homeostasis as sotatercept Rho kinase inhibitors, for example and preferably fasudil, Y-27632, SLx-2119, BF-66851, BF-66852, BF-66853, KI-23095 or BA-1049;

anti-obstructive agents as used, for example, for the therapy of chronic-obstructive pulmonary disease (COPD) or bronchial asthma, for example and preferably inhalatively or systemically administered beta-receptor mimetics (e.g. salbutamol, salmeterol) or inhalatively administered anti-muscarinergic substances (e.g. ipratropium, tiotropium);

antiinflammatory and/or immunosuppressive agents as used, for example for the therapy of chronic-obstructive pulmonary disease (COPD), of bronchial asthma or pulmonary fibrosis, for example and preferably systemically or inhalatively administered corticosteroids, flutiform, pirfenidone, acetylcysteine, azathioprine or BIBF-1120, nintedanib or treprostinil;

active compounds used for the systemic and/or inhalative treatment of pulmonary disorders, for example for cystic fibrosis (alpha-1-antitrypsin, aztreonam, ivacaftor, lumacaftor, ataluren, amikacin, levofloxacin), chronic obstructive pulmonary diseases (COPD) (Tiotropium, LABA/LAMA, LAS40464, PT003, SUN-101), acute respiratory distress syndrome (ARDS) and acute lung injury (ALI) (interferon-beta-la, traumakines, PEG-Adrenomedullin, inhaled sGC modulators e.g. BAY2111163), obstructive sleep apnoe (VI-0521, TASK channel blocker and ADRA2C antagonists), bronchiectasis (mannitol, ciprofloxacin), Bronchiolitis obliterans (cyclosporine, aztreonam);

antithrombotic agents, for example and preferably from the group of platelet aggregation inhibitors, anticoagulants or profibrinolytic substances.

Antithrombotic agents are preferably to be understood as compounds from the group of platelet aggregation inhibitors, anticoagulants or profibrinolytic substances.

In a preferred embodiment of the invention, the compounds according to the invention are administered in combination with a platelet aggregation inhibitor, for example and preferably aspirin, clopidogrel, ticlopidine or dipyridamole.

In a preferred embodiment of the invention, the compounds according to the invention are administered in combination with a thrombin inhibitor, for example and preferably ximelagatran, melagatran, dabigatran, bivalirudin or Clexane.

In a preferred embodiment of the invention, the compounds according to the invention are administered in combination with a GPIIb/IIIa antagonist, for example and preferably tirofiban or abciximab.

In a preferred embodiment of the invention, the compounds according to the invention are administered in combination with a factor Xa inhibitor, for example and preferably rivaroxaban, apixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, for example and preferably coumarin.

The agents for lowering pulmonary blood pressure are preferably to be understood as compounds from the group of calcium antagonists, PDE5 inhibitors, sGC stimulators and activators, prostacyclin analogs and IP receptor agonists, and endothelin receptor antagonists.

In a preferred embodiment of the invention, the compounds according to the invention are administered in combination with a calcium antagonist, for example and preferably nifedipine, amlodipine, verapamil or diltiazem.

In a preferred embodiment of the invention, the compounds according to the invention are administered in combination with an endothelin receptor antagonist, for example and preferably bosentan, darusentan, ambrisentan or sitaxsentan.

DETAILED DESCRIPTION OF THE INVENTION

Formulations for Inhalation

The present invention further relates to medicaments that contain at least one crystalline form of compound of formula (I) according to the invention, preferably monohydrate I of formula (I-M-I) or monohydrate II of formula (I-M-II), particular preferably monohydrate I of formula (I-M-I) usually together with one or more inert, non-toxic, pharmaceutically suitable excipients, and use thereof for the aforementioned purposes.

A preferred embodiment of the present invention is a pharmaceutical composition comprising the Monohydrate I of the compound of the formula (I) mainly and no significant fractions of another form of the compound of the formula (I) and optionally further pharmaceutically acceptable excipients. More preferably the pharmaceutical composition contains more than 85 percent by weight, more preferably more than 90 percent by weight, most preferably more than 95 percent by weight, of the Monohydrate I of the compound of the formula (I) related to the total amount of all forms of the compound of the formula (I) present in the composition.

Active Ingredient

Solid preparations according to the present invention for dry powder inhalation contain an amount of active ingredient (i.e. (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I, preferably (5S)—{[2-(4-carboxyphenyl)ethyl][2-(2-{[3-chloro-4'-(trifluoromethyl)biphenyl-4-yl]methoxy}phenyl)-ethyl]-amino}-5,6,7,8-tetrahydroquinoline-2-carboxylic acid in form of monohydrate I of formula (I-M-I)) or (5S)—{[2-(4-carboxyphenyl)ethyl][2-(2-{[3-chloro-4'-(trifluoromethyl)biphenyl-4-yl]methoxy}phenyl)-ethyl]-amino}-5,6,7,8-tetrahydroquinoline-2-carboxylic acid in form of monohydrate II of formula (I-M-II)), particularly preferable (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid in form of monohydrate I of formula (I-M-I)) in a matrix of a suitable inhalation grade carrier for the active compound which is not more than about 20%. Usually the amount of active ingredient is between 0.5% and 20%, preferably between 0.75% and 10%. The amount of active ingredient therein is usually at least 0.75%, or at least 3%, or at least 5% or at least 10% by weight based on the preparation ready for use. Very preferable are amount of active ingredient of 3%, 10% or 20%.

Solid preparations according to the present invention for dry powder inhalation contain the active ingredient (i.e. (5S)—{[2-(4-carboxyphenyl)ethyl][2-(2-{[3-chloro-4'-(trifluoromethyl)biphenyl-4-yl]methoxy}-phenyl)ethyl]-amino}-5,6,7,8-tetrahydroquinoline-2-carboxylic acid of formula I, preferably (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid in form of monohydrate I of formula (I-M-I)) or (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid in form of monohydrate II of formula (I-M-II)), particularly preferable (5S)—{[2-(4-carboxyphenyl)ethyl][2-(2-{[3-chloro-4'-(trifluoromethyl)biphenyl-4-yl]methoxy}-phenyl)ethyl]-amino}-5,6,7,8-tetrahydroquinoline-2-carboxylic acid in form of monohydrate I of formula (I-M-I)) in a certain particle size, suitable for inhalative application.

The particle size distribution for the active ingredient ((5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid, preferably (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid in form of monohydrate I of formula (I-M-I) or (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid in form of monohydrate II of formula (I-M-II)) particularly preferable (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid in form of monohydrate I of formula (I-M-I)) according to the invention is defined as in below table.

TABLE 1

| Particle size distribution of active ingredient, e.g. compound of formula (I-M-I) or (I-M-II) | |
|---|---|
| Particle size upper X90 | max. 6 µm |
| Particle size mean X50 | 1-3 µm |
| Particle size lower X10 | max. 1 µm |

For inhalative drug products it is important to guarantee a homogeneous drug substance with defined particle size <5 µm to secure delivery to the deep lung compartments. This technical requirement can be achieved by micronization of the drug substance particles (see experimental part B, ex. 8). Appropriate specifications for a particle size distribution of the active ingredient to achieve this requirement were set as specified in table 1.

Therefore in order to secure a suitable delivery of the active at the target site, esp. the deep airways and aeveoli the present inventors found that is essential to provide the active ingredient (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I, preferably (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid in form of monohydrate I of formula (I-M-I)) or in form of monohydrate II of formula (I-M-II)), preferably in form of monohydrate I of formula (I-M-I)) in a particle size of X90=6 µm and/or X50 1-3 µm and/or X10 max. 1 µm.

Lactose Carrier

Solid preparations according to the invention for dry powder inhalation generally contain an amount of a suitable carrier for the active compound which is not more than about 99.25%. Usually the amount of inhalation grade carrier is between 99.25% and 80%, preferably between 99.25% and 90%. The amount of carrier therein is usually at least 99.25%, or at least 97%, or at least 95% or at least 90% by weight based dry powder blend.

Different materials of inhalation grade carriers are principally available.

The present inventors found that the excellent aerosol performance of the formulations for inhalation according to the present invention is achieved by choosing lactose as carrier material.

Lactose for inhalation is available in different particle size ranges and different characteristics.

One would expect that a coarse lactose carrier alone with a particle size distribution centered at higher particle sizes compared to the active ingredient may lead to poor aerosol performance due to relatively strong binding of the fine drug particles to active sites of the coarse carrier particles (Paolo Colombo, Daniela Traini and Francesca Buttini "Inhalation Drug Delivery—Techniques and Products" (published by Wiley-Blackwell 2013). Advanced aerosol performance is characterized by increased fine particle dose and fraction as well as delivered dose with related to the nominal dose. This is expected by an equilibrium between drug to carrier adhesion and subsequent segregation once the powder is aerosolized, often also described as powder or drug dispersion. One may also expect that the aerosol performance behavior will improve with the addition of fine carrier particles or by use of lactose materials that contain intrinsic portions of lactose fines, although the extent cannot be predicted (de Boer et al 2012, Grasmejier et al 2015). As an expression of the improvement of drug dispersion and release from the carrier, measurements by cascade impactors are the established method of choice for fine particle dose (alternatively fine particle mass) as well as for fine particle fraction (percentage fraction of drug mass with a defined particle size upper limit, e.g. 5 µm or 4.5 µm in relation to the delivered dose or nominal dose of the single dosage unit). These methods are also established as mandatory quality control methods for inhalation products in current pharmacopoeia (e.g. Pharmacopoeia Europaea (Pharm Eur.) or United States Pharmacopoeia (USP).

However, the potential effect of addition of fine lactose and its magnitude cannot be predicted as there may be other major effects within the dry powder adhesive mixture that superimpose the lactose fines effect. Very importantly the properties of the micronized drug itself can have an impact on the adhesive and cohesive properties (e.g. cohesive: adhesive balance (CAB) or surface energy) of a binary or ternary mixture of particles of a specific drug molecule which makes a prediction even more difficult.

The present inventors found that the excellent aerosol performance of the formulations for inhalation according to the present invention is achieved by choosing fine lactose and coarse lactose as carrier material with specific particle sizes.

The coarse lactose material according to the present invention is a sieved or milled, crystalline, α-lactose monohydrate with low fine particle content (e.g. commercially available as Lactohale® 100 or Lactohale®206).

Coarse lactose according to the invention having a similar particle size distribution may also be selected from other brands e.g. Meggle Inhalac® 120 or DFE Respitose® SV010.

To select a primary coarse carrier, a lactose quality was selected that would have a particle size X90 larger by at least the factor of 10 compared to the X90 of the active ingredient and a low intrinsic fines content to allow for consistent quality of the major part of the carrier.

Fine lactose was selected to improve the aerosol performance. The present inventors assumed that a particle size similar to the active ingredient could be suitable to control the temporary binding of the active ingredient particles to the coarse carrier particles although other fine lactose particle size specifications were potentially also suitable. A selection of a fine lactose product with a particle size of X90<10 µm or X90<30 µm or X50≤5 µm or 1.0-3.0 µm was therefore regarded adequate to compose the lactose carrier.

The fine lactose material according to the present invention is a milled or micronized, crystalline, a-lactose monohydrate with a low particle size ("Lactose fines") of X90≤10 µm (e.g. commercially available as Lactohale® 300) or X90<30 µm or X50≤5 µm or 1.0-3.0 µm (e.g. commercially available as Lactohale® 230). Fine milled or micronized lactose with similar properties and particle size may also be selected e.g. Meggle Inhalac® 500. Particle size distribution of materials and powder mixtures are usually measured by laser diffraction spectroscopy, microscopic techniques or conventional sieve analysis and classification [B. Y. Shekunov, P. Chattopadhyay, H. H. Y. Tong and A. H. L. Chow, Particle size analysis in pharmaceutics, *Pharm. Res.* 2007, 24 (2), S203-S227] (see also D.4).

The particle size distributions for commercial available Lactose for inhalation qualities according to the invention (e.g. Lactohale® 100, Lactohale® 300) are summarized in below table 2.

TABLE 2

Particle size distribution (specifications) for lactose for inhalation according to the invention

| | Coarse lactose | Fine Lactose |
|---|---|---|
| Trade name | Lactohale ® 100 | Lactohale ® 300 |
| Particle size upper X90 | 200-250 µm | ≤10 µm |
| Particle size mean X50 | 125-145 µm | ≤5 µm |
| Particle size lower X10 | 45-65 µm | not defined |
| Trade name | Lactohale ® 200 | |
| Particle size upper X90 | 120-160 µm | |
| Particle size mean X50 | 50-100 µm | |
| Particle size lower X10 | 5-15 µm | |
| Trade name | Lactohale ® 206 | Lactohale ® 230 |
| Particle size upper X90 | 115-170 µm | <30 µm |
| Particle size mean X50 | 75-95 µm | <10 µm |
| Particle size lower X10 | 20-50 µm | 1.0-3.0 µm |

Solid preparations according to the invention for dry powder inhalation contain a mixture of coarse lactose The present inventors found out that the coarse lactose particle size can be varied over a certain range without jeopardizing the aerosol performance or the blend uniformity of the carrier based formulations according to the present invention.

According to the present invention the coarse lactose has a particle size of X90=200-250 µm or 120-160 µm or 115-170 µm, or 115-250 µm. Furthermore according to the present invention the coarse lactose has a particle size of X90≤250 µm or ≤170 µm or ≤160 µm. Furthermore according to the present invention the coarse lactose has a particle size of X90 being at least or ≥115 µm or being at least or 120 µm or being at least or ≥200 µm.

According to the present invention the coarse lactose has a particle size of X50=125-145 µm or 50-100 µm or 75-95 µm or 50-145 µm. Furthermore according to the present invention the coarse lactose has a particle size of X50≤145 µm or ≤100 µm or ≤95 µm. Furthermore according to the present invention the coarse lactose has a particle size of X50 being at least or ≥50 µm or being at least or ≥75 µm or being at least or ≥125 µm and/or X10=45-65 µm or 5-15 µm or 20-50 µm.

According to the present invention the fine lactose has a particle size of X90=≤10 µm or <30 µm, X50≤5 µm or 1.0-3.0 µm. By utilizing the Lactohale200® with an inherent content of fine particles there is no need to add any further fine lactose particles to the lactose carrier. Therefore the present carrier based formulation may be formulated with Lactohale 200® or similar Lactose product with intrinsic lactose fines content.

According to the present invention, Lactohale 100® and Lactohale 300® are preferred.

Furthermore the present inventors found that the excellent aerosol performance of the formulations for inhalation according to the present invention is achieved by adjusting a specific content of fine lactose and a specific content of coarse lactose within the dry powder blend.

The present inventors identified the fine lactose content of the lactose carrier as an important parameter. In order to obtain the formulations for inhalation according to the present invention characterized by an excellent aerosol performance the content of fine lactose should be selected within a certain range. For example a higher content of fine lactose in the powder blend/lactose carrier, e.g. a content of 20% or more was found to have a negative impact on the blend uniformity (see e.g. comparative example 20). It was shown that the powder blends and formulations according to the present invention can have a varying content of fine lactose within a range of between 1% and 10%, also between 5% and 10% whereas the fine lactose content may also be an intrinsic part of the lactose for inhalation, i.e. calculated as an X10 of 5-15 µm as in the case of Lactohale 2000® (see emb. 34) without jeopardizing the aerosol performance.

According to the present invention the content of fine lactose in the powder blend is between 1% and 10%, preferably between 5% and 10%, preferably between 2.5% and 7.5%, preferably between 5% and 7.5%, more preferably 5%.

The present inventors identified the coarse lactose content of the powder blend also as an important parameter. In order to obtain the formulations for inhalation according to the present invention characterized by an excellent aerosol performance the content of coarse lactose should be selected within a certain range.

According to the present invention the content of coarse lactose in the powder blend is between 98.25% and 75%, preferably between 94.25% and 75%, preferably between 92.00% and 75%, more preferably from 90.00% to 75% and especially preferably from 90% to 85%.

As the dry powder blend according to the present invention is a ternary mixture all three components need to be provided in form of defined maximum particle sizes and in certain specific ratios.

The present inventors found that the excellent aerosol performance of the formulations for inhalation according to the present invention is achieved by choosing a specific ratio of fine lactose and coarse lactose and active ingredient.

According to the present invention the ratio of the coarse lactose to fine lactose in the powder blend is between 445:5 and 65:5, preferably 94.25:5 and 65:5, preferably 94.25:5 and 75:5, 91.75:7.5 and 89.25:10, preferably between 92:5 and 75:5, particular preferred are ratios of 92:5, 85:5 as well as 75:5.

According to the present invention the ratio of the active ingredient of formula (I) or (I-M-I) to Coarse Lactose in the powder blend is between 1:126 and 1:3.8., preferably between 1:31 and 1:3.8.

According to the present invention the ratio of the active ingredient of formula (I) or (I-M-I) to Fine Lactose in the powder blend is from 1:13 and 1:0.1, preferably between 1:13 and 1:0.25, preferably between 1:1.67 and 1:0.25.

Further Excipients

The preparations according to the invention can generally contain further pharmacologically acceptable excipients, including, inter alia, carriers (e.g. inhalation grade lactose, lactose monohydrate, mannitol), dispersants, wetting agents, lubricants (e.g. magnesium stearate), surface active compounds (e.g. sodium lauryl sulfate, Disteaorylphosphatidycholine), ionic compounds (e.g. calcium chloride, sodium chloride, potassium chloride), synthetic and natural polymers (for example carrageenan, hydroxypropylmethylcellulose, gelatine) or pH modifiers (e.g. sodium hydroxide, sodium chloride, citric acid salts Trisodium citrate) colorants (e.g. inorganic pigments such as, for example, iron or titanium oxides).

Cavity

According to the present invention the dry powder blend comprising the active ingredient in form of its monohydrate forms I-M-I or I-M-II and lactose can be administered via dry powder inhalers such as single-unit dose inhalers in which each dose is loaded into the device before use, multi-unit dose inhalers in which several single doses are individually sealed (pre-metered) and can be discharged in a dosing chamber prior to each actuation or reservoir multi-unit dose inhalers in which a bulk supply of drug is pre-loaded into the device and discharged (metered by device) in a dosing chamber prior to each actuation. Preferably the dry powder blend according to the present invention is administered via a single-unit dose inhaler which is equipped/loaded with cavities, such as capsules or blisters comprising the dry powder blend. Preferably the cavities are individual capsules, preferably hard capsules of gelatin or of hydroxypropylmethylcellulose, most preferably hydroxypropylmethylcellulose capsules.

The dry powder blends comprising the active ingredient, e.g. the monohydrate I of formula (I-M-I) or the monohydrate II of formula (I-M-II), according to examples 2 or 4, micronized are filled into hard capsules (hydroxypropylmethylcellulose=Hypromellose=HPMC, e.g. in size 3) or alternative capsules from hard gelatine or other suitable materials. Pharmaceutical hard capsule sizes are standardized and characterized by defined measures, where e.g. a size 3 capsule has a length of 157 mm a and a diameter of 57 mm, whereas a size 2 capsule has a length of 176 mm and a diameter of 62 mm and a size 1 capsule has a length of 194 mm and a diameter of 68 mm.

Depending on the fill weight and active ingredient concentration different nominal dose can be achieved. Exemplary compositions for capsules with different nominal doses of active ingredient, e.g. the monohydrate I of formula (I-M-I) or the monohydrate II of formula (I-M-II), according to examples 2 or 4, are given in exemplary embodiments 1-3 and are displayed in below table 3

TABLE 3 examples of formulations according to the present invention with defined nominal dose (filled powder in hard capsules).

|  | Exemplary Embodiment 1 | Exemplary Embodiment 2 | Exemplary Embodiment 3 |
|---|---|---|---|
| Nominal dose | 120 µg | 480 µg | 1000 µg |
| concentration of active ingredient (example 4) in powder blend | 0.75% | 3% | 10% |
| Fill weight | 16 mg | 16 mg | 10 mg |

On intrapulmonary administration, the amount of active ingredient (nominal dose), (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid, preferably (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I (see example 4) is about 10 µg to 50000 µg per inhalation, preferably about 100 µg to 10000 µg per inhalation, further preferably about 100 to 6000 µg per inhalation, further preferably about 120 to 4000 µg per inhalation, further preferably about 200 to 4000 µg per inhalation, very particularly preferably about 240 µg to 4000 µg, very particularly preferably about 240 µg to 2000 µg, very particularly preferably about 240 µg to 1000 µg, very particularly preferably about 240 µg to 480 µg, very particularly preferably about 480 µg to 4000 µg, very particularly preferably about 480 µg to 2000 µg, very particularly preferably about 480 µg to 1000 µg, very particularly preferably about 1000 µg to 4000 µg, very particularly preferably about 1000 mg to 2000 µg, very particularly preferably about 1000 µg, very particularly preferably about 2000 µg, very particularly preferably about 4000 µg.

The cavity, preferably a hard capsule, very preferably a HMPC based hard capsule, size 3 according to the present invention contains a filled mass of 8-40 mg of the formulation for inhalation, preferably a filled mass of 10-30 mg of the formulation for inhalation, more preferably a filled mass of 10-20 mg of the formulation for inhalation, more preferably a filled mass of 16-20 mg of the formulation for inhalation.

According to the present invention, mostly preferred are the following compositions:

TABLE 4 final capsule formulations according to the present invention comprising dry powder blends, percentage based

| Nominal dose | Capsule, e.g. HMPC | Powder Fill mass | API content (%) in powder blend | Coarse Lactose content (%) | Fine Lactose content (%) | Ratio API:Coarse Lactose | Ratio API:Fine Lactose |
|---|---|---|---|---|---|---|---|
| 480 µg | Size 3 | 16 mg | 3% | 92% | 5% | 1:31 | 1:1.67 |
| 1000 µg | Size 3 | 10 mg | 10% | 89% | 1% | 1:8.9 | 1:0.1 |
| 1000 µg | Size 3 | 10 mg | 10% | 87.5% | 2.5% | 1.8.75 | 1:0.25 |
| 1000 µg | Size 3 | 10 mg | 10% | 85% | 5% | 1:8.5 | 1:0.5 |
| 2000 µg | Size 3 | 20 mg | 10% | 85% | 5% | 1:8.5 | 1:0.5 |
| 3000 µg | Size 3 | 30 mg | 10% | 85% | 5% | 1:8.5 | 1:0.5 |
| 4000 µg | Size 3 | 40 mg | 10% | 85% | 5% | 1:8.5 | 1:0.5 |
| 2000 µg | Size 3 | 10 mg | 20% | 75% | 5% | 1:3.8 | 1:0.25 |
| 3000 µg | Size 3 | 15 mg | 20% | 75% | 5% | 1:3.8 | 1:0.25 |
| 4000 µg | Size 3 | 20 mg | 20% | 75% | 5% | 1:3.8 | 1:0.25 |

According to the present invention a powder blend with a content of 3% active ingredient of formula (I) or (I-M-I) in the powder blend comprises 480 µg active ingredient of formula (I) or (I-M-I), 92% coarse lactose and 5% fine lactose and might be filled as a mass of 16 mg powder blend in a hard capsule, preferably a HMPC capsule of size 3 and which might then be administered via a "single unit dose" Inhaler, e.g. preferable Plastiape (Berry) RS01 low resistance device.

According to the present invention a powder blend with a content of 10% active ingredient of formula (I) or (I-M-I) in the powder blend comprises 1000 μg, 2000 μg, 3000 μg or 4000 μg active ingredient of formula (I) or (I-M-I), 85% coarse lactose and 5% fine lactose and might be filled (as a corresponding mass of 10 mg, 20 mg, 30 mg or 40 mg powder blend) in a hard capsule, preferably a HMPC capsule of size 3 and which might then be administered via a "single unit dose" Inhaler, e.g. preferable Plastiape (Berry) RS01 low resistance device.

According to the present invention a powder blend with a content of 20% active ingredient of formula (I) or (I-M-I) in the powder blend comprises 2000 μg, 3000 μg or 4000 μg active ingredient of formula (I) or (I-M-I), 75% coarse lactose and 5% fine lactose and might be filled (as a corresponding mass of 10 mg, 15 mg or 20 mg powder blend) in a hard capsule, preferably a HMPC capsule of size 3 and which might then be administered via a "single unit dose" Inhaler, e.g. preferable Plastiape (Berry) RS01 low resistance device.

TABLE 5 final capsule formulations according to the present invention comprising dry powder blends, mass based characterization:

| Nominal dose | Capsule | Powder Fill mass | API content (mg/g) in powder blend | Coarse Lactose content (mg) | Fine Lactose content (mg) | Ratio API:Coarse Lactose | Ratio API:Fine Lactose |
|---|---|---|---|---|---|---|---|
| 480 μg | Size 3 | 16 mg | 30 mg/g | 14.72 mg | 0.8 mg | 1:31 | 1:1.67 |
| 1000 μg | Size 3 | 10 mg | 100 mg/g | 8.9 mg | 0.1 mg | 1:8.9 | 1:0.1 |
| 1000 μg | Size 3 | 10 mg | 100 mg/g | 8.75 mg | 0.25 mg | 1.8.75 | 1:0.25 |
| 1000 μg | Size 3 | 10 mg | 100 mg/g | 8.5 mg | 0.5 mg | 1:8.5 | 1:0.5 |
| 2000 μg | Size 3 | 20 mg | 100 mg/g | 17.0 mg | 1.0 mg | 1:8.5 | 1:0.5 |
| 3000 μg | Size 3 | 30 mg | 100 mg/g | 25.5 mg | 1.5 mg | 1:8.5 | 1:0.5 |
| 4000 μg | Size 3 | 40 mg | 100 mg/g | 34.0 mg | 2.0 mg | 1:8.5 | 1:0.5 |
| 2000 μg | Size 3 | 10 mg | 200 mg/g | 7.5 mg | 0.5 mg | 1:3.8 | 1:0.25 |
| 3000 μg | Size 3 | 15 mg | 200 mg/g | 11.25 mg | 0.75 mg | 1:3.8 | 1:0.25 |
| 4000 μg | Size 3 | 20 mg | 200 mg/g | 15.0 mg | 1.0 mg | 1:3.8 | 1:0.25 |

According to the present invention a powder blend with a content of 30 mg/g active ingredient of formula (I) or (I-M-I) in the powder blend comprises 480 μg active ingredient of formula (I) or (I-M-I), 14.72 mg coarse lactose and 0.8 mg fine lactose and might be filled as a mass of 16 mg powder blend in a hard capsule, preferably a HMPC capsule of size 3 and which might then be administered via a "single unit dose" Inhaler, e.g. preferable Plastiape (Berry) RS01 low resistance device.

According to the present invention a powder blend with a content of 100 mg/g active ingredient of formula (I) or (I-M-I) in the powder blend comprises 1000 μg, 2000 μg, 3000 μg or 4000 μg active ingredient of formula (I) or (I-M-I), 8.9 mg, 8.75 mg, 8.5 mg, 17.0 mg, 25.5 mg or 34.0 mg coarse lactose and 0.1 mg, 0.25 mg, 0.5 mg, 1.0 mg, 1.5 mg or 2.0 mg fine lactose and might be filled (as a corresponding mass of 10 mg, 20 mg, 30 mg or 40 mg powder blend) in a hard capsule, preferably a HMPC capsule of size 3 and which might then be administered via a "single unit dose" Inhaler, e.g. preferable Plastiape (Berry) RS01 low resistance device.

According to the present invention a powder blend with a content of 200 mg/g active ingredient of formula (I) or (I-M-I) in the powder blend comprises 2000 μg, 3000 μg or 4000 μg active ingredient of formula (I) or (I-M-I), 7.5 mg, 11.25 mg or 15.0 mg coarse lactose and 0.5 mg, 0.75 mg or 1.0 mg fine lactose and might be filled (as a corresponding mass of 10 mg, 15 mg or 20 mg powder blend) in a hard capsule, preferably a HMPC capsule of size 3 and which might then be administered via a "single unit dose" Inhaler, e.g. preferable Plastiape (Berry) RS01 low resistance device.

Manufacturing Process

The preparations according to the invention can generally be produced—as is usual in the production of inhalable free-flowing medicaments in powder form, by micronizing the active ingredient and optionally blending the micronized active ingredient with inactive carrier compounds.

The compounds according to the invention can be converted into the stated administration forms. This can take place in a manner known per se by mixing with inert, non-toxic, pharmaceutically suitable excipients. The dry powder formulation and finished products (dry powder blend filled hard capsules) are manufactured according to FIG. 66 and the below description.

Step 1:

The fine lactose portion was weighed and layered in between two layers of coarse lactose prior to start of mixing.

Step 2:

Mixing of the lactose pre-blend was performed in a tumble mixer 2 times (2 cycles) at 72 rpm, 67 rpm or 34 rpm or 32 rpm or 30 rpm, preferably 32 rpm for 20 min. The lactose pre-blend was sieved through a 500 μg sieve between the cycles.

Step 3:

active ingredient: monohydrate I or II, example 2 or 4, micronized was sieved through a 500 μm sieve and added to the pre-blended lactose. Prior to start of mixing cycles, the lactose pre-blend and active ingredient were layered alternating with 6 layers of lactose pre-blend and 5 layers of active ingredient (monohydrate I or II, example 2 or 4) in between.

Step 4:

The components were mixed in cycles, e.g. 3-5 cycles, preferably 3 cycles in a tumble mixer, e.g. glass or stainless steel, preferably stainless steel. Each cycle was conducted at 72 rpm, 67 rpm, 34 rpm or 32 rpm preferably 32 rpm for 20-30 minutes, preferably 30 minutes (90 min overall mixing time), preferably 32 rpm for 30 minutes with a rest time of 10 minutes between the mixing cycles. If necessary (e.g. visual agglomerates) the blend maybe sieved between blending cycles, respectively.

Step 5:

The blend was left to rest at room temperature (15-25° C.) and 35-65% relative humidity in a stainless steel container for a certain period of time, preferably 24-72 hours, more preferably 48 h.

Step 6:

Using a capsule filling machine (e.g. MG2 Flexalab) the blend was filled into capsules at the desired fill weight.

Inhaler Device

In the context of the present invention the sGC activator, e.g. example 2 or 4 is applied as dry powder or dry powder formulation by means of a dry powder Inhaler device.

The preferred dry powder Inhaler device within the context of the present invention is defined as a capsule based single-unit dose inhaler which is a pre-metered inhalation device (see FIGS. 1a and 1b). In the context of the present invention doses were applied using the Plastiape (Berry) RS01 low resistance device. This device (in a higher resistance type) is disclosed and described in publications (ELKINS et al. Inspiratory Flows and Volumes in Subjects with Cystic Fibrosis Using a New Dry Powder Inhaler Device, The Open Respiratory Medicine Journal, 2014, 8, 1-7 and ELKINS et al. Inspiratory Flows and Volumes in Subjects with Non-CF Bronchiectasis Using a New Dry Powder Inhaler Device, The Open Respiratory Medicine Journal, 2014, 8, 8-13) relating to treatment of other patient populations, e.g. cystic fibrosis (CF) or non-CF bronchiectasis.

The inhaler is operated by inserting a single capsule filled with the dry powder formulation into the device. Two buttons (pushbuttons) are pressed to puncture the capsule and the user places his/her mouth around the mouthpiece and inhales deeply and forcefully. The energy from the inhalation pulls the drug preparation out of the capsule, disperses the powder as an aerosol, the active ingredient particles are released from the lactose carrier particles and carried it into the respiratory tract. The used capsule is removed and discarded. The device may be reused depending upon the patient's therapy requirements and corresponding labeling of the clinical devices. The number of capsules administered determines the dose of medication.

Other pre-metered dry powder inhalation devices such as blister strip based multi-unit dose devices may also be used for the preferred method of application and may lead to comparable results if the aerosol path has similar design or properties (e.g. device resistance and pressure drop at defined flow rates).

In the context of the invention there are also disclosed devices which contain preparations containing example 1 or can have a receptacle to incorporate these preparations in a capsule or blister and which are suitable for the administration by inhalation thereof in solid form, i.e. aerosolizers which are able to administer preparations containing active ingredient: e.g. monohydrate I or II, example 2 or 4, by inhalation in solid form (powder inhalers).

Human Dose Estimation

The formulation according to the invention can be characterized regarding delivered dose (DD), determined by filter collection tube method and fine particle dose (FPD) determined by cascade impaction. The analytical methods to determine delivered dose and fine particle dose are generally described in Pharmacopoeia as these are harmonized for inhalable dosage forms e.g. dry powder inhalation formulations and constitute conventions for quality control for e.g. release of DPI products for clinical use.

It has been discovered that different formulations with different nominal doses lead to a different delivered dose and, more importantly, to a certain fine particle dose that characterize the effective dose as this is being delivered into the deep lung to the site of action. In theory the delivered dose and fine particle dose and fraction would have a linear relationship in correlation to the filled powder dose, but due to several interacting factors this cannot be predicted reliably, may practically differ and requires associated studies. It is desirable that a delivered dose is as close to the nominal dose as possible. In practice, the delivered dose will never match the nominal by 100% as residuals are always left to some degree on surfaces of inhalation capsules and on the aerosol path of the used dry powder inhaler. Of course, this property is highly depending on the physicochemical properties of the active ingredient and its release behavior from the powder blend. Analogously the fine particle dose and fine particle fraction are desired to be as high as possible in relation to filled nominal active ingredient content to exploit the available drug amount as good as possible and to reduce loss of active ingredient or to decrease portions delivered to other compartments than the deep lung (e.g. by swallowing via oral impact of larger drug particles).

Due to the nature of inhalable formulations and in contrast to e.g. oral solid formulations not all of the nominal content will be delivered into the lung. Several fractions can be defined that are characterized by specific analytical methods in-vitro and support the estimation of dose fractions delivered to the patient during inhalation (delivered dose or emitted dose) and the fraction of fine particles below e.g. 5 µm or 4.5 µm (size cutoff in µm is depending on definition of FPD) as that is expected to reach the deep airways and alveoli (fine particle dose). For an overview refer to the table below.

TABLE 7

Definition of terms with respect to dosages of inhalative drug products

| Terminology | Abbreviation | Definition | Synonyms or equivalent terms |
|---|---|---|---|
| Nominal Dose | ND | Total dose of API filled in the capsule (clinical studies) or nebulizer (pharmacological animal experiments). | Capsule dose, Capsule strength, Quantity of drug substance labeled on the capsule. |
| Emitted Dose | ED | Dose that actually leaves the device at the mouthpiece under defined laboratory test conditions. | Corresponds to the delivered dose |
| Delivered Dose | DD | Dose that is estimated or calculated to be inhaled by the animal (from the tip of the nose/mouth up to the alveoli) or quantity of drug substance that is available to the human, ex-device, on a per dose basis. | Corresponds to the emitted dose |

TABLE 7-continued

Definition of terms with respect to dosages of inhalative drug products

| Terminology | Abbreviation | Definition | Synonyms or equivalent terms |
|---|---|---|---|
| Lung Deposited Dose | LDD/LD | Dose that is considered to reach the lung (tracheobronchial and pulmonary deposition) of the respective animal or human. | It is considered that the FPD (measured in-vitro) is corresponding to the lung deposited dose in humans. |
| Fine Particle Dose | FPD | Parameter calculated from the aerodynamic particle size distribution (ASPD) function determined by in-vitro cascade impaction analysis The mass of active pharmaceutical ingredient (API) per actuation or dose delivery of the inhaler contained in particles finer than 4.5-5 µm aerodynamic diameter (e.g. according to European Pharmacopoeia). | For DPI, it is assumed that the FPD is basically equivalent to the human lung deposited dose |
| Fine Particle Fraction | FPF | The fraction of fine particle mass according to FPD related to the ED/DD or to the nominal dose (in %) | |

Evaluation of Pharmacokinetic/Pharmacodynamic (PK/PD) Relationship

The anesthetized thromboxane A2 challenged PAH-minipig model (see experimental part E-1) is considered to be the most relevant and sensitive model for the prediction of the human minimal effective and effective doses (MED, ED). To determine effective LDs, experiments were repeated with the difference that absorbing filters were attached at the end of the tubes to determine the deposited lung dose. Nebulization of example 1 resulted in a mean nebulization efficiency of 5% of nominally applied doses resulting in LDs of about 0.15 µg/kg (3 µg/kg ND), 0.5 µg/kg (10 µg/kg ND), 1.5 µg/kg (30 µg/kg ND) and 5 µg/kg (100 µg/kg ND). Assuming a minimal effective ND of 3 µg/kg (5% reduction in PAP) the minimal effective deposited LD is considered as 0.15 µg/kg.

The nominal doses of 3, 10, 30 and 100 µg/kg of the minipig model were multiplied by the filter deposition factor of 5% resulting in 0.15, 0.5, 1.5 and 5 µg/kg lung deposited doses in the minipig. These values were multiplied by 60 kg to achieve the lung dose in humans. Thus, the FPD reflecting the PAP reduction for a 60 kg human are calculated to be 9, 30, 90 and 300 µg.

Thus, via a direct up-scaling from minipig, the predictive MED (5% PAP reduction) for a human based on a 60 kg body weight is calculated to be 9 µg LDD, not considering protein binding within the respiratory tract. As a surrogate for unbound concentrations, which are the likely active concentrations in the lung, we considered respective differences in fractions unbound in plasma of minipig and human. This consideration results in a minimum effective lung dose (LD) for a 60 kg participant of 41 µg LDD for the assumed 5% reduction on PAP. Consequently, the predictive minimal human effective dose is in the range from 9 µg LDD to 41 µg LDD based on a 60 kg body weight (see FIG. 3).

TABLE 8

Effective lung dose with and without consideration of interspecies differences in protein binding

| | Total lung deposited dose in a 60 kg human [µg] | |
|---|---|---|
| Relative lung deposited dose in minipig [µg/kg] | Interspecies difference in protein binding not considereda | Interspecies difference in protein binding consideredb |
| 0.15 µg/kg (3 µg/kg nominal dose) | 9 | 41 |
| 0.50 µg/kg (10 µg/kg nominal dose) | 30 | 137 |
| 1.5 µg/kg (30 µg/kg nominal dose) | 90 | 410 |
| 5.0 µg/kg (100 µg/kg nominal dose) | 300 | 1370 | aCalculation (relative lung deposited dose in minipig x 60 kg)
bCalculation (relative lung deposited dose in minipig x 60 kg x 4.55 (ratio of fraction unbound minipig (plasma fu 0.348%)/ human (plasma fu 0.0764%))

This translation was also conducted for effective doses (effective PAP reduction >five up to 35 percent for longer time periods up to the complete observation period of 4 hrs) based on the relative lung deposited doses in minipigs as listed in Table 8.

Thus, effective lung deposited doses in humans based on the minipig data were expected in the range of 9 µg to 1370 µg.

Considering 100 µg/kg as highest effective dose in the minipig model without systemic side effects (BP reduction), with a corresponding maximal effective human LDD of 1370 µg, 9-1370 µg lung deposited dose is postulated as effective doses, depending on different interspecies protein binding (see table 7). For DPI products, it is assumed that the fine particle dose (FPD) is basically equivalent to the human lung deposited dose.

To address the need for a wide range of lung deposited doses and translate them into technical specifications for fine particle dose (FPD targets) of the dry powder inhalation capsules to be manufactured, some calculations and approximations were done. Generally, an inhalable product based on a powder blend carrier formulation is considered to have an excellent performance if a fine particle fraction of greater than 20% of the nominal dose is achieved. Further, a high FPF(%) related to the delivered dose is desired for a high performance inhalation product and was targeted at ≥30%. Taking technical and practical considerations into account (active concentration in powder blend and capsule fill mass of the blends) the FPD targets were subsequently used to establish defined nominal doses for the finished dry powder inhalation capsules. FPD and DD targets as well as corresponding nominal doses are outlined in the following two tables 9 and 10.

TABLE 9

Nominal dose targets and targets for fine particle dose and % fraction (ds)

| Capsule nominal dose [µg] | Mean FPF (FPD % of nominal) | Mean FPF (FPD % of DD) | Mean FPD <4.5 µm (targeta) [µg] | Min FPD <4.5 µm (65% of targetb) [µg] |
|---|---|---|---|---|
| 60 | ≥20% | ≥30% | 12 | 8 |
| 75 | ≥20% | ≥30% | 15 | 10 |
| 120 | ≥20% | ≥30% | 24 | 16 |
| 480 | ≥20% | ≥30% | 96 | 62 |
| 500 | ≥20% | ≥30% | 100 | 65 |
| 1000 | ≥20% | ≥30% | 200 | 130 |
| 2000 | ≥20% | ≥30% | 400 | 260 |
| 3000 | ≥20% | ≥30% | 600 | 390 |
| 6000 | ≥20% | ≥30% | 1200 | 780 |
| 9000 | ≥20% | ≥30% | 1800 | 1170 | a)target value calculated from FPF % of nominal target
b)minimum targets were established due to expected variability in manufacturing and analytical determinations.

For the relation between delivered and nominal dose there is no general binding (e.g. compendial) requirement as this cannot be defined due to the very different nature of different active ingredients, having different properties and the manufactured pharmaceutical formulations thereof. Rather the uniformity of delivered dose is defined by pharmacopoeia to assure dose-to-dose consistency. The target delivered dose is an empirical parameter resulting from multiple determinations of a defined dosage form with a defined dry powder inhalation device under standardized conditions. The expected mean delivered dose should fall within 85-115% of the target DD. The minimum delivered dose requirement accounts for the 85% lower limit of the mean delivered dose range. A target delivered dose percentage (from ≥50% to ≥65% of nominal) was defined for all nominal doses which is not linear and needs to take into consideration the relatively higher content of active ingredient adhesion on e.g. capsule and device surfaces specifically with lower nominal filled doses.

TABLE 10

Nominal doses, DD targets and related min delivered dose

| Capsule nominal dose [µg] | Mean DD (% of nominal) | Mean DD (targetA) [µg] | Min DD (85% of target) [µg] |
|---|---|---|---|
| 60 | ≥50% | 30 | 26 |
| 75 | ≥50% | 38 | 32 |
| 120 | ≥60% | 72 | 61 |
| 480 | ≥60% | 288 | 245 |
| 500 | ≥60% | 300 | 255 |
| 1000 | ≥65% | 650 | 553 |

TABLE 10-continued

Nominal doses, DD targets and related min delivered dose

| Capsule nominal dose [µg] | Mean DD (% of nominal) | Mean DD (targetA) [µg] | Min DD (85% of target) [µg] |
|---|---|---|---|
| 2000 | ≥65% | 1300 | 1105 |
| 3000 | ≥65% | 1950 | 1658 |
| 6000 | ≥65% | 3900 | 3315 |
| 9000 | ≥65% | 5850 | 4973 |

Surprisingly preclinical experiments revealed for the sGC activator (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I as well as its pseudopolymorphic forms, like e.g. (I-M-I) and (I-M-II) (see E-1) an improved lung selectivity and extended duration of action (prolonged selective pulmonary arterial pressure (=PAP) reduction without systemic blood pressure (=BP) reducing effects after inhaled application) in PAH animal models (see experimental part E-1). Furthermore the prediction of duration of action and prediction of human dose has been investigated. Considering 100 µg/kg as effective dose in the minipig model, 300-1370 µg lung deposited dose is postulated as effective dose, depending on the consideration of different interspecies protein binding.

Finally the pharmacological effects of different pseudopolymorphic forms of the active ingredients have been investigated. All dry powder formulations comprising crystalline forms of comp. example 11, e.g. sesquihydrate example 6e selectively and dose-dependently reduced PAP after inhaled application in this model of acute PAH with a long duration of action of at least 4 h. A clear dose-response curve was observed for increasing applied doses (see E-1).

Furthermore we found for the sGC activator (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid especially in the form of its monohydrate II (example 2) in first clinical studies (see experimental part E-2.1) increased cGMP levels as second messenger molecule of sGC activation as surrogate for drug concentration in the lung (indicative of target engagement) as well as beneficial bronchodilatory properties in healthy volunteers over a time period of more than 12 hrs, up to 24 hrs after dry powder application, e.g. a decrease of total specific airway resistance (sRaw), a parameter indicating bronchodilative activity in the lung, supporting the long lung retention time clinically as well as the suitability of (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid especially in the form of its monohydrate II (example 2) to be successfully used in the treatment of cardiopulmonary diseases. Up to a dose of 4000 µg no clinically meaningful effect on systemic blood pressure were observed in healthy volunteers.

Moreover, we found a selective decrease in pulmonary arterial pressure and pulmonary vascular resistance in patients with pulmonary hypertension without clinically relevant effects on systemic blood pressure at doses up to 4000 µg (including). The effect was sustained with no decrease in response until the end of the measurement period of 3 h (a measurement period of >3 h was technically not feasible). A lung retention time beyond the 3 h of measurement (presumably over a time period of more than 12 hrs, up to 24 hrs after dry powder application) can be concluded from the long plasma half-life of example 4 measured in this study (see experimental part E-2.4).

Additionally the analysis of plasma concentrations after oral, intravenous and inhalative administration of the drug substance (example 4) showed the longest half-life of the active ingredient after inhaled application (E-2.3). The emitted (lung) dose has been determined to be 720 μg after inhalation of 1000 μg in humans. The outcome from this investigation confirms the lung dose and that the half-life is adequate for an inhaled dry powder administration enabling a once daily treatment for a sufficient 24 h drug coverage of example 4 in the lung.

In conclusion all results show that (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I as well as its pseudopolymorphic forms, like e.g. (I-M-I) and (I-M-II), especially the monohydrate I of formula (I-M-I) are suitable in particular for the treatment of pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP) and are adequate for an inhaled dry powder administration enabling a once daily treatment for a sufficient 24 h drug coverage of example 4 in the lung.

Additionally we found that (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid especially in the form of its monohydrate I (example 4) has beneficial physicochemical properties e.g. protein binding and CACO flux (see experimental part E-3.1 (Caco permeability) and E-3.2 (protein binding) which make (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid especially in the form of its monohydrate I (example 4) a suitable compound for local treatment of cardiopulmonary diseases by dry powder inhalation to the lung. Moreover, our data indicate that (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid especially in the form of its monohydrate I (example 4) (I-M-I) not only shows effective reduction of the PAP via selective vasodilation in the lungs but also showed longer lasting bronchodilatory properties compared to cinaciguat which may be beneficial in the once or twice daily inhalative treatment of PH patients with chronic lung diseases (PH group 3) or even have a potential in the treatment of patients with restricted lung function, e.g. asthmatics.

Therefore the drug substance, e.g. (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula (I), as well as its pseudopolymorphic forms (I-M-I) and (I-M-II) according to the present invention have excellent primary pharmacological properties:

(5S)—{[2-(4-carboxyphenyl)ethyl][2-(2-{[3-chloro-4'-(trifluoromethyl)biphenyl-4-yl]methoxy}-phenyl)ethyl]-amino}-5,6,7,8-tetrahydroquinoline-2-carboxylic acid is a potent and selective sGC activator and provides a new approach in the treatment of PH after inhalation.

(5S)—{[2-(4-carboxyphenyl)ethyl][2-(2-{[3-chloro-4'-(trifluoromethyl)biphenyl-4-yl]methoxy}-phenyl)ethyl]-amino}-5,6,7,8-tetrahydroquinoline-2-carboxylic acid selectively decreased elevated PAP after inhaled application in different disease relevant animal models (thromboxane and hypoxia challenged rats, pigs, and dogs) with a long duration of action, suggesting a twice daily application.

In an unilateral ventilated minipig model as a proxy of VQ-mismatch, (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid after inhaled application, lowered PAP without negative effects on oxygenation in contrast to systemic applied vasodilators.

On top of PAH standard-of-care (SoC) (e.g. bosentan, sildenafil, Ilomedin, and riociguat), (5S)—{[2-(4-carboxyphenyl)ethyl][2-(2-{[3-chloro-4'-(trifluoromethyl)biphenyl-4-yl]methoxy}phenyl)-ethyl]-amino}-5,6,7,8-tetrahydroquinoline-2-carboxylic acid selectively decreased elevated PAP after inhaled application in the PAH-minipig model.

The efficacy of (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid was enhanced under experimental conditions of oxidative stress (1H-[1,2,4]Oxadiazolo[4,3-a]quinoxalin-1-one, a highly selective, irreversible, heme-site inhibitor of soluble guanylyl cyclase [ODQ], L-Nω-Nitroarginine methyl ester [L-NAME] treatment).

With respect to ventilation, (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid showed a bronchodilatory effect (acetylcholine [ACh] rat model) and an inhibitory effect on airway hyper-responsiveness and inflammation (chronic ovalbumin asthma mice model).

Plasma concentrations of (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid especially in the form of its monohydrate I (example 4) were measured after three different types of administrations (oral, intravenous, inhalation) and revealed the longest elimination half-life after inhaled application.

The emitted (lung) dose has been determined to be 720 μg after inhalation of 1000 μg in humans.

First studies in humans with the sGC activator (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid in form of its crystalline form monohydrate I of formula (I-M-I) (example 4) showed sGC activation and long lung retention time combined with bronchodilatory properties and selective decrease of pulmonary arterial pressure and pulmonary vascular resistance at a good local and systemic tolerability up to the highest tested dose of 4000 μg (including).

Therefore the drug substance, e.g. (5S)—{[2-(4-carboxyphenyl)ethyl][2-(2-{[3-chloro-4'(trifluoromethyl)biphenyl-4-yl]methoxy}phenyl)ethyl]-amino}-5,6,7,8-tetrahydroquinoline-2-carboxylic acid of formula (I), as well as its pseudopolymorphic forms (I-M-I) and (I-M-II) according to the present invention has excellent primary pharmacological and pharmacodynamic properties in patients including reduction of pulmonary artery pressure (mPAP) and pulmonary vascular resistance (PVR), bronchodilation as measured by e.g. FEV1, pulmonary selectivity with low to no systemic adverse effects (especially on systemic hemodynamics, such as clinically relevant changes in blood pressure or heart rate) and low to no increase of VQ-mismatch to avoid relevant desaturation, furthermore sufficient lung retention time and/or sufficient duration of action following intrapulmonary administration.

Therefore the pharmaceutical dry powder formulations according to the present invention are suitable medicaments for treatment of cardiopulmonary disorders, such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

The weight data in the tests and examples which follow are, unless stated otherwise, percentages by weight; parts are parts by weight. Solvent ratios, dilution ratios and concentration data of liquid/liquid solutions are based on each case on the volume.

Specific Embodiments of the Invention
(Pseudopolymorphic Forms)

Monohydrate I

1. A compound that is (5S)—{[2-(4-carboxyphenyl)ethyl] [2-(2-{[3-chloro-4'-(trifluoromethyl)biphenyl-4-yl] methoxy}phenyl)ethyl]amino}-5,6,7,8-tetrahydroquinoline-2-carboxylic acid in crystalline modification monohydrate I of the formula (I-M-I)

(I-M-I)

wherein the X-ray powder diffractogram (measured at 25° C. and with Cu—K alpha 1 as radiation source) of the compound comprises peaks at least at 12.8 and 29.2, or at least at 6.9, 7.2, 7.3, 12.8 and 29.2 at diffraction angle 2Θ value±0.2°.

2. A compound that is (5S)—{[2-(4-carboxyphenyl)ethyl] [2-(2-{[3-chloro-4'-(trifluoromethyl)biphenyl-4-yl] methoxy}phenyl)ethyl]amino}-5,6,7,8-tetrahydroquinoline-2-carboxylic acid in crystalline modification monohydrate I of the formula (I-M-I)

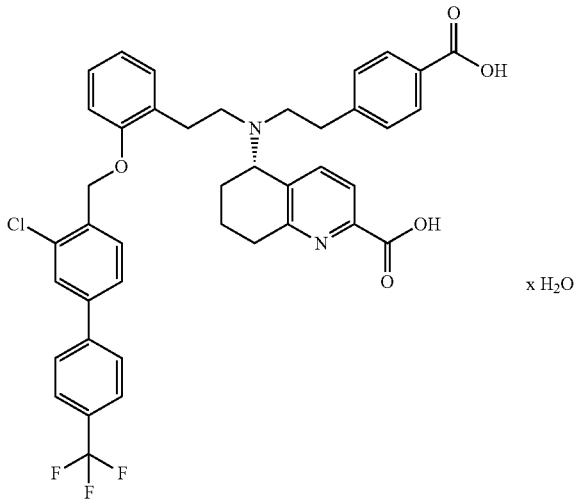

(I-M-I)

wherein the X-ray powder diffractogram (measured at 25° C. and with Cu—K alpha 1 as radiation source) of the compound comprises peaks at least at 12.8, 16.0 and 25.8, or at least at 6.9, 7.2, 7.3, 12.8, 16.0 and 25.8 at diffraction angle 2Θ value±0.2°.

3. A compound that is (5S)—{[2-(4-carboxyphenyl)ethyl] [2-(2-{[3-chloro-4'-(trifluoromethyl)biphenyl-4-yl] methoxy}phenyl)ethyl]amino}-5,6,7,8-tetrahydroquinoline-2-carboxylic acid in crystalline modification monohydrate I of the formula (I-M-I)

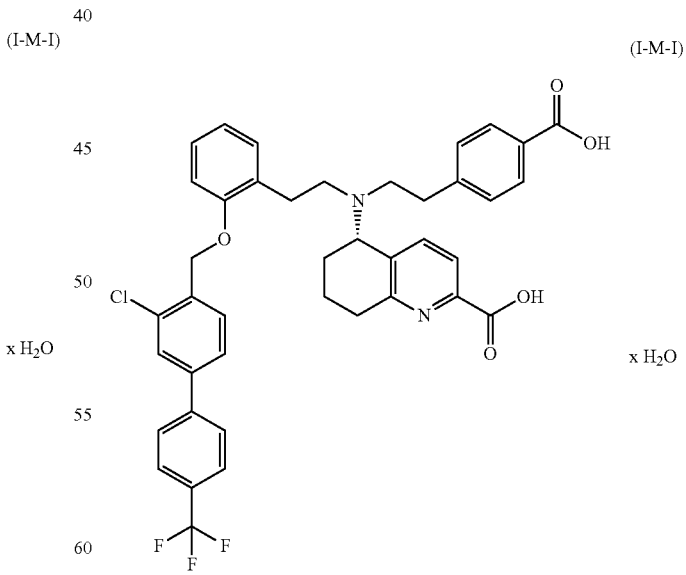

(I-M-I)

wherein the X-ray powder diffractogram (measured at 25° C. and with Cu—K alpha 1 as radiation source) of the compound comprises peaks at least at 12.8, 20.5 and 25.8, or at least at 6.9, 7.2, 7.3, 12.8, 20.5 and 25.8 at diffraction angle 2Θ value±0.2°.

4. A compound that is (5S)—{[2-(4-carboxyphenyl)ethyl] [2-(2-{[3-chloro-4'-(trifluoromethyl)biphenyl-4-yl] methoxy}phenyl)ethyl]amino}-5,6,7,8-tetrahydroquinoline-2-carboxylic acid in crystalline modification monohydrate I of the formula (I-M-I)

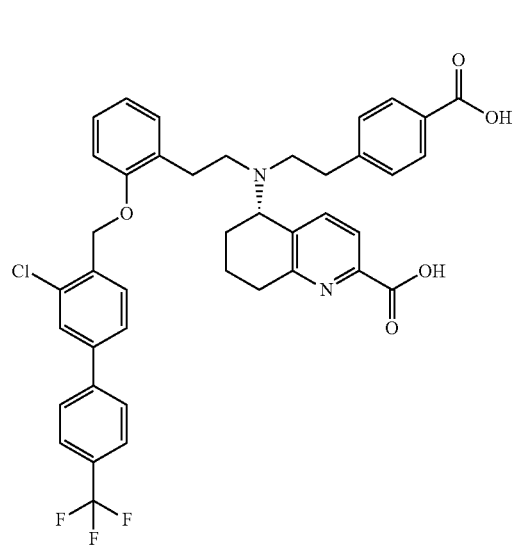

(I-M-I)

x H₂O wherein the X-ray powder diffractogram (measured at 25° C. and with Cu—K alpha 1 as radiation source) of the compound comprises at least peaks at 12.8, 5.7, 6.9, 7.2, 7.3 and 9.9, at diffraction angle 2Θ value±0.2°.

5. A compound that is (5S)—{[2-(4-carboxyphenyl)ethyl] [2-(2-{[3-chloro-4'-(trifluoromethyl)biphenyl-4-yl] methoxy}phenyl)ethyl]amino}-5,6,7,8-tetrahydroquinoline-2-carboxylic acid in crystalline modification monohydrate I of the formula (I-M-I)

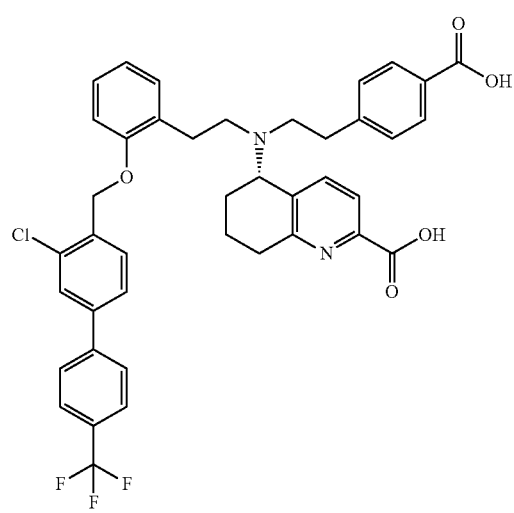

(I-M-I)

x H₂O wherein the X-ray powder diffractogram (measured at 25° C. and with Cu—K alpha 1 as radiation source) of the compound comprises at least peaks at 12.8, 5.7 and 16.0, or at least at 6.9, 7.2, 7.3, 12.8, 5.7 and 16.0 at diffraction angle 2Θ value±0.2°.

6. A compound that is (5S)—{[2-(4-carboxyphenyl)ethyl] [2-(2-{[3-chloro-4'-(trifluoromethyl)biphenyl-4-yl] methoxy}phenyl)ethyl]amino}-5,6,7,8-tetrahydroquinoline-2-carboxylic acid in crystalline modification monohydrate I of the formula (I-M-I)

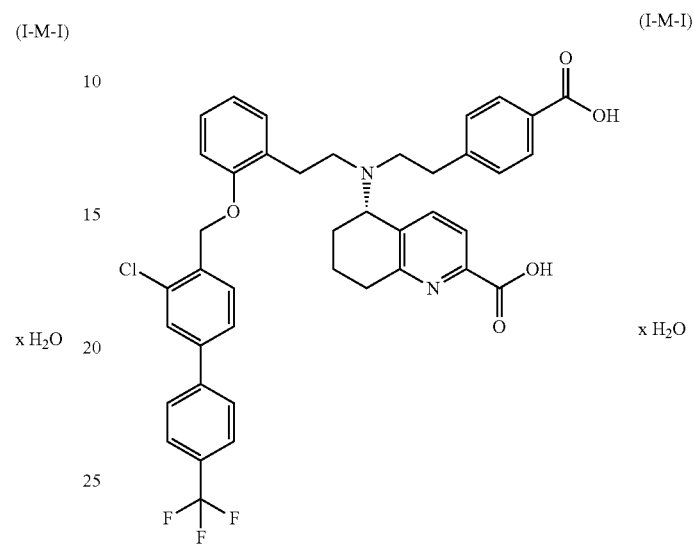

(I-M-I)

x H₂O wherein the X-ray powder diffractogram (measured at 25° C. and with Cu—K alpha 1 as radiation source) of the compound comprises at least peaks at 12.8, 5.7 and 20.5, or at least at 6.9, 7.2, 7.3, 12.8, 5.7 and 20.5 at diffraction angle 2Θ value±0.2°.

7. A compound that is (5S)—{[2-(4-carboxyphenyl)ethyl] [2-(2-{[3-chloro-4'-(trifluoromethyl)biphenyl-4-yl] methoxy}phenyl)ethyl]amino}-5,6,7,8-tetrahydroquinoline-2-carboxylic acid in crystalline modification monohydrate I of the formula (I-M-I)

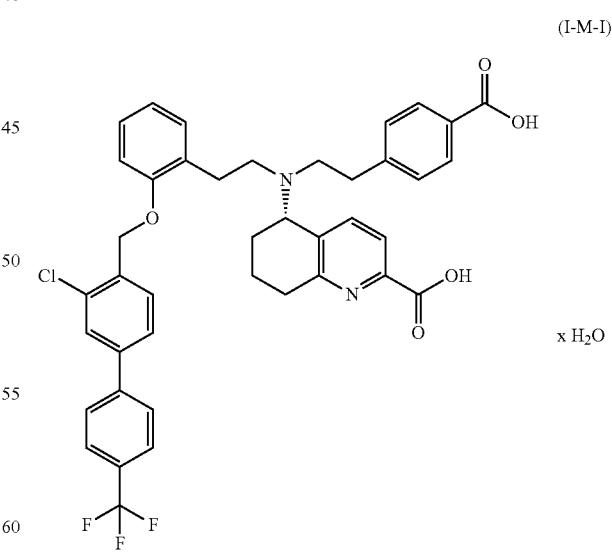

(I-M-I)

x H₂O wherein the X-ray powder diffractogram (measured at 25° C. and with Cu—K alpha 1 as radiation source) of the compound comprises at least peaks at 12.8, 5.7 and 29.2, or at least at 6.9, 7.2, 7.3, 12.8, 5.7 and 29.2 at diffraction angle 2Θ value±0.2°.

8. The compound of one of claims 8 to 14 wherein the x-ray powder diffractogram further comprises peaks at 23.0, 15.2, 25.8 and 25.1.

9. A compound that is (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid in crystalline modification monohydrate I of the formula (I-M-I)

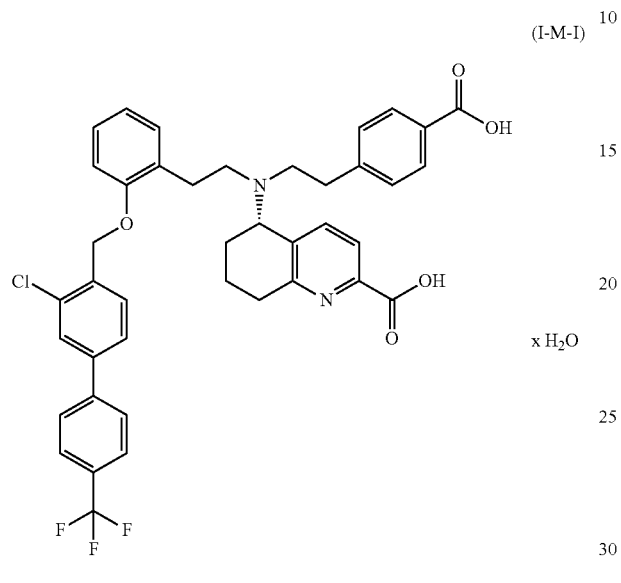

(I-M-I)

x H₂O having an X-ray powder diffraction pattern as shown in FIG. 6 (measured at 25° C. and with Cu—K alpha 1 as radiation source).

10. The compound of any one of claims 8 to 16, wherein the crystalline form is stable during micronization.

11. A compound that is (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid in crystalline modification monohydrate I of the formula (I-M-I)

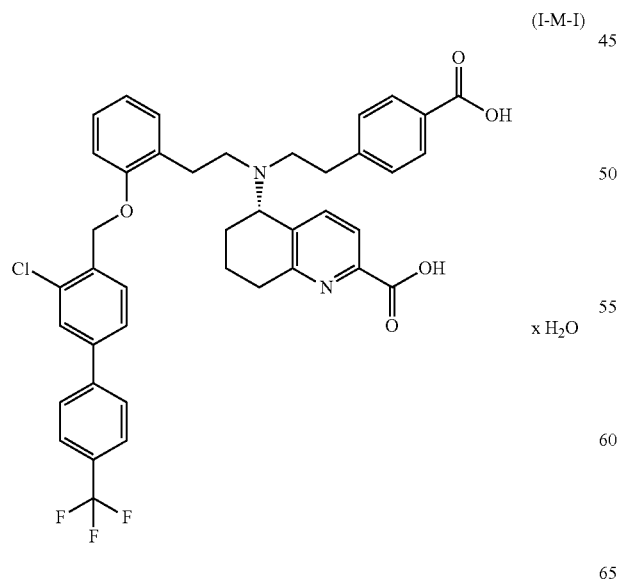

(I-M-I)

x H₂O wherein the X-ray powder diff-actogram (measured at 25° C. and with Cu—K alpha 1 as radiation source) of the compound comprises a peak at least at 12.8, at diffraction angle 2Θ value±0.2°, and the compound has a DSC thermogram as shown in FIG. 27.

12. A compound that is (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid in crystalline modification monohydrate I of the formula (I-M-I)

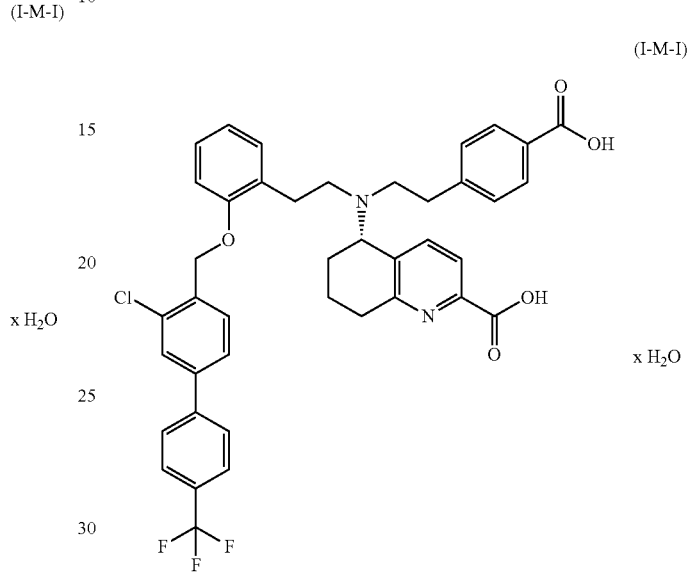

(I-M-I)

x H₂O wherein the X-ray powder diffractogram (measured at 25° C. and with Cu—K alpha 1 as radiation source) of the compound comprises a peak at least at 12.8 and lacks peaks at 27.2 and 27.5, at diffraction angle 2θ value±0.2°.

13. A compound that is (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid in crystalline modification monohydrate I of the formula (I-M-I)

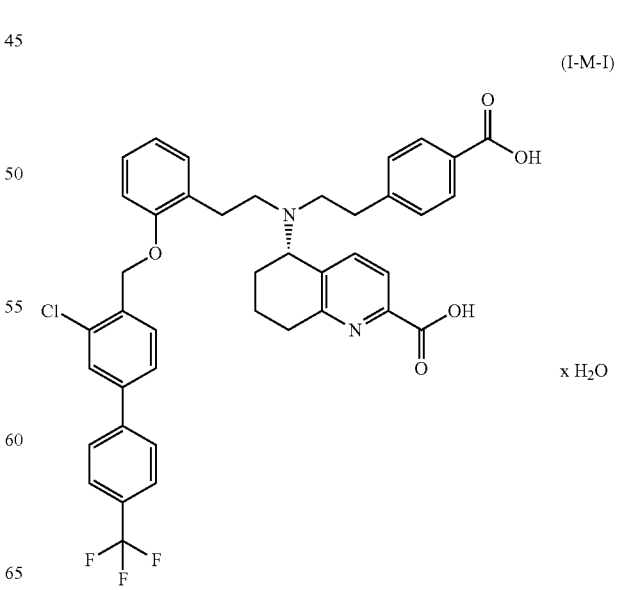

(I-M-I)

x H₂O wherein the X-ray powder diffractogram (measured at 25° C. and with Cu—K alpha 1 as radiation source) of the compound comprises peaks at least at 12.8 and 5.7 and lacks peaks at 8.5 and 6.1, at diffraction angle 2Θ value±0.2°.

14. A pharmaceutical composition comprising the compound of any one of claims 1 to 13 and a pharmaceutically acceptable excipient.

15. The compound of any one of claims 1 to 13 for use in the treatment and/or prophylaxis of cardiopulmonary diseases.

16. The pharmaceutical composition of claim 15 for use in the treatment and/or prophylaxis of cardiopulmonary disorders, such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

17. Use of the compound as defined in any one of claims 1 to 13 for the manufacture of a pharmaceutical composition for the treatment or prevention of cardiopulmonary disorders, such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

18. Use of the compound of any one of claims 1 to 13 for the manufacture of a stable inhalative dosage form for use in a dry powder inhaler.

19. A method of treating or preventing cardiopulmonary disorders, wherein the cardiopulmonary disorder is selected from the group consisting of pulmonary arterial hypertension (PAH), chronic thromboembolic pulmonary hypertension (CTEPH) and pulmonary hypertension (PH) associated with chronic lung disease (PH group 3) including pulmonary hypertension in chronic obstructive pulmonary disease (PH-COPD) and pulmonary hypertension with idiopathic interstitial pneumonia (PH-IIP), comprising administering to a mammal in need thereof a therapeutically effective amount of the compound of any one of claims 1 to 13.

20. The method of claim 19, wherein the cardiopulmonary disorder is pulmonary hypertension in chronic obstructive pulmonary disease (PH-COPD) or pulmonary hypertension with idiopathic interstitial pneumonia (PH-LIP).

Monohydrate II

1. A compound that is (5S)—{[2-(4-carboxyphenyl)ethyl] [2-(2-{[3-chloro-4'-(trifluoromethyl)biphenyl-4-yl] methoxy}phenyl)ethyl]amino}-5,6,7,8-tetrahydroquinoline-2-carboxylic acid in crystalline modification monohydrate II of the formula (I-M-II)

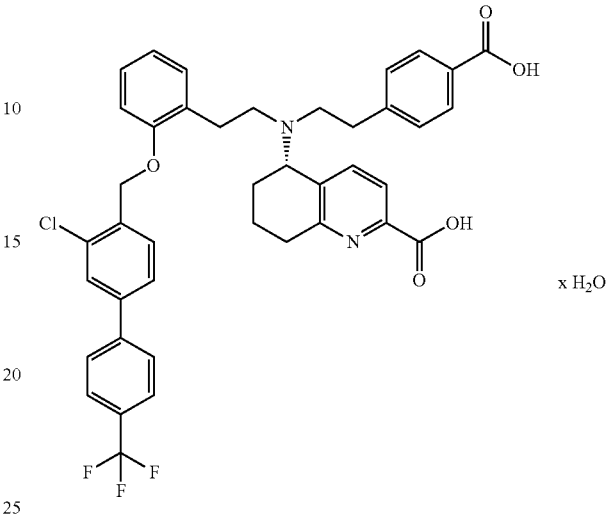

wherein the X-ray powder diffractogram (measured at 25° C. and with Cu—K alpha 1 as radiation source) of the compound comprises peaks at least at 12.7, 13.9, 21.7, and 16.4, at diffraction angle 2Θ value±0.2°.

2. A compound that is (5S)—{[2-(4-carboxyphenyl)ethyl] [2-(2-{[3-chloro-4'-(trifluoromethyl)biphenyl-4-yl] methoxy}phenyl)ethyl]amino}-5,6,7,8-tetrahydroquinoline-2-carboxylic acid in crystalline modification monohydrate II of the formula (I-M-II)

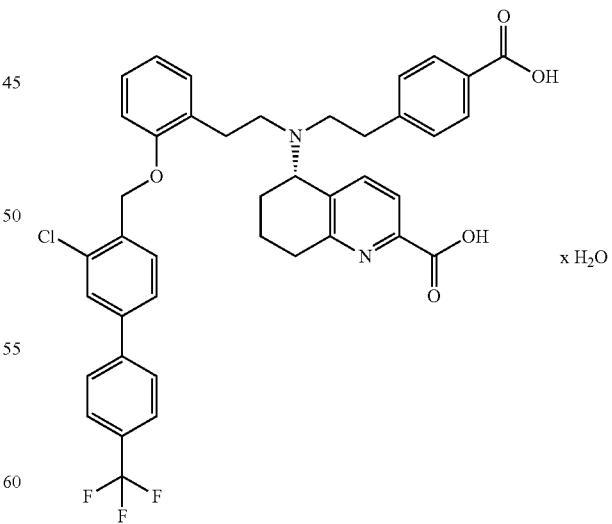

wherein the X-ray powder diffractogram (measured at 25° C. and with Cu—K alpha 1 as radiation source) of the compound comprises peaks at least at 12.7, 13.9, 21.7, and 24.4, at diffraction angle 2Θ value±0.2°.

3. A compound that is (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid in crystalline modification monohydrate II of the formula (I-M-II)

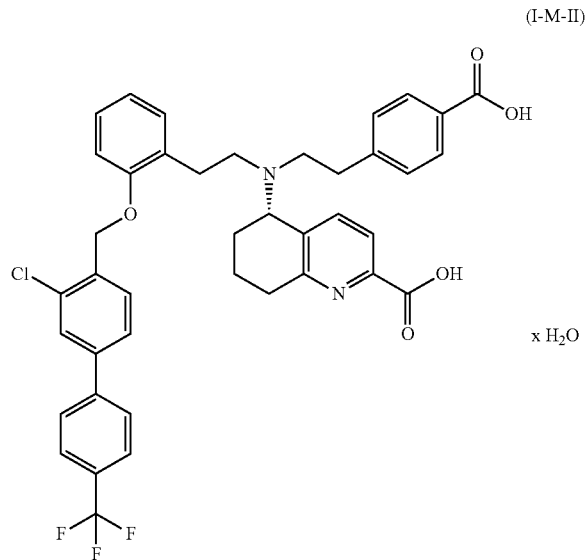 [SMILES: O=C(O)c1ccc(CCN(CCc2ccccc2OCc2ccc(-c3ccc(C(F)(F)F)cc3)cc2Cl)[C@H]2CCCc3nc(C(=O)O)ccc32)cc1]

(I-M-II)

x H₂O wherein the X-ray powder diffractogram (measured at 25° C. and with Cu—K alpha 1 as radiation source) of the compound comprises peaks at least at 12.7, 21.7, and 25.5, at diffraction angle 2Θ value±0.2°.

4. A compound that is (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid in crystalline modification monohydrate II of the formula (I-M-II)

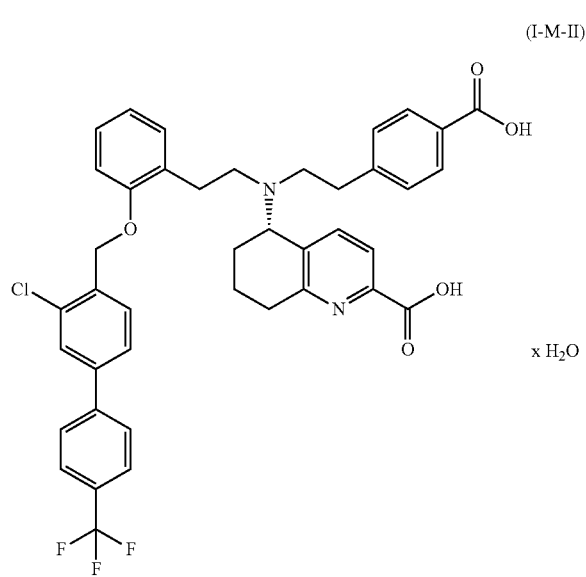 [SMILES: O=C(O)c1ccc(CCN(CCc2ccccc2OCc2ccc(-c3ccc(C(F)(F)F)cc3)cc2Cl)[C@H]2CCCc3nc(C(=O)O)ccc32)cc1]

(I-M-II)

x H₂O wherein the X-ray powder diffractogram (measured at 25° C. and with Cu—K alpha 1 as radiation source) of the compound comprises peaks at least at 12.7, 5.7, 6.1, and 7.1, at diffraction angle 2Θ value±0.2°.

5. A compound that is (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid in crystalline modification monohydrate II of the formula (I-M-II)

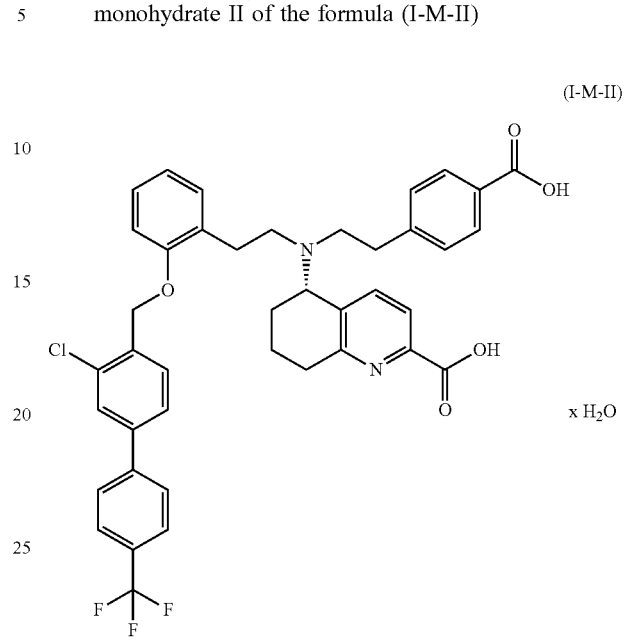

(I-M-II)

x H₂O wherein the X-ray powder diffractogram (measured at 25° C. and with Cu—K alpha 1 as radiation source) of the compound comprises peaks at least at 12.7, 5.7, and 8.5, at diffraction angle 2Θ value±0.2°.

6. A compound that is (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid in crystalline modification monohydrate II of the formula (I-M-II)

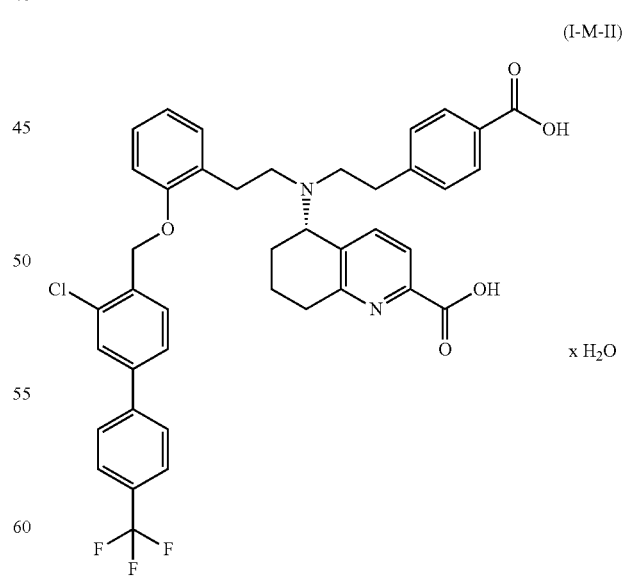

(I-M-II)

x H₂O wherein the X-ray powder diffractogram (measured at 25° C. and with Cu—K alpha 1 as radiation source) of the compound comprises peaks at least at 12.7, 6.1, and 9.9, at diffraction angle 2Θ value±0.2°.

7. A compound that is (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid in crystalline modification monohydrate II of the formula (I-M-II)

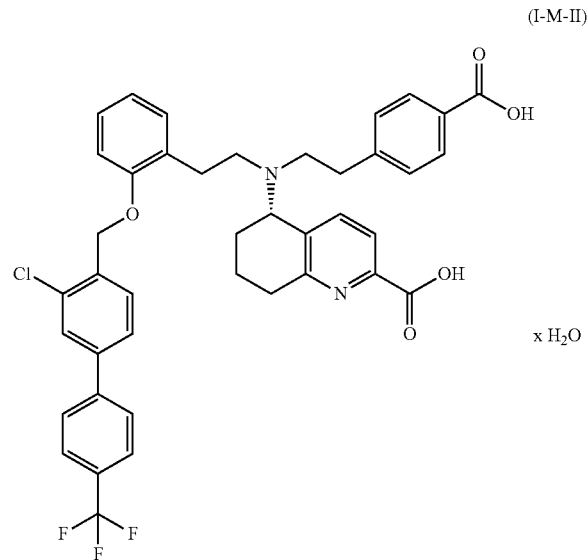 [SMILES: O=C(O)c1ccc(CCN(CCc2ccccc2OCc2ccc(-c3ccc(C(F)(F)F)cc3)cc2Cl)[C@H]2CCCc3nc(C(=O)O)ccc32)cc1]

(I-M-II)

wherein the X-ray powder diffractogram (measured at 25° C. and with Cu—K alpha 1 as radiation source) of the compound comprises peaks at least at 12.7, 7.1, and 8.5, at diffraction angle 2Θ value±0.2°.

8. A compound that is (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid in crystalline modification monohydrate II of the formula (I-M-II)

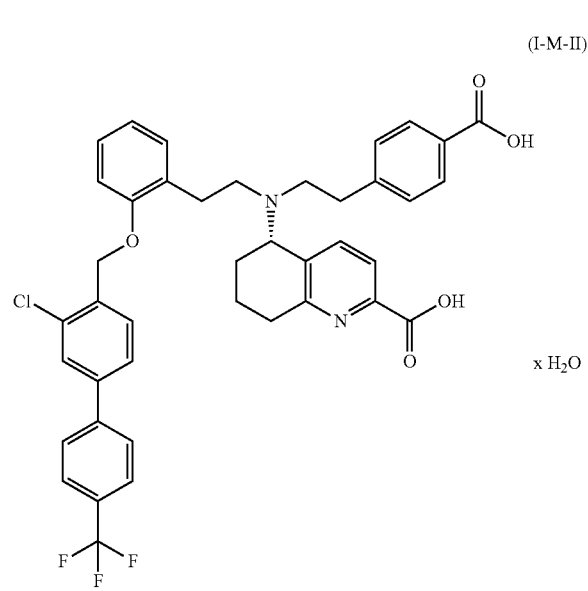 [SMILES: O=C(O)c1ccc(CCN(CCc2ccccc2OCc2ccc(-c3ccc(C(F)(F)F)cc3)cc2Cl)[C@H]2CCCc3nc(C(=O)O)ccc32)cc1]

(I-M-II)

wherein the X-ray powder diffractogram (measured at 25° C. and with Cu—K alpha 1 as radiation source) of the compound comprises peaks at least at 12.7, 7.1, and 6.1, at diffraction angle 2Θ value±0.2°.

9. A compound that is (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid in crystalline modification monohydrate II of the formula (I-M-II)

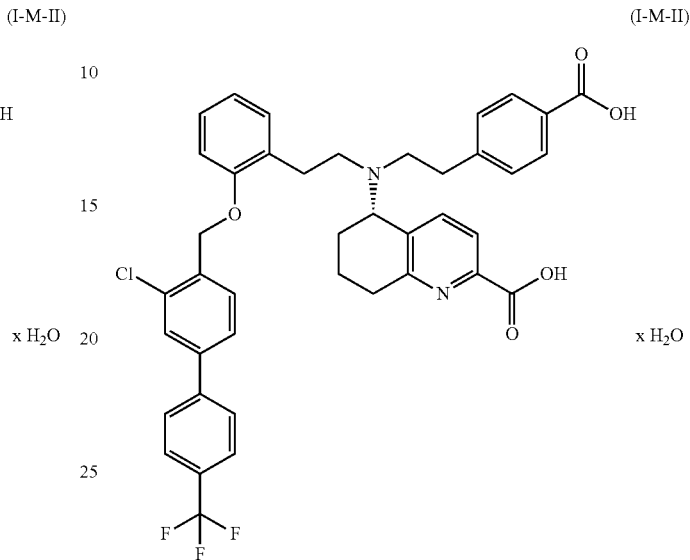

(I-M-II)

having an X-ray powder diffraction pattern as shown in FIG. 7 (measured at 25° C. and with Cu—K alpha 1 as radiation source).

10. A compound that is (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid in crystalline modification monohydrate II of the formula (I-M-II)

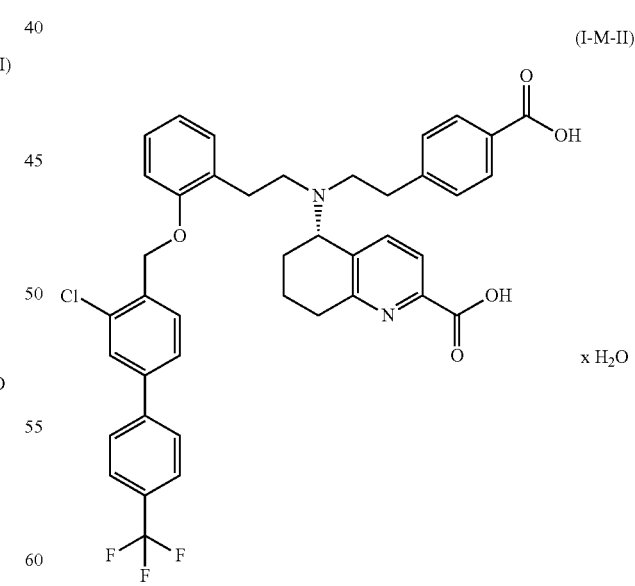

(I-M-II)

wherein the X-ray powder diffractogram (measured at 25° C. and with Cu—K alpha 1 as radiation source) of the compound comprises a peak at least at 12.7, at diffraction angle 2Θ value±0.2°, and the compound has a DSC thermogram as shown in FIG. 28.

11. A compound that is (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid in crystalline modification monohydrate II of the formula (I-M-II)

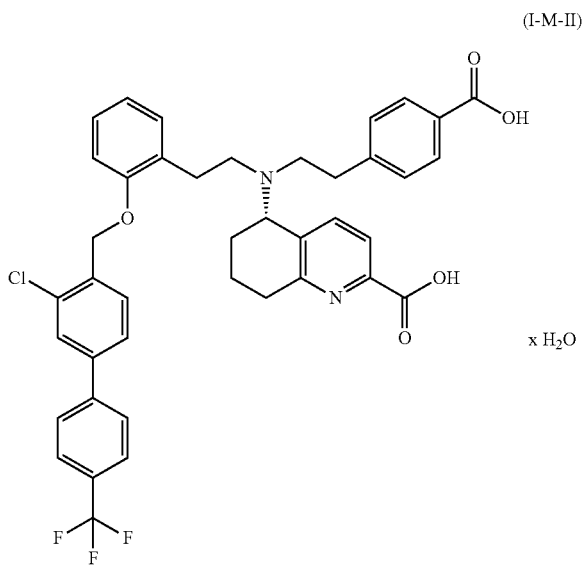 [SMILES: O=C(O)c1ccc(CCN(CCc2ccccc2OCc2ccc(-c3ccc(C(F)(F)F)cc3)cc2Cl)[C@H]2CCCc3nc(C(=O)O)ccc32)cc1]

(I-M-II)

x H₂O wherein the X-ray powder diffractogram (measured at 25° C. and with Cu—K alpha 1 as radiation source) of the compound comprises a peak at least at 12.7 and lacks peaks at (1) 11.1 and 20.5, (2) 11.1 and 29.2, (3) 20.5 and 29.2, (4) 11.1 and 16.0, (5) 11.1 and 16.9, and/or (6) 16.0 and 16.9, at diffraction angle 2Θ value±0.2°.

12. The compound of claim 11 that lacks peaks at 11.1 and 29.2, at diffraction angle 2Θ value 0.2°.
13. The compound of claim 11 that lacks peaks at 11.1 and 20.5, at diffraction angle 2Θ value±0.2°.
14. The compound of one of claims 1 to 13, wherein the x-ray powder diffractogram comprises peaks at 12.7, 23.9, 13.9, 23.0 and 12.2, at diffraction angle 2Θ value±0.2°.
15. A pharmaceutical composition comprising the compound of any one of claims 1 to 14 and a pharmaceutically acceptable excipient.
16. The compound of any one of claims 1 to 14 for use in the treatment and/or prophylaxis of cardiopulmonary diseases.
17. The pharmaceutical composition of claim 15 for use in the treatment and/or prophylaxis of cardiopulmonary disorders, such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).
18. Use of the compound as defined in any one of claims 1 to 14 for the manufacture of a pharmaceutical composition for the treatment or prevention of cardiopulmonary disorders, such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).
19. Use of the compound of any one of claims 1 to 14 for the manufacture of a stable inhalative dosage form for use in a dry powder inhaler.
20. A method of treating or preventing cardiopulmonary disorders, wherein the cardiopulmonary disorder is selected from the group consisting of pulmonary arterial hypertension (PAH), chronic thromboembolic pulmonary hypertension (CTEPH) and pulmonary hypertension (PH) associated with chronic lung disease (PH group 3) including pulmonary hypertension in chronic obstructive pulmonary disease (PH-COPD) and pulmonary hypertension with idiopathic interstitial pneumonia (PH-IIP), comprising administering to a mammal in need thereof a therapeutically effective amount of the compound of any one of claims 1 to 14.
21. The method of claim 20, wherein the cardiopulmonary disorder is pulmonary hypertension in chronic obstructive pulmonary disease (PH-COPD) or pulmonary hypertension with idiopathic interstitial pneumonia (PH-IIP).

Sesquihydrate

1. A compound that is (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid of the formula (I)

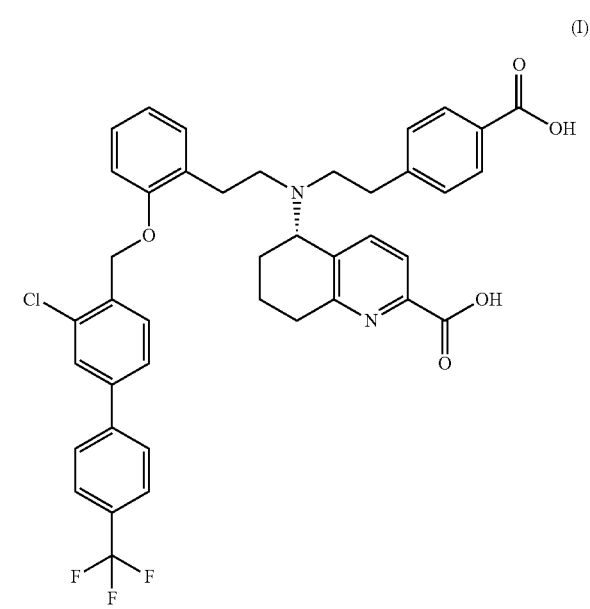 [SMILES: O=C(O)c1ccc(CCN(CCc2ccccc2OCc2ccc(-c3ccc(C(F)(F)F)cc3)cc2Cl)[C@H]2CCCc3nc(C(=O)O)ccc32)cc1]

(I)

in crystalline modification sesquihydrate wherein the X-ray powder diffractogram (measured at 25° C. and with Cu—K alpha 1 as radiation source) of the compound comprises peaks at least at 12.2 and 7.6, at diffraction angle 2Θ value±0.2°.

2. A compound that is (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid of the formula (I)

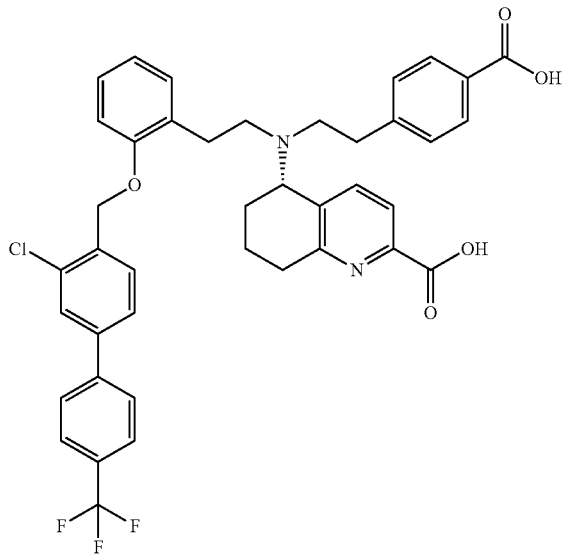

(I)

in crystalline modification sesquihydrate wherein the X-ray powder diffractogram (measured at 25° C. and with Cu—K alpha 1 as radiation source) of the compound comprises peaks at least at 12.2, 5.1 and 26.4, at diffraction angle 2Θ value±0.2°.

3. A compound that is (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid of the formula (I)

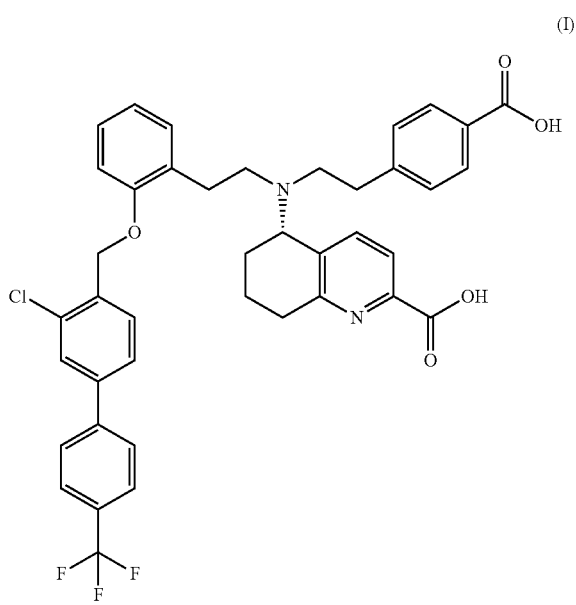 [SMILES: O=C(O)c1ccc(CCN(CCc2ccccc2OCc2ccc(-c3ccc(C(F)(F)F)cc3)cc2Cl)[C@H]2CCCc3nc(C(=O)O)ccc32)cc1]

(I)

in crystalline modification sesquihydrate wherein the X-ray powder diffractogram (measured at 25° C. and with Cu—K alpha 1 as radiation source) of the compound comprises peaks at least at 12.2, 8.6 and 14.5, at diffraction angle 2Θ value±0.2°.

4. A compound that is (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid of the formula (I)

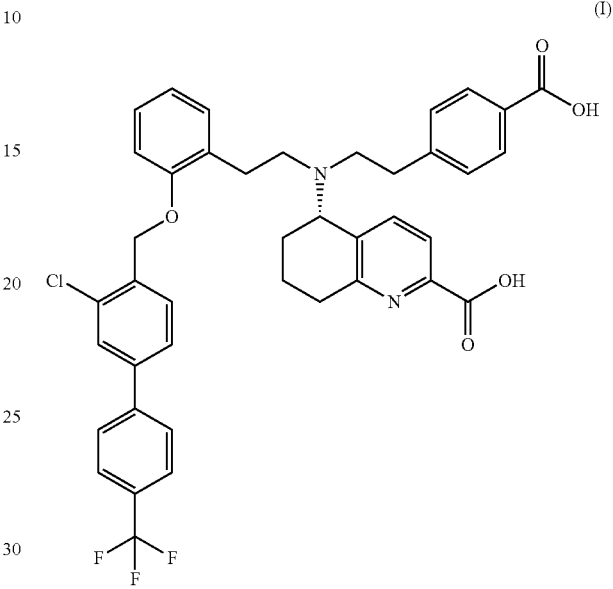

(I)

in crystalline modification sesquihydrate having an X-ray powder diffraction pattern as shown in FIG. 9 (measured at 25° C. and with Cu—K alpha 1 as radiation source).

5. A compound that is (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid of the formula (I)

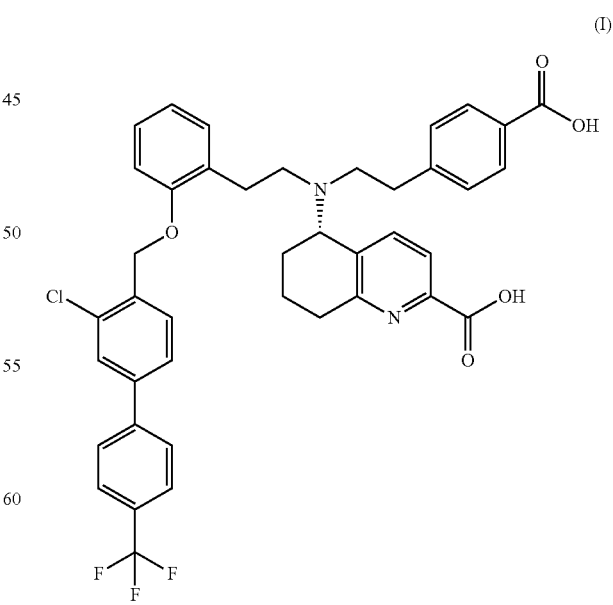

(I)

in crystalline modification sesquihydrate wherein the X-ray powder diffractogram (measured at 25° C. and with Cu—K alpha 1 as radiation source) of the compound comprises a peak at least at 12.2, at diffraction angle 2Θ value±0.2°, and the compound has a DSC thermogram as shown in FIG. 30.

6. A compound that is (5S)—{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid of the formula (I)

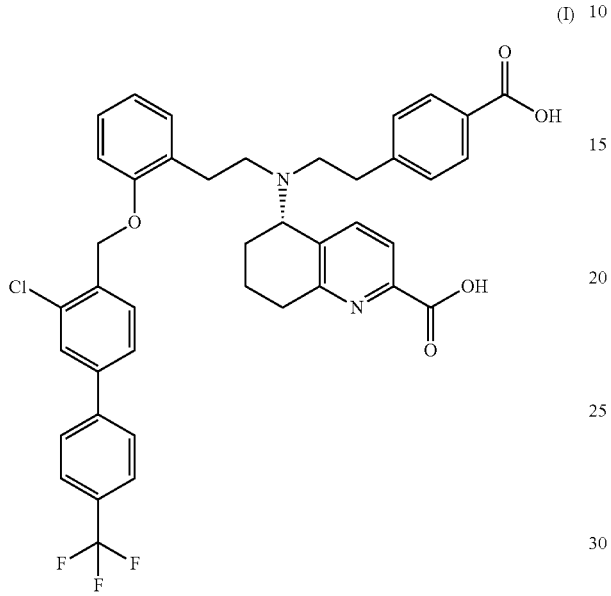

in crystalline modification sesquihydrate wherein the X-ray powder diffractogram (measured at 25° C. and with Cu—K alpha 1 as radiation source) of the compound comprises a peak at least at 12.2 and lacks peaks at (1) 10.6, (2) 25.8 and 6.7 (3) 25.8 and 7.1, (4) 25.8 and 10.6, (5) 10.4, (6) 5.7 and 6.7 and/or (6) 25.5, 5.7 and 6.7, at diffraction angle 2Θ value±0.2°.

7. The compound of claim 6 that lacks a peak at 10.6, at diffraction angle 2Θ value±0.2°.

8. The compound of claim 6 that lacks peaks at 5.7 and 6.7, at diffraction angle 2Θ value±0.2°.

9. The compound of one of claims 1 to 8, wherein the x-ray powder diffractogram comprises peaks at 12.2, 14.5, 18.7, 25.1, and 27.0, at diffraction angle 2Θ value±0.2°.

10. A pharmaceutical composition comprising the compound of any one of claims 1 to 9 and a pharmaceutically acceptable excipient.

11. The compound of any one of claims 1 to 9 for use in the treatment and/or prophylaxis of cardiopulmonary diseases.

12. The pharmaceutical composition of claim 10 for use in the treatment and/or prophylaxis of cardiopulmonary disorders, such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

13. Use of the compound as defined in any one of claims 1 to 9 for the manufacture of a pharmaceutical composition for the treatment or prevention of cardiopulmonary disorders, such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

14. Use of the compound of any one of claims 1 to 9 for the manufacture of a stable inhalative dosage form for use in a dry powder inhaler.

15. A method of treating or preventing cardiopulmonary disorders, wherein the cardiopulmonary disorder is selected from the group consisting of pulmonary arterial hypertension (PAH), chronic thromboembolic pulmonary hypertension (CTEPH) and pulmonary hypertension (PH) associated with chronic lung disease (PH group 3) including pulmonary hypertension in chronic obstructive pulmonary disease (PH-COPD) and pulmonary hypertension with idiopathic interstitial pneumonia (PH-IIP), comprising administering to a mammal in need thereof a therapeutically effective amount of the compound of any one of claims 1 to 9.

16. The method of claim 15, wherein the cardiopulmonary disorder is pulmonary hypertension in chronic obstructive pulmonary disease (PH-COPD) or pulmonary hypertension with idiopathic interstitial pneumonia (PH-IIP).

EXPERIMENTAL PART

Abbreviations and Acronyms abs. absolute
acac acetylacetonato
BINAP (2,2'-bis(diphenylphosphino)-1,1'-binaphthyl)
cat. catalytic
CI chemical ionization (in MS)
coe cyclooctene
d day(s)
TLC thin layer chromatography
DCM dichloromethane
DMA dimethylacetamide
DMF dimethylformamide
DMSO dimethyl sulfoxide
ee enantiomeric excess
EI electron impact ionization (in MS)
ent enantiomer/enantiomerically pure
eq equivalent(s)
ESI electrospray ionization (in MS)
EtOAc ethyl acetate
GC-MS gas chromatography-coupled mass spectrometry
% by weight percent by weight
h hour(s)
HPLC high-pressure, high-performance liquid chromatography
ID internal diameter
iPrOAc isopropyl acetate
iPrOH isopropanol
conc. concentrated
LC-MS liquid chromatography-coupled mass spectrometry
LDA lithium diisopropylamide
LiHMDS lithium bis(trimethylsilyl)amide
min minute(s)
MS mass spectrometry
MTBE 2-methoxy-2-methylpropane
NMR nuclear magnetic resonance spectrometry
NMP N-methyl-2-pyrrolidone Ph phenyl
pTsOH p-toluenesulfonic acid
Rf retention index (in TLC)
RP-HPLC reversed phase high performance liquid chromatography
RRT relative retention time
Rt retention time
RT room temperature
TESCl chlorotriethylsilane
THF tetrahydrofuran
v/v volume to volume ratio (of a solution)
aq. aqueous, aqueous solution
Tinternal internal temperature
Tsheath sheath temperature Analytical Methods

DSC/TG

DSC thermograms were recorded using Differential Scanning Calorimeters (model DSC7, Pyris-1 or Diamond) from Perkin-Elmer. The measurements were performed with a heating rate of 20 Kmin-1 using non-gastight aluminium pans. Flow gas was nitrogen. There was no sample preparation.

TGA thermograms were recorded using thermobalances (model TGA7 and Pyris 1) from Perkin-Elmer. The measurements were performed with a heating rate of 10 Kmin-1 using open platinum pans. Flow gas was nitrogen. There was no sample preparation.

XRPD

X-Ray diffraction patterns were recorded at room temperature using XRD-diffractometers X'Pert PRO (PANalytical) and STOE STADI-P (radiation Cu K alpha 1, wavelength 1.5406 Å). There was no sample preparation. All X-Ray reflections are quoted as 020 (theta) values (peak maxima) with a resolution of ±0.2°.

Raman

Raman spectra were recorded at room temperature using FT-Raman-spectrophotometers (model RFS 100 and MultiRam) from Bruker. Resolution was 2 cm-1. Measurements were performed in glass vials or aluminium discs. There was no sample preparation.

IR

IR-ATR-spectra were recorded at room temperature using a FT-IR-spectrophotometer Tensor 37 with universal diamond ATR device from Bruker. Resolution was 4 cm-1. There was no sample preparation.

LC-MS Methods

Method A

Instrument: Waters ACQUITY SQD UPLC System; column: Waters Acquity UPLC HSS T3 1.8 µm 50×1 mm; eluent A: 1 l Wasser+0.25 ml 99% ige formic acid, eluent B: 1 l acetonitrile+0.25 ml 99% ige formic acid; gradient: 0.0 min 90% A→1.2 min 5% A→2.0 min 5% A oven: 50° C.; flow: 0.40 ml/min; UV-detection: 210 nm.

HPLC Methods

Method B

High performance liquid chromatograph with thermostatized column oven, UV detector and data evaluation system, measuring wavelength 206 nm, bandwidth: 6 nm, oven temperature 30° C., column: chiralpak AD-H, length: 250 mm, inner diameter: 4.6 mm, grain size: 5 µm, mobile Phase: A: N-heptane, B: ethanol+0.1% diethylamine, gradient program: start 1 ml/min 70% eluent a, 30% eluent B; 12 min 1 ml/min 40% eluent A, 60% eluent B. Sample solvent: ethanol+0.1% diethylamine, Test solution: approx. 1.0 mg/ml of the substance, dissolved with sample solvents, injection volume: 5 µl RT: Enantiomer 1: 5.8 min (RRT 1.00), Enantiomer 2: 7.2 min RRT1.25

Method C

High performance liquid chromatograph with thermostatized column oven, UV detector and data evaluation system, measuring wavelength 204 nm, bandwidth: 6 nm, oven temperature 45° C., column: chiralpak AD-H, length: 250 mm, inner diameter: 4.6 mm, grain size: 5 µm, mobile Phase: A: N-heptane, B: ethanol+0.2% trifluoroacetic acid+0.1% diethylamine, gradient program: 1.5 ml/min 60% eluent a, 40% eluent b; Sample solvent: ethanol, test solution: approx. 1.0 mg/ml of the substance, dissolved with sample solvents, injection volume: 10 µl RT: Enantiomer 1 2.9 min RRT 1.00 Enantiomer 2 3.7 min RRT 1.28

Method L

Device type MS: Waters Synapt G2S; Device type UPLC: Waters Acquity I-CLASS; Column: Waters, HSST3, 2.1×50 mm, C18 1.8 µm; Eluent A: 1 l water+0.01% formic acid; Eluent B: 1 l acetonitrile+0.01% formic acid; Gradient: 0.0 min 2% B→2.0 min 2% B→13.0 min 90% B→15.0 min 90% B; Oven: 50° C.; Flow rate: 1.20 ml/min; UV detection: 210 nm Method M High-performance liquid chromatograph with thermostated column oven, UV detector and data evaluation system, measuring wavelength 226 nm, bandwidth: 40 nm. Column: Zorbax Bonus-RP, length: 150 mm, inner diameter: 3.0 mm, grain size: 3.5 µm, mobile phase: A: Water+0.1% TFA, B: ACN+0.1% TFA/methanol=2+1, gradient program: 0.0 min 50% B→12.0 min 70% B→17.0 min 90% B→25.0 min 90% B; Flow rate: 0.60 ml/min; Sample solvent: isopropanol+0.1% diethylamine, test solution: dissolve approx. 35 mg of the substance in 25 ml ACN and fill up to 50 ml with water+0.1% TFA. (0.7 mg/mL); Injection volume: 3 µL New Method M High-performance liquid chromatograph with thermostated column oven, UV detector and data evaluation system, measuring wavelength 226 nm, bandwidth: 40 nm. Column: XBridge Phenyl length: 50 mm, inner diameter:4.6 mm, grain size: 2.5 µm; column oven temperature: 22° C.

mobile phase: A: buffer pH7 (0.66 g/L (NH4)2HPO4 and 0.58 g/L NH4H2PO4); B: ACN gradient program: 0.00 min=95% A, 5% B; t 8.3–11=20% A, 80% B Flow rate: 1.2 mL/min.; UV-Lampe: 210 nm Method N High-performance liquid chromatograph with thermostated column oven, UV detector and data evaluation system, measuring wavelength 210 nm. Column: XBridge BEH Phenyl length: 50 mm, inner diameter: 4.6 mm, grain size: 2.5 µm, mobile phase: A: 0.66 g (NH4)2HPO4 and 0.58 g (NH4)H2PO4 in 1 l millipore water; B: ACN, gradient program: 0.00 min 95% B→8.3 min 80% B→11.0 min 80%; Flow rate: 1.2 ml/min; Sample solvent: ACN+Water, Injection volume: 3 µL.

A—CHEMICAL EXAMPLES

Starting Materials and Intermediates

Example 1A (5S)-5-([2-(2-{[3-chloro-4'-(trifluoromethyl)[biphenyl]-4-yl]methoxy}phenyl)ethyl]{2-[4-(methoxycarbonyl)phenyl]ethyl}amino)-5,6,7,8-tetrahydroquinoline-2-carboxylate (Enantiomer 2)

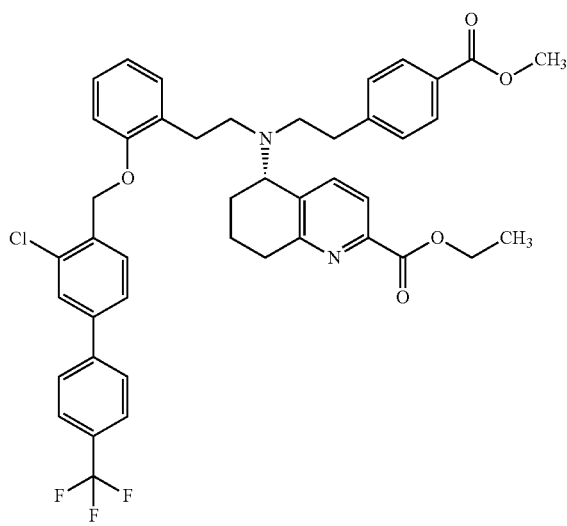 [SMILES: CCOC(=O)c1ccc2c(n1)CCC[C@@H]2N(CCc1ccc(C(=O)OC)cc1)CCc1ccccc1OCc1ccc(-c2ccc(C(F)(F)F)cc2)cc1Cl]

The compound was synthesized according to procedures as disclosed in example 92A, WO 2014/012934.

Example 2A

Butyl-(5S)-5-({2-[4-(butoxycarbonyl)phenyl]ethyl}[2-(2-hydroxyphenyl)ethyl]amino)-5,6,7,8-tetrahydrochinoline-2-carboxylate

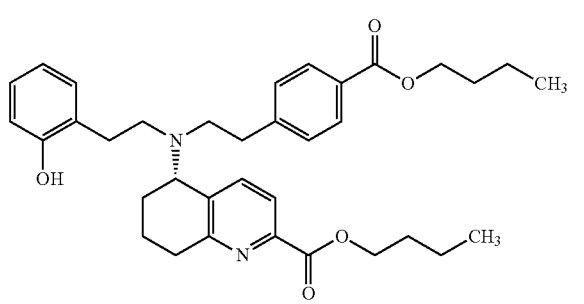 [SMILES: CCCCOC(=O)c1ccc(CCN(CCc2ccccc2O)[C@H]2CCCc3nc(C(=O)OCCCC)ccc32)cc1]

The compound was synthesized according to procedures as disclosed in example 10, WO2021/233783.

Example 3A

Butyl-(5S)-5-({2-[4-(butoxycarbonyl)phenyl]ethyl}[2-(2-{[3-chloro-4'-(trifluoromethyl)[biphenyl]-4-yl]methoxy}phenyl)ethyl]amino)-5,6,7,8-tetrahydrochinoline-2-carboxylate

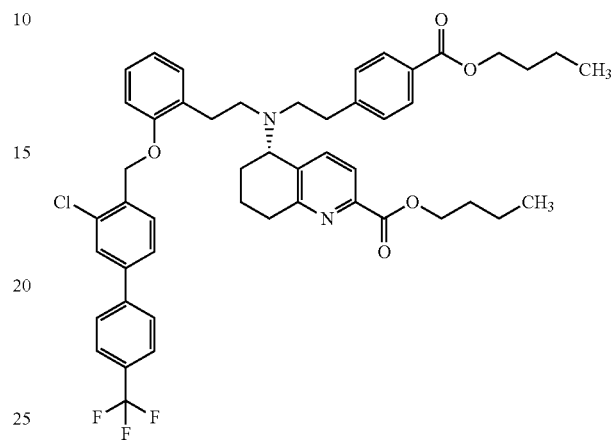

The compound was synthesized according to procedures as disclosed in example 11, WO2021/233783.

A further starting material 4-(Bromomethyl)-3-chloro-4'-(trifluoromethyl)[biphenyl] (compound of the formula XI) is commercial available.

Example 4A

Naphthalene-1,5-disulfonic acid-butyl-(5S)-5-({2-[4-(butoxycarbonyl) phenyl] ethyl} [2-(2-{[3-chloro-4'-(trifluoromethyl) [biphenyl]-4-yl] methoxy} phenyl) ethyl] amino)-5,6,7,8-tetrahydroquinoline-2-carboxylate (1:1) Adduct

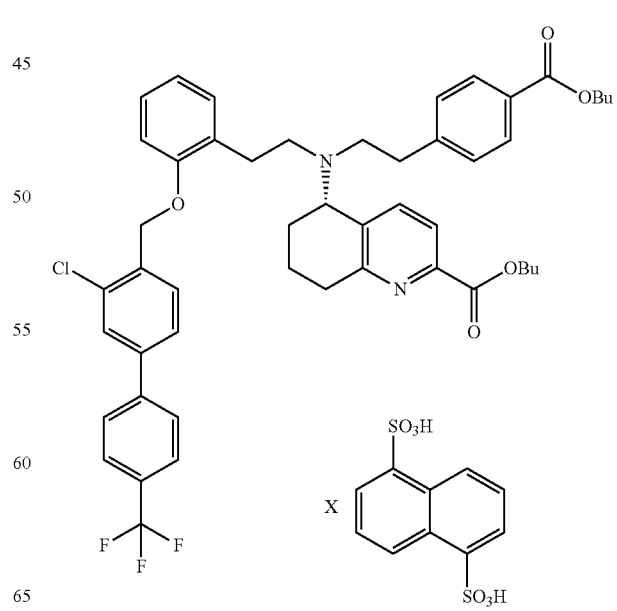

In a 3 L flask, 889.1 g (1.06 mol) of butyl-(5S)-5-({2-[4-(butoxycarbonyl) phenyl] ethyl} [2-(2-{[3-chloro-4'-(trifluoromethyl) [biphenyl]-4-yl] methoxy} phenyl) ethyl] amino)-5,6,7,8-tetrahydroquinoline-2-carboxylate (oil) dissolved in 1850 ml of tetrahydrofuran. 304.6 g (1.06 mol) of naphthalene-1,5-disulfonic acid were added at room temperature, the mixture was stirred until it was completely dissolved. Subsequently the solution was concentrated on a rotary evaporator at 40° C. The residue (solid) was dried to 1126.3 g in a vacuum drying cabinet at 40° C. in a stream of nitrogen.

Yield (raw-product): 1126.3 g; 94.4% of the theoretical yield

Enantiomeric purity (HPLC method B): 95.3% ee

Purity (area): 81.8% (Method N), Rt 16.11 (BP-Diester))

Examples 4B-4E

Trials to form stable salts of Butyl-(5S)-5-({2-[4-(butoxycarbonyl)phenyl]ethyl}[2-(2-{[3-chloro-4'-(trifluoromethyl) [biphenyl]-4-yl] methoxy} phenyl)ethyl]amino)-5,6,7,8-tetrahydrochinoline-2-carboxylate with different acids 4B: Addition of (+)-di-p-toluoyl-D-tartaric acid 4 g (0.005 mol) of butyl-(5S)-5-({2-[4-(butoxycarbonyl) phenyl] ethyl} [2-(2-{[3-chloro-4'-(trifluoromethyl) [biphenyl]-4-yl] methoxy} phenyl) ethyl] amino)-5,6,7,8-tetrahydroquinoline-2-carboxylate (oil) were gradually dissolved in a total amount of 75 ml of methanol at a temperature of 50° C. A warm solution of 1.8 g (0.005 mol) (+)-di-p-toluoyl-D-tartaric acid in 2.5 ml methanol was added. Finally the mixture was stirred over the weekend.

To smaller parts of the reaction mixture different solvents were added to initiate crystallization. The following solvents were tried without any effect: MTBE, MIBK, methylenchloride, toluene. After addition of a mixture of cyclohexane, n-hexane and methylcyclohexane two layers formed.

A few drops of the reaction mixture were dried on a watchglass and the resulting dried mass was scraped off and stirred finally in a mixture of cyclohexane, n-hexane and methylcyclohexane. The resulting solids melted.

With methylcyclohexane a solid separated. HPLC analysis of the solids revealed tartaric acid.

After addition of water to another part of the reaction mixture a solid separated. The solids were difficult to be separated.

The reaction mixture was stripped off the solvents. 3.1 g of yellowish foam crystals were obtained.

To the foam crystals 31 ml of methylcyclohexane were added and stirred for 4 hours. 2.8 g of light-yellowish solids were obtained.

No defined salt could be detected.

4C: Addition of Trifluoro Acetic Acid (=TFA)

0.21 g (0.2 mmol) of butyl-(5S)-5-({2-[4-(butoxycarbonyl) phenyl] ethyl} [2-(2-{[3-chloro-4'-(trifluoromethyl) [biphenyl]-4-yl] methoxy} phenyl) ethyl] amino)-5,6,7,8-tetrahydroquinoline-2-carboxylate (oil) were dissolved in 2 ml of acetonitrile. 0.1 ml of TFA was added. An orange solution was formed. The solvents were evaporated in vacuo to yield an orange oil.

No salt formation observable.

4D: Addition of Methane Sulfonic Acid 0.26 g (0.3 mmol) of butyl-(5S)-5-({2-[4-(butoxycarbonyl) phenyl] ethyl} [2-(2-{[3-chloro-4'-(trifluoromethyl) [biphenyl]-4-yl] methoxy} phenyl) ethyl] amino)-5,6,7,8-tetrahydroquinoline-2-carboxylate (oil) were dissolved in 1.5 ml of dichloromethane. 20.1 µl of methane sulfonic acid was added. An orange solution was formed. After stirring for 1 hour at room temperature no crystallization.

The solvents were evaporated in vacuo at 40° C. to yield yellow foam crystals.

Several solvents were screened to initiate either crystallization or purification.

Dichloromethane, MIBK, MTBE, ethylacetate, acetone, acetonitrile, dioxane, n-butanol, methanol, ethanol, tetrahydrofurane, toluene resulted in a solution at room temperature.

Diisopropylether, water, diethylether, cyclohexane resulted in a sticky mass.

Further stirring in n hexane at room temperature resulted again in a sticky mass.

No salt isolatable.

4E: Addition of Camphor Sulfonic Acid 0.29 g (0.34 mmol) of butyl-(5S)-5-({2-[4-(butoxycarbonyl) phenyl] ethyl} [2-(2-{[3-chloro-4'-(trifluoromethyl) [biphenyl]-4-yl] methoxy} phenyl) ethyl] amino)-5,6,7,8-tetrahydroquinoline-2-carboxylate (oil) were dissolved in 1.5 ml of dichloromethane. 80.05 µg of camphor sulfonic acid was added. An orange solution was formed.

The solvents were evaporated in vacuo at 40° C. to yield yellow foam crystals.

Several solvents were screened to initiate either crystallization or purification.

Dichloromethane, MIBK, ethylacetate, acetone, acetonitrile, dioxane, n-butanol, methanol, ethanol, tetrahydrofurane, toluene resulted in a solution at room temperature.

MTBE addition resulted in oily drops formation.

Water, diisopropylether, diethylether, cyclohexane and n heptane all afforded only sticky masses.

No salt isolatable.

Example 5A and Example 6A

Ethyl 5-{(tert-butoxycarbonyl)[2-(2-{[3-chloro-4'-(trifluoromethyl)biphenyl-4-yl]methoxy}phenyl)-ethyl]amino}-5,6,7,8-tetrahydroquinoline-2-carboxylate (Enantiomers 1 and 2)

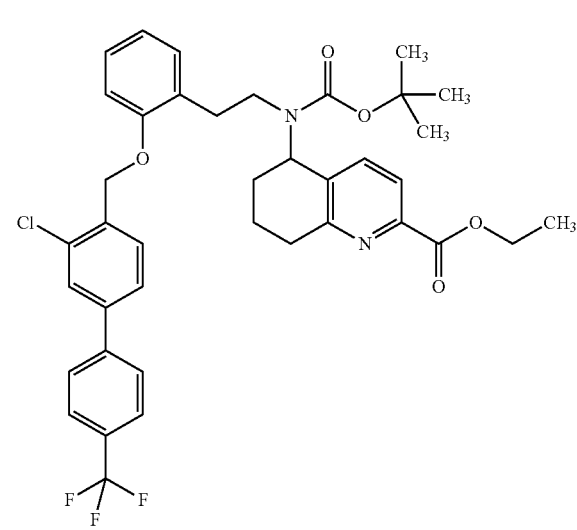 [SMILES: CCOC(=O)c1ccc2c(n1)CCCC2N(CCc1ccccc1OCc1ccc(-c2ccc(C(F)(F)F)cc2)cc1Cl)C(=O)OC(C)(C)C]

15 g (21.42 mmol) of the racemic ethyl 5-{(tert-butoxy-carbonyl)[2-(2-{[3-chloro-4'-(trifluoromethyl)-biphenyl-4-yl]methoxy}phenyl)ethyl]amino}-5,6,7,8-tetrahydroquinoline-2-carboxylate (Example 22A) were separated by supercritical fluid chromatography (SFC) on a chiral phase into the enantiomers [column: Chiralpak OD-H, 20 μm, 400 mm×50 mm; mobile phase: carbon dioxide/isopropanol 70:30 (v/v); flow rate: 400 ml/min; pressure: 80 bar; UV detection: 220 nm; temperature: 37° C.]:

Example 5A (Enantiomer 1)

Yield: 5830 mg
Rt=2.83 min; chemical purity ≥99.9%; ≥99% ee
[column: Chiralpak OD-H, 5 μm, 250 mm×4.6 mm; mobile phase: carbon dioxide/isopropanol 70:30 (v/v); flow rate: 3 ml/min; UV detection: 210 nm].

Example 6A (Enantiomer 2)

Yield: 6330 mg
Rt=5.30 min; chemical purity ≥99%; ≥98% ee
[column: Chiralpak OD-H, 5 μm, 250 mm×4.6 mm; mobile phase: carbon dioxide/isopropanol 70:30 (v/v); flow rate: 3 ml/min; UV detection: 210 nm].

Example 7A

Ethyl 5-{[2-(2-{[3-chloro-4'-(trifluoromethyl)biphenyl-4-yl]methoxy}phenyl)ethyl]amino}-5,6,7,8-tetrahydroquinoline-2-carboxylate dihydrochloride (Enantiomer 1)

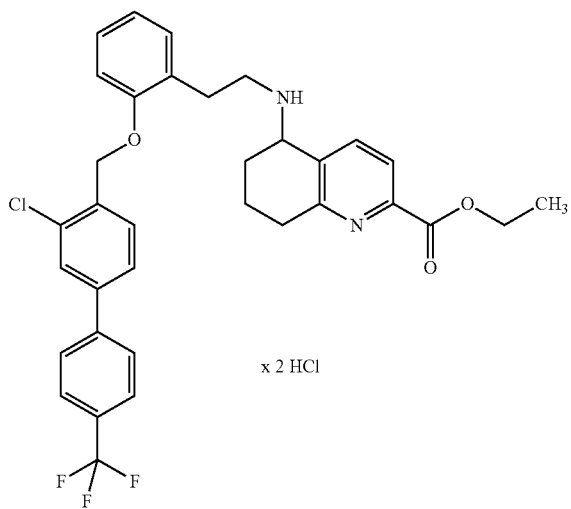 [SMILES: CCOC(=O)c1ccc2c(n1)CCCC2NCCc1ccccc1OCc1ccc(-c2ccc(C(F)(F)F)cc2)cc1Cl]

x 2 HCl 3208 ml of a 4 N solution of hydrogen chloride in dioxane, diluted with a further 2240 ml of dioxane, were added to 455 g (641.56 mmol) of ethyl 5-{(tert-butoxycarbonyl)[2-(2-{[3-chloro-4'-(trifluoromethyl)-biphenyl-4-yl]methoxy}phenyl)ethyl]amino}-5,6,7,8-tetrahydroquinoline-2-carboxylate (Enantiomer 1, Example 1A), and the mixture was stirred at room temperature overnight. The reaction solution was then concentrated to dryness and the residue was dried under high vacuum overnight. This gave 448.7 g (641.59 mmol, about 100% of theory) of the target product.

LC-MS (Method A): Rt=1.06 min; m/z=609/611 (M+H)+.

Example 8A

Ethyl 5-{[2-(2-{[3-chloro-4'-(trifluoromethyl)biphenyl-4-yl]methoxy}phenyl)ethyl]amino}-5,6,7,8-tetrahydroquinoline-2-carboxylate (Enantiomer 1)

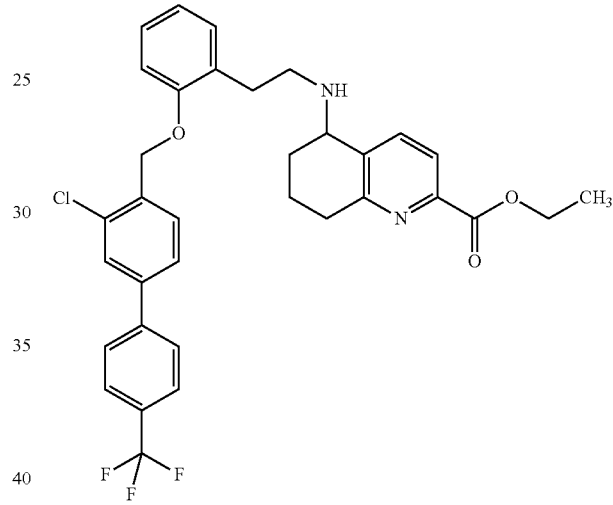

448.7 g (641.59 mmol) of ethyl 5-{[2-(2-{[3-chloro-4'-(trifluoromethyl)biphenyl-4-yl]methoxy}phenyl)-ethyl]amino}-5,6,7,8-tetrahydroquinoline-2-carboxylate dihydrochloride (Enantiomer 1, Example 3A) were taken up in 6869 ml of THF, 268 ml of triethylamine were added and the mixture was stirred at room temperature for 1 h. The precipitated triethylammonium chloride crystals were then filtered off and washed with THF. The filtrate obtained was evaporated to dryness. The residue was dissolved in ethyl acetate, washed twice with 10% strength aqueous sodium chloride solution, dried over magnesium sulphate, filtered and once more evaporated to dryness. This gave 391 g (620.59 mmol, 97% of theory) of the target compound.

LC-MS (Method A): Rt=1.08 min; m/z=609/611 (M+H)+.
1H-NMR (400 MHz, DMSO-d6, δ/ppm): 1.27 (t, 3H), 1.57-1.72 (m, 2H), 1.76-1.87 (m, 1H), 1.87-1.95 (m, 1H), 1.95-2.07 (m, 1H), 2.65-2.88 (m, 6H), 3.75 (br. s, 1H), 4.28 (q, 2H), 5.19 (s, 2H), 6.92 (t, 1H), 7.08 (d, 1H), 7.16-7.26 (m, 2H), 7.65-7.77 (m, 3H), 7.84 (d, 3H), 7.89 (s, 1H), 7.95 (d, 2H).

Example 9A

Ethyl 5-([2-(2-{[3-chloro-4'-(trifluoromethyl)biphenyl-4-yl]methoxy}phenyl)ethyl] {2-[4-(methoxycarbonyl)phenyl]ethyl}amino)-5,6,7,8-tetrahydroquinoline-2-carboxylate (Enantiomer 1)

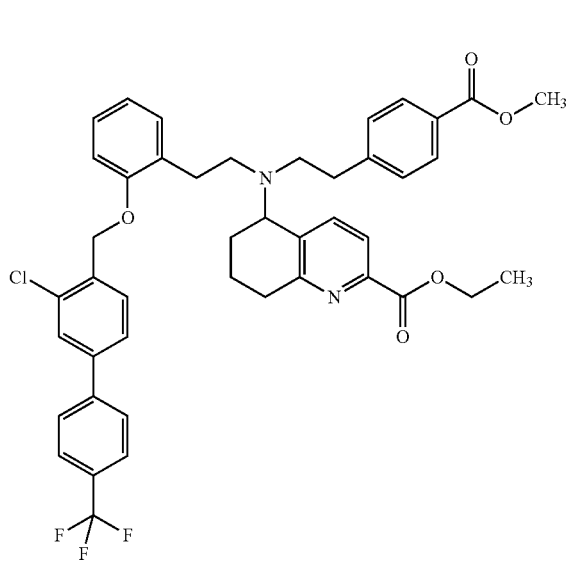 [SMILES: CCOC(=O)c1ccc2c(n1)CCCC2N(CCc1ccc(C(=O)OC)cc1)CCc1ccccc1OCc1ccc(-c2ccc(C(F)(F)F)cc2)cc1Cl]

A suspension of 378 g (620.59 mmol) of ethyl 5-{[2-(2-{[3-chloro-4'-(trifluoromethyl)biphenyl-4-yl]methoxy}phenyl)ethyl]amino}-5,6,7,8-tetrahydroquinoline-2-carboxylate (Enantiomer 1, Example 4A), 360 g (1241.19 mmol) of methyl 4-(2-iodoethyl)benzoate and 98.66 g (930.89 mmol) of anhydrous sodium carbonate in 8191 ml of dry acetonitrile was stirred at a bath temperature of 110° C. overnight. A further 360 g (1241.19 mmol) g of methyl 4-(2-iodoethyl)benzoate and 128.65 g (930.89 mmol) of powdered potassium carbonate were then added, and the mixture was heated under reflux for another 72 h. After cooling of the reaction mixture, the inorganic salts were filtered off and the filtrate obtained was evaporated to dryness. The resulting residue was taken up in ethyl acetate, washed twice with 10% strength aqueous sodium chloride solution, dried over magnesium sulphate, filtered and then once more evaporated to dryness. The residue obtained was purified chromatographically on silica gel (9 kg) in 2 portions (mobile phase: petroleum ether/ethyl acetate 8:2→7:3). This gave 397 g (551.32 mmol, 89% of theory) of the target compound.

LC-MS (Method A): Rt=1.67 min; m/z=771/773 (M+H)+.

1H-NMR (400 MHz, DMSO-d6, δ/ppm): 1.27 (t, 3H), 1.37-1.52 (m, 1H), 1.52-1.67 (m, 1H), 1.85-1.96 (m, 1H), 1.96-2.05 (m, 1H), 2.56-2.80 (m, 10H), 3.81 (s, 3H), 3.97-4.09 (m, 1H), 4.26 (q, 2H), 5.07 (m, 2H), 6.87 (t, 1H), 7.01-7.16 (m, 4H), 7.23 (t, 1H), 7.35-7.48 (m, 2H), 7.53 (d, 1H), 7.61 (d, 1H), 7.74 (d, 2H), 7.77-7.89 (m, 5H).

COMPARATIVE EXAMPLES

Comparative Example 11

(5S)-5-{[2-(4-carboxyphenyl)ethyl][2-(2-{[3-chloro-4'-(trifluoromethyl)[biphenyl]-4-yl]methoxy}phenyl)ethyl]amino}-5,6,7,8-tetrahydroquinoline-2-carboxylic acid

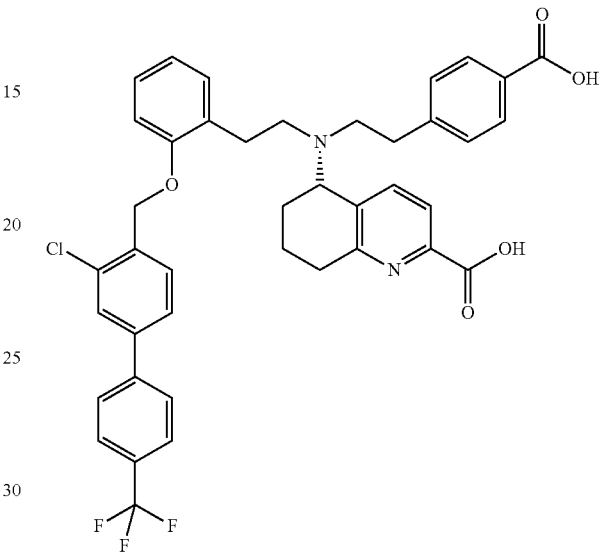

2450 mg (3.18 mmol) of ethyl (5S)-5-([2-(2-{[3-chloro-4'-(trifluoromethyl)[biphenyl]-4-yl]methoxy}phenyl)ethyl] {2-[4-(methoxycarbonyl)phenyl]ethyl}amino)-5,6,7,8-tetrahydroquinoline-2-carboxylate (example 1A, Enantiomer 2) were dissolved in 25 ml of dioxane, 9.5 ml of 1 N aqueous sodium hydroxide solution were added and the mixture was then stirred at room temperature overnight. After the reaction had gone to completion, the dioxane was removed on a rotary evaporator and the mixture that remained was diluted with about 50 ml of water. The mixture was then acidified to pH 4-5 using acetic acid. The precipitated solid was filtered off with suction and washed repeatedly with water (about 50 ml of water in total). The solid was then taken up in 50 ml of water and stirred at room temperature overnight. After another filtration with suction, the solid was again washed with water and then dried under high vacuum overnight at 40° C. In this manner, 2300 mg (2.9 mmol, 93% purity, contains unknown amounts of mono sodium salt, having same retention time) of the title compound were obtained.

LC-MS (Method A): Rt=1.37 min; m/z=729/731 (M+H)+.

1H-NMR (400 MHz, DMSO-d6): δ [ppm]=1.38-1.71 (m, 2H), 1.84-2.08 (m, 2H), 2.59-2.84 (m, 10H), 3.97-4.11 (m, 1H), 4.99-5.16 (m, 2H), 6.87 (t, 1H), 7.05 (br. d, 2H), 7.12 (br. d, 2H), 7.23 (br. t, 1H), 7.38-7.48 (m, 2H), 7.54 (d, 1H), 7.62 (d, 1H), 7.71-7.91 (m, 7H), 11.90-13.60 (br. s, about 2H).

XRPD: amorphous phase, see FIG. 33

Determination of the absolute configuration of comparative example 11 via VCD spectroscopy:

Vibrational circular dichroism (VCD) is an established methodology to determine absolute configuration of chiral molecules (see United States Pharmacopeial Convention (USP) and The National Formulary (USP—NF), second suppl. USP—NF 34, chapters 782 and 1782, Jun. 1, 2016 and Abs. config. by VCD, white paper BioTools, 2017).

The steps involved in determination are as follows:
1. The experimental VCD spectrum was measured using DMSO. The sample, example 1 was measured at a concentration of 5.5 mg/0.15 ml.
2. The VCD of one of the enantiomers is calculated using ab initio calculations using Gaussian09™ (commercially available software package). The VCD spectrum of the other enantiomer is then obtained by reversing the signs of all the bands or calculating the VCD of the mirror-image structure.
3. The last step is a comparison of the experimental spectrum to the two calculated spectra to determine the enantiomer that gives the best correlation between the signs and the signal intensities. The confidence level of overlap between two such spectra can be calculated using CompareVOA™ software.

VCD spectrometer: ChiralIR-2X w/DualPEM
Concentration: 5.5 mg/0.15 ml of example 1 in DMSO
Resolution: 4 cm-1
PEM setting: 1400 cm-1
Number of scans/measurement time: 20 hours
Sample cell: BaF2
Path length: 100 □m Calculation Details:
Gaussian version: Gaussian 09
Total low-energy conformer used for Boltzman sum: 92
Methodology and basis set for DFT calculation: B3LYP/ 6-31G(d)
Absolute configuration calculated: S Absolute configuration of comparative example 11 was assigned as (S)-enantiomer based on the agreement of VCD spectra. The confidence level of assignment was 94%.

Determination of thermal stability of comparative example 11:

0.3 mg of the comparative example 11 were solved in 0.1 ml dimethylsulfoxide and 0.4 ml acetonitrile. Then 1.0 ml water was added. For complete dissolution the HPLC vial was shaken and sonicated. This solution was immediately analyzed by HPLC (reference at t0). 0.3 mg of the test compound was weighed into another HPLC vial. The vial was capped and stored for 7 days in a heating block at 90° C.

After this time the vial was decapped and 0.1 ml dimethylsulfoxide and 0.4 ml acetonitrile were added to the stressed compound. Then 1.0 ml water was added. For complete dissolution the HPLC vial was shaken and sonicated. The sample was analyzed by HPLC (sample after 1 week). The peak areas in percentage are used for quantification.

TABLE 11

| HPLC-method eluent: | A = 5 ml HClO4/L water B = ACN | gradient: | Time (min.) | % B | flow (mL/min.) |
|---|---|---|---|---|---|
| column: | Nucleodur 100 C18ec 3 μm 50 * 2 mm | | 0.00 | 2.0 | 0.750 |
| Temp.: | 30 ° C. | | 1.00 | 2.0 | 0.750 |
| UV WL.: | 210 nm | | 9.00 | 98.0 | 0.750 |
| HPLC flow: | 0.750 mL/min. | | 13.00 | 98.0 | 0.750 |
| | | | 13.50 | 2.0 | 0.750 |
| | | | 15.00 | 2.0 | 0.750 |

Comparative example 11 was found to be stable during the test period.

In addition, several examples disclosed in WO 14/012934-A1 do only show limited thermal stability (at 90° C., 7 days): e.g. example 2 (comparative example 5, experimental part), 24 (comparative example 6, experimental part), 25 (comparative example 7, experimental part), 28 (comparative example 8, experimental part), 29 (comparative example 9, experimental part) and for example 31 (comparative example 10, experimental part).

Comparative Example 12

(5R)-5-{[2-(4-carboxyphenyl)ethyl][2-(2-{[3-chloro-4'-(trifluoromethyl)[biphenyl]-4-yl]methoxy}phenyl)ethyl]amino}-5,6,7,8-tetrahydroquinoline-2-carboxylic acid (Enantiomer 1)

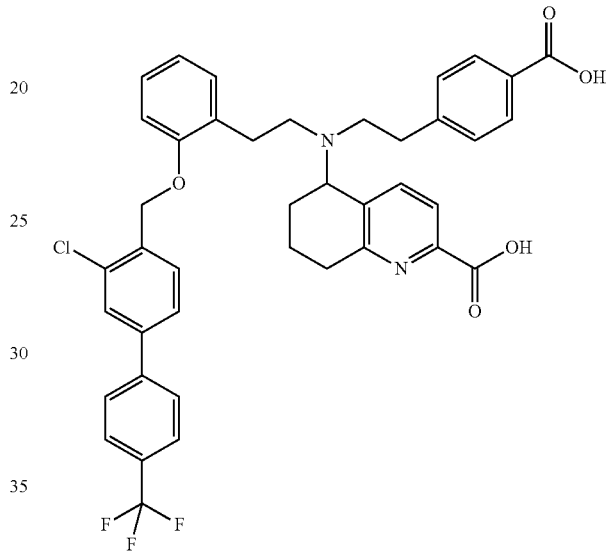

291 g (377.29 mmol) of ethyl 5-([2-(2-{[3-chloro-4'-(trifluoromethyl)biphenyl-4-yl]methoxy}phenyl)-ethyl]{2-[4-(methoxycarbonyl)phenyl]ethyl}amino)-5,6,7,8-tetrahydroquinoline-2-carboxylate (Enantiomer 1, Example 5A) were dissolved in 3000 ml of dioxane, 1132 ml of 1 N aqueous sodium hydroxide solution were added and the mixture was then stirred at room temperature overnight. After the reaction had gone to completion, the dioxane was removed on a rotary evaporator and the mixture that remained was diluted with about 6000 ml of water. The mixture was then acidified to pH 4-5 using acetic acid. The precipitated solid was filtered off with suction and washed repeatedly with water (about 3000 ml of water in total). The solid was then dried under high vacuum 3 d at room temperature using the drying agent phosphorus pentoxide. The drying agent was then removed and the solid was dried at 40° C. for a further 48 h. In this manner, 249 g (342.15 mmol, 91% of theory) of the title compound were obtained.

LC-MS (Method A): Rt=1.33 min; m/z=729/731 (M+H)+.

1H-NMR (400 MHz, DMSO-d6): δ [ppm]=1.37-1.66 (m, 2H), 1.84-2.05 (m, 2H), 2.56-2.81 (m, 10H), 3.98-4.08 (m, 1H), 5.01-5.14 (m, 2H), 6.87 (t, 1H), 7.05 (d, 2H), 7.12 (d, 2H), 7.23 (t, 1H), 7.39-7.47 (m, 2H), 7.54 (d, 1H), 7.62 (d, 1H), 7.71-7.90 (m, 7H), 11.60-13.85 (br. s, about 2H).

As for comparative example 11 the absolute configuration was determined to be (5S) the corresponding absolute configuration of comparative example 12 should be the opposite, i.e. (5R).

Comparative Example 13

Mono sodium (5R)-5-{[2-(4-carboxyphenyl)ethyl][2-(2-{[3-chloro-4'-(trifluoromethyl)[biphenyl]-4-yl]methoxy}phenyl)ethyl]amino}-5,6,7,8-tetrahydroquinoline-2-carboxylate (Enantiomer 1)

A vessel was charged with 60 g amorphous (5R)-5-([2-(2-{[3-chloro-4'-(trifluoromethyl)[biphenyl]-4-yl]methoxy}phenyl)ethyl]{2-[4-(methoxycarbonyl)phenyl]ethyl}amino)-5,6,7,8-tetrahydroquinoline-2-carboxylate (comparative example 12) and 800 g acetone. The vessel was heated to reflux temperature. The solid which formed under reflux temperature, was filtered after cooling to room temperature.

Yield: 8 g of dry product, 13% o. th.
Enantiomeric purity (HPLC method C): 100% ee
(ICP): sodium content: 3.1% sodium Comparative Example 14 (5R)-5-{[2-(4-carboxyphenyl)ethyl][2-(2-{[3-chloro-4'-(trifluoromethyl)[biphenyl]-4-yl]methoxy}phenyl)ethyl]amino}-5,6,7,8-tetrahydroquinoline-2-carboxylic acid monohydrate II (Enantiomer 1)

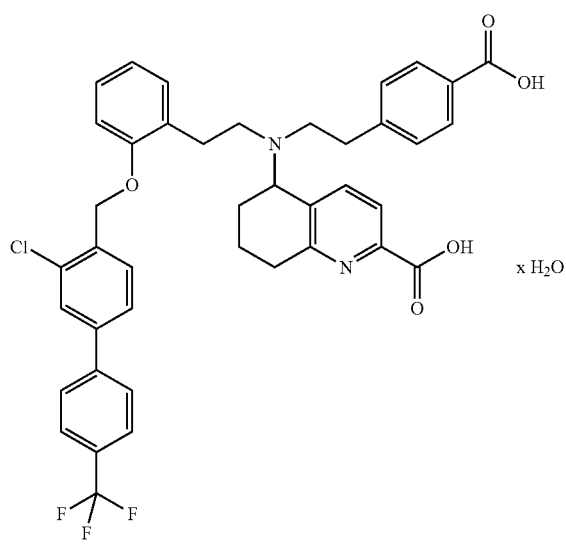 [SMILES: O=C(O)c1ccc(CCN(CCc2ccccc2OCc2ccc(-c3ccc(C(F)(F)F)cc3)cc2Cl)C2CCCc3nc(C(=O)O)ccc32)cc1]

174.2 g comparative example 12 were stirred under reflux with 2003.3 g acetone. The mixture was cooled to 20° C. and insoluble solid (19.5 g after drying) was filtered off. 273 g acetone were added to the filtrate, it was heated to 57° C. and 1101.4 g water and 0.4 g seed crystals of monohydrate II, R enantiomer (prepared from small scale pre experiments analogously to the present procedure) were added. Further 1101.4 g water were added and it was stirred overnight at room temperature. The product was filtered off and dried at 55° C. in vacuum (30 mbar) to 143.8 g.

Further 20.3 g have been obtained from 21.0 g comparative example 12 prepared according to the same procedure.

The solids were combined to 164.1 g and 161.0 g of these solids were stirred under reflux with 1993.0 g acetone. At this temperature 930.0 g water and 0.8 g seed crystals of monohydrate II, R enantiomer (prepared from small scale pre experiments analogously to the present procedure) were added and it was cooled to 50° C. Further 200.0 g water and 400.0 g acetone were added to improve stirrability. It was stirred for 1 h at 50° C., 1263.0 g water were added, it was stirred for 30 min, cooled within 2 h to 20° C. and stirred overnight at room temperature. The product was filtered off and dried at 55° C. in vacuum (30 mbar) to 154.4 g.

A part of the solid (95.0 g) was dissolved at 40° C. in 916.7 g of acetone, cooled to room temperature and the solution was filtered for clarification. 170.1 g of water were added, after 30 min seed crystals of monohydrate II, R enantiomer (prepared from small scale pre experiments analogously to the present procedure) were added and it was stirred overnight. The thin suspension was heated to 50° C., the resulting solution was cooled to room temperature, inoculated with seed crystals of monohydrate II, R enantiomer (prepared from small scale pre experiments analogously to the present procedure) and stirred overnight. The solid was filtered off, washed with a mixture of 76.0 g acetone and 19.0 g water (8:2) and sucked dry to 68.4 g.

The filtrate was concentrated at 40° C./250 to 15 mbar and the precipitated solid was filtered off. 28.2 g solid were dissolved in 157.2 g acetone water mixture (9:1 w/w) at 55° C., cooled to 15° C. After addition of 10 g water it was inoculated with seed crystals of monohydrate II, R enantiomer (prepared from small scale pre experiments analogously to the present procedure) and stirred overnight at 15° C. The suspension was heated to 50° C., stirred for 30 min and cooled to 20° C. within 4 h. It was again heated to 50° C. within 1 h, cooled to 15° C. within 4.5 h and stirred overnight at 15° C. The solid was filtered off, washed with 28 g of an acetone water (8:2 w/w) mixture and sucked dry to 20.6 g.

The solids were combined to 87.0 g of the target compound.

Enantiomeric purity (HPLC method C): 99.8% ee
Purity (Method M, area): 99.7%, Rf 9.33 min
XRPD: Monohydrate II

EXAMPLES

Example 1

(5S)—{[2-(4-Carboxyphenyl)ethyl][2-(2-{[3-chloro-4'-(trifluoromethyl)biphenyl-4-yl]methoxy}phenyl)-ethyl]amino}-5,6,7,8-tetrahydroquinoline-2-carboxylic acid monohydrate II (Seed Crystals)

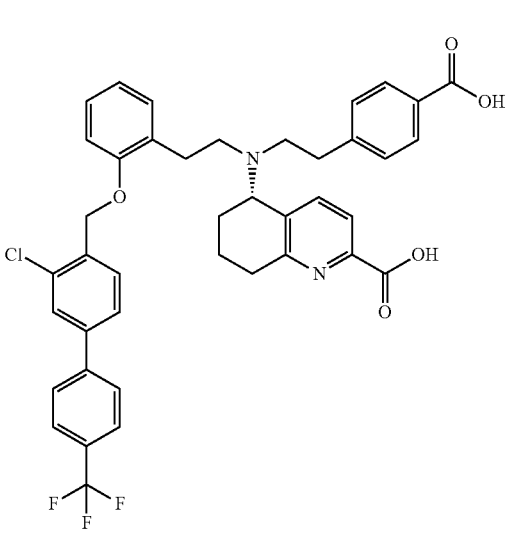

(I-M-II)

2.0 g of (5S)—{[2-(4-Carboxyphenyl)ethyl][2-(2-{[3-chloro-4'-(trifluoromethyl)biphenyl-4-yl]methoxy}-phenyl)ethyl]amino}-5,6,7,8-tetrahydroquinoline-2-carboxylic acid of formula (I) (manufactured in analogy to comparative example 11) were dissolved in 16.2 g acetone and 1.8 g water (8:1 mixture), there were more 1.8 g of water added. The clear solution was stirred overnight and crystallization began after 1.5 h. The solid was filtered off with suction, washed with 2 g of acetone/water (8:2) and dried overnight at 60° C. in vacuo with nitrogen air:

Yield: 1.5 g of white solid, 75% of theory

XRPD: monohydrate II, X-Ray powder diffractogram is shown in FIG. 34

| Reflections (Peak maxima) [°2 Theta] |
|---|
| 5.7 |
| 6.1 |
| 7.1 |
| 8.5 |
| 9.4 |
| 9.9 |
| 10.2 |
| 10.8 |
| 11.4 |
| 11.6 |
| 11.7 |
| 12.2 |
| 12.7 |
| 13.0 |
| 13.9 |
| 14.2 |
| 14.5 |
| 15.1 |
| 15.3 |
| 15.7 |
| 15.9 |
| 16.1 |
| 16.4 |
| 17.1 |
| 17.3 |
| 17.7 |
| 17.9 |
| 18.3 |
| 18.5 |
| 18.7 |
| 19.1 |
| 19.7 |
| 19.8 |
| 20.2 |
| 20.4 |
| 20.8 |
| 21.1 |
| 21.2 |
| 21.6 |
| 22.0 |
| 22.3 |
| 22.8 |
| 23.0 |
| 23.4 |
| 23.8 |
| 24.2 |
| 24.4 |
| 24.4 |
| 25.1 |
| 25.5 |
| 26.2 |
| 26.4 |
| 27.1 |
| 27.4 |
| 27.7 |
| 28.0 |
| 28.5 |
| 28.9 |
| 29.2 |
| 29.5 |
| 29.7 |
| 30.0 |
| 30.4 |
| 30.6 |
| 31.2 |
| 31.6 |
| 32.2 |
| 32.4 |
| 32.8 |

Example 2

(5S)—{[2-(4-Carboxyphenyl)ethyl][2-(2-{[3-chloro-4'-(trifluoromethyl) biphenyl-4-yl]methoxy}phenyl)-ethyl]amino}-5,6,7,8-tetrahydroquinoline-2-carboxylic acid as Monohydrate II (Route 3, Crystallization from Acetone, Methanol and Water)

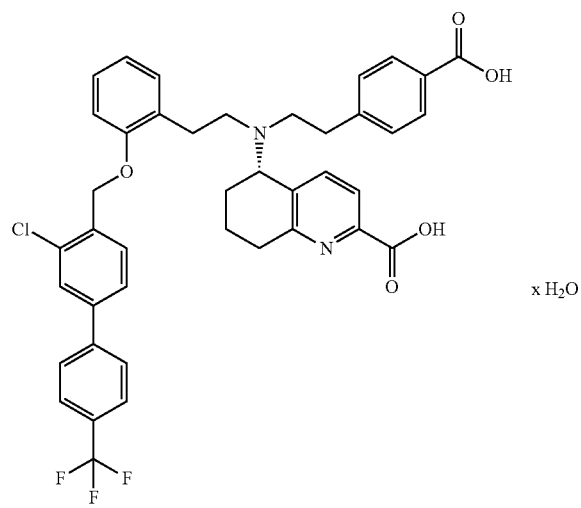 [SMILES: O=C(O)c1ccc(CCN(CCc2ccccc2OCc2ccc(-c3ccc(C(F)(F)F)cc3)cc2Cl)[C@H]2CCCc3nc(C(=O)O)ccc32)cc1]

1067 g of tetrahydrofuran were placed in a 6 L glass stirring apparatus and 333 g (0.396 mol) of naphthalene-1,5-disulfonic acid-butyl (5S)-5-({2-[4-(butoxycarbonyl) phenyl] ethyl} [2-(2-{[3-chloro-4'-(trifluoromethyl)[biphenyl]-4-yl]methoxy}phenyl)ethyl]amino)-5,6,7,8-tetrahydroquinoline-2-carboxylate (1:1) adduct (example 4A) added in portions with stirring. 1335 ml of water and then aqueous ammonia (27%) were added at 20° C. to 25° C. until a pH of 7.8 to 8.2 was reached (approx. 46 g). 1440 g of diisopropyl ether were added, the aqueous phase was separated off, the organic phase was washed again with 1335 ml of water/1 ml of 27% ammonia water and then with 1335 ml of water. The organic phase was filtered through a Seitz filter plate covered with 200 g of sodium sulfate (anhydrous), it was rinsed with 200 g of diisopropyl ether and the filtrate was concentrated in vacuo at 40° C. to give 267 g of evaporation residue.

The residue after evaporation was dissolved in 848 g of dioxane, 1583 g of 1N sodium hydroxide solution were added and the mixture was stirred at 60° C. for 5.5 h. 1480 g of ethyl acetate were then added at 20° C., the aqueous product phase (disodium salt solution) was separated off, washed with 1480 g of ethyl acetate and residual ethyl acetate was distilled off at a maximum of 40° C. in vacuo. The residue was diluted with 2500 g of water and a portion of the disodium salt solution (1178 g) was added dropwise to a mixture of 1095 g of tetrahydrofuran and 137 g of 10% hydrochloric acid until a pH of 4.0 was reached.

The consumption of disodium salt solution is set in relation to the amount of hydrochloric acid submitted and the amount of hydrochloric acid for the conversion of the further partial amounts is calculated. The second aliquot of the disodium salt solution (1789 g) was added dropwise to the calculated amounts of tetrahydrofuran (1789 g) and 10% strength hydrochloric acid (208 g) until a pH of 4.0 was reached.

The third aliquot of the disodium salt solution (1510 g) was added dropwise to the calculated amounts of tetrahydrofuran (1505 g) and 10% strength hydrochloric acid (175 g) until a pH of 4.0 was reached.

The combined organic phases were concentrated in vacuo at a maximum of 40° C. until solvent-free water condensed on the reflux condenser. The precipitated solid was filtered off with suction and washed with 750 g of water.

Using the same procedure, a 2nd and 3rd part each 333 g of naphthalene-1,5-disulphonic acid butyl-(5S)-5-({2-[4-(butoxycarbonyl) phenyl] ethyl} [2-(2-{[3-chloro-4'-(trifluoromethyl) [biphenyl]-4-yl]methoxy} phenyl) ethyl] amino)-5,6,7,8-tetrahydroquinoline-2-carboxylate (1:1) adduct (example 4A) were converted according to the procedure described above.

The combined moist products were dried at 60° C. in a stream of nitrogen under vacuum to give 587 g (ca. 91% o.th.) of target compound of formula I.

Crystallization:

The solid (587 g) was heated to 50° C. with a mixture of 3674 g of acetone and 470 g of water. The solution obtained was filtered through a Seitz filter plate and heated to 40° C. The filtrate was mixed with 1.5 g of seed crystals of (5S)-5-{[2-(4-carboxyphenyl) ethyl] [2-(2-{[3-chloro-4'-(trifluoromethyl) [biphenyl]-4-yl] methoxy} phenyl) ethyl] amino}-5,6,7,8-tetrahydroquinoline-2-carboxylic acid monohydrate II (example 1), cooled to 20° C. in 2 h, stirred for 0.5 h and within 2 h heated again to 50° C. The mixture was stirred for 0.5 h, cooled to 20° C. in 3 h, stirred for 0.5 h and heated again to 50° C. over the course of 2 h. It was cooled to 20° C. in 3 h, stirred for 0.5 h and the solid was filtered off with suction. The moist product was washed with a mixture of 800 g of acetone and 90 g of water and dried to a constant weight of 361 g at 25° C. in a stream of nitrogen under vacuum.

The in-process control of the quality and modification of the product received did not meet the requirements. Therefore, it was re-crystallized again.

The solid (361 g) was heated to 50° C. with a mixture of 1949 g of acetone and 217 g of water. The solution obtained was filtered through a Seitz filter plate and heated to 50° C. It was mixed with 1.5 g of seed crystals of (5S)-5-{[2-(4-carboxyphenyl) ethyl] [2-(2-{[3-chloro-4'-(trifluoromethyl) [biphenyl]-4-yl]methoxy} phenyl) ethyl] amino}-5,6,7,8-tetrahydroquinoline-2-carboxylic acid monohydrate II (example 1), cooled to 20° C. in 3 h, stirred for 0.5 h and within 3 h heated again to 50° C. The mixture was stirred for 0.5 h, cooled to 20° C. in 3 h, stirred for 0.5 h and again heated to 50° C. over 3 h and stirred for 0.5 h. It was cooled to 20° C. in 3 h, stirred for 0.5 h and the solid was filtered off with suction. The moist product was dried at 25° C. in a stream of nitrogen under vacuum to constant weight of 271 g.

The in-process control confirmed sufficient quality, but not the desired modification of the product obtained. Therefore, it was recrystallized again.

The solid (271 g) was heated to 50° C. with a mixture of 1668 g of acetone and 75 g of water. The solution obtained was filtered through a Seitz filter plate and heated to 50° C. It was cooled to 45° C., 1.5 g of seed crystals of (5S)-5-{[2-(4-carboxyphenyl) ethyl] [2-(2-{[3-chloro-4'-(trifluoromethyl) [biphenyl]-4-yl] methoxy} phenyl) ethyl] amino}-5,6,7,8-tetrahydroquinoline-2-carboxylic acid monohydrate II (example 1), cooled to 20° C. in 3 h, stirred for 0.5 h and heated to 40° C. within 1 h. The suspension was stirred for 0.5 h, cooled to 20° C. in 3 h and stirred, and the solid was filtered off with suction. The moist product was dried to constant weight at 25° C. in a stream of nitrogen under vacuum.

The in-process control confirmed the quality and modification of the product in accordance with the requirements.

Yield: 117 g monohydrate II; 18% of the theoretically yield.
Enantiomeric purity (HPLC method C): 99.6% ee
Purity (area): 99.8% (Method M, Rt 9.33 min)
XRPD: monohydrate II, X-Ray powder diffractogram is shown in FIG. 35
after micronization:
Enantiomeric purity (HPLC method C): 100.0% ee
Purity (area): 99.7% (Method M, Rt 9.35 min)
XRPD: monohydrate II with partial amorphization, X-Ray powder diffractogram is shown in FIG. 36

Monohydrate II Before Micronization: See FIG. 35

| Reflections (Peak maxima) [°2 Theta] |
| --- |
| 5.7 |
| 6.1 |
| 6.3 |
| 7.1 |
| 8.5 |
| 9.9 |
| 10.1 |
| 10.2 |
| 10.8 |
| 11.4 |
| 11.6 |
| 11.8 |
| 12.2 |
| 12.7 |
| 13.0 |
| 13.9 |
| 14.3 |
| 14.5 |
| 15.1 |
| 15.3 |
| 15.7 |
| 15.9 |
| 16.2 |
| 16.4 |
| 17.1 |
| 17.3 |
| 17.7 |
| 17.9 |
| 18.3 |
| 18.5 |
| 18.8 |
| 19.2 |
| 19.8 |
| 20.3 |
| 20.5 |
| 20.8 |
| 21.1 |
| 21.3 |
| 21.6 |
| 22.0 |
| 22.4 |
| 22.8 |
| 23.1 |
| 23.3 |
| 23.5 |
| 23.8 |
| 24.2 |
| 24.5 |
| 25.1 |
| 25.4 |
| 25.6 |
| 26.2 |
| 26.4 |
| 26.7 |
| 27.1 |
| 27.4 |
| 27.7 |
| 28.1 |
| 28.3 |
| 28.5 |
| 28.9 |
| 29.2 |
| 29.5 |
| 29.8 |
| 30.0 |
| 30.6 |
| 30.7 |
| 31.2 |
| 31.7 |
| 32.2 |
| 32.4 |
| 32.8 |
| 34.8 |
| 35.3 |
| 36.3 |

Monohydrate II after Micronization (Partial Amorphization), FIG. 36

| Reflections (Peak maxima) [°2 Theta] |
| --- |
| 5.7 |
| 6.1 |
| 7.1 |
| 8.5 |
| 9.9 |
| 10.1 |
| 10.8 |
| 11.5 |
| 11.6 |
| 12.2 |
| 12.7 |
| 13.0 |
| 13.9 |
| 14.2 |
| 15.2 |
| 15.3 |
| 15.7 |
| 16.4 |
| 17.2 |
| 17.3 |
| 17.7 |
| 18.0 |
| 18.3 |
| 18.5 |
| 18.8 |
| 19.1 |
| 19.8 |
| 20.2 |
| 20.8 |
| 21.1 |
| 21.3 |
| 21.6 |
| 22.1 |
| 22.4 |
| 23.1 |
| 23.4 |
| 23.5 |
| 23.9 |
| 24.3 |
| 24.5 |
| 25.2 |
| 25.4 |
| 25.6 |
| 26.3 |

| Reflections (Peak maxima) [°2 Theta] |
|---|
| 27.1 |
| 27.5 |
| 28.9 |
| 29.5 |
| 30.6 |
| 32.4 |

Example 3

(5S)—{[2-(4-Carboxyphenyl)ethyl][2-(2-{[3-chloro-4'-(trifluoromethyl)biphenyl-4-yl]methoxy}phenyl)-ethyl]amino}-5,6,7,8-tetrahydroquinoline-2-carboxylic acid monohydrate I (Seed Crystals)

2.0 g (5S)—{[2-(4-Carboxyphenyl)ethyl][2-(2-{[3-chloro-4'-(trifluoromethyl)biphenyl-4-yl]methoxy}-phenyl)ethyl]amino}-5,6,7,8-tetrahydroquinoline-2-carboxylic acid of formula (I) (manufactured in analogy to comparative example 11) were dissolved in 8.1 g of methanol and 1.8 g of water, 8.1 g of acetone and a further 1.8 g of water were added. It was stirred overnight. The solid was filtered off with suction, washed with 2 g of acetone/water (8:2) and dried overnight at 60° C. in vacuo with nitrogen air.

Yield: 1.8 g of white solid, 90% of theory.

Enantiomeric purity (HPLC method C): 92.0% ee

Purity (area): 97.3% (Method M, Rt 8.94 min)

XRPD: monohydrate I, see FIG. 37

| Reflections (Peak maxima) [°2 Theta] |
|---|
| 5.7 |
| 7.1 |
| 9.9 |
| 10.2 |
| 10.7 |
| 11.4 |
| 12.2 |
| 12.8 |
| 14.0 |
| 15.1 |
| 15.6 |
| 15.9 |
| 17.2 |
| 17.7 |
| 19.2 |
| 19.5 |
| 19.8 |
| 20.2 |
| 20.3 |
| 20.7 |
| 21.0 |
| 22.2 |
| 22.9 |
| 23.4 |
| 23.8 |
| 24.2 |
| 24.5 |
| 25.0 |
| 25.7 |
| 26.0 |
| 26.4 |
| 28.8 |
| 29.1 |

| Reflections (Peak maxima) [°2 Theta] |
|---|
| 30.5 |
| 32.1 |

Example 4

(5S)—{[2-(4-Carboxyphenyl)ethyl][2-(2-{[3-chloro-4'-(trifluoromethyl) biphenyl-4-yl]methoxy}phenyl)-ethyl]amino}-5,6,7,8-tetrahydroquinoline-2-carboxylic acid as Monohydrate I Release of Dibutylester from NSA Salt:

800 g of tetrahydrofuran were placed in a 6 L glass stirring apparatus and 250 g (0.30 mol) of naphthalene-1,5-disulfonic acid-butyl-(5S)-5-({2-[4-(butoxycarbonyl) phenyl]ethyl} [2-(2-{[3-chloro-4'-(trifluoromethyl) [biphenyl]-4-yl]methoxy} phenyl) ethyl] amino)-5,6,7,8-tetrahydroquinoline-2-carboxylate (1:1) (example 4A) was added in portions with stirring. 1 L of water and then 27% ammonia water were added at 20° C. to 25° C. until a pH of 7.8 to 8.2 was reached (approx. 27 g). 1080 g of diisopropyl ether were added, the aqueous phase was separated off, the organic phase was extracted again with 1 L of water/0.8 ml of 27% ammonia water and then washed with 1 L of water. The organic phase was filtered through a Seitz filter plate covered with 150 g of sodium sulfate (anhydrous), it was rinsed with 150 g of diisopropyl ether and the filtrate was concentrated at 40° C. in vacuo to 192 g of evaporation residue.

Saponification of Dibutylester:

The evaporation residue was dissolved in 610 g of tetrahydrofuran, 1139 g of 1N sodium hydroxide solution were added and the mixture was stirred at 60° C. for 24 h. 875 g of ethyl acetate were then added at 20° C., the aqueous product phase (disodium salt solution) was separated off and residual ethyl acetate was distilled off at a maximum of 40° C. in vacuo.

Formation of Free Acid of Formula I:

The residue was diluted with 1875 g of water, filtered through a Seitz filter plate and a portion of the disodium salt solution (835 g) was added dropwise to a mixture of 821 g of tetrahydrofuran and 103 g of 10% hydrochloric acid until a pH value of 4.0 was reached. 174 g of sodium chloride and 420 g of tetrahydrofuran were added and the organic product phase was separated off.

The consumption of disodium salt solution is set in relation to the amount of hydrochloric acid submitted and the amount of hydrochloric acid for the conversion of the further partial amounts is calculated. The second aliquot of the disodium salt solution (2000 g) was added dropwise to the calculated amounts of tetrahydrofuran (2116 g) and 10% strength hydrochloric acid (246 g) until a pH of 4.0 was reached. 174 g of sodium chloride and 420 g of tetrahydrofuran were added and the organic product phase was separated off. The combined aqueous phases were added with 261 g of sodium chloride and 1043 g of tetrahydrofuran and the organic product phase was separated off. The combined organic phases were concentrated in vacuo to a residual volume of 800 ml at a maximum of 40° C.

Crystallization:

184 g of tetrahydrofuran were added and a mixture of 646 g of methanol and 291 g of water was added at 20° C. with stirring added dropwise. It was mixed with 0.8 g of (5S)-5-{[2-(4-carboxyphenyl) ethyl] [2-(2-{[3-chloro-4'-(trifluoromethyl) [biphenyl]-4-yl] methoxy} phenyl) ethyl] amino}-5,6,7,8-tetrahydroquinoline-2-carboxylic acid monohydrate I (example 3) and stirred for 12 h. The solid was separated and washed with a mixture of 112 g of methanol and 112 g of water. The solid was then dried to 127 g in vacuo at 20° C. A second portion of 128 g was prepared using the same procedure.

The combined solids were heated to 50° C. with a mixture of 1020 g acetone and 1020 g methanol and cooled to 20° C. The solution obtained was filtered through a Seitz filter plate, heated to 50° C. and 460 g of water were added dropwise over a period of 30 minutes. It was inoculated with 1.5 g of seed crystals of monohydrate I (example 3), stirred for 30 min, cooled to 20° C. in at least 30 min and the solid was filtered off with suction. The moist product was stirred with 2550 g of water for 12 hours, then filtered off with suction and washed twice with 510 g of water. The moist product was dried to constant weight at 20° C. in a stream of nitrogen under vacuum.

Yield: 230 g monohydrate I, (I-M-I); 71% o. Th.
Purity (area): 96.0% (Method M, Rt 8.94 min)
Enantiomeric purity (HPLC method C): 99.3% ee
XRPD: monohydrate form I; see FIG. 38

| Reflections (Peak maxima) [°2 Theta] |
| --- |
| 5.7 |
| 6.9 |
| 7.2 |
| 7.4 |
| 9.9 |
| 10.7 |
| 11.1 |
| 11.5 |
| 12.0 |
| 12.2 |
| 12.4 |
| 12.8 |
| 13.7 |
| 14.1 |
| 14.3 |
| 15.2 |
| 15.6 |
| 16.0 |
| 16.9 |
| 17.2 |
| 17.5 |
| 17.7 |
| 18.0 |
| 18.4 |
| 18.8 |
| 19.1 |
| 19.9 |
| 20.3 |
| 20.5 |
| 20.7 |
| 20.9 |
| 21.3 |
| 21.9 |
| 22.2 |
| 22.5 |
| 23.0 |
| 23.2 |
| 23.4 |
| 23.7 |
| 24.1 |
| 24.4 |
| 25.1 |
| 25.8 |
| 26.1 |
| 26.5 |
| 26.8 |
| 28.8 |
| 29.4 |
| 30.0 |
| 30.6 |
| 31.0 |
| 32.2 |
| 35.4 |

Example 5

(5S)—{[2-(4-Carboxyphenyl)ethyl][2-(2-{[3-chloro-4'-(trifluoromethyl) biphenyl-4-yl]methoxy}phenyl)-ethyl]amino}-5,6,7,8-tetrahydroquinoline-2-carboxylic acid as Monohydrate I In an inertized 2 L reactor, butyl (5S)-5-({2-[4-(butoxycarbonyl) phenyl] ethyl} [2-(2-hydroxyphenyl) ethyl] amino)-5,6,7,8-tetrahydroquinoline-2-carboxylate (example 2A, WO2021/233783) was dissolved at Tsheatht=22° C. (50.8 g, 1.0 eq.) in acetonitrile (380 mL). The solution was distilled at Tsheatht=50° C. and 120 mbar. Then again acetonitrile (380 ml) was added and the mixture was distilled again under the same conditions. Acetonitrile (660 mL) was added to the solution and stirred for 5 min. Then 4-(bromomethyl)-3-chloro-4'-(trifluoromethyl)[biphenyl] (biarylbenzylbromide) (53.5 g, 1.2 eq.) was added and the mixture was again stirred for 5 min until it was dissolved. Then cesium carbonate (83.1 g, 2.0 eq.) was added and the mixture was stirred for 4 hours. Cesium carbonate (20.8 g, 0.5 eq.) was added again to the suspension and the mixture was stirred for 1 h. The product suspension was clarified by filtration and the filter cake was washed once over a kettle with acetonitrile (110 mL). The filter cake was disposed of.

The organic reaction solution was concentrated in the inerted 2 L reactor at 90 mbar and Tsheath=45° C. until the distillate has dried up. When Tsheath=23° C., THF (425 mL) was added. The solution was concentrated at 150 mbar and Tsheath=45° C. until the distillate has dried up. THF (425 mL) and 4% NaOH (680 mL) were added to the solution. The emulsion was heated to Tinternal=60° C. and stirred for a further 20 hours.

The solution was cooled to Tinternal=23° C. and deionized water (800 ml) and ethyl acetate (435 ml) were added and the mixture was stirred for 15 min. The phases were separated. The organic phase was discarded and the aqueous phase was extracted with ethyl acetate (435 mL). The organic phase was discarded and the aqueous phase was distilled at 140-160 mbar and Tsheath=45-40° C. to Tinternal=36° C. The product solution was clarified by filtration and the filter cake was washed once with deionized water (80 mL). The residue was disposed of.

The product solution was titrated. For this purpose, 25% HCl, deionized water and THF were placed in the inerted 4-liter reactor. The organic product solution was added at Tinternal=20° C. f 5° C. up to pH 3.8-4.2. THF (360 mL) and sodium chloride (471 g) were then added and the mixture was stirred for 30 min. The phases were separated and the aqueous phase was extracted with THF (450 mL). The aqueous phase was disposed of and the organic phase was crystallized. For this purpose, it was concentrated to the sump mass at 200 mbar and ΔT=30° C. THF was then added and the mixture was again distilled to 4 times the theoretical yield under the same conditions. At Tinternal=22° C., a mixture of deionized water (49 mL, 49 g) and methanol (144 ml, 114 g) was metered in, inoculated and stirred for 15 min. A mixture of deionized water (113 ml, 113 g) and Methanol (335 mL, 265 g) was further metered in and the mixture was stirred overnight. The suspension was filtered and the product was washed once over a kettle with a mixture of deionized water and methanol (1:1). It was then dried at 40-50° C. and 40-30 mbar.

Yield: 23.4 g, 67% of theory
Purity (area): 99.3% (new method M, Rt 6.28)
XRPD: monohydrate I, see FIG. 39

Example 6

Study to Investigate Crystalline/Polymorphic Forms of (5S)—{[2-(4-Carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid of Formula I Example 6a (5S)—{[2-(4-Carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid semihydrate 2.9 g (5S)—{[2-(4-Carboxyphenyl)ethyl][2-(2-{[3-chloro-4'-(trifluoromethyl)biphenyl-4-yl]methoxy}-phenyl)ethyl]amino}-5,6,7,8-tetrahydroquinoline-2-carboxylic acid monohydrate I (material prepared in analogy to example 3/4) were suspended in 20 ml of acetone. The suspension was stirred at ambient conditions for three days. The residue was filtered and the resulting solid was dried at ambient conditions.
water content: 1.5% water
Raman: see table 13, see FIG. 12
IR: see table 14, see FIG. 19
XRPD: see table 12, see FIG. 5

Example 6b (5S)—{[2-(4-Carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid monohydrate I The target compound was prepared in analogy to example 3 (monohydrate I).
water content: 3.9% before and 2.4% water after drying
Raman: see table 13, see FIG. 13
IR: see table 14, see FIG. 20
XRPD: see table 12, see FIG. 6

Example 6 c (5S)—{[2-(4-Carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid monohydrate II The target compound was prepared in analogy to example 1 (monohydrate II).
water content: 3.9% before and 2.4% water after drying
Raman: see table 13, see FIG. 14
IR: see table 14, see FIG. 21
XRPD: see table 12, see FIG. 7

Example 6 d (5S)—{[2-(4-Carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid 1.25 hydrate 3 g (5S)—{[2-(4-Carboxyphenyl)ethyl][2-(2-{[3-chloro-4'-(trifluoromethyl)biphenyl-4-yl]methoxy}-phenyl)ethyl]amino}-5,6,7,8-tetrahydroquinoline-2-carboxylic acid monohydrate I, (material prepared in analogy to example 3/4) were suspended in 20 mL of an isopropanole/water mixture (1:1). The suspension was stirred at 60° C. for eight days. The residue was filtered and the resulting solid was dried at ambient conditions.
water content: 2.9% water
Raman: see table 13, see FIG. 15
IR: see table 14, see FIG. 22
XRPD: see table 12, see FIG. 8

Example 6e (5S)—{[2-(4-Carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid sesquihydrate 3 g (5S)—{[2-(4-Carboxyphenyl)ethyl][2-(2-{[3-chloro-4'-(trifluoromethyl)biphenyl-4-yl]methoxy}-phenyl)ethyl]amino}-5,6,7,8-tetrahydroquinoline-2-carboxylic acid monohydrate I, (material prepared in analogy to example 3/4) were suspended in 15 mL of an isopropanole/water mixture (1:1). The suspension was stirred at 80° C. for four weeks. Additional 10 mL of the solvent mixture were added to improve the stirring properties of the suspension. The residue was filtered and the resulting solid was dried at ambient conditions.
water content: 3.7% water
Raman: see table 13, see FIG. 16
IR: see table 14, see FIG. 23
XRPD: see table 12, see FIG. 9

Example 6f (5S)—{[2-(4-Carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid dihydrate 3 g (5S)—{[2-(4-Carboxyphenyl)ethyl][2-(2-{[3-chloro-4'-(trifluoromethyl)biphenyl-4-yl]methoxy}-phenyl)ethyl]amino}-5,6,7,8-tetrahydroquinoline-2-carboxylic acid monohydrate I, (material prepared in analogy to example 3/4) were suspended in 20 mL of methanol. The suspension was stirred at ambient conditions for eight days. The residue was filtered and the resulting solid was dried at ambient conditions.
water content: 4.8% water
Raman: see table 13, see FIG. 17
IR: see table 14, see FIG. 24
XRPD: see table 12, see FIG. 10
After drying the dihydrate form went amorphous.
XRPD: amorphous form, see FIG. 10*a*

Example 6g (5S)—{[2-(4-Carboxyphenyl)ethyl][2-(2-{[3-chloro-4'-(trifluoromethyl)biphenyl-4-yl]methoxy}phenyl)-ethyl]amino}-5,6,7,8-tetrahydroquinoline-2-carboxylic acid The amorphous form was prepared in analogy to comparative example 11.
Raman: see table 13, see FIG. 18
IR: see table 14, see FIG. 25
XRPD: see table 12, see FIG. 11

Physical Characterization of Polymorphic Forms of (5S)—{[2-(4-Carboxyphenyl)ethyl][2-(2-{[3-chloro-4'-(trifluoromethyl) biphenyl-4-yl]methoxy}phenyl) ethyl]amino}-5,6,7,8-tetrahydroquinoline-2-carboxylic acid of Formula (I)

Table 12: XRPD (X-ray powder diffraction) data of pseudopolymorphic forms of compound of formula (I)
XRPD were recorded according to the general procedure described under the headline methods.

TABLE 12

| Reflections (Peak maxima) [2 Theta] | | | | | |
|---|---|---|---|---|---|
| Semihydrate | Monohydrate I | Monohydrate II | 1,25-Hydrate | Sesquihydrate | Dihydrate |
| 3.1 | 5.7 | 5.7 | 5.9 | 5.1 | 6.1 |
| 5.3 | 6.9 | 6.1 | 6.1 | 6.3 | 6.8 |
| 6.7 | 7.2 | 7.1 | 7.9 | 7.6 | 10.1 |
| 7.1 | 7.3 | 8.5 | 10.5 | 8.6 | 10.5 |
| 9.3 | 9.9 | 9.9 | 11.9 | 11.4 | 11.2 |
| 10.6 | 10.4 | 10.2 | 12.2 | 12.2 | 11.3 |
| 12.4 | 10.6 | 10.8 | 12.5 | 12.5 | 12.3 |
| 14.3 | 11.1 | 11.4 | 13.2 | 12.9 | 12.5 |
| 16.1 | 11.5 | 11.6 | 13.6 | 13.3 | 13.1 |
| 19.7 | 12.0 | 11.8 | 13.7 | 14.3 | 13.6 |
| 20.8 | 12.3 | 12.0 | 14.4 | 14.5 | 14.6 |
| 24.0 | 12.4 | 12.2 | 15.2 | 15.2 | 14.8 |
| 31.1 | 12.8 | 12.7 | 15.3 | 15.5 | 15.5 |
| | 13.7 | 13.0 | 15.4 | 15.8 | 16.2 |
| | 14.1 | 13.9 | 15.7 | 16.2 | 16.4 |
| | 14.3 | 14.2 | 15.9 | 16.4 | 16.8 |
| | 15.2 | 15.2 | 16.5 | 16.7 | 17.1 |
| | 15.6 | 15.3 | 16.9 | 17.3 | 17.3 |
| | 16.0 | 15.7 | 17.2 | 17.5 | 17.9 |
| | 16.9 | 16.4 | 17.4 | 17.7 | 18.5 |
| | 17.2 | 17.3 | 17.6 | 18.3 | 18.8 |
| | 17.5 | 17.7 | 17.8 | 18.7 | 19.5 |
| | 17.7 | 17.9 | 18.3 | 19.4 | 20.2 |
| | 18.0 | 18.3 | 18.6 | 20.5 | 20.5 |
| | 18.4 | 18.5 | 18.7 | 20.7 | 21.1 |
| | 18.8 | 18.8 | 19.0 | 20.8 | 21.4 |
| | 19.2 | 19.2 | 19.5 | 21.4 | 22.2 |
| | 19.9 | 19.8 | 19.6 | 21.51 | 23.2 |
| | 20.2 | 20.2 | 19.8 | 21.8 | 24.3 |
| | 20.5 | 20.8 | 20.5 | 22.4 | 25.1 |
| | 20.7 | 21.1 | 20.7 | 22.9 | 25.4 |
| | 21.3 | 21.7 | 21.0 | 23.4 | 25.6 |
| | 21.9 | 22.0 | 21.4 | 24.0 | 26.3 |
| | 22.2 | 22.4 | 22.0 | 24.7 | 26.9 |
| | 22.5 | 22.8 | 23.2 | 25.1 | 27.4 |
| | 23.0 | 23.1 | 23.8 | 26.1 | 28.5 |
| | 23.4 | 23.4 | 24.0 | 26.4 | 28.7 |
| | 23.7 | 23.9 | 24.4 | 27.0 | 29.6 |
| | 24.1 | 24.2 | 24.6 | 27.4 | |
| | 25.1 | 24.4 | 25.0 | 28.5 | |
| | 25.8 | 25.1 | 25.2 | 32.2 | |
| | 26.0 | 25.5 | 25.6 | 36.5 | |
| | 26.4 | 25.7 | 26.1 | | |
| | 28.9 | 26.2 | 26.8 | | |
| | 29.2 | 26.4 | 27.4 | | |
| | 29.4 | 26.8 | 27.6 | | |
| | 30.6 | 27.2 | 28.4 | | |
| | 31.1 | 27.5 | 28.8 | | |
| | 32.2 | 28.9 | 30.2 | | |
| | 35.3 | 30.0 | 30.7 | | |
| | | 30.1 | 31.1 | | |
| | | 30.6 | 31.6 | | |
| | | 32.2 | 32.3 | | |
| | | 32.4 | | | |

TABLE 13

Raman data of pseudopolymorphic forms of compound of formula (I)
Raman spectra were recorded according to the general procedure described under the headline Methods.

| Bands [Peak maxima in cm−1] | | | | | | |
|---|---|---|---|---|---|---|
| Semihydrate | Monohydrate I | Monohydrate II | 1,25-Hydrate | Sesquihydrate | Dihydrate | Amorphous |
| 3069 | 3073 | 3073 | 3064 | 3081 | 3073 | 3069 |
| 2941 | 2950 | 3042 | 2954 | 3064 | 2971 | 3008 |
| 2917 | 2937 | 3003 | 2933 | 3019 | 2940 | 2938 |
| 2862 | 2906 | 2950 | 2907 | 2993 | 2897 | 2869 |
| 2825 | 2892 | 2936 | 2858 | 2979 | 2877 | 2732 |
| 1700 | 2852 | 2892 | 2828 | 2965 | 2864 | 1769 |
| 1689 | 1685 | 2854 | 1765 | 2924 | 1689 | 1708 |
| 1617 | 1616 | 1685 | 1694 | 2897 | 1617 | 1617 |
| 1528 | 1527 | 1615 | 1610 | 2873 | 1611 | 1610 |
| 1496 | 1451 | 1526 | 1528 | 2858 | 1573 | 1587 |
| 1487 | 1440 | 1458 | 1492 | 2805 | 1527 | 1527 |
| 1452 | 1420 | 1451 | 1459 | 2736 | 1497 | 1489 |
| 1423 | 1384 | 1441 | 1449 | 1690 | 1460 | 1450 |
| 1372 | 1374 | 1420 | 1439 | 1616 | 1454 | 1372 |
| 1349 | 1328 | 1384 | 1430 | 1530 | 1443 | 1326 |
| 1329 | 1293 | 1372 | 1381 | 1463 | 1433 | 1279 |
| 1294 | 1278 | 1328 | 1369 | 1453 | 1422 | 1263 |
| 1283 | 1259 | 1294 | 1327 | 1440 | 1384 | 1231 |
| 1269 | 1228 | 1279 | 1283 | 1421 | 1372 | 1205 |
| 1260 | 1191 | 1259 | 1258 | 1370 | 1332 | 1194 |
| 1229 | 1162 | 1228 | 1233 | 1330 | 1296 | 1162 |
| 1207 | 1153 | 1196 | 1197 | 1291 | 1282 | 1126 |
| 1196 | 1128 | 1162 | 1166 | 1274 | 1259 | 1072 |
| 1163 | 1116 | 1153 | 1128 | 1263 | 1228 | 1054 |
| 1131 | 1056 | 1128 | 1116 | 1231 | 1196 | 1037 |
| 1074 | 1042 | 1057 | 1053 | 1199 | 1169 | 1015 |
| 1054 | 1033 | 1043 | 1041 | 1183 | 1149 | 960 |
| 1042 | 1015 | 1016 | 1015 | 1169 | 1128 | 926 |
| 1014 | 997 | 998 | 999 | 1148 | 1115 | 883 |
| 1002 | 937 | 894 | 938 | 1131 | 1059 | 859 |
| 936 | 922 | 861 | 922 | 1115 | 1042 | 843 |
| 885 | 893 | 843 | 887 | 1096 | 1015 | 804 |
| 860 | 86 | 837 | 858 | 1071 | 1003 | 777 |
| 844 | 844 | 808 | 840 | 1060 | 937 | 766 |
| 819 | 808 | 777 | 817 | 1040 | 924 | 755 |
| 804 | 793 | 757 | 806 | 964 | 891 | 738 |
| 776 | 776 | 750 | 775 | 944 | 873 | 692 |
| 745 | 756 | 701 | 755 | 928 | 861 | 638 |
| 702 | 750 | 693 | 746 | 911 | 835 | 457 |
| 693 | 703 | 655 | 739 | 863 | 806 | 440 |
| 657 | 692 | 638 | 701 | 850 | 777 | 408 |
| 638 | 655 | 569 | 658 | 835 | 757 | 183 |
| 572 | 638 | 473 | 637 | 826 | 750 | 107 |
| 476 | 568 | 463 | 605 | 814 | 741 | |
| 464 | 473 | 439 | 587 | 805 | 703 | |
| 439 | 464 | 419 | 571 | 767 | 692 | |
| 423 | 439 | 410 | 477 | 757 | 658 | |
| 407 | 419 | 394 | 462 | 743 | 652 | |
| 395 | 410 | 357 | 441 | 701 | 637 | |
| 349 | 393 | 323 | 421 | 693 | 601 | |
| 300 | 359 | 302 | 403 | 678 | 571 | |
| 242 | 323 | 281 | 333 | 656 | 465 | |

TABLE 13-continued

Raman data of pseudopolymorphic forms of compound of formula (I)
Raman spectra were recorded according to the general
procedure described under the headline Methods.
Bands [Peak maxima in cm−1]

| Semihy-drate | Monohy-drate I | Monohy-drate II | 1,25-Hy-drate | Sesquihy-drate | Dihy-drate | Amor-phous |
|---|---|---|---|---|---|---|
| 176 | 301 | 233 | 316 | 634 | 438 | |
| 145 | 281 | 208 | 297 | 491 | 422 | |
| 110 | 230 | 195 | 282 | 464 | 410 | |
| | 197 | 148 | 226 | 440 | 399 | |
| | 149 | 117 | 177 | 422 | 360 | |
| | 117 | | 142 | 409 | 314 | |
| | | | 102 | 394 | 287 | |
| | | | | 372 | 226 | |
| | | | | 349 | 190 | |
| | | | | 341 | 152 | |
| | | | | 326 | 103 | |
| | | | | 301 | | |
| | | | | 271 | | |
| | | | | 251 | | |
| | | | | 243 | | |
| | | | | 224 | | |
| | | | | 187 | | |
| | | | | 156 | | |
| | | | | 113 | | |

TABLE 14

IR data of pseudopolymorphic forms of compound of formula (I)
IR spectra were recorded according to the general
procedure described under the headline Methods.
Bands [Peak maxima in cm−1]

| Semihy-drate | Monohy-drate I | Monohy-drate II | 1,25-Hy-drate | Sesquihy-drate | Dihy-drate | Amor-phous |
|---|---|---|---|---|---|---|
| 3032 | 3660 | 3659 | 3426 | 3516 | 3395 | 3405 |
| 2937 | 3416 | 3416 | 3044 | 3404 | 3197 | 3036 |
| 2864 | 3038 | 3039 | 2921 | 3073 | 3037 | 2941 |
| 2648 | 2933 | 2934 | 2854 | 2939 | 2938 | 2864 |
| 1761 | 2863 | 2892 | 2832 | 2922 | 2865 | 2644 |
| 1695 | 2809 | 2862 | 2650 | 2895 | 2646 | 1701 |
| 1640 | 2644 | 2809 | 1767 | 2876 | 1684 | 1685 |
| 1590 | 1761 | 2733 | 1692 | 2854 | 1597 | 1599 |
| 1558 | 1678 | 2647 | 1602 | 2815 | 1558 | 1559 |
| 1528 | 1595 | 1762 | 1511 | 2733 | 1539 | 1494 |
| 1495 | 1539 | 1679 | 1497 | 2650 | 1497 | 1453 |
| 1452 | 1498 | 1595 | 1448 | 1683 | 1453 | 1419 |
| 1418 | 1454 | 1539 | 1429 | 1668 | 1431 | 1371 |
| 1373 | 1419 | 1498 | 1376 | 1607 | 1419 | 1325 |
| 1325 | 1375 | 1454 | 1325 | 1594 | 1376 | 1272 |
| 1293 | 1327 | 1431 | 1275 | 1559 | 1327 | 1238 |
| 1241 | 1292 | 1419 | 1237 | 1533 | 1270 | 1166 |
| 1166 | 1272 | 1375 | 1178 | 1503 | 1241 | 1112 |
| 1112 | 1242 | 1327 | 1158 | 1450 | 1167 | 1072 |
| 1072 | 1167 | 1292 | 1128 | 1377 | 1106 | 1057 |
| 1059 | 1110 | 1272 | 1109 | 1330 | 1072 | 1036 |
| 1038 | 1072 | 1242 | 1066 | 1302 | 1037 | 1014 |
| 1014 | 1062 | 1167 | 1040 | 1242 | 1013 | 925 |
| 924 | 1039 | 1110 | 1014 | 1171 | 954 | 882 |
| 883 | 1014 | 1072 | 939 | 1152 | 924 | 845 |
| 844 | 956 | 1062 | 924 | 1136 | 886 | 821 |
| 818 | 938 | 1039 | 887 | 1105 | 844 | 805 |
| 750 | 923 | 1014 | 858 | 1073 | 819 | 751 |
| 703 | 887 | 938 | 840 | 1060 | 804 | 704 |
| 692 | 858 | 923 | 815 | 1036 | 750 | 692 |
| 656 | 845 | 888 | 805 | 1013 | 703 | 669 |
| 635 | 818 | 858 | 783 | 992 | 691 | 654 |
| 591 | 806 | 845 | 748 | 954 | 656 | 637 |
| 582 | 742 | 818 | 701 | 928 | 634 | 609 |
| 569 | 703 | 806 | 692 | 910 | 608 | 589 |
| | 692 | 756 | 657 | 881 | 575 | 577 |
| | 654 | 742 | 646 | 862 | 564 | 558 |
| | | 637 | 703 | 641 | 849 | 558 |
| | | 608 | 692 | 635 | 819 | |

TABLE 14-continued

IR data of pseudopolymorphic forms of compound of formula (I)
IR spectra were recorded according to the general
procedure described under the headline Methods.
Bands [Peak maxima in cm−1]

| Semihy-drate | Monohy-drate I | Monohy-drate II | 1,25-Hy-drate | Sesquihy-drate | Dihy-drate | Amor-phous |
|---|---|---|---|---|---|---|
| | 575 | 654 | 604 | 802 | | |
| | 559 | 637 | 577 | 778 | | |
| | | 609 | 560 | 755 | | |
| | | 576 | | 740 | | |
| | | 558 | | 700 | | |
| | | | | 692 | | |
| | | | | 655 | | |
| | | | | 640 | | |
| | | | | 632 | | |
| | | | | 606 | | |
| | | | | 566 | | |
| | | | | 559 | | |

B—PROPERTIES OF PSEUDOPOLYMORPHIC FORMS

Example 7

Properties of Pseudopolymorphic Forms of [(5S)—{[2-(4-carboxyphenyl)ethyl][2-(2-{[3-chloro-4'-(trifluoromethyl)biphenyl-4-yl]methoxy}phenyl)-ethyl]amino}-5,6,7,8-tetrahydroquinoline-2-carboxylic acid of the Formula (I), e.g Monohydrate II of Formula (I-M-II)

Storage Stability

Compound stability and uniformity is a key requirement for a pharmaceutical and a prerequisite for an approval by health authorities. It increases the safety and quality of preparations and formulations comprising of the compound of the formula (I) and thus reduces the risk to the patient.

(5S)—{[2-(4-carboxyphenyl)ethyl][2-(2-{[3-chloro-4'-(trifluoromethyl)biphenyl-4-yl]methoxy}phenyl)-ethyl]amino}-5,6,7,8-tetrahydroquinoline-2-carboxylic acid of the formula (I) in form of the monohydrate II was used for storage stability studies under various conditions for one, three and six months:

TABLE 15 storage stability study results, monohydrate II

| example | Container | Temperature | Relative humidity | Result |
|---|---|---|---|---|
| 7a | Brown glass snap on closure | 25° C. | 60% | monohydrate II |
| 7b | Polyethylene | 25° C. | 60% | monohydrate I |
| 7c | Polyethylene | 40° C. | 75% | monohydrate I |
| 7d | Brown glass closed with paper filter disc | 40° C. | 75% | monohydrate I |

Under most of these storage conditions the monohydrate II (starting material, see FIG. 40) underwent conversion to monohydrate I (see e.g. FIG. 41: example 7b, XRPD).

In comparison the monohydrate I of formula (I-M-I) was stable under these conditions.

In particular the monohydrate I of the compound of the formula (I) ensures that an undesired conversion into another form of the compound of formula (I) and an associated change in the properties as described above is prevented.

Example 8

Properties of Pseudopolymorphic Forms of [(5S)—{[2-(4-carboxyphenyl)ethyl][2-(2-{[3-chloro-4'-(trifluoromethyl)biphenyl-4-yl]methoxy}-phenyl)-ethyl]amino}-5,6,7,8-tetrahydroquinoline-2-carboxylic acid of the Formula (I), e.g Monohydrate II of Formula (I-M-II)

Micronization

For inhalative drug products it is important to guarantee a homogeneous drug substance with defined particle size <5 μm to secure delivery to the deep lung compartments. This technical requirement can be afforded by micronization of the drug substance particles.

Appropriate specifications for a particle size distribution of the active ingredient to achieve this requirement were set as specified in table 16a.

TABLE 16a

| Particle size distribution of active ingredient, e.g. compound of formula (I-M-I) or (I-M-II) | |
| --- | --- |
| Particle size upper X90 | max. 6 μm |
| Particle size mean X50 | 1-3 μm |
| Particle size lower X10 | max. 1 μm |

In order to investigate the feasibility of monohydrate II of formula (I-M-II) for drug product manufacturing several micronization conditions were tested. Generally no amorphization even partial nor form conversion should happen during the necessary micronization step. Even a partial amorphization during micronization could lead to the risk of recrystallization of active ingredient and/or later of active ingredient in final drug product during storage.

The corresponding batches (examples 8a-8 d) were micronized using a 50 mm spiral jet mill and pressurized nitrogen with the following parameters (see table 16b).

TABLE 16b

| | different micronization conditions, mononohydrate II as starting material | | | | | | |
| --- | --- | --- | --- | --- | --- | --- | --- |
| example | mill type | Temperature | Injector pressure | Grinding pressure | Throughput | PSD | observation |
| 8a | VA jet mill | 25° C. | 4.5 bar | 4.0 bar | 4.5 g/min | X10: 0.4 μm, X50: 1.7 μm, X90: 4.2 μm (dry measurement 4 bar) | transformation to monohydrate I |
| 8b | PTFE coated jet mill | 25° C. | 4.5 bar | 4.0 bar | 4.5 g/min | X10: 0.7 μm, X50: 1.9 μm, X90: 5.0 μm (dry measurement 4 bar) | partial amorphization of monohydrate II |
| 8c | VA jet mill | −65° C. | 4.5 bar | 4.0 bar | 5.5 g/min | X10: 0.4 μm, X50: 1.8 μm, X90: 4.8 μm (dry measurement 4 bar) | partial amorphization of monohydrate II |
| 8d | VA jet mill (Low stress conditions) | −65° C. | 4.5 bar | 3.0 bar | 10.6 g/min | X10: 0.5 μm, X50: 2.3 μm, X90: 9.6 μm (dry measurement 4 bar) | partial amorphization of monohydrate II |

Firstly it was found during an orienting experiment under standard conditions (VA jet mill (50 mm) at a temperature of 25° C.) that monohydrate II could be principally micronized to obtain the desired particle size distribution (see tables 16a and 16b, ex. 8a).

During micronization of monohydrate II of formula (I-M-II) partial amorphization occurred under several conditions, even under "low stress" (see table 16b above and FIG. 42, XRPD).

XRPD: monohydrate II with partial amorphization, example 8b

Additionally it was found that besides partial amorphization also a transformation from monohydrate II to monohydrate I occurred under micronization with a VA jet mill (diameter 50 mm), 25° C. (see table 16b, example 8a and FIG. 43, XRPD).

As all studied conditions showed either a form transformation to form I or a partial amorphization of form II the monohydrate I was further investigated in order to check feasibility of monohydrate I for a reliable drug manufacturing.

The corresponding batches were micronized using a 100 mm spiral jet mill and pressurized nitrogen with the following parameters (see table 16c).

II of formula (I-M-II) (example 2), were formulated and manufactured into pharmaceutical dry powder preparations in the following ways:

Manufacturing Process

The dry powder formulation and finished products (dry powder blend filled hard capsules) were manufactured according to the below description.

Step 1: The fine lactose portion was weighed and layered in between two layers or coarse lactose prior to start of mixing.

Step 2: Mixing of the lactose pre-blend was performed for 2×20 minutes with 32 rpm. The lactose pre-blend was sieved through a 500 µg sieve between the cycles.

Step 3: active ingredient, e.g. the monohydrate I of formula (I-M-I), example 4 or the monohydrate II of formula (I-M-II), example 2, micronized was sieved through a 500 µm sieve and added to the pre-blended lactose. Prior to start of mixing cycles, the lactose pre-blend and active ingredient were layered alternating with 6 layers of lactose pre-blend and 5 layers of active ingredient, e.g. the monohydrate I of formula (I-M-I), example 4 or the monohydrate II of formula (I-M-II), example 2 in between.

TABLE 16c large batch micronization conditions, monohydrate I as starting material

| example | mill type | temperature | Injector pressure | Grinding pressure [bar] | Throughput | PSD | observation |
| --- | --- | --- | --- | --- | --- | --- | --- |
| 8e | PTFE coated jet mill | 25° C. | 5 bar | 4.5 bar | 22.8 g/min | X10: 0.7 µm, X50: 2.1 µm, X90: 6.1 µm (dry measurement 4 bar) | monohydrate I |
| 8f | PTFE coated jet mill | −65° C. | 5 bar | 4.0 bar | 23 to 28 g/min | X10: 0.6 µm, X50: 2.4 µm, X90: 6.3 µm (dry measurement 3 bar, N = 3) | monohydrate I |
| 8g | VA (stainless steel) jet mill | 25° C. | 6 bar | 4.5 bar | 8.5 g/min | X10: 0.5 µm, X50: 1.8 µm, X90: 3.9 µm (dry measurement 3 bar) | monohydrate I |

All measurements cited in the above tables were obtained by laser diffraction with dry dispersion using compressed air. Measuring in aqueous suspension with surfactants may lead to smaller particle sizes (×90 up to 1 µm smaller).

In comparison the monohydrate I of formula (I-M-I) was stable under micronization conditions.

XRPD: monohydrate form I; see FIG. 44

C—PHARMACEUTICAL COMPOSITIONS

C-1 Dry Powder Preparations for Inhalation

The compounds according to the invention e.g. the monohydrate I of formula (I-M-I) (example 4) or the monohydrate Step 4: The components were mixed in cycles in a tumble mixer. Each cycle was conducted at 32 rpm for 30 minutes with a rest time of 10 minutes between the mixing cycles. If necessary (e.g. visual agglomerates) the blend maybe sieved between blending cycles, respectively.

Step 5: The blend was left to rest at room temperature (15-25° C.) and 35-65% relative humidity in a stainless steel container for at least 48 hours Step 6: Using a capsule filling machine (e.g. MG2 Flexalab) the blend was filled into capsules at the desired fill weight.

Dry Powder Blends for Inhalation:

TABLE 17 composition (lactose content/ratio) of exemplary embodiments 1-3

| | Exemplary Embodiment 1 Low strength blend (0.75% active, 300 g) | | Exemplary Embodiment 2 Medium strength blend (3% active, 300 g) | | Exemplary Embodiment 3 High strength blend (10% active, 300 g) | |
|---|---|---|---|---|---|---|
| | Amount (g) | Amount (%) | Amount (g) | Amount (%) | Amount (g) | Amount (%) |
| active ingredient: monohydrate I, example 4* | 2.25 | 0.75% | 9.00 | 3% | 30.00 | 10% |
| Coarse Lactose (Lactohale 100) | 282.75 | 94.25% | 276.00 | 92% | 255.00 | 85% |
| Fine Lactose (Lactohale 300) | 15.00 | 5% | 15.00 | 5% | 15.00 | 5% |
| Total | 300.00 | | 300.00 | | 300.00 | |
| Blend Uniformity Assay (RSD %) | | 99% (2.1%) | | 102% (2.2%) | | 102% (4.4%) |
| LH 300 fines content in Lactose Mixture ** | | 5.0% | | 5.2% | | 5.6% |
| Ratio Active ingredient:LH 100 | | 1:126 | | 1:31 | | 1:8.5 |
| Ratio Active ingredient:LH 300* | | 1:6.7 | | 1:1.67 | | 1:0.5 |

*used as monohydrate I.
** the ratio of fine lactose (LH 300) to coarse Lactose (LH 100) is varying slightly as for practical reasons the actual amount of fine lactose in the powder blend is kept constant and the varying amounts of API (compound 1) is adjusted by the LH 100 coarse lactose content being reduced. The percent content of fine lactose (LH 300) is constant in all formulations, the ratio of active ingredient to fine lactose portion and coarse lactose portion varies in the indicated ranges.

For inhalative drug products it is important to guarantee a homogeneous drug substance with defined particle size ≤5 µm to secure delivery to the deep lung compartments. This technical requirement can be afforded by micronization of the drug substance particles.

Appropriate specifications for a particle size distribution of the active ingredient to achieve this requirement were set as specified in table 18.

The particle size distribution for the active ingredient (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I of formula (I-M-I), example 4) according to the invention is defined as in below table 18.

TABLE 18 particle size distribution of example 4

| Particle size upper X90 | max. 6 µm |
|---|---|
| Particle size mean X50 | 1-3 µm |
| Particle size lower X10 | max. 1 µm |

Lactose for inhalation is used according to the invention in different particle size ranges and different characteristics.

The coarse lactose material according to the present invention is a sieved, crystalline, a-lactose monohydrate with low fine particle content (e.g. commercially available as Lactohale® 100).

A different medium coarse lactose is the milled Lactohale® 200 which already contains considerable amount of lactose fines which can be basically tailored for customers to a desired particle size and fines content.

A further different coarse lactose is Lactohale® 206, a milled a-lactose with tightly controlled particle size, without any fine particles.

The fine lactose material according to the present invention is a micronized, crystalline, a-lactose monohydrate with a low particle size ("Lactose fines") of X90≤10 µm (e.g. commercially available as Lactohale® 300). Fine micronized lactose according to the invention with similar properties and particle size may also be selected e.g. Meggle Inhalac® 500.

A different fine lactose material is Lactohale 230®, a α-lactose monohydrate with a low particle size, X90<30 µm, milled, with irregular shaped particles;

The particle size distribution for Lactose for inhalation according to the invention (e.g. Lactohale® 100, Lactohale® 300 and others) is defined as in below table 19.

TABLE 19 particle size distribution of lactose carrier components

| | Coarse lactose | Fine lactose |
|---|---|---|
| | Lactohale ® 100 | Lactohale ® 300 |
| Particle size upper X90 | 200-250 µm | ≤10 µm |
| Particle size mean X50 | 125-145 µm | ≤5 µm |
| Particle size lower X10 | 45-65 µm | not defined |

TABLE 19-continued particle size distribution of lactose carrier components

|  | Coarse lactose | Fine lactose |
| --- | --- | --- |
| Lactohale ® 200* | | |
| Particle size upper X90 | 120-160 μm | |
| Particle size mean X50 | 50-100 μm | |
| Particle size lower X10 | 5-15 μm | |

|  | Lactohale ® 206** | Lactohale ® 230*** |
| --- | --- | --- |
| Particle size upper X90 | 115-170 μm | <30 μm |
| Particle size mean X50 | 75-95 μm | <10 μm |
| Particle size lower X10 | 20-50 μm | 1.0-3.0 μm |

*as used for comparative example 20 and exemplary embodiments 34-35
**as used for exemplary embodiments 39-44
***as used for exemplary embodiments 36-38 and 42-44

The quality of the blends were assessed by measuring the blend assay and uniformity as described under D.3.

As quality requirement the blends according to the present invention should fulfill the following criteria:

a blend assay of 90-110%, preferably 95-105% (in % content of active ingredient)
and a blend uniformity of RSD (=relative standard deviation) (n=10) of NMT (=not more than) 10% preferably 7.5% more preferably 5%.

Dry Powder Blends in Capsules (Finished Formulation for Inhalation):

The dry powder blends comprising the active ingredient (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid, preferably (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I (example 4) micronized as well as the lactose carrier components: fine lactose and coarse lactose were filled into hard capsules (hydroxypropylmethylcellulose=Hypromellose=HPMC, e.g. in size 3) or alternative capsules made from hard gelatine or other suitable materials.

Depending on the fill weight and active ingredient concentration different nominal dose can be achieved. Exemplary compositions for capsules with different nominal doses of example 4 (monohydrate I) are displayed in below table. The final products (dry powder compositions in hard gel capsules) were assessed for their corresponding aerosol performance (see table 20).

TABLE 20 aerosol performance of exemplary embodiments 1-3

|  | Exemplary Embodiment 1 | Exemplary Embodiment 2 | Exemplary Embodiment 3 |
| --- | --- | --- | --- |
| Nominal dose | 120 μg | 480 μg | 1000 μg |
| concentration of active ingredient, example 4 in powder blend | 0.75% | 3% | 10% |
| Fill weight | 16 mg | 16 mg | 10 mg |
| Delivered Dose (DD) | 71 μg | 316 μg | 705 μg |
| DD (% of nominal) | 59% | 66% | 71% |
| Fine Particle Dose <4.5 μm (FPD) | 32 μg | 128 μg | 258 μg |
| FPF (% of nominal) | 27% | 27% | 26% |
| FPF (% of DD) | 45% | 41% | 37% |

The aerosol performance includes parameters like the delivered dose (DD), the fine particle dose (=FPD) and the fine particle fraction (=FPF). The DD was measured according to method D.1, the fine particle dose (=FPD) and the fine particle fraction (=FPF) were measured according to method D.2 (Aerodynamic particle size distribution).

As quality requirement the dry powder blends in capsules according to the present invention should fulfill the following criteria:

a FPF (% of nominal dose of active, ≤4.5 μm) of 20% and a FPF(% of DD of active ≤4.5 μm) of ≥30% of active ingredient As shown in tables above the exemplary embodiments 1-3 demonstrate excellent aerosol performance and appropriate uniformity of the blend and good chemical stability (see stability data).

Further dry powder blends were manufactured using (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I of formula (I-M-I) (example 2) as active ingredient and using a partially different manufacturing process.

The particle size distribution for the active ingredient (5S)—{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate II of formula (I-M-II), example 2) according to the invention is defined as in below table 21.

TABLE 21

Particle size distribution of example 2

| Particle size upper X90 | max. 6 μm |
| --- | --- |
| Particle size mean X50 | 1-3 μm |
| Particle size lower X10 | max. 1 μm |

The exemplary embodiments 4-6 are summarized in the below table 22.

TABLE 22 composition (lactose contents) of exemplary embodiments 4-6 comprising example 2

|  | Exemplary Embodiment 4 | | Exemplary Embodiment 5 | | Exemplary Embodiment 6 | |
| --- | --- | --- | --- | --- | --- | --- |
|  | API concentration and batch size | | | | | |
|  | (0.75% active, 300 g) | | (3% active, 300 g) | | (10% active, 300 g) | |
|  | Amount (g) | Amount (%) | Amount (g) | Amount (%) | Amount (g) | Amount (%) |
| Active ingredient: (example 2)* | 3.75 | 0.75% | 9.00 | 3% | 20.00 | 10% |

TABLE 22-continued composition (lactose contents) of exemplary embodiments 4-6 comprising example 2

| | Exemplary Embodiment 4 | | Exemplary Embodiment 5 | | Exemplary Embodiment 6 | |
|---|---|---|---|---|---|---|
| | API concentration and batch size | | | | | |
| | (0.75% active, 300 g) | | (3% active, 300 g) | | (10% active, 300 g) | |
| | Amount (g) | Amount (%) | Amount (g) | Amount (%) | Amount (g) | Amount (%) |
| Coarse Lactose (Lactohale 100) | 471.25 | 94.25% | 276.00 | 92% | 170.00 | 85% |
| Fine Lactose (Lactohale 300) | 25.00 | 5% | 15.00 | 5% | 10.00 | 5% |
| Total | 500.00 | | 300.00 | | 200.00 | |
| Blend Uniformity Assay (RSD %) | | 96% (1.5%) | | 98% (0.8%) | | 103% (4.4%) |
| LH 300 fines content Lactose Mixture** | | 5.0% | | 5.2% | | 5.6% |
| Ratio Active ingredient:LH 100** | | 1:126 | | 1:31 | | 1:8.5 |
| Ratio Active ingredient:LH 300** | | 1:6.7 | | 1:1.67 | | 1:0.5 |

*used as Monohydrate II
**the ratio of fine lactose (LH 300) to coarse Lactose (LH 100) is explained in the section for the exemplary embodiments 1-3 according to the invention.

The manufacturing process of the exemplary embodiments 4-6 differed in Steps 2, 3 and 4

Step 2: Mixing of the lactose pre-blend was performed for 2×20 minutes with 67 rpm (72 rpm for low strength blend of exemplary embodiment 4). The lactose pre-blend was sieved through a 500 μg sieve between the cycles.

Step 3: active ingredient: monohydrate II, example 2 micronized was added to the pre-blended lactose without sieving. Prior to start of mixing cycles, the lactose pre-blend and active ingredient were layered alternating with 4 layers of lactose pre-blend and 3 layers of active ingredient (example 2, monohydrate II compound 1) in between.

Step 4: The layered mix was sieved through a 500 μm sieve before start of the first mixing cycle. The components were mixed in 3 cycles in a tumble mixer. Each cycle was conducted at 67 rpm (72 rpm for low strength blend of exemplary embodiment 4) for 30 minutes and sieved through a 500 μm sieve between the mixing cycles.

The following results from filled capsules of the exemplary embodiments 4-6 were obtained.

TABLE 23

Aerosol performance of exemplary embodiments 4-6

| | Exemplary Embodiment 4.1 + 4.2 (low/high powder fill) | | Exemplary Embodiment 5 | Exemplary Embodiment 6 |
|---|---|---|---|---|
| Nominal dose | 60 μg | 120 μg | 480 μg | 1000 μg |
| concentration of active ingredient, example 2 in powder blend | 0.75% | 0.75% | 3% | 10% |
| Fill weight | 8 mg | 16 mg | 16 mg | 10 mg |
| Delivered Dose (DD) | 30 μg | 82 μg | 316 μg | 671 μg |
| DD (% of nominal) | 50% | 68% | 66% | 67% |
| Fine Particle Dose <4.5 μm (FPD) | 12 μg | 31 μg | 126 μg | 242 μg |
| FPF (% of nominal) | 20% | 26% | 26% | 24% |
| FPF (% of DD) | 40% | 38% | 40% | 36% |

Results from exemplary embodiments 4-6 show that similar favorable aerosol performance can be achieved using (5S)—{[2-(4-carboxyphenyl)ethyl][2-(2-{[3-chloro-4'-(trifluoromethyl)biphenyl-4-yl]methoxy}-phenyl)ethyl]-amino}-5,6,7,8-tetrahydroquinoline-2-carboxylic acid monohydrate II of formula (I-M-II) form, example 2 to formulate dry powder blends according to the invention.

Stability Test

Stability studies were conducted with one clinical batch each of a low strength (120 μg, according to the invention, exemplary embodiment 1) and high strength (1000 μg according to the invention, exemplary embodiment 3). Stability testing was carried out with respect to appearance, delivered dose, aerodynamic particle size distribution, assay and degradation products as well as physical form (high strength batch only). The study was carried out according to the protocol outlined in tables 24 and 25.

TABLE 24

Stability protocol - long-term capsule for inhalation comprising example 4 (clinical batch)

| Storage condition | Storage [months] | | | | | | | | |
|---|---|---|---|---|---|---|---|---|---|
| | 0 | 1 | 3 | 6 | 9 | 12 | 18 | 24 | 36 |
| 25° C./60% RH | x | x | x | x | (x) | x | x | x | (x) |

RH relative humidity
x test station
(x) optional test station

Throughout the tested period no signs of significant changes in any of the tested parameters was observed. Therefore the powder blend formulations according to the invention are sufficiently stable for the intended use and storage period. Stability data are presented in the following table 25.

TABLE 25

Stability data - long-term capsule for inhalation comprising example 4

| Test Acceptance criterion | Storage time [months] | Embodiment 1 (120 µg) | Embodiment 2 (1000 µg) |
|---|---|---|---|
| Formulation (hard capsule, clear & colorless no marking) | Initial | complies | complies |
| | 1 | complies | complies |
| | 3 | complies | complies |
| | 6 | complies | complies |
| | 12 | complies | complies |
| | 18 | complies | complies |
| | 24 | complies | complies |
| Appearance of capsule content (white to off-white powder) | Initial | white powder | off-white powder |
| | 1 | white powder | white powder |
| | 3 | white powder | white powder |
| | 6 | white powder | white powder |
| | 12 | white powder | white powder |
| | 18 | white powder | white powder |
| | 24 | white powder | white powder |
| Delivered Dose Uniformity Mean delivered dose 120 µg: 64-92 µg 1000 µg: 550-750 µg | Initial | 71 | 625 |
| | 1 | 67 | 659 |
| | 3 | 75 | 691 |
| | 6 | 70 | 625 |
| | 12 | 66 | 644 |
| | 18 | 63 | 646 |
| | 24 | 68 | 660 |
| Tier 1 (n = 10) (9 of 10 must lie between 75% and 125% and 10 of 10 lie between 65% and 135% of the mean) | Initial | complies | complies |
| | 1 | complies | complies |
| | 3 | complies | complies |
| | 6 | complies | complies |
| | 12 | complies | complies |
| | 18 | complies | complies |
| | 24 | complies | complies |
| Tier 2 (n = 30) (Not more than 3 of all 30 values lie outside the limits of 75% to 125% and no value lies outside the limit of 65% to 135% of the mean) | Initial | n.a. | n.a. |
| | 1 | n.a. | n.a. |
| | 3 | n.a. | n.a. |
| | 6 | n.a. | n.a. |
| | 12 | n.a. | n.a. |
| | 18 | n.a. | n.a. |
| | 24 | n.a. | n.a. |
| Aerodynamic Particle Size Distribution MMAD (1.8-5.0 µm) | Initial | 3.2 | 3.1 |
| | 1 | 3.3 | 3.1 |
| | 3 | 3.4 | 3.2 |
| | 6 | 3.3 | 3.1 |
| | 12 | 3.5 | 3.1 |
| | 18 | 3.5 | 3.3 |
|

Step 4: The pH was adjusted to 12.0 (11.8-12.2) with an appropriate amount of sodium hydroxide 1 N.

Step 5: The weighed quantity of the active ingredient, example 4 (monohydrate I of formula (I-M-I) was transferred to the vessel, the solution was stirred until completeness of dissolution.

Step 6: The weighed quantity of sodium chloride was transferred to the vessel, the solution was stirred until completeness of dissolution.

Step 7: The pH was adjusted to 7.8 (7.7-7.9) with an appropriate amount of hydrochloric acid 10%.

Step 8: The amount of water for final weight was calculated and the required amount of water for injections was added while stirring.

Step 9: The solution was prefiltered (filter 1, bioburden-reduction filter) and sterile filtered (filter 2) prior to aseptic filling into glass vials through a membrane filter (pore size 0.2 μm).

Step 10: The solution was filled into sterile, depyrogenized 20 mL brown glass injection vials.

Step 11: The vials were capped and crimped for complete closure.

D—ANALYTICAL METHODS (DELIVERED DOSE, FINE PARTICLE DOSE, BLEND ASSAY & UNIFORMITY)

Below the analytical methods to determine the delivered dose and the fine particle dose are described in detail.

| | |
|---|---|
| D.1: Delivered Dose (DD) | The method is performed with the dry powder inhaler (see description, page 94, FIGS. 1a and 1b) and the inhalation capsule (for preparation of capsules see C.) according to Ph. Eur. Monograph Preparations for Inhalation - Powders for inhalation, using the specified sample collection tube (dose unit sampling adapter = DUSA), a digital flow meter and a vacuum pump. Sampling is performed at a flow of 90 L/min for 2.4 sec corresponding to 3.6 L inhaled volume. DD sample preparation is perfomed at 20° C. and 40-55% RH. Samples are measured using High-performance liquid chromatography with UV-detection (summarized below) |
| D.2 Aerodynamic particle size distribution (APSD) (for determination of FPD) | The method is performed with the dry powder inhaler (see description, page 86, FIGS. A and B) and the inhalation capsule (for preparation of capsules see C.) according to Ph. Eur. 2.9.18 aerodynamic assessment of fine particles using apparatus E (Next Generation Impactor, NGI) a digital flow meter and a vacuum pump. NGI sampling cups are coated each with 2 mL of a solution of 1% silicone oil in hexane. Sampling is performed at a flow of 90 L/min for 2.4 sec corresponding to 3.6 L inhaled volume. DD sample preparation is perfomed at 20° C. and 40-55% RH. For 120 μg capsules 5 individual cpasules are fired consecutively into the NGI as described above, for higher dose strengths (e.g. 480 μg, 1000 μg) one capsule is sufficient for each NGI analysis. Samples are measured using a reversed phase high performance liquid chromatography with UV-detection (summarized below) |
| RP-HPLC-UV method (for samples from APSD and DD testing and capsule assay) | The assay method is used for assay of the content of example 2 or 4 or comparative example 14 in samples prepared during delivered dose uniformity (by DUSA sampling tube) and aerodynamic particle size determination (by next generation impactor). |
| Equipment | High-performance liquid chromatograph with thermostated column oven, UV-detector or diode array detector and chromatography data system |
| Column | HPLC Column Poroshell 120 EC-C8, 2.7 μm, 150 × 4.6 mm. |
| Sample diluent [Sol] | Acetonitrile/Water/Phosphoric acid 50/50/0.35 (for APSD & DD) |
| Acidified Water | Phosphoric acid/Water (7:1000 (v:v)) |
| Sample preparation | The required no of capsules are emptied into a volumetric flask containing acidified water. The capsules are rinsed with ethanol and the solution including capsule shells transferred to the vol. flask. The resulting solution has a concentration of 6 μg/mL. Samples for APSD are prepared by extraction of the NGI cups with acetonitrile. Samples for DD are prepared by washing of the sample tube with sample diluent. |
| HPLC conditions | |
| Eluent | A) 52:48 H2O:MeCN with 0.3% phosphoric acid. B) 5:95 H2O:MeCN with 0.3% phosphoric acid. |
| Elution | Gradient |

-continued

|  | Time (min) | % A | % B |
|---|---|---|---|
|  | 0.0 | 100 | 0 |
|  | 6.0 | 100 | 0 |
|  | 6.5 | 0 | 100 |
|  | 8.0 | 0 | 100 |
|  | 8.5 | 100 | 0 |
|  | 11.0 | 100 | 0 |

| | |
|---|---|
| Chromatogram run time | 11 minutes |
| Flow rate | 1.5 mL/minute |
| Temperature of column oven | 35° C. (±2° C.) |
| Detection | Spectrophotometer at 260 nm |
| Injection volume | 100 µL |
| D.3 Blend assay/uniformity (HPLC) | High-performance liquid chromatography (HPLC) with UV-detection. |
| Equipment | 1. High-performance liquid chromatograph with thermostated column oven, UV-detector or diode array detector and chromatography data system.<br>2. HPLC Column Poroshell 120 EC-C8, 2.7 µm, 150 × 4.6 mm.<br>3. Ultrasonic bath. |
| Reagents | 1. Phosphoric acid (e.g. Merck).<br>2. Acetonitrile (MeCN) (HPLC-grade).<br>3. Demineralized water (e.g. Millipore). |
| Sample diluent [Sol] | Acetonitrile/Water/Phosphoric acid 50/50/0.35 |
| Acidified water | Phosphoric acid/Water (7:1000 (v:v)) |
| Test solution [TS] | Prepare the test solutions 10 times. All test solutions are stable for 7 days under ambient/light conditions. |
| 7.5 µg/mg blend strength (1.2 µg/mL sample solution) Target capsule strength: 60 µg | Accurately weigh approximately 8.0 mg of 7.5 µg/mg bulk blend into a 50 mL volumetric flask. Dissolve and make to volume with diluent to produce 1.2 µg/mL example 2 or 4 or comparative example 14 solution. |
| 7.5 µg/mg blend strength (1.2 µg/mL sample solution) Target capsule strength: 120 µg | Accurately weigh approximately 16.0 mg of 7.5 µg/mg bulk blend into a 100 mL volumetric flask. Dissolve and make to volume with diluent to produce 1.2 µg/mL example 2 or 4 or comparative example 14 solution. |
| 30 µg/mg blend strength (4.8 µg/mg stock solution, (1.44 µg/mL sample solution) Target capsule strength: 480 µg | Accurately weigh approximately 16.0 mg of bulk 30 µg/mg blend into a 100 mL volumetric flask. Dissolve and make to volume with diluent and dilute 3.0 mL to 10 mL with diluent to produce 1.4 µg/mL example 2 or 4 or comparative example 14 solution. |
| 100 µg/mg blend strength (5 µg/mg stock solution, 1.5 µg/mL sample solution) Target capsule strength: 1000 µg | Accurately weigh approximately 10.0 mg of bulk blend into a 200 mL volumetric flask. Dissolve and make to volume with diluent, and dilute 6.0 mL to 20 mL with diluent to produce 1.5 µg/mL example 2 or 4 or comparative example 14 solution. |
| Standard stock solution [SSS] (15 µg/mL) | Weigh, in duplicate, the amount of example 2 or 4 or comparative example 14 reference standard required to make an approximate 15 µg/mL solution and transfer into a 100 mL volumetric flask. Sonicate and dilute to volume with diluent. Label stock solutions as SSS 1 and SSS 2. Different weights of standard substances and different dilution steps may be used if they lead to the same final concentrations. |
| Standard solution [SS] (1.5 µg/mL) | Dilute 5.0 mL of each of the stock standards to 50 mL using diluent and mix well to produce the working standard solutions. |
| HPLC conditions | As described for Delivered dose and fine particle dose. |
| D.4 Particle Size Distribution (Laser Diffraction) | Applied for e.g. API or Lactose |
| Principle | A representative sample, dispersed at an adequate concentration in a suitable liquid or gas, is passed through a beam of monochromatic light, usually a laser. The light scattered by the particles at various angles is measured by a multi-element-detector. The scattering pattern values are then transformed, using an appropriate optical model and mathematical procedure, to yield the proportion of total volume to a discrete number of size classes forming a volumetric particle size distribution |
| Equipment | Sympatec HELOS with RODOS dry dispersion unit |
| Parameter | Pressure: 4 bar<br>Feed Rate: 18%<br>Focal Length (RODOS): 100 mm |
| Precision | Coefficient of variation max 5% |

| Alternative configuration for laser diffraction measurement | |
| --- | --- |
| Equipment | Malvern Mastersizer 3000 with dry dispersion unit |
| Parameter | Pressure: 3.5 bar<br>Feed rate: 20%<br>Focal length: 300 mm<br>Sampling Time: 3 s |
| Precision | Coefficient of variation: max 5% |

The particle size analysis data are usually reported as cumulative undersized distribution by volume. The symbol x is used to denote the particle size, which is defined as diameter of a volume equivalent sphere. Most common characteristic values are calculated from the particle size distribution by interpolation. Frequently used are the particle sizes at the undersize values of 10%, 50% and 90% of the volume distribution, denoted as x10, x50 and x90. x50 is also known as median particle size. The symbol d is widely used to designate the particle size, thus the symbol x may be replaced by the symbol d.

D.5 Additional Stability Test methods

| | |
| --- | --- |
| Appearance | Visual Test |
| RP-HPLC-UV method (for degradation products) | Reversed phase high performance liquid chromatography (HPLC) with UV-detection at 260 nm and external calibration. |
| Equipment | High-performance liquid chromatograph with thermostated column oven, UV-detector or diode array detector and chromatography data system |
| Column | HPLC Column Poroshell 120 EC-C8, 2.7 µm, 150 × 4.6 mm. |
| Sample diluent [Sol] | Acetonitrile/Water/Phosphoric acid 50/50/0.35 |
| Acidified Water | Phosphoric acid/Water (7:1000 (v:v)) |
| Sample preparation | The required no of capsules are emptied into a volumetric flask containing acidified water. The capsules are rinsed with acetonitrile and the solution without capsule shells transferred to the vol. flask. Make the volumetric flask to volume with acetonitrile to produce 60 µg/mL example 4 solution. |
| HPLC conditions | |
| Eluent | A) 55:45 H2O:MeCN with 0.3% phosphoric acid.<br>B) 5:95 H2O:MeCN with 0.3% phosphoric acid. |
| Elution | Gradient |

| Time (min) | % A | % B |
| --- | --- | --- |
| 0.0 | 100 | 0 |
| 12.0 | 100 | 0 |
| 32.0 | 0 | 100 |
| 35.0 | 0 | 100 |
| 35.1 | 100 | 0 |
| 42.0 | 100 | 0 |

| | |
| --- | --- |
| Chromatogram run time | 42 minutes |
| Flow rate | 1.5 mL/minute |
| Temperature of column oven | 35° C. (±2° C.) |
| Detection | Spectrophotometer at 260 nm |
| Injection volume | 100 µL |

D.6 Additional Method to Characterize Particle Distributions and Sizes of API and Lactose Particles in Finished Dry Powder Blends

| | |
| --- | --- |
| Principle of the method | Automated optical and Raman microscopy integrated system to analyze morphology/particle size and number of a composite powder sample concurrently with identification of chemical nature of the components of a powder blend. |
| Apparatus: | Malvern Morphologi 4-ID |
| Dry dispersion (exmplary settings): | Volume: 5 mm$^3$<br>Pressure: 3 bar<br>Dispersion time: 3 ms<br>Settling Time: 60 s |
| Morphology (exemplary settings): | Light Source: Diascopic<br>Objective (magnification) ×50<br>Scan area 784 mm$^2$ |
| Raman (exemplary settings): | Acquisition time: 15 s<br>Spectral masking: in region 0.520 cm$^{-1}$ and 790-1740 cm$^{-1}$ |

E—BIOLOGICAL EXAMPLES

E-1 Haemodynamics in the Anesthetized Thromboxane Challenged Minipig

Lung Selectivity and Duration of Action

Healthy Göttingen Minipigs® Ellegaard (Ellegaard, Denmark) of both sexes and having a weight of 2-6 kg were used. The animals were sedated by i.m. administration of about 25 mg/kg ketamine and about 10 mg/kg azaperone. Anaesthesia was initiated by i.v. administration of about 2 mg/kg ketamine and about 0.3 mg/kg midazolam. Maintenance of anaesthesia was by i.v. administration of about 7.5-30 mg/kg/h ketamine and about 1-4 mg/kg/h midazolam (rate of infusion 1-4 ml/kg/h) and about 150 µg/kg/h pancuronium bromide (for example Pancuronium-Actavis). After intubation, the animals were ventilated by the ventilator at a constant respiratory volume (10-12 ml/kg, 35 breaths/min; Avea®, Viasys Healthcare, USA, or Engström Carestation, GE Healthcare, Freiburg, Germany) such that an end-tidal CO2 concentration of about 5% was achieved. Ventilation was performed with room air, enriched with about 40% oxygen (normoxia). For the measurement of the haemodynamic parameters such as pulmonary arterial pressure (PAP), blood pressure (BP) and heart rate (HR), catheters were inserted into the carotid artery to measure the blood pressure, and a Swan-Ganz® catheter was introduced in a flow-directed manner via the jugular vein into the pulmonary artery. The haemodynamic signals were recorded and evaluated by means of pressure transducers (Combi-transducer, B. Braun, Melsungen, Germany)/amplifiers and Ponemah® as data acquisition software.

After the instruments have been placed into the animals, continuous infusion of a thromboxane A2 analog was initiated to increase the pulmonary arterial pressure. About 0.3-0.75 µg/kg/min of 9,11-didesoxy-9α,11α-epoxymethanoprostaglandine F2α (U-44069; Sigma, cat. no. D0400, or Cayman Chemical Company, cat. no. 16440), dissolved in physiological saline, were infused to achieve an increase of the mean pulmonary arterial pressure to values of over 25 mmHg. 30 minutes after the start of the infusion, a plateau was reached, and the experiment was started.

The test substances were administered as i.v. infusion or by inhalation. For the preparation of the solution for inhalation, the following procedure was adopted: For an animal having a weight of 4 kg, to prepare the stock solution (300 μg/kg), 1.2 mg of the test compound were weighed out and dissolved in a total volume of 3 ml (1% DMSO, 99% 0.2% strength citric acid solution, 1 n aqueous sodium hydroxide solution to adjust the pH to 8). The solution was then diluted to the concentration employed using 0.2% strength citric acid which had been adjusted to pH 8 beforehand with aqueous sodium hydroxide solution. In each test, 3 ml of the solution of test compound per 4 kg animal were nebulized in the inhalation arm of the respiratory circuit using the Aeroneb® Pro nebulizer system. The mean nebulization time was about 7 min from the start of the nebulization.

Prediction of Duration of the Effect in Humans

With respect to a prediction of the duration of action for human studies comparative example 11 was compared in the PAH minipig model after inhaled application to Ventavis® (=Iloprost, 10 μg/kg nominal dose), which we used as a clinical reference. Ventavis® had a maximal duration of action of about 40 min. All doses of comparative example 11 showed dose dependent efficacy during the whole 240 min observation interval (see FIG. 45). Therefore, the duration of action is more than 6 times longer compared to Ventavis in this preclinical animal model. In clinical studies Ventavis showed a duration of action on haemodynamics (PVR) of about 60 min (Ref: Favorable Effects of Inhaled Treprostinil in Severe Pulmonary Hypertension Results From Randomized Controlled Pilot Studies Robert Voswinckel, MD,* Beate Enke, MD,* Frank Reichenberger, MD,* Markus Kohstall, MD,*Andree Kreckel, MD,* Stefanie Krick, MD,* Henning Gall, MD,* Tobias Gessler, MD, PHD, *Thomas Schmehl, PHD,* Hossein A. Ghofrani, MD,* Ralph Theo Schermuly, PHD,*Friedrich Grimminger, MD, PHD,* Lewis J. Rubin, MD,† Werner Seeger, MD,* Horst Olschewski, MD*‡Journal of the American College of Cardiology Vol. 48, No. 8, 2006) which is in good correlation of our observed duration of action of about 40 min.

Under the assumption that the duration of action for comparative example 11 is comparable between the PAH minipig model and humans, as similarly shown and described for Ventavis, the duration of action of comparative example 11 in humans is supposed to be at least 6 hours or even longer.

TABLE 27

Effects of vehicle solution, comparative example 11 (10, 30 and 100 μg/kg nominal dose) and Ventavis (10 μg/kg nominal dose) after inhaled application in the PAH minipigs model. % changes in PAP vs baseline (10 min interval prior to start of nebulization). Data are mean ± SD.
PAP % changes vs prevalue

| | Vehicle n = 4 | | Ventavis ® n = 3 | | Comparative example 11 10 μg/kg n = 3 | | Comparative example 11 30 μg/kg n = 3 | | Comparative example 11 100 μg/kg n = 3 | |
|---|---|---|---|---|---|---|---|---|---|---|
| Time | mean | SD | mean | SD | mean | SD | Mean | SD | mean | SD |
| 0 | 0 | 0 | 0 | 0 | 0 | 0 | 0 | 0 | 0 | 0 |
| 10 | −0.2 | 2.7 | −30.3 | 9.0 | 0.6 | 0.5 | 0.3 | 0.6 | −2.1 | 2.7 |
| 20 | −0.4 | 6.3 | −20.7 | 21.6 | 0.2 | 0.3 | −2.0 | 1.0 | −7.2 | 3.8 |
| 30 | 0.5 | 6.5 | −6.9 | 13.5 | −0.7 | 0.4 | −4.6 | 0.8 | −14.6 | 6.0 |
| 40 | 2.4 | 4.1 | 1.7 | 2.9 | −1.5 | 2.2 | −7.8 | 0.9 | −18.1 | 6.9 |

TABLE 27-continued

Effects of vehicle solution, comparative example 11 (10, 30 and 100 μg/kg nominal dose) and Ventavis (10 μg/kg nominal dose) after inhaled application in the PAH minipigs model. % changes in PAP vs baseline (10 min interval prior to start of nebulization). Data are mean ± SD.
PAP % changes vs prevalue

| | Vehicle n = 4 | | Ventavis ® n = 3 | | Comparative example 11 10 μg/kg n = 3 | | Comparative example 11 30 μg/kg n = 3 | | Comparative example 11 100 μg/kg n = 3 | |
|---|---|---|---|---|---|---|---|---|---|---|
| Time | mean | SD | mean | SD | mean | SD | Mean | SD | mean | SD |
| 50 | 4.3 | 4.0 | 4.9 | 0.9 | −2.3 | 2.7 | −9.8 | 0.6 | −22.2 | 8.6 |
| 60 | 5.6 | 4.6 | | | −3.5 | 3.3 | −11.8 | 1.0 | −25.1 | 7.9 |
| 70 | 6.2 | 5.2 | | | −4.2 | 3.2 | −14.1 | 0.7 | −27.0 | 7.4 |
| 80 | 6.2 | 5.2 | | | −3.7 | 4.2 | −14.2 | 0.7 | −27.9 | 7.3 |
| 90 | 7.0 | 5.3 | | | −4.3 | 4.6 | −14.4 | 0.2 | −28.9 | 9.1 |
| 100 | 7.0 | 5.3 | | | −5.3 | 4.9 | −14.8 | 0.3 | −31.1 | 8.8 |
| 110 | 7.0 | 5.7 | | | −6.2 | 4.9 | −15.3 | 0.3 | −30.8 | 8.4 |
| 120 | 7.6 | 5.5 | | | −6.7 | 5.4 | −15.3 | 1.0 | −31.3 | 8.4 |
| 130 | 7.9 | 5.9 | | | −6.2 | 4.9 | −15.5 | 1.9 | −31.2 | 9.1 |
| 140 | 7.7 | 5.5 | | | −7 | 5.0 | −15.3 | 2.2 | −31.6 | 8.7 |
| 150 | 7.9 | 5.1 | | | −7.6 | 5.3 | −16.3 | 1.7 | −31.1 | 8.2 |
| 160 | 8.9 | 4.8 | | | −7.6 | 6.1 | −16.3 | 2.3 | −30.1 | 8.5 |
| 170 | 9 | 5.8 | | | −8.2 | 5.9 | −14.9 | 2.1 | −31.1 | 8.9 |
| 180 | 8.6 | 6.0 | | | −8.0 | 4.4 | −14.7 | 2.1 | −31.1 | 9.2 |
| 190 | 9.2 | 6.0 | | | −7.8 | 4.7 | −15.1 | 2.1 | −30.5 | 8.5 |
| 200 | 8.9 | 5.7 | | | −7.3 | 3.6 | −15.3 | 2.6 | −30.9 | 8.6 |
| 210 | 9.4 | 6.0 | | | −7.5 | 4.5 | −13.8 | 2.3 | −30.6 | 8.9 |
| 220 | 9.9 | 5.3 | | | −7.2 | 3.7 | −13.6 | 2.2 | −31.6 | 9.2 |
| 230 | 9.1 | 4.7 | | | −7.2 | 3.4 | −12.8 | 2.4 | −31.2 | 7.4 |
| 240 | 8.4 | 4.1 | | | −7.6 | 2.7 | −13.4 | 1.9 | −31.0 | 8.0 |

Prediction of Human Dose

In order to generate a human dose estimate, experiments in the PAH minipig model for comparative example 11 were repeated with the difference that absorbing filters were attached at the end of the tubes to determine the deposited lung dose. Nebulization of comparative example 11 resulted in a nebulization efficiency of 3-6% of nominally applied doses. The arithmetic mean of the aerosol fraction deposited on the filters is 5% based on all results of the filter experiments, resulting in relative lung deposited doses of about 0.15 μg/kg (3 μg/kg nominal dose), 0.5 μg/kg (10 μg/kg nominal dose), 1.5 μg/kg (30 μg/kg nominal dose) and 5 μg/kg (100 μg/kg nominal dose). Assuming a minimal effective nominal dose of 3 μg/kg for a 5% reduction in PAP and a mean nebulization efficiency of 5%, the minimal effective deposited lung dose is considered as 0.15 μg/kg based on the PAH minipig model. Therefore, for a human patient of 60 kg body weight a minimal effective lung deposited dose of 9-41p g, depending on whether or not an effect of different protein binding (see table 28) is postulated. Considering 100 μg/kg as effective dose in the minipig model, 300-1370 μg lung deposited dose is postulated as effective dose, again depending on the consideration of different interspecies protein binding.

TABLE 28

Effective lung dose with and without consideration of interspecies differences in protein binding

| | Total lung deposited dose in a 60 kg human [µg] | |
|---|---|---|
| Relative lung deposited dose in minipig [µg/kg] | Interspecies difference in protein binding not considered[a] | Interspecies difference in protein binding considered[b] |
| 0.15 µg/kg (3 µg/kg nominal dose) | 9 | 41 |
| 0.50 µg/kg (10 µg/kg nominal dose) | 30 | 137 |
| 1.5 µg/kg (30 µg/kg nominal dose) | 90 | 410 |
| 5.0 µg/kg (100 µg/kg nominal dose) | 300 | 1370 |

[a]Calculation (relative lung deposited dose in minipig × 60 kg)
[b]Calculation (relative lung deposited dose in minipig × 60 kg × 4.55 (ratio of fraction unbound minipig (plasma fu 0.348%)/human (plasma fu 0.0764%))

Effects of Dry Powder Formulations

After characterization of the effects of comparative example 11 after nebulization of compound solutions, in a further step the effects of crystalline forms of comp. example 11, e.g. sesquihydrate, e.g. example 6e on PAP and BP after inhaled application of different dry powder lactose formulations (table 29) were studied in anesthetized PAH minipigs.

TABLE 29

| Dry powder formulations of crystalline forms of comparative example 11, e.g. sesquihydrate, e.g. example 6e applied in minipig experiments | | | |
|---|---|---|---|
| Formulation | Drug load % (w/w) | Dry powder/ drug dose applied per animal | crystalline forms of comparative example 11 dose applied |
| Lactose formulation I of cryst. form of comp. ex. 11 in lactose | 2 | 1.5 mg/ 30 μg | 7.5 μg/kg |
| Lactose formulation II of cryst. form of comp. ex. 11 in lactose | 6 | 1.5 mg/ 90 μg | 22.5 μg/kg |

TABLE 29-continued

| Dry powder formulations of crystalline forms of comparative example 11, e.g. sesquihydrate, e.g. example 6e applied in minipig experiments | | | |
|---|---|---|---|
| Formulation | Drug load % (w/w) | Dry powder/ drug dose applied per animal | crystalline forms of comparative example 11 dose applied |
| sesquihydrate ex. 6e, micronized | 100 | 1.5 mg/ 1500 μg | 375 μg/kg | w/w: weight/weight 1.5 mg/4 kg animal weight lactose vehicle (LH300/LH200 20/78 or LH300/LH200 20/80), lactose formulation I (LH300/LH200 20/78 comprising 2 w-% cryst. form of comp. ex. 11), lactose formulation II (LH300/LH200 20/80 comprising 6 w-% cryst. form of comp. ex. 11 or micronized crystalline form of comp. ex. 11, e.g. sesquihydrate, e.g. example 6e were applied intratracheally (i.t.) via the Penn-Century® dry powder insufflator attached to the air pump. In all animals, lactose application led to an increase in PAP without any effects on BP (FIG. 46-49). After i.t. application of lactose formulation I (2% w/w), lactose formulation 11 (6% w/w) or as micronized crystalline form of complex. 11, e.g. sesquihydrate example 6e a decrease of PAP without any effects on BP was observed (FIG. 46-48). As shown in FIG. 49 the onset of the effect was slow reaching the maximum effect with lactose formulation 1(2% w/w) after approximately 190 min, with lactose formulation II (6% w/w) after approximately 170 min and with micronized sesquihydrate example 6e after approximately 80 min after i.t. application. The selective effect on PAP lasted for all doses for the complete 4 h observation interval. The maximal effect, achievable in this animal model under these experimental conditions, was reached in this model with lactose formulation II as well as the micronized sesquihydrate example 6e. As the lactose formulation I was already effective, the MED of comparative example 11 as well as its pseudopolymorphic forms, e.g. sesquihydrate and monohydrate I or monohydrate II (similar efficacy of the different pseudopolymorphic forms of compound of formula I has been shown in below tests) is ≤7.5 μg/kg which is well in line with the experiments for the derivation of human dose prediction with liquid solution (MED3 μg/kg). Lower doses were not applicable due to technical limitations.

TABLE 30

Effects after intratracheal application of different lactose vehicles, lactose formulation I (7.5 μg/kg), lactose formulation II (22.5 μg/kg) and micronized sesquihydrate, e.g. example 6e (375 μg/kg). Data are shown as absolute values for PAP and BP [mmHg] (n = 3)

| | Lactose 1.5 mg/4 kg (@0 min) + lactose formulation I 2% 1.5 mg/4 kg (@90 min) | | | | | | Lactose 1.5 mg/4 kg (@0 min) + lactose formulation II 6% 1.5 mg/4 kg (@90 min) | | | | | |
|---|---|---|---|---|---|---|---|---|---|---|---|---|
| time | PAP | | | BP | | | PAP | | | BP | | |
| 0 | 38.8 | 37.1 | 37.2 | 101 | 106 | 119 | 38.6 | 36.8 | 40.0 | 110 | 115 | 93 |
| 10 | 37.3 | 37.7 | 37.6 | 95 | 110 | 118 | 39.4 | 37.1 | 39.2 | 111 | 112 | 92 |
| 20 | 35.3 | 36.8 | 38.4 | 96 | 106 | 119 | 39.9 | 37.9 | 39.1 | 113 | 117 | 88 |
| 30 | 40.4 | 37.2 | 38.7 | 101 | 105 | 119 | 40.3 | 37.4 | 39.8 | 114 | 115 | 89 |
| 40 | 41.8 | 37.8 | 39.4 | 103 | 105 | 119 | 40.9 | 38.5 | 40.9 | 113 | 116 | 92 |
| 50 | 41.9 | 39.4 | 39.2 | 105 | 102 | 118 | 41.7 | 38.1 | 41.0 | 113 | 115 | 93 |
| 60 | 41.9 | 40.9 | 39.7 | 107 | 100 | 118 | 42.4 | 38.0 | 39.8 | 112 | 114 | 91 |
| 70 | 40.9 | 41.2 | 39.6 | 108 | 101 | 116 | 42.8 | 39.2 | 41.6 | 112 | 113 | 95 |
| 80 | 37.6 | 42.4 | 37.4 | 108 | 94 | 111 | 43.3 | 39.5 | 40.6 | 111 | 113 | 93 |
| 90 | 35.5 | 42.3 | 38.4 | 111 | 97 | 111 | 43.0 | 39.2 | 40.2 | 111 | 110 | 93 |
| 100 | 38.1 | 43.8 | 37.5 | 113 | 100 | 110 | 43.2 | 40.0 | 42.5 | 110 | 112 | 94 |
| 110 | 38.8 | 43.8 | 36.5 | 114 | 93 | 107 | 44.2 | 38.5 | 40.4 | 110 | 111 | 94 |
| 120 | 40.9 | 43.8 | 35.3 | 115 | 96 | 107 | 42.7 | 36.5 | 40.1 | 110 | 111 | 96 |
| 130 | 40.9 | 43.6 | 34.2 | 115 | 89 | 106 | 40.8 | 36.4 | 38.6 | 110 | 109 | 96 |
| 140 | 41.3 | 42.3 | 33.5 | 116 | 86 | 105 | 40.6 | 35.6 | 35.6 | 109 | 110 | 96 |

TABLE 30-continued

Effects after intratracheal application of different lactose vehicles, lactose formulation
I (7.5 μg/kg), lactose formulation II (22.5 μg/kg) and micronized sesquihydrate,
e.g. example 6e (375 μg/kg). Data are shown as absolute values for PAP and BP [mmHg] (n = 3)

| | | | | | | | | | | | | |
|---|---|---|---|---|---|---|---|---|---|---|---|---|
| 150 | 41.3 | 39.5 | 33.2 | 117 | 89 | 104 | 39.9 | 35.0 | 35.9 | 110 | 108 | 98 |
| 160 | 40.4 | 39.0 | 32.9 | 116 | 87 | 103 | 38.8 | 34.1 | 34.1 | 110 | 107 | 98 |
| 170 | 40.9 | 38.1 | 32.9 | 116 | 86 | 102 | 37.1 | 34.8 | 32.5 | 110 | 106 | 97 |
| 180 | 40.9 | 38.1 | 32.6 | 114 | 88 | 101 | 35.5 | 31.6 | 32.6 | 109 | 105 | 98 |
| 190 | 41.5 | 39.7 | 33.6 | 116 | 90 | 102 | 34.4 | 31.7 | 30.8 | 108 | 106 | 96 |
| 200 | 39.3 | 39.7 | 32.5 | 112 | 89 | 103 | 34.5 | 31.7 | 30.5 | 108 | 106 | 95 |
| 210 | 40.2 | 39.7 | 32.3 | 112 | 90 | 102 | 34.5 | 31.5 | 30.3 | 107 | 106 | 96 |
| 220 | 38.6 | 38.7 | 31.5 | 110 | 89 | 104 | 34.2 | 29.9 | 28.6 | 106 | 104 | 95 |
| 230 | 39.3 | 38.7 | 31.5 | 111 | 88 | 105 | 32.7 | 29.5 | 28.6 | 106 | 104 | 96 |
| 240 | 38.2 | 38.5 | 30.5 | 109 | 89 | 104 | 32.2 | 28.6 | 28.0 | 106 | 104 | 96 |
| 250 | 40.3 | 38.1 | 31.2 | 110 | 90 | 103 | 31.6 | 29.1 | 27.4 | 105 | 102 | 96 |
| 260 | 39.6 | 36.4 | 30.0 | 107 | 90 | 100 | 29.6 | 28.7 | 27.7 | 105 | 102 | 97 |
| 270 | 38.7 | 36.9 | 29.3 | 108 | 94 | 98 | 28.8 | 27.9 | 26.6 | 104 | 103 | 94 |
| 280 | 39.6 | 36.2 | 28.9 | 106 | 91 | 98 | 32.5 | 27.2 | 26.2 | 105 | 102 | 93 |
| 290 | 40.1 | 37.0 | 28.3 | 107 | 91 | 95 | 31.5 | 26.6 | 26.6 | 105 | 100 | 91 |
| 300 | 38.2 | 37.9 | 28.0 | 104 | 90 | 92 | 30.6 | 26.6 | 25.7 | 104 | 101 | 94 |
| 310 | 40.0 | 37.1 | 27.4 | 105 | 91 | 92 | 30.6 | 26.3 | 26.0 | 105 | 97 | 93 |
| | | | | | | | 30.3 | 26.2 | 26.1 | 104 | 95 | 93 |
| | | | | | | | 30.2 | 26.0 | 25.7 | 103 | 95 | 93 |
| | | | | | | | 29.7 | 25.3 | 26.5 | 102 | 90 | 94 |

Lactose 1.5 mg/4 kg (@30 min) + cryst. form of sesquihydrate
ex. 6e micronized 1.5 mg/4 kg (@90 min)

| time | PAP | | | BP | | |
|---|---|---|---|---|---|---|
| 0 | | | | | | |
| 10 | | | | | | |
| 20 | 42.0 | 36.4 | 37.5 | 99 | 107 | 119 |
| 30 | 41.9 | 37.1 | 37.5 | 99 | 104 | 117 |
| 40 | 42.0 | 37.3 | 38.6 | 99 | 108 | 119 |
| 50 | 41.4 | 37.4 | 39.8 | 99 | 109 | 118 |
| 60 | 41.4 | 36.8 | 41.2 | 100 | 107 | 118 |
| 70 | 41.0 | 37.4 | 41.3 | 100 | 109 | 118 |
| 80 | 40.9 | 38.1 | 40.8 | 101 | 114 | 119 |
| 90 | 40.4 | 39.5 | 40.7 | 102 | 116 | 118 |
| 100 | 40.7 | 38.7 | 39.6 | 99 | 111 | 117 |
| 110 | 36.5 | 37.6 | 35.4 | 101 | 112 | 116 |
| 120 | 34.3 | 36.4 | 30.8 | 101 | 114 | 115 |
| 130 | 32.3 | 35.7 | 28.6 | 101 | 114 | 115 |
| 140 | 30.8 | 35.0 | 27.5 | 99 | 120 | 114 |
| 150 | 30.3 | 29.0 | 26.6 | 99 | 121 | 114 |
| 160 | 29.0 | 30.3 | 26.9 | 100 | 122 | 114 |
| 170 | 28.0 | 28.3 | 25.1 | 101 | 121 | 115 |
| 180 | 25.8 | 30.8 | 25.3 | 99 | 119 | 115 |
| 190 | 25.1 | 30.8 | 23.9 | 99 | 123 | 114 |
| 200 | 25.5 | 30.6 | 24.6 | 98 | 116 | 113 |
| 210 | 25.0 | 30.8 | 24.2 | 99 | 117 | 116 |
| 220 | 24.3 | 32.9 | 23.6 | 97 | 123 | 114 |
| 230 | 24.0 | 31.5 | 23.6 | 97 | 119 | 114 |
| 240 | 24.3 | 31.0 | 23.5 | 97 | 119 | 112 |
| 250 | 24.2 | 31.3 | 22.9 | 97 | 118 | 111 |
| 260 | 24.0 | 31.5 | 23.5 | 96 | 116 | 112 |
| 270 | 24.5 | 29.8 | 22.6 | 99 | 115 | 109 |
| 280 | 23.9 | 29.8 | 22.8 | 97 | 111 | 110 |
| 290 | 23.5 | 30.3 | 22.0 | 97 | 110 | 107 |
| 300 | 24.6 | 30.0 | 22.2 | 98 | 109 | 108 |
| 310 | 23.9 | 29.6 | 21.9 | 97 | 109 | 105 |
| | 25.3 | 29.1 | 22.5 | 94 | 108 | 105 |
| | 25.1 | 28.5 | 21.6 | 97 | 108 | 105 |

TABLE 31

Effects after intratracheal application of different lactose vehicles, lactose formulation I (7.5 μg/kg), lactose formulation II (22.5 μg/kg) and micronized sesquihydrate, e.g. example 6e (375 μg/kg). Data are shown as % changes vs. baseline on PAP as absolute values for each animal.

| time | Lactose formulation I 2% | | | Lactose LH300/LH200 20:78 m/m | | | Lactose formulation II 6% | | | Lactose LH300/LH200 20:80 m/m | | |
|---|---|---|---|---|---|---|---|---|---|---|---|---|
| 80 | 100.0 | 100.0 | 100.0 | 100.0 | 100.0 | 100.0 | 100.0 | 100.0 | 100.0 | 100.0 | 100.0 | 100.0 |
| 90 | 97.6 | 100.8 | 99.8 | 96.0 | 101.5 | 101.0 | 100.7 | 101.9 | 105.7 | 102.0 | 100.7 | 97.9 |
| 100 | 89.7 | 103.8 | 94.3 | 90.9 | 99.3 | 103.2 | 102.8 | 98.0 | 100.6 | 103.3 | 102.9 | 97.6 |
| 110 | 84.7 | 103.6 | 96.8 | 103.9 | 100.2 | 104.0 | 99.3 | 93.0 | 99.7 | 104.3 | 101.5 | 99.4 |
| 120 | 90.9 | 107.1 | 94.6 | 107.7 | 101.9 | 105.7 | 95.1 | 92.7 | 96.0 | 105.8 | 104.6 | 102.0 |
| 130 | 92.6 | 107.1 | 92.0 | 107.9 | 106.3 | 105.4 | 94.6 | 90.6 | 88.5 | 108.0 | 103.6 | 102.3 |
| 140 | 97.5 | 107.1 | 88.8 | 108.0 | 110.1 | 106.7 | 92.8 | 89.1 | 89.4 | 109.8 | 103.3 | 99.5 |
| 150 | 97.5 | 106.7 | 86.0 | | | | 90.2 | 86.9 | 84.7 | 110.8 | 106.4 | 103.8 |
| 160 | 98.6 | 103.5 | 84.3 | | | | 86.3 | 88.6 | 80.7 | 112.1 | 107.4 | 101.3 |
| 170 | 98.4 | 96.6 | 83.7 | | | | 82.6 | 80.5 | 81.1 | 111.2 | 106.6 | 100.4 |
| 180 | 96.4 | 95.5 | 82.9 | | | | 80.1 | 80.8 | 76.7 | 111.9 | 108.6 | 106.1 |
| 190 | 97.6 | 93.3 | 82.9 | | | | 80.4 | 80.9 | 76.0 | | | |
| 200 | 97.6 | 93.3 | 82.1 | | | | 80.2 | 80.1 | 75.4 | | | |
| 210 | 98.8 | 97.1 | 84.6 | | | | 79.6 | 76.1 | 71.0 | | | |
| 220 | 93.7 | 97.3 | 81.9 | | | | 76.1 | 75.2 | 71.2 | | | |
| 230 | 95.8 | 97.3 | 81.3 | | | | 74.9 | 72.9 | 69.6 | | | |
| 240 | 92.1 | 94.6 | 79.4 | | | | 73.5 | 74.1 | 68.2 | | | |
| 250 | 93.7 | 94.6 | 79.3 | | | | 68.9 | 73.1 | 68.9 | | | |
| 260 | 91.0 | 94.1 | 76.8 | | | | 66.9 | 71.1 | 66.1 | | | |
| 270 | 96.1 | 93.1 | 78.5 | | | | 75.6 | 69.4 | 65.1 | | | |
| 280 | 94.5 | 89.2 | 75.5 | | | | 73.4 | 67.8 | 66.1 | | | |
| 290 | 92.3 | 90.2 | 73.7 | | | | 71.2 | 67.9 | 64.0 | | | |
| 300 | 94.3 | 88.6 | 72.8 | | | | 71.2 | 67.1 | 64.7 | | | |
| 310 | 95.7 | 90.5 | 71.3 | | | | 70.6 | 66.7 | 65.0 | | | |
| 320 | 91.0 | 92.8 | 71.3 | | | | 70.2 | 66.3 | 63.9 | | | |
| 330 | 95.4 | 90.8 | 69.1 | | | | 69.2 | 64.5 | 66.0 | | | |

| time | sesquihydrate example 6e micronized | | | Lactose LH300/LH200 20:80 m/m | | |
|---|---|---|---|---|---|---|
| 80 | 100.0 | 100.0 | 100.0 | 100.0 | 100.0 | 100.0 |
| 90 | 98.9 | 103.6 | 99.8 | 99.7 | 101.8 | 100.1 |
| 100 | 99.5 | 101.4 | 97.3 | 100.0 | 102.3 | 103.2 |
| 110 | 89.3 | 98.7 | 86.8 | 98.6 | 102.5 | 106.3 |
| 120 | 84.0 | 95.6 | 75.7 | 98.6 | 101.0 | 110.1 |
| 130 | 78.9 | 93.7 | 70.2 | 97.7 | 102.6 | 110.1 |
| 140 | 75.2 | 91.8 | 67.5 | 97.4 | 104.6 | 108.8 |
| 150 | 74.0 | 76.0 | 65.4 | | | |
| 160 | 71.0 | 79.5 | 65.9 | | | |
| 170 | 68.5 | 74.3 | 61.5 | | | |
| 180 | 63.2 | 80.8 | 62.0 | | | |
| 190 | 61.5 | 80.8 | 58.6 | | | |
| 200 | 62.3 | 80.3 | 60.2 | | | |
| 210 | 61.0 | 80.7 | 59.4 | | | |
| 220 | 59.5 | 86.3 | 57.8 | | | |
| 230 | 58.6 | 82.6 | 57.8 | | | |
| 240 | 59.3 | 81.5 | 57.6 | | | |
| 250 | 59.3 | 82.2 | 56.1 | | | |
| 260 | 58.8 | 82.7 | 57.6 | | | |
| 270 | 59.9 | 78.3 | 55.4 | | | |
| 280 | 58.4 | 78.3 | 55.9 | | | |
| 290 | 57.4 | 79.6 | 53.9 | | | |
| 300 | 60.1 | 78.7 | 54.5 | | | |
| 310 | 58.4 | 77.6 | 53.7 | | | |
| 320 | 61.8 | 76.3 | 55.1 | | | |
| 330 | 61.3 | 74.8 | 53.0 | | | |

In summary all dry powder formulations comprising crystalline forms of comp. example 11, e.g. sesquihydrate example 6e selectively and dose-dependently reduced PAP after inhaled application of the dry powder in this model of acute PAH with a long duration of action of at least 4 h. A clear dose-response curve was observed for increasing doses of crystalline form of comp. example 11. Compared to nebulized liquid formulations (maximum effect about 90 min after start inhalation) the maximum effect was delayed to later time points (lactose formulation I (2% w/w)~190 min. lactose formulation II (6% w/w)~170 min) with the dry powder formulations (see FIG. 49).

Evaluation of Efficacy of Different Hydrates of Dry Powder

In addition, to evaluate efficacy of different hydrates of comparative example 11, comparative example 11 at the dose of 1.5 mg/4 kg (=375 μg/kg) was intratracheally applied as micronized monohydrate II (example 2), micronized semihydrate (in analogy to example 6a), as well as micronized sesquihydrate (in analogy to example 6e) via the PennCentury® dry powder insufflator in PAH minipigs. As reference pure Lactose vehicle was applied in the beginning of each experiment. All 3 hydrates showed comparable efficacy with regard to PAP reduction as well as to systemic BP reduction (see FIGS. 50 and 51). Systemic blood pressure was slightly affected with all 3 hydrates within the last hour of the observation interval. This slight systemic BP decrease might be caused via systemic overspill of the drug, applied at a relatively high dose of nominally 375 μg/kg i.t. It also might reflect some decrease in BP in anaesthetized animals over the course of duration of anaesthesia.

TABLE 32

Effects of comparative example 11 after intratracheal application of different hydrates micronized monohydrate II (example 2), micronized semihydrate (example 6a) and micronized sesquihydrate (example 6e) on BP and PAP. Data are shown as absolute values [mmHg] as mean ± SEM (n = 3)

| time | Monohydrate II (example 2) | | | | | | Semihydrate (example 6a) | | | | | |
|---|---|---|---|---|---|---|---|---|---|---|---|---|
| | BP (mean) | | | PAP(mean) | | | BP (mean) | | | PAP(mean) | | |
| −10 | 116 | 126 | 139 | 37.9 | 37.8 | 39.4 | 99 | 85 | 86 | 38.7 | 40.6 | 38.7 |
| 0 | 109 | 127 | 136 | 35.8 | 38.7 | 39.7 | 101 | 85 | 85 | 39.6 | 40.8 | 38.5 |
| 10 | 110 | 126 | 135 | 35.8 | 38.7 | 37.1 | 103 | 83 | 79 | 40.2 | 41.1 | 41.1 |
| 20 | 117 | 128 | 139 | 38.9 | 38.2 | 40.2 | 101 | 83 | 84 | 40.4 | 41.3 | 41.3 |
| 30 | 121 | 128 | 139 | 39.8 | 38.6 | 40.0 | 100 | 81 | 88 | 40.2 | 41.3 | 41.3 |
| 40 | 123 | 127 | 137 | 40.4 | 39.0 | 40.7 | 98 | 81 | 90 | 40.4 | 41.8 | 41.0 |
| 50 | 120 | 127 | 135 | 39.7 | 39.2 | 40.2 | 99 | 78 | 89 | 40.7 | 41.7 | 40.9 |
| 60 | 121 | 127 | 136 | 39.9 | 39.2 | 40.8 | 100 | 79 | 86 | 41.2 | 42.0 | 40.9 |
| 70 | 124 | 126 | 137 | 39.1 | 36.0 | 37.2 | 102 | 78 | 87 | 38.8 | 40.6 | 40.1 |
| 80 | 123 | 124 | 135 | 39.1 | 36.1 | 35.9 | 102 | 79 | 90 | 34.1 | 39.9 | 37.7 |
| 90 | 122 | 125 | 134 | 37.9 | 35.2 | 34.5 | 101 | 81 | 92 | 30.1 | 37.7 | 36.6 |
| 100 | 122 | 124 | 132 | 36.8 | 33.2 | 32.7 | 100 | 80 | 95 | 28.3 | 35.9 | 35.0 |
| 110 | 122 | 125 | 133 | 35.5 | 31.9 | 31.2 | 99 | 79 | 99 | 27.2 | 34.8 | 34.0 |
| 120 | 121 | 125 | 132 | 34.8 | 30.2 | 29.8 | 99 | 79 | 96 | 26.4 | 34.1 | 32.9 |
| 130 | 120 | 124 | 131 | 34.2 | 29.7 | 29.3 | 98 | 81 | 97 | 25.7 | 33.7 | 31.7 |
| 140 | 119 | 125 | 131 | 34.3 | 29.3 | 28.6 | 99 | 82 | 98 | 25.3 | 33.2 | 31.3 |
| 150 | 117 | 124 | 130 | 33.7 | 28.4 | 28.4 | 97 | 82 | 97 | 25.0 | 32.9 | 30.7 |
| 160 | 117 | 121 | 130 | 33.7 | 27.8 | 27.8 | 96 | 81 | 97 | 24.5 | 32.5 | 30.2 |
| 170 | 116 | 120 | 129 | 33.5 | 27.5 | 28.0 | 95 | 79 | 95 | 24.0 | 32.4 | 29.9 |
| 180 | 114 | 117 | 132 | 33.5 | 27.1 | 28.1 | 94 | 79 | 94 | 23.7 | 31.9 | 29.7 |
| 190 | 112 | 116 | 133 | 33.6 | 26.7 | 28.3 | 94 | 85 | 93 | 24.4 | 32.4 | 29.2 |
| 200 | 109 | 115 | 131 | 33.5 | 26.8 | 28.0 | 92 | 85 | 92 | 24.8 | 32.4 | 29.4 |
| 210 | 110 | 117 | 130 | 33.4 | 26.3 | 27.6 | 90 | 81 | 91 | 24.8 | 31.9 | 29.2 |
| 220 | 110 | 116 | 128 | 33.7 | 26.3 | 27.1 | 89 | 79 | 89 | 24.7 | 31.7 | 29.1 |
| 230 | 111 | 115 | 129 | 33.8 | 26.0 | 27.6 | 87 | 78 | 89 | 24.0 | 31.3 | 28.6 |
| 240 | 111 | 113 | 121 | 33.3 | 26.6 | 26.8 | 87 | 77 | 87 | 24.1 | 31.3 | 28.1 |
| 250 | 109 | 110 | 123 | 33.2 | 26.0 | 26.3 | 85 | 76 | 85 | 24.2 | 30.7 | 28.1 |
| 260 | 109 | 108 | 119 | 33.4 | 26.3 | 26.7 | 85 | 76 | 84 | 24.1 | 30.6 | 28.1 |
| 270 | 108 | 106 | 119 | 33.6 | 25.9 | 26.3 | 85 | 76 | 87 | 24.4 | 30.6 | 27.8 |
| 280 | 108 | 104 | 116 | 33.4 | 26.3 | 26.2 | 85 | 75 | 84 | 24.3 | 30.7 | 28.0 |
| 290 | 106 | 102 | 114 | 33.2 | 25.9 | 25.8 | 84 | 75 | 83 | 24.1 | 30.7 | 27.6 |
| 300 | 105 | 101 | 114 | 33.1 | 25.9 | 25.7 | 83 | 77 | 82 | 23.7 | 30.5 | 27.7 |

| time | Sesquihydrate (example 6e) | | | | | |
|---|---|---|---|---|---|---|
| | BP (mean) | | | PAP(mean) | | |
| −10 | 99 | 107 | 119 | 42.0 | 36.4 | 37.5 |
| 0 | 99 | 104 | 117 | 41.9 | 37.1 | 37.5 |
| 10 | 99 | 108 | 119 | 42.0 | 37.3 | 38.6 |
| 20 | 99 | 109 | 118 | 41.4 | 37.4 | 39.8 |
| 30 | 100 | 107 | 118 | 41.4 | 36.8 | 41.2 |
| 40 | 100 | 109 | 118 | 41.0 | 37.4 | 41.3 |
| 50 | 101 | 114 | 119 | 40.9 | 38.1 | 40.8 |
| 60 | 102 | 116 | 118 | 40.4 | 39.5 | 40.7 |
| 70 | 99 | 111 | 117 | 40.7 | 38.7 | 39.6 |
| 80 | 101 | 112 | 116 | 36.5 | 37.6 | 35.4 |
| 90 | 101 | 114 | 115 | 34.3 | 36.4 | 30.8 |
| 100 | 101 | 114 | 115 | 32.3 | 35.7 | 28.6 |
| 110 | 99 | 120 | 114 | 30.8 | 35.0 | 27.5 |
| 120 | 99 | 121 | 114 | 30.3 | 29.0 | 26.6 |
| 130 | 100 | 122 | 114 | 29.0 | 30.3 | 26.9 |
| 140 | 101 | 121 | 115 | 28.0 | 28.3 | 25.1 |
| 150 | 99 | 119 | 115 | 25.8 | 30.8 | 25.3 |
| 160 | 99 | 123 | 114 | 25.1 | 30.8 | 23.9 |
| 170 | 98 | 116 | 113 | 25.5 | 30.6 | 24.6 |
| 180 | 99 | 117 | 116 | 25.0 | 30.8 | 24.2 |
| 190 | 97 | 123 | 114 | 24.3 | 32.9 | 23.6 |
| 200 | 97 | 119 | 114 | 24.0 | 31.5 | 23.6 |
| 210 | 97 | 119 | 112 | 24.3 | 31.0 | 23.5 |
| 220 | 97 | 118 | 111 | 24.2 | 31.3 | 22.9 |
| 230 | 96 | 116 | 112 | 24.0 | 31.5 | 23.5 |
| 240 | 99 | 115 | 109 | 24.5 | 29.8 | 22.6 |
| 250 | 97 | 111 | 110 | 23.9 | 29.8 | 22.8 |
| 260 | 97 | 110 | 107 | 23.5 | 30.3 | 22.0 |
| 270 | 98 | 109 | 108 | 24.6 | 30.0 | 22.2 |
| 280 | 97 | 109 | 105 | 23.9 | 29.6 | 21.9 |

TABLE 32-continued

Effects of comparative example 11 after intratracheal application of different hydrates micronized monohydrate II (example 2), micronized semihydrate (example 6a) and micronized sesquihydrate (example 6e) on BP and PAP. Data are shown as absolute values [mmHg] as mean ± SEM (n = 3)

| 290 | 94 | 108 | 105 | 25.3 | 29.1 | 22.5 |
|---|---|---|---|---|---|---|
| 300 | 97 | 108 | 105 | 25.1 | 28.5 | 21.6 |

TABLE 33

Effects of comparative example 11 after intratracheal application of different hydrates micronized monohydrate II (example 2), micronized semihydrate (in analogy to example 6a) and micronized sesquihydrate (in analogy to example 6e) on BP and PAP. Data are shown as % changes vs. prevalues as absolute values for each animal.

| | Monohydrate II (example 2) | | | | | | Semihydrate (example 6a) | | | | | |
|---|---|---|---|---|---|---|---|---|---|---|---|---|
| time | PAP | | | BP | | | PAP | | | BP | | |
| 50 | 99.1 | 99.2 | 98.5 | 99.1 | 100.1 | 100.0 | 99.3 | 98.7 | 98.9 | 99.6 | 98.4 | 100.6 |
| 60 | 99.7 | 99.3 | 99.8 | 99.9 | 100.1 | 100.7 | 100.7 | 99.4 | 99.2 | 100.6 | 99.7 | 97.2 |
| 70 | 97.7 | 91.1 | 91.0 | 102.4 | 99.3 | 101.4 | 94.7 | 96.1 | 97.0 | 102.6 | 98.4 | 98.4 |
| 80 | 97.7 | 91.3 | 88.0 | 101.6 | 97.7 | 100.0 | 83.4 | 94.5 | 91.2 | 102.6 | 99.7 | 101.8 |
| 90 | 94.7 | 89.1 | 84.5 | 100.7 | 98.5 | 99.2 | 73.4 | 89.2 | 88.7 | 101.6 | 102.2 | 104.0 |
| 100 | 91.8 | 84.0 | 80.0 | 100.7 | 97.7 | 97.7 | 69.0 | 85.0 | 84.7 | 100.6 | 101.0 | 107.4 |
| 110 | 88.8 | 80.9 | 76.3 | 100.7 | 98.5 | 98.5 | 66.5 | 82.4 | 82.1 | 99.6 | 99.7 | 111.9 |
| 120 | 87.0 | 76.6 | 73.0 | 99.9 | 98.5 | 97.7 | 64.4 | 80.8 | 79.7 | 99.6 | 99.7 | 108.6 |
| 130 | 85.5 | 75.2 | 71.7 | 99.1 | 97.7 | 97.0 | 62.8 | 79.9 | 76.7 | 98.6 | 102.2 | 109.7 |
| 140 | 85.6 | 74.3 | 70.0 | 98.3 | 98.5 | 97.0 | 61.8 | 78.7 | 75.7 | 99.6 | 103.5 | 110.8 |
| 150 | 84.1 | 71.9 | 69.4 | 96.6 | 97.7 | 96.3 | 60.9 | 78.0 | 74.3 | 97.6 | 103.5 | 109.7 |
| 160 | 84.1 | 70.4 | 68.1 | 96.6 | 95.3 | 96.3 | 59.9 | 77.1 | 73.1 | 96.6 | 102.2 | 109.7 |
| 170 | 83.8 | 69.8 | 68.5 | 95.8 | 94.5 | 95.5 | 58.6 | 76.7 | 72.3 | 95.6 | 99.7 | 107.4 |
| 180 | 83.8 | 68.7 | 68.9 | 94.1 | 92.2 | 97.7 | 58.0 | 75.4 | 71.8 | 94.6 | 99.7 | 106.3 |
| 190 | 83.9 | 67.7 | 69.3 | 92.5 | 91.4 | 98.5 | 59.5 | 78.4 | 70.7 | 94.6 | 108.5 | 105.2 |
| 200 | 83.7 | 67.9 | 68.5 | 90.0 | 90.6 | 97.0 | 60.5 | 76.8 | 71.1 | 92.6 | 107.3 | 104.0 |
| 210 | 83.4 | 66.5 | 67.7 | 90.8 | 92.2 | 96.3 | 60.6 | 75.5 | 70.8 | 90.6 | 102.2 | 102.9 |
| 220 | 84.0 | 66.7 | 66.2 | 90.8 | 91.4 | 94.8 | 60.3 | 75.1 | 70.3 | 89.6 | 99.7 | 100.6 |
| 230 | 84.5 | 65.8 | 67.6 | 91.6 | 90.6 | 95.5 | 58.7 | 74.1 | 69.1 | 87.6 | 98.4 | 100.6 |
| 240 | 83.2 | 67.3 | 65.6 | 91.6 | 89.0 | 89.6 | 58.9 | 74.2 | 68.0 | 87.6 | 97.2 | 98.4 |
| 250 | 83.0 | 65.7 | 64.3 | 90.0 | 86.7 | 91.1 | 59.0 | 72.7 | 67.9 | 85.5 | 95.9 | 96.1 |
| 260 | 83.3 | 66.7 | 65.4 | 90.0 | 85.1 | 88.1 | 58.8 | 72.5 | 68.0 | 85.5 | 95.9 | 95.0 |
| 270 | 83.8 | 65.6 | 64.3 | 89.2 | 83.5 | 88.1 | 59.6 | 72.4 | 67.3 | 85.5 | 95.9 | 98.4 |
| 280 | 83.3 | 66.5 | 64.1 | 89.2 | 81.9 | 85.9 | 59.3 | 72.6 | 67.8 | 85.5 | 94.6 | 95.0 |
| 290 | 82.8 | 66.5 | 63.1 | 87.5 | 80.4 | 84.4 | 58.8 | 72.6 | 66.7 | 84.5 | 94.6 | 93.9 |
| 300 | 82.7 | 65.7 | 62.9 | 86.7 | 79.6 | 84.4 | 57.9 | 72.2 | 67.1 | 83.5 | 97.2 | 92.7 |

| | Sesquihydrate (example 6e) | | | | | |
|---|---|---|---|---|---|---|
| time | PAP | | | BP | | |
| 50 | 98.3 | 96.2 | 101.2 | 101.4 | 98.5 | 100.3 |
| 60 | 97.2 | 99.6 | 101.1 | 102.5 | 100.3 | 99.4 |
| 70 | 97.8 | 97.5 | 98.5 | 99.4 | 96.0 | 98.6 |
| 80 | 87.8 | 94.9 | 87.9 | 101.4 | 96.8 | 97.7 |
| 90 | 82.5 | 92.0 | 76.6 | 101.4 | 98.5 | 96.9 |
| 100 | 77.6 | 90.1 | 71.1 | 101.4 | 98.5 | 96.9 |
| 110 | 74.0 | 88.3 | 68.4 | 99.4 | 103.7 | 96.1 |
| 120 | 72.8 | 73.1 | 66.2 | 99.4 | 104.6 | 96.1 |
| 130 | 69.8 | 76.4 | 66.8 | 100.4 | 105.5 | 96.1 |
| 140 | 67.3 | 71.4 | 62.2 | 101.4 | 104.6 | 96.9 |
| 150 | 62.1 | 77.7 | 62.8 | 99.4 | 102.9 | 96.9 |
| 160 | 60.4 | 77.7 | 59.3 | 99.4 | 106.3 | 96.1 |
| 170 | 61.3 | 77.3 | 61.0 | 98.4 | 100.3 | 95.2 |
| 180 | 60.0 | 77.6 | 60.1 | 99.4 | 101.1 | 97.7 |
| 190 | 58.5 | 83.0 | 58.5 | 97.4 | 106.3 | 96.1 |
| 200 | 57.6 | 79.4 | 58.5 | 97.4 | 102.9 | 96.1 |
| 210 | 58.3 | 78.3 | 58.3 | 97.4 | 102.9 | 94.4 |
| 220 | 58.3 | 79.0 | 56.8 | 97.4 | 102.0 | 93.5 |
| 230 | 57.8 | 79.6 | 58.3 | 96.4 | 100.3 | 94.4 |
| 240 | 58.9 | 75.3 | 56.1 | 99.4 | 99.4 | 91.8 |
| 250 | 57.4 | 75.3 | 56.6 | 97.4 | 96.0 | 92.7 |
| 260 | 56.4 | 76.5 | 54.6 | 97.4 | 95.1 | 90.2 |
| 270 | 59.1 | 75.7 | 55.2 | 98.4 | 94.2 | 91.0 |
| 280 | 57.4 | 74.6 | 54.4 | 97.4 | 94.2 | 88.5 |
| 290 | 60.8 | 73.3 | 55.8 | 94.4 | 93.4 | 85.9 |
| 300 | 60.3 | 72.0 | 53.7 | 101.4 | 90.8 | 84.3 |

E-2.1 Inhalative Administration of sGC Activators in Healthy Male Subjects for 7 Days—cGMP and Bronchodilatation Healthy White male subjects, aged 18 to 45 years and with a body mass index (BMI) above/equal 18.5 and below/equal 29.9 kg/m2 were treated in a clinical pharmacological phase I study on seven days with inhaled once daily doses of 480 µg or 1000 µg or 2000 µg (2 capsules of 1000 µg) (nominal dose) of dry powder formulations comprising example 2 or Placebo. The subjects inhaled the drug powder from capsules (see under C-1, e.g. tables 22 and 23) inserted into a handheld inhalation device by one deep inhalative breath. The dry powder formulation of the drug is dispersed into the airstream and fine particles are transported into the deep parts of the lung where it is intended to cause a vasodilation of the blood vessels in PH patients for a substantial reduction of increased blood pressure in the central pulmonary blood vessels in PAH patients or other subtypes of PH. This effect cannot be shown in subjects with healthy lungs. In addition inhaled drug causes a dilation of the bronchial airways and thus also improves disease states of lung diseases in PH patients with pathological bronchoconstriction. This effect was measured via bodyplethysmography as reduction of Specific Airway Resistance in healthy subjects. After the deep inhalative breath the subjects hold breath for 2 seconds, so that the dry powder drug condenses from the airstream onto the surface of the deeper lung areas where it is deposited close to its site of intended pharmacological action. The drug dissolutes over the day and equilibrates the lung via lining fluid. As surrogate for drug concentration in the lung, plasma concentrations over time were analysed and showed a maximum blood concentration 2.0 to 2.5 h after inhalation. that thereafter supports drug equilibration of the lung via bloodstream. After first inhalation a measurable plasma concentration was generated that persisted for 48 h as seen for all doses administered, to generate a steady state drug concentration over 24 h after 14 days of once daily inhalation and thus supporting an 24/7 activity of the drug after od inhalation.

Drug activity in healthy men was controlled in the healthy subjects by analysing blood samples for cGMP, the immediate product of sGC pharmacological activation prior after the first and after the last drug inhalation of the 7 days treatment in comparison to measurements on the pretreatment day for all doses.

The analysis of changes from baseline of this parameter showed dose-dependent increases of cGMP, starting at approximately 2 h after first inhalation with a peak at 6 h (480 and 1000 µg dose) and 8 h (2000 µg dose) after administration of example 2 (see FIGS. 52-56). This prolonged activity in comparison to systemic drug concentration is caused by the mode of administration as inhaled dry powder, that deposits drug in the deeper part of the lung leading to an active drug concentration over 24 h after a once daily inhalation. The peak mean±SD cGMP values observed at the first profile day were 8.84±1.35, 11.69±1.86, and 16.52±4.24 nmol/L after administration of 480, 1000, and 2000 µg example 2.

After repeated dosing for 7 days, a further increase of mean peak values for cGMP were observed with 11.96±2.80, 16.70±2.96, and 32.67±9.48 nmol/L after administration of the resp. doses. At 10 days after the first treatment, mean cGMP concentrations had returned close to the concentration observed at the pre-dosing day. The cGMP data show that a once-daily inhalation of the drug example 2 causes the intended dose dependent effect at the sGC target (see FIG. 56).

TABLE 34

Cyclic guanosine monophosphate changes from baseline (nmol/L) (SAF)

| | Placebo | 480 µg, ex. 2 | 1000 µg, ex. 2 | 2000 µg, ex. 2 |
|---|---|---|---|---|
| −0 D 22 H 00 M | 0.47 ± 0.90 | 1.17 ± 1.00 | 0.08 ± 1.41 | 0.66 ± 0.79 |
| −0 D 20 H 00 M | −0.11 ± 1.13 | 0.52 ± 0.95 | −0.24 ± 1.75 | 0.48 ± 0.71 |
| −0 D 18 H 00 M | 0.71 ± 1.41 | 0.21 ± 1.74 | −0.87 ± 1.44 | 0.17 ± 0.78 |
| −0 D 16 H 00 M | −0.26 ± 1.89 | 0.41 ± 0.96 | −0.43 ± 1.49 | 0.29 ± 1.17 |
| −0 D 12 H 00 M | −0.11 ± 1.34 | 0.22 ± 1.17 | −0.77 ± 1.72 | 0.28 ± 0.97 |
| −0 D 09 H 00 M | −0.67 ± 1.25 | 0.20 ± 1.59 | −0.84 ± 2.04 | −0.18 ± 0.90 |
| 0 D 00 H 00 M | −0.77 ± 1.27 | 0.11 ± 1.10 | −0.11 ± 1.62 | 0.68 ± 1.14 |
| 0 D 02 H 00 M | 0.42 ± 0.52 | 1.73 ± 0.82 | 3.26 ± 2.04 | 4.78 ± 1.35 |
| 0 D 04 H 00 M | −0.68 ± 2.23 | 3.04 ± 1.39 | 5.64 ± 2.54 | 9.18 ± 2.50 |
| 0 D 06 H 00 M | −0.40 ± 2.23 | 3.33 ± 1.39 | 6.78 ± 2.79 | 11.04 ± 3.21 |
| 0 D 08 H 00 M | 0.33 ± 2.56 | 2.94 ± 1.38 | 5.94 ± 2.65 | 11.69 ± 2.78 |
| 0 D 12 H 00 M | −0.24 ± 2.07 | 2.10 ± 1.18 | 4.86 ± 2.91 | 8.56 ± 2.19 |
| 0 D 15 H 00 M | −0.58 ± 2.14 | 1.53 ± 1.50 | 3.70 ± 2.59 | 7.54 ± 2.32 |
| 1 D 00 H 00 M | −0.18 ± 2.06 | 0.84 ± 0.89 | 1.26 ± 1.98 | 3.48 ± 0.90 |
| 2 D 00 H 00 M | −0.30 ± 2.26 | 0.74 ± 1.59 | 0.33 ± 1.99 | 1.57 ± 0.86 |
| 3 D 00 H 00 M | −0.14 ± 2.10 | 1.00 ± 1.92 | 2.31 ± 2.68 | 5.17 ± 1.51 |
| 4 D 00 H 00 M | 0.31 ± 1.99 | 1.46 ± 1.24 | 2.86 ± 2.63 | 9.33 ± 2.55 |
| 5 D 00 H 00 M | 0.27 ± 2.34 | 1.50 ± 0.98 | 3.59 ± 2.51 | 11.10 ± 3.49 |
| 6 D 00 H 00 M | 0.71 ± 2.21 | 1.92 ± 1.21 | 4.32 ± 2.82 | 11.71 ± 2.66 |
| 7 D 00 H 00 M | 0.21 ± 0.83 | 1.68 ± 0.85 | 4.74 ± 2.98 | 11.36 ± 3.37 |
| 7 D 02 H 00 M | 0.07 ± 0.81 | 4.22 ± 2.29 | 6.93 ± 2.99 | 17.33 ± 4.18 |
| 7 D 04 H 00 M | 0.20 ± 0.71 | 5.39 ± 2.34 | 10.84 ± 2.91 | 22.23 ± 4.75 |
| 7 D 06 H 00 M | 0.72 ± 1.06 | 6.44 ± 2.26 | 11.79 ± 3.70 | 27.39 ± 6.93 |
| 7 D 08 H 00 M | 1.26 ± 1.68 | 5.19 ± 1.64 | 11.00 ± 4.58 | 27.83 ± 7.77 |
| 7 D 12 H 00 M | 0.59 ± 1.00 | 3.71 ± 1.79 | 9.19 ± 5.26 | 23.33 ± 5.53 |
| 7 D 15 H 00 M | 0.02 ± 0.73 | 3.04 ± 2.09 | 8.00 ± 4.41 | 19.08 ± 4.95 |
| 8 D 00 H 00 M | 0.81 ± 0.54 | 1.69 ± 2.65 | 4.47 ± 3.81 | 11.17 ± 3.69 |
| 8 D 12 H 00 M | 0.66 ± 1.11 | 0.69 ± 1.53 | 2.30 ± 3.05 | 8.02 ± 2.45 |
| 9 D 00 H 00 M | 0.08 ± 0.73 | 0.13 ± 1.97 | 1.38 ± 2.59 | 5.64 ± 1.36 |
| 9 D 12 H 00 M | 0.70 ± 1.64 | 1.10 ± 1.01 | 1.02 ± 2.24 | 4.57 ± 2.15 |
| 10 D 00 H 00 M | 0.89 ± 1.47 | −0.00 ± 0.64 | 1.42 ± 2.87 | 3.26 ± 1.07 |

TABLE 35

Means (N = 9 each for Placebo, 480, 1000 and 2000 µg, example 2) for cGMP over time: prior to drug inhalation (baseline) (−1 d 02 h-0 d 00 h) after first inhalation day (0 d 00 h-2 d 00 h), trough measurements after inhalations on days 3 d 00 h-7 d 00 h and after last of 7 days of inhalation (7 d 00 h-10 d 00 h).

| | Placebo | 480 µg, ex. 2 | 1000 µg, ex. 2 | 2000 µg, ex. 2 |
|---|---|---|---|---|
| −1 D 02 H 00 M | 5.83 ± 2.01 | 5.40 ± 1.41 | 5.02 ± 1.59 | 4.16 ± 1.70 |
| −0 D 22 H 00 M | 6.30 ± 2.42 | 6.57 ± 1.22 | 5.10 ± 1.46 | 4.81 ± 2.22 |
| −0 D 20 H 00 M | 5.72 ± 2.00 | 5.92 ± 0.83 | 4.78 ± 1.37 | 4.63 ± 1.86 |
| −0 D 18 H 00 M | 6.54 ± 2.68 | 5.61 ± 0.71 | 4.16 ± 0.92 | 4.32 ± 1.33 |
| −0 D 16 H 00 M | 5.58 ± 2.13 | 5.81 ± 1.09 | 4.59 ± 1.06 | 4.44 ± 2.15 |
| −0 D 12 H 00 M | 5.72 ± 2.17 | 5.62 ± 1.26 | 4.26 ± 0.99 | 4.43 ± 2.24 |
| −0 D 09 H 00 M | 5.17 ± 1.90 | 5.60 ± 1.08 | 4.18 ± 0.82 | 3.98 ± 1.91 |
| 0 D 00 H 00 M | 5.07 ± 1.90 | 5.51 ± 1.00 | 4.91 ± 1.27 | 4.83 ± 2.52 |
| 0 D 02 H 00 M | 5.49 ± 2.03 | 7.24 ± 1.25 | 8.17 ± 1.07 | 9.61 ± 3.65 |
| 0 D 04 H 00 M | 4.39 ± 1.20 | 8.56 ± 1.45 | 10.56 ± 1.47 | 14.01 ± 4.51 |
| 0 D 06 H 00 M | 4.67 ± 1.25 | 8.84 ± 1.35 | 11.69 ± 1.86 | 15.88 ± 5.09 |
| 0 D 08 H 00 M | 5.40 ± 1.70 | 8.46 ± 1.59 | 10.86 ± 1.66 | 16.52 ± 4.24 |
| 0 D 12 H 00 M | 4.82 ± 1.35 | 7.61 ± 1.01 | 9.77 ± 2.11 | 13.39 ± 4.01 |
| 0 D 15 H 00 M | 4.49 ± 0.90 | 7.04 ± 1.50 | 8.61 ± 1.63 | 12.38 ± 4.17 |
| 1 D 00 H 00 M | 4.89 ± 1.16 | 6.36 ± 1.10 | 6.17 ± 1.05 | 8.31 ± 2.88 |
| 2 D 00 H 00 M | 4.77 ± 0.74 | 6.26 ± 2.17 | 5.24 ± 1.28 | 6.40 ± 2.09 |
| 3 D 00 H 00 M | 4.92 ± 0.87 | 6.51 ± 2.62 | 7.22 ± 2.04 | 10.00 ± 3.51 |
| 4 D 00 H 00 M | 5.38 ± 1.06 | 6.97 ± 1.96 | 7.77 ± 1.87 | 14.17 ± 4.36 |
| 5 D 00 H 00 M | 5.33 ± 1.07 | 7.01 ± 1.72 | 8.50 ± 2.13 | 15.93 ± 5.52 |
| 6 D 00 H 00 M | 5.78 ± 1.42 | 7.43 ± 1.69 | 9.23 ± 2.12 | 16.54 ± 4.60 |
| 7 D 00 H 00 M | 5.28 ± 1.86 | 7.19 ± 1.47 | 9.66 ± 2.30 | 16.19 ± 5.02 |
| 7 D 02 H 00 M | 5.13 ± 1.97 | 9.73 ± 3.00 | 11.84 ± 2.18 | 22.17 ± 6.07 |

TABLE 35-continued

Means (N = 9 each for Placebo, 480, 1000 and 2000 µg, example 2) for cGMP over time: prior to drug inhalation (baseline) (−1 d 02 h-0 d 00 h) after first inhalation day (0 d 00 h-2 d 00 h), trough measurements after inhalations on days 3 d 00 h-7 d 00 h and after last of 7 days of inhalation (7 d 00 h-10 d 00 h).

|  | Placebo | 480 µg, ex. 2 | 1000 µg, ex. 2 | 2000 µg, ex. 2 |
|---|---|---|---|---|
| 7 D 04 H 00 M | 5.27 ± 2.05 | 10.90 ± 3.12 | 15.76 ± 2.29 | 27.07 ± 7.01 |
| 7 D 06 H 00 M | 5.79 ± 2.16 | 11.96 ± 2.80 | 16.70 ± 2.96 | 32.22 ± 8.83 |
| 7 D 08 H 00 M | 6.32 ± 3.30 | 10.70 ± 2.27 | 15.91 ± 3.86 | 32.67 ± 9.48 |
| 7 D 12 H 00 M | 5.66 ± 2.17 | 9.22 ± 2.37 | 14.10 ± 4.55 | 28.17 ± 7.50 |
| 7 D 15 H 00 M | 5.09 ± 1.97 | 8.56 ± 2.80 | 12.91 ± 3.72 | 23.91 ± 6.59 |
| 8 D 00 H 00 M | 5.88 ± 2.07 | 7.20 ± 3.23 | 9.38 ± 3.11 | 16.00 ± 5.77 |
| 8 D 12 H 00 M | 5.72 ± 2.10 | 6.20 ± 2.00 | 7.21 ± 2.24 | 12.86 ± 3.96 |
| 9 D 00 H 00 M | 5.14 ± 1.60 | 5.64 ± 2.53 | 6.29 ± 1.86 | 10.48 ± 3.49 |
| 9 D 12 H 00 M | 5.77 ± 3.38 | 6.61 ± 1.80 | 5.93 ± 1.39 | 9.40 ± 3.10 |
| 10 D 00 H 00 M | 5.96 ± 2.26 | 5.51 ± 1.39 | 6.33 ± 2.30 | 8.09 ± 2.81 |

Measurement of lung function parameters via bodyplethysmography showed a decrease of total specific airway resistance sRaw, a parameter for bronchodilative activity in the healthy lung, of −0.142 to −0.296 kPa/sec, measured at 6 h after first dosing example 2 compared to baseline and was observed in all dose groups (see FIG. 57 and table 36).

TABLE 36

Means (N = 9 each for Placebo, 480, 1000 and 2000 µg, example 2) for total specific airway resistance (kPa/sec) over time: screening 1/2, pretreatment day (−1 d 00 h-0 d 00 h) first inhalation day (0 d 00 h-0 d 06 h), measurements after inhalations 2 d 02 h-6 d 04 h) and after last of 7 days inhalation (7 d 00 h-7 d 06 h).

|  | Placebo | 480 µg, ex. 2 | 1000 µg, ex. 2 | 2000 µg, ex. 2 |
|---|---|---|---|---|
| SCREENING | 0.829 ± 0.494 | 0.844 ± 0.327 | 0.867 ± 0.376 | 0.899 ± 0.150 |
| SCREENING 2 | 0.934 ± 0.522 | 0.832 ± 0.280 | 1.009 ± 0.340 | 0.957 ± 0.140 |
| −1 D 00 H 00 M | 0.896 ± 0.301 | 0.939 ± 0.344 | 0.996 ± 0.194 | 0.962 ± 0.266 |
| −0 D 22 H 00 M | 0.916 ± 0.332 | 0.928 ± 0.392 | 0.903 ± 0.255 | 0.933 ± 0.165 |
| −0 D 18 H 00 M | 0.942 ± 0.302 | 0.921 ± 0.305 | 0.901 ± 0.187 | 0.943 ± 0.245 |
| 0 D 00 H 00 M | 0.991 ± 0.341 | 1.078 ± 0.375 | 0.967 ± 0.233 | 0.947 ± 0.143 |
| 0 D 02 H 00 M | 0.948 ± 0.307 | 0.839 ± 0.182 | 0.859 ± 0.143 | 0.677 ± 0.139 |
| 0 D 06 H 00 M | 0.876 ± 0.268 | 0.800 ± 0.187 | 0.824 ± 0.180 | 0.651 ± 0.149 |
| 2 D 02 H 00 M | 0.913 ± 0.211 | 0.883 ± 0.310 | 0.797 ± 0.141 | 0.748 ± 0.155 |
| 4 D 02 H 00 M | 0.902 ± 0.197 | 0.807 ± 0.200 | 0.853 ± 0.172 | 0.709 ± 0.178 |
| 6 D 04 H 00 M | 0.872 ± 0.192 | 0.798 ± 0.193 | 0.787 ± 0.168 | 0.722 ± 0.168 |
| 7 D 00 H 00 M | 0.978 ± 0.261 | 0.823 ± 0.274 | 0.917 ± 0.227 | 0.844 ± 0.097 |
| 7 D 02 H 00 M | 0.872 ± 0.223 | 0.777 ± 0.282 | 0.764 ± 0.140 | 0.716 ± 0.089 |
| 7 D 06 H 00 M | 0.918 ± 0.212 | 0.803 ± 0.280 | 0.787 ± 0.188 | 0.730 ± 0.151 |

E-2.2 Inhalative Administration of sGC Activators in Healthy Male Subjects for 14 Days to Evaluate Steady State Pharmacokinetics Healthy white male subjects, aged 18 to 45 years and with a body mass index (BMI) above/equal 18.5 and below/equal 29.9 kg/m2 were treated in a clinical pharmacological phase I study for 14 days with inhaled once daily doses of 1000 µg (nominal dose) of Placebo or of dry powder formulation containing example 4. The subjects inhaled the drug powder from capsules (see under C, e.g. tables 17 and 20) inserted into a handheld inhalation device by one deep inhalative breath into the deep parts of the lung. The intended substantial reduction of increased blood pressure in the central pulmonary blood vessels cannot be evaluated in subjects without pathophysiological impairment of lung function. As surrogate for drug concentration in the lung, plasma concentrations over time have been analysed. This analysis after the doses administered for 14 days to generate a steady state drug concentration over 24 h once daily inhalations showed that steady state was reached after 7 to 11 days of inhalation. Drug activity/target engagement in healthy men was controlled in the healthy subjects by analysing blood samples for cGMP. Results are shown in as mean in table 37 and change to baseline in FIG. 58 and table 38 with maximum values after 1 week treatment and showing that steady state of cGMP concentration was reached at latest after 11 days of treatment as biomarker for a constant target engagement.

TABLE 37

Means +/− standard deviation for Placebo (N = 4) and 1000 µg, (N = 17) example 4) for cGMP concntration over time (nmol/L) on pretreatment day (−1 d 00 h--0 d 09 h) first inhalation day (−0 d 02 h-1 d 00 h;), prior and after inhalations on days 2 d 00 h-2 d 12 h, 6 d 00 h-6 d 12 h, 10 d 00 h-10 d 12 h (profiles), at trough prior inhalation on days 3 d-5 d, 7 d-9 d, 11 d-12 d and prior to and after last of 14 days inhalation (12 d 22 h-20 d 00 h).

| Mean | Placebo (n = 4) | 1000 µg, (n = 17) ex. 4 |
|---|---|---|
| −1 D 02 H 00 M | 4775.0 +/− 1530.5 | 5264.7 +/− 2006.8 |
| −0 D 22 H 00 M | 4800.0 +/− 469.0 | 5164.7 +/− 1680.0 |
| −0 D 20 H 00 M | 4175.0 +/− 1345.1 | 4311.8 +/− 1956.4 |
| −0 D 18 H 00 M | 4925.0 +/− 797.4 | 5011.8 +/− 1875.5 |
| −0 D 16 H 00 M | 5250.0 +/− 914.7 | 5941.2 +/− 2641.7 |
| −0 D 12 H 00 M | 7900.0 +/− 3763.9 | 5570.6 +/− 2087.4 |
| −0 D 09 H 00 M | 6400.0 +/− 1180.4 | 5488.2 +/− 1654.9 |

TABLE 37-continued

Means +/− standard deviation for Placebo (N = 4) and 1000 µg, (N = 17) example 4) for cGMP concntration over time (nmol/L) on pretreatment day (−1 d 00 h--0 d 09 h) first inhalation day (−0 d 02 h-1 d 00 h;), prior and after inhalations on days 2 d 00 h-2 d 12 h, 6 d 00 h-6 d 12 h, 10 d 00 h-10 d 12 h (profiles), at trough prior inhalation on days 3 d-5 d, 7 d-9 d, 11 d-12 d and prior to and after last of 14 days inhalation (12 d 22 h-20 d 00 h).

| Mean | Placebo (n = 4) | 1000 µg, (n = 17) ex. 4 |
|---|---|---|
| −0 D 02 H 00 M | 3900.0 +/− 668.3 | 4329.4 +/− 1509.5 |
| 0 D 02 H 00 M | 6200.0 +/− 1930.5 | 9170.6 +/− 2348.3 |
| 0 D 04 H 00 M | 4625.0 +/− 1173.0 | 11623.5 +/− 2636.9 |
| 0 D 06 H 00 M | 4000.0 +/− 559.8 | 14276.5 +/− 3557.1 |
| 0 D 08 H 00 M | 4500.0 +/− 469.0 | 14888.2 +/− 3618.2 |
| 0 D 12 H 00 M | 4500.0 +/− 1409.5 | 11812.5 +/− 2708.5 |
| 0 D 15 H 00 M | 4750.0 +/− 1443.4 | 11064.7 +/− 2963.1 |
| 1 D 00 H 00 M | 4425.0 +/− 590.9 | 7305.9 +/− 1593.5 |
| 2 D 00 H 00 M | 4200.0 +/− 697.6 | 8876.5 +/− 2507.6 |
| 2 D 03 H 00 M | 5366.7 +/− 1150.4 | 17282.4 +/− 4749.9 |
| 2 D 08 H 00 M | 4700.0 +/− 1493.3 | 20770.6 +/− 6604.0 |

TABLE 37-continued

Means +/− standard deviation for Placebo (N = 4) and 1000 μg, (N = 17) example 4) for cGMP concntration over time (nmol/L) on pretreatment day (−1 d 00 h-−0 d 09 h) first inhalation day (−0 d 02 h-1 d 00 h;), prior and after inhalations on days 2 d 00 h-2 d 12 h, 6 d 00 h-6 d 12 h, 10 d 00 h-10 d 12 h (profiles), at trough prior inhalation on days 3 d-5 d, 7 d-9 d, 11 d-12 d and prior to and after last of 14 days inhalation (12 d 22 h-20 d 00 h).

| Mean | Placebo (n = 4) | 1000 μg, (n = 17) ex. 4 |
| --- | --- | --- |
| 2 D 12 H 00 M | 4233.3 +/− 1436.4 | 16941.2 +/− 5408.8 |
| 3 D 00 H 00 M | 4033.3 +/− 1050.4 | 9488.2 +/− 2238.5 |
| 4 D 00 H 00 M | 3466.7 +/− 1429.5 | 10694.1 +/− 2193.0 |
| 5 D 00 H 00 M | 3166.7 +/− 1059.9 | 10252.9 +/− 2390.4 |
| 6 D 00 H 00 M | 4566.7 +/− 2285.5 | 9423.5 +/− 2613.1 |
| 6 D 03 H 00 M | 3800.0 +/− 608.3 | 17735.3 +/− 4290.1 |
| 6 D 08 H 00 M | 4266.7 +/− 1222.0 | 24452.9 +/− 7374.6 |
| 6 D 12 H 00 M | 4266.7 +/− 750.6 | 18194.1 +/− 4785.2 |
| 7 D 00 H 00 M | 3700.0 +/− 1058.3 | 10511.8 +/− 2026.4 |
| 8 D 00 H 00 M | 3733.3 +/− 1331.7 | 10529.4 +/− 1910.7 |
| 9 D 00 H 00 M | 3800.0 +/− 173.2 | 10911.8 +/− 2620.6 |
| 10 D 00 H 00 M | 3766.7 +/− 1011.6 | 10776.5 +/− 2286.0 |
| 10 D 03 H 00 M | 4200.0 +/− 1212.4 | 17058.8 +/− 4319.2 |
| 10 D 08 H 00 M | 4666.7 +/− 1703.9 | 21858.8 +/− 6188.5 |
| 10 D 12 H 00 M | 3800.0 +/− 655.7 | 17329.4 +/− 4529.3 |
| 11 D 00 H 00 M | 3966.7 +/− 1357.7 | 11270.6 +/− 2814.9 |
| 12 D 00 H 00 M | 4400.0 +/− 1389.2 | 12388.2 +/− 3016.4 |
| 12 D 22 H 00 M | 4466.7 +/− 1021.4 | 11276.5 +/− 3261.8 |
| 13 D 02 H 00 M | 3800.0 +/− 700.0 | 13447.1 +/− 2802.9 |
| 13 D 04 H 00 M | 3200.0 +/− 624.5 | 17276.5 +/− 4328.9 |
| 13 D 06 H 00 M | 3633.3 +/− 461.9 | 21370.6 +/− 5581.2 |
| 13 D 08 H 00 M | 3933.3 +/− 901.8 | 22047.1 +/− 5535.0 |
| 13 D 12 H 00 M | 3700.0 +/− 964.4 | 17217.6 +/− 4806.0 |
| 13 D 15 H 00 M | 3433.3 +/− 896.3 | 16382.4 +/− 4045.9 |
| 14 D 00 H 00 M | 3300.0 +/− 1053.6 | 9735.3 +/− 2740.0 |
| 15 D 00 H 00 M | 3433.3 +/− 960.9 | 6852.9 +/− 1222.3 |
| 15 D 12 H 00 M | 4533.3 +/− 1680.3 | 7370.6 +/− 1654.8 |
| 16 D 00 H 00 M | 3666.7 +/− 665.8 | 6329.4 +/− 1357.3 |
| 16 D 12 H 00 M | 4800.0 +/− 1500.0 | 6735.3 +/− 1394.6 |
| 17 D 00 H 00 M | 2866.7 +/− 577.4 | 4729.4 +/− 995.5 |
| 20 D 00 H 00 M | 4033.3 +/− 1893.0 | 5518.8 +/− 1505.2 |
| FOLLOW-UP | 4566.7 +/− 1078.6 | 5847.1 +/− 2013.4 |

TABLE 38 cGMP changes from baseline (nmol/L) on pretreatment day (−1 d 00 h-−0 d 09 h) first inhalation day (−0 d 02 h-1 d 00 h;), after inhalations on days 2 d 00 h-2 d 12 h, 6 d 00 h-6 d 12 h, 10 d 00 h-10 d 12 h (profile days), at trough prior inhalation on days 3 d-5 d, 7 d-9 d, 11 d-12 d) and after last of 14 days inhalation (12 d 22 h-20 d 00 h)

| Delta baseline | Placebo (n = 4) | 1000 μg, (n = 17) ex. 4 |
| --- | --- | --- |
| −1 D 02 H 00 M | baseline | baseline |
| −0 D 22 H 00 M | 25.0 +/− 1408.0 | −100.0 +/− 1403.1 |
| −0 D 20 H 00 M | −600.0 +/− 2219.6 | −952.9 +/− 1984.7 |
| −0 D 18 H 00 M | 150.0 +/− 2120.5 | −252.9 +/− 1345.9 |
| −0 D 16 H 00 M | 475.0 +/− 2091.8 | 676.5 +/− 1844.1 |
| −0 D 12 H 00 M | 3125.0 +/− 2742.7 | 305.9 +/− 1880.3 |
| −0 D 09 H 00 M | 1625.0 +/− 2118.8 | 223.5 +/− 1396.2 |
| −0 D 02 H 00 M | baseline | baseline |
| 0 D 02 H 00 M | 2300.0 +/− 1529.7 | 4841.2 +/− 2006.9 |
| 0 D 04 H 00 M | 725.0 +/− 981.1 | 7294.1 +/− 2972.3 |
| 0 D 06 H 00 M | 100.0 +/− 516.4 | 9947.1 +/− 3796.2 |
| 0 D 08 H 00 M | 600.0 +/− 778.9 | 10558.8 +/− 3607.1 |
| 0 D 12 H 00 M | 600.0 +/− 1067.7 | 7531.3 +/− 3057.2 |
| 0 D 15 H 00 M | 850.0 +/− 1097.0 | 6735.3 +/− 2917.4 |
| 1 D 00 H 00 M | 525.0 +/− 1158.7 | 2976.5 +/− 1785.2 |
| 2 D 00 H 00 M | 300.0 +/− 1067.7 | 4547.1 +/− 2374.4 |
| 2 D 03 H 00 M | 1600.0 +/− 1058.3 | 12952.9 +/− 4814.8 |
| 2 D 08 H 00 M | 933.3 +/− 1059.9 | 16441.2 +/− 6525.1 |
| 2 D 12 H 00 M | 466.7 +/− 1527.5 | 12611.8 +/− 5555.1 |
| 3 D 00 H 00 M | 266.7 +/− 1594.8 | 5158.8 +/− 2554.4 |
| 4 D 00 H 00 M | −300.0 +/− 1833.0 | 6364.7 +/− 2482.9 |
| 5 D 00 H 00 M | −600.0 +/− 1646.2 | 5923.5 +/− 2801.2 |
| 6 D 00 H 00 M | 800.0 +/− 2330.2 | 5094.1 +/− 2382.9 |
| 6 D 03 H 00 M | 33.3 +/− 945.2 | 13405.9 +/− 4568.6 |
| 6 D 08 H 00 M | 500.0 +/− 1819.3 | 20123.5 +/− 7302.6 |
| 6 D 12 H 00 M | 500.0 +/− 1081.7 | 13864.7 +/− 4528.5 |
| 7 D 00 H 00 M | −66.7 +/− 1429.5 | 6182.4 +/− 2095.9 |
| 8 D 00 H 00 M | −33.3 +/− 1934.8 | 6200.0 +/− 2018.7 |
| 9 D 00 H 00 M | 33.3 +/− 776.7 | 6582.4 +/− 2425.7 |
| 10 D 00 H 00 M | 0.0 +/− 1311.5 | 6447.1 +/− 2255.0 |
| 10 D 03 H 00 M | 433.3 +/− 1450.3 | 12729.4 +/− 4182.7 |
| 10 D 08 H 00 M | 900.0 +/− 1907.9 | 17529.4 +/− 6277.2 |
| 10 D 12 H 00 M | 33.3 +/− 1184.6 | 13000.0 +/− 4616.5 |
| 11 D 00 H 00 M | 200.0 +/− 1915.7 | 6941.2 +/− 2865.1 |
| 12 D 00 H 00 M | 633.3 +/− 2064.8 | 8058.8 +/− 2949.8 |
| 12 D 22 H 00 M | 700.0 +/− 1200.0 | 6947.1 +/− 3016.4 |
| 13 D 02 H 00 M | 33.3 +/− 503.3 | 9117.6 +/− 2994.0 |
| 13 D 04 H 00 M | −566.7 +/− 251.7 | 12947.1 +/− 4570.3 |
| 13 D 06 H 00 M | −133.3 +/− 896.3 | 17041.2 +/− 5998.9 |
| 13 D 08 H 00 M | 166.7 +/− 1422.4 | 17717.6 +/− 5772.9 |
| 13 D 12 H 00 M | −66.7 +/− 1331.7 | 12888.2 +/− 4847.5 |
| 13 D 15 H 00 M | −333.3 +/− 1159.0 | 12052.9 +/− 3938.8 |
| 14 D 00 H 00 M | −466.7 +/− 1550.3 | 5405.9 +/− 3158.2 |
| 15 D 00 H 00 M | −333.3 +/− 1436.4 | 2523.5 +/− 1666.0 |
| 15 D 12 H 00 M | 766.7 +/− 1628.9 | 3041.2 +/− 1792.7 |
| 16 D 00 H 00 M | −100.0 +/− 1058.3 | 2000.0 +/− 1581.1 |
| 16 D 12 H 00 M | 1033.3 +/− 2003.3 | 2405.9 +/− 1555.4 |
| 17 D 00 H 00 M | −900.0 +/− 964.4 | 400.0 +/− 1434.8 |
| 20 D 00 H 00 M | 266.7 +/− 2542.3 | 1218.8 +/− 1715.1 |
| FOLLOW-UP | 800.0 +/− 1743.6 | 1517.6 +/− 2343.9 |

E-2.3 Inhalative, Oral and Intravenous Administration of Single Doses of sGC an Activator in Healthy Male Subjects—Lung Deposition Healthy white male subjects, aged 18 to 45 years with a body mass index (BMI) above/equal 18.5 and below/equal 29.9 kg/m² were treated in a clinical phase I study with a single inhaled dose of 1000 μg (nominal dose), a single inhaled dose of 1000 μg (nominal dose)+charcoal block, a single oral dose of 1000 μg and a single infusion over 2 h of 100 μg of example 4. As the bioavailability of an intravenous application is generally 100% per definition and therefore higher than in case of an oral or intravenous administration, the intravenous dose was carefully selected to be lower than the oral and inhaled dose to avoid higher plasma concentration resulting from a high IV dose and potential side effect, e.g. reduction in blood pressure or syncope. Therefore, 100 μg was selected for the IV dose in this investigation. Seven days washout period between treatments was applied. The subjects swallowed a solution for oral administration (20 ml comprising 1000 μg, see under C-2, table 26). The subjects received a solution as a single infusion over 2 hours (2 ml comprising 100 μg, see under C-2 table 26). The subjects inhaled the drug powder from capsules (see under C-1, tables 17 and 20) inserted into a handheld inhalation device by one deep inhalative breath. After inhalation of the dry powder formulation of this drug, some parts of the nominal dose remain in the capsule and the device, the dose which reaches the body at the mouthpiece is called the emitted dose. The emitted dose can be calculated/determined as followed: nominal dose−(remains in the capsule+remains in the device). After inhalation of the dry powder, one part of the emitted dose enters the gastrointestinal tract (GIT) and is called the oral part of the emitted dose, the other part of the emitted dose which reaches the lung through the respiratory airways is called the lung dose and represents the lung deposited dose. As the lung is the target organ of the effect, the lung deposited dose must be quantified. Lung deposition can be indirectly estimated, by determining the part of the nominal dose which reaches the GIT and the remains in the capsule and the device. To investigate and determine lung deposition, the following investigations were done (see also FIG. 59):

1—Inhaled application of a single dose of 1000 µg of the dry powder.
2—Inhaled application of a single dose of 1000 µg of the dry powder in combination with oral administration of charcoal block. The charcoal block capped the oral absorption of GIT part of the dose, as example 4 completely adsorbed to charcoal block. This implies that the concentrations of example 4 measured reach the systemic circulation via the lung.
3—Administration of a single oral dose of 1000 g example 4 to determine the oral absorption.
4—Administration of a 2 h infusion of example 4 to investigate the elimination.

Plasma concentrations of example 4 were measured after all different types of administrations, in addition the remains in the device and the capsule were measured after inhaled application. The analysis of plasma concentrations showed a rapid elimination of example 4 after intravenous administration with an elimination half-life of 0.26 h. The elimination half-life after oral administration was 4.43 h. The elimination half-life after inhaled application with/without charcoal was 16.1 h and 15.1 h, respectively, see FIG. 60. The longer terminal half-life after inhalation can be explained by the formation of a pulmonary depot of example 4 in the lungs from which the substance is continuously transferred to the circulatory system.

The absolute bioavailability of the dry powder formulation administered with charcoal was 16.3% and 18.8% for example 4 administered without charcoal. This means 16.3% of the nominal dose of dry powder of example 4 reached the lung considered as the lung dose, and the total part of the dry powder reaching the body is 18.8% of the nominal dose. The relative bioavailability of example 4 after inhaled application with charcoal block to inhaled administration without charcoal block is 86.9%. This indicates that the oral part of the dose is approximately 13% of the nominal dose. See tables 39 and 40. The emitted dose is calculated to be 720 µg, as the remains in the capsule were 160 µg and the remains in the device were 120 g, see FIG. 61.

The outcome from this investigation confirms the lung dose and that the half-life is adequate for an inhaled dry powder administration enabling a once daily treatment for a sufficient 24 h drug coverage of example 4 in the lung.

TABLE 39

Geometric mean of plasma concentrations (in µg/L) over time of example 4 and (geometric standard deviation SD in %) after administration of 1000 µg inhale, 1000 µg inhale + charcoal and 1000 µg oral

| time after | 1000 µg ex. 4, inhale + Charcoal Block N = 16 | | 1000 µg ex. 4, inhale N = 16 | | 1000 µg ex. 4, oral N = 16 | |
|---|---|---|---|---|---|---|
| dose (h) | geo. mean | geo. SD | geo. mean | geo. SD | geo. mean | geo. SD |
| 0 | >0.0500 | n.a. | >0.0500 | n.a. | >0.0500 | n.a. |
| 0.25 | 0.0583 | (1.78) | 0.0628 | (1.79) | 0.777 | (1.44) |

TABLE 39-continued

Geometric mean of plasma concentrations (in µg/L) over time of example 4 and (geometric standard deviation SD in %) after administration of 1000 µg inhale, 1000 µg inhale + charcoal and 1000 µg oral

| time after | 1000 µg ex. 4, inhale + Charcoal Block N = 16 | | 1000 µg ex. 4, inhale N = 16 | | 1000 µg ex. 4, oral N = 16 | |
|---|---|---|---|---|---|---|
| dose (h) | geo. mean | geo. SD | geo. mean | geo. SD | geo. mean | geo. SD |
| 0.5 | 0.261 | (1.56) | 0.316 | (1.32) | 3.64 | (1.30) |
| 0.75 | 0.491 | (1.46) | 0.622 | (1.32) | 5.28 | (1.32) |
| 1 | 0.662 | (1.43) | 0.869 | (1.29) | 5.68 | (1.35) |
| 1.5 | 0.900 | (1.39) | 1.16 | (1.30) | 4.69 | (1.31) |
| 2 | 0.969 | (1.38) | 1.20 | (1.31) | 3.32 | (1.33) |
| 2.5 | 1.02 | (1.31) | 1.18 | (1.32) | 2.26 | (1.31) |
| 3 | 0.933 | (1.33) | 1.07 | (1.32) | 1.60 | (1.36) |
| 4 | 0.812 | (1.29) | 0.927 | (1.31) | 1.01 | (1.46) |
| 6 | 0.508 | (1.31) | 0.583 | (1.30) | 0.424 | (1.33) |
| 8 | 0.373 | (1.37) | 0.415 | (1.36) | 0.233 | (1.31) |
| 12 | 0.220 | (1.43) | 0.250 | (1.37) | 0.126 | (1.38) |
| 15 | 0.157 | (1.46) | 0.181 | (1.43) | 0.0714 | (1.60) |
| 24 | 0.0931 | (1.81) | 0.106 | (1.69) | n.a. | n.a. |
| 28 | 0.0761 | (1.69) | 0.0793 | (1.77) | n.a. | n.a. |
| 32 | 0.0696 | (1.63) | 0.0698 | (1.79) | n.a. | n.a. |
| 36 | 0.054 | (1.79) | 0.058 | (1.86) | n.a. | n.a. |

TABLE 40

Geometric mean of plasma concentrations (in µg/L) over time of example 4 and (geometric standard deviation SD in %) after administration of 100 µg intravenously

| time after | 100 µg ex. 4, IV mg N = 15 | |
|---|---|---|
| dose (h) | geo. Mean | geo. SD |
| 0 | >0.0500 | n.a. |
| 0.25 | 1.76 | (1.20) |
| 0.5 | 2.52 | (1.11) |
| 0.75 | 2.68 | (1.14) |
| 1 | 2.99 | (1.12) |
| 1.5 | 3.15 | (1.17) |
| 2 | 3.07 | (1.19) |
| 2.083 | 2.57 | (1.16) |
| 2.25 | 1.42 | (1.20) |
| 2.5 | 0.559 | (1.19) |
| 2.75 | 0.264 | (1.23) |
| 3 | 0.132 | (1.24) |

E-2.4 Inhaled Administration of Single Doses to Patients with PAH or CTEPH to Investigate the Reduction of Pulmonary Vascular Resistance (PVR)

Patients with PAH or CTEPH aged 18 to 80 years were treated in a clinical phase 1b study with orally inhaled single doses* of 240 µg (2 capsules of 120 µg), 480 µg (1 capsule of 480 µg), 1000 µg (1 capsule of 1000 µg), 2000 µg (2 capsules of 1000 µg) or 4000 µg (4 capsules of 1000 µg) of a dry powder formulation comprising example 4 (see C-1, e.g. tables 17 and 20) inserted into a handheld inhalation device, inhaled by deep inhalative breath into the deep parts of the lung (*single dose means the administration of one dosage form/capsule as well as administration of two or more dosage forms/capsules simultaneously or consecutively within a short time period). The included patients had no background treatment with standard of care (SoC) medication for PAH or CTEPH (such as endothelin antagonists, prostanoids, phosphodiesterase type 5 inhibitor or soluble guanylate cyclase stimulators). Patients in this study underwent invasive right heart catheterization as medically indicated routine diagnostic. Primary objective of the study was to investigate the peak percent reduction from baseline in PVR. Patients had to have a baseline pulmonary artery pressure (mPAP) of ≥25 mmHg and a PVR of ≥400 dyn·sec·cm$^{-5}$ (5 Wood Units) and were not to show vasoresponsiveness to initial iNO inhalation testing to be included in the per protocol analysis. Plasma concentrations (pharmacokinetics) of the administered drug at several time points after administration were measured and safety and tolerability was assessed.

The study is divided into two parts, Part A and Part B. In Part A escalating aforementioned single doses were administered to patients without background treatment with standard of care (SoC) medication for PAH or CTEPH (such as endothelin antagonists, prostanoids, phosphodiesterase type 5 inhibitor or soluble guanylate cyclase stimulators). In Part B, after finalization of Part A, a selected dose from PartA will be tested in further patients without background SoC treatment (group 1) and additionally in patients on monotherapy with SoC (group 2) and on dual combination therapy with SoC (group 3).

The PVR is a derived parameter from parameters directly measured during the right heart catheterization procedure. The direct parameters included in the calculation are: mean pulmonary arterial pressure [mmHg](mPAP), pulmonary capillary wedge pressure [mmHg] (PCWP), and cardiac output [1/min] (CO). The PVR is calculated according to the formula: PVR [dyn*sec*cm$^{-5}$]=80*(mPAP−PCWP)/CO.

The study design is shown in FIG. 62 and the summary of the finalized Part A is shown in FIG. 63.

Overall 38 patients received a dose of dry powder of example 4. A total of 4 patients in each dose group were included into the per protocol set as planned (total 20 patients). A dose-dependent mean change of PVR from baseline could be clearly observed peaking in an enduring mean change of approximately −30% in the 2000 µg and 4000 µg groups (for details of PVR see FIG. 64 and table 41). The decreases in PVR were predominantly driven by decreases in pulmonary arterial pressure (for details of mean PAP see FIG. 65 and table 42). A mean peak change level of −20%—as the predefined relevant threshold level—was clearly exceeded peaking in the 2000 µg and 4000 µg groups (mean peak changes were: −21.0%, −16.1%, −25.9%, −38.1%, −36.3% for 240, 480, 1000, 2000, and 4000 µg, respectively). The magnitude of mean change in PVR of −30% from baseline was at the same level as for the inhaled competitor Treprostinil (Tyvaso®) after single administration in a historical comparison [Voswinckel et al, *Journal of American College of Cardiology* Vol. 48, No. 8, 2006 Oct. 17, 2006:1672-81]. However, the effect after example 4 was advantageously sustained with no decrease in response until the end of the measurement period of 3 h (a measurement period of >3 h was technically not feasible for the patients with right heart catheter in the study). A lung retention time beyond the 3 h of measurement (presumably over a time period of more than 12 hrs, up to 24 hrs after dry powder application) can be concluded from the long plasma half-life of example 4 measured in this study. Increase of systemic cGMP (cyclic Guanosine Monophosphate) confirmed strong target engagement of sGC activation. Overall good tolerability was seen including the highest dose of 4000 µg. Observed changes of systemic blood pressure, heart rate and oxygen saturation did not represent a safety concern at any dose. Overall, the observed changes of the pulmonary haemodynamic parameters (PVR and mPAP) without relevant changes in systemic hemodynamics are in well accordance with the desired effect of selective pulmonary vasodilation.

TABLE 41

Means and SDs for pulmonary vascular resistance (PVR) over time at baseline (0 D 00 H 00 M) and after inhalation (0 D 00 H 30 M until 0 D 03 H 00 M) of example 4 in patients with PAH or CTEPH (N = 4 each for 240, 480, 1000, 2000 and 4000 µg group, per protocol set). Relative changes from baseline are shown in FIG. 64.

|  | 240 µg, N = 4 | 480 µg, N = 4 | 1000 µg, N = 4 | 2000 µg, N = 4 | 4000 µg, N = 4 |
| --- | --- | --- | --- | --- | --- |
| 0 D 00 H 00 M | 788.338 ± 416.914 | 1055.863 ± 317.077 | 608.898 ± 135.153 | 468.608 ± 20.537 | 713.998 ± 117.204 |
| 0 D 00 H 30 M | 749.012 ± 398.928 | 1003.264 ± 300.639 | 645.387 ± 211.946 | 464.586 ± 58.200 | 616.894 ± 97.774 |
| 0 D 01 H 00 M | 734.427 ± 396.799 | 1007.504 ± 290.883 | 558.324 ± 169.860 | 421.730 ± 81.602 | 542.417 ± 97.103 |
| 0 D 01 H 30 M | 726.362 ± 364.099 | 1031.647 ± 252.210 | 542.130 ± 187.227 | 340.782 ± 82.566 | 573.812 ± 123.865 |
| 0 D 02 H 00 M | 710.844 ± 410.668 | 908.704 ± 252.569 | 487.951 ± 144.546 | 339.924 ± 105.884 | 501.071 ± 97.979 |
| 0 D 02 H 30 M | 716.209 ± 419.311 | 1038.344 ± 263.837 | 537.812 ± 204.640 | 338.404 ± 87.381 | 526.648 ± 144.679 |
| 0 D 03 H 00 M | 657.829 ± 291.191 | 909.265 ± 259.510 | 535.636 ± 235.678 | 327.284 ± 25.882 | 493.103 ± 130.480 |

TABLE 42

Means and SDs for mean pulmonary arterial pressure (mPAP) over time at baseline (0 D 00 H 00 M) and after inhalation (0 D 00 H 30 M until 0 D 03 H 00 M) of example 4 in patients with PAH or CTEPH (N = 4 each for 240, 480, 1000, 2000 and 4000 µg group, per protocol set). Relative changes from baseline are shown in FIG. 65.

|  | 240 µg, N = 4 | 480 µg, N = 4 | 1000 µg, N = 4 | 2000 µg, N = 4 | 4000 µg, N = 4 |
| --- | --- | --- | --- | --- | --- |
| 0 D 00 H 00 M | 42.8 ± 11.1 | 55.0 ± 8.6 | 34.3 ± 4.9 | 33.5 ± 3.4 | 46.0 ± 8.1 |
| 0 D 00 H 30 M | 42.5 ± 11.0 | 52.3 ± 8.4 | 33.8 ± 7.5 | 33.3 ± 6.3 | 43.0 ± 4.6 |
| 0 D 01 H 00 M | 44.3 ± 10.4 | 53.8 ± 9.1 | 31.8 ± 7.4 | 30.8 ± 5.6 | 41.3 ± 4.6 |
| 0 D 01 H 30 M | 43.0 ± 8.0 | 55.0 ± 8.0 | 32.0 ± 8.9 | 28.5 ± 7.3 | 40.3 ± 5.1 |
| 0 D 02 H 00 M | 39.5 ± 7.9 | 52.5 ± 7.9 | 32.3 ± 9.0 | 27.0 ± 6.1 | 40.0 ± 5.3 |
| 0 D 02 H 30 M | 42.0 ± 6.5 | 54.0 ± 9.7 | 33.5 ± 10.7 | 27.3 ± 6.0 | 39.8 ± 3.0 |
| 0 D 03 H 00 M | 39.0 ± 4.2 | 56.0 ± 11.1 | 34.0 ± 11.6 | 27.5 ± 5.2 | 39.8 ± 4.1 |

E-3. Further Characterization
E-3.1 Caco-2 Permeability Test

The in vitro permeation of a test compound across a Caco-2 cell monolayer is a well-established assay system to predict the permeability from the gastro-intestinal tract (1). The permeability of the compounds of the present invention in such Caco-2 cells was determined as described below:

Human caco-2 cells were seeded on 24-well insert plates and were allowed to grow for 14-16 days. For permeability studies, the test compounds were dissolved in DMSO and diluted to the final test concentration of 2 μM with transport buffer [Hanks' Buffered Salt Solution, Gibco/Invitrogen, further supplemented with glucose and HEPES]. For determination of the apical to basolateral permeability (PappA-B), the test compound solution was added to the apical side of the cell monolayer and transport buffer to the basolateral side of the monolayer; for determination of the basolateral to apical permeability (PappB-A), the test compound solution was added to the basolateral side of the cell monolayer and transport buffer to the apical side of the monolayer. Samples were taken from the donor compartment at the beginning of the experiment to confirm mass balance. After an incubation of 2 h at 37° C., samples were taken from both compartments. Samples were analyzed by LC-MS/MS, and the apparent permeability coefficients were calculated. Lucifer Yellow permeability was assayed for each cell monolayer to ensure cell monolayer integrity, and the permeability of Atenolol (low permeability marker) and Sulfasalazine (marker for active excretion) was determined for each batch as quality control.

TABLE 43

Permeability test

| Caco-2 (2 μM) | Papp A − B (nm/s) (mean +/− SD) | Papp B − A (nm/s) (mean +/− SD) | Efflux ratio |
|---|---|---|---|
| comparative example 11 (2.0 μM) | 15.1 ± 1.7 | 9.7 ± 0.6 | 0.64 ± 0.1 |
| Comparative example 2 (Riociguat) (2.4 μM) | 35 ± 8.4 | 367 ± 75 | 11 ± 3.3 |
| Comparative example 1 (Cinaciguat) (2.0 μM) | 31 ± 3.9 | 631 ± 71 | 20 ± 3.5 |

All three examples showed moderate permeability in Caco-2 cells.

In comparison to comparative example 2 (Riociguat) and comparative example 1 (Cinaciguat), comparative example 11 shows the lowest permeability with 15.1+/−1.7 nm/s. Additionally comparative example 11 does not show an efflux ratio. Efflux ratios are indicating transporter involvement in e.g. the gut and or the liver. Transporter proteins as e.g. permeability glycoprotein (=PgP) or Breast Cancer Resistance Protein (=BCRP) could influence the systemic exposure of a drug.

Comparative example 11 shows here a clear benefit, because it shows the lowest permeability and no transporter involvement seems to be present thus showing its suitability for a local inhalative treatment with a potentially very low systemic exposure.

E-3.2 Protein Binding
Protein Binding of Comparative Example 11 and Comparative Example 1 was Analyzed Via Transil Assay, Described Below.

The distribution of a test substance between Transil® (phosphatidylcholine lipid bilayers immobilized on silica beads) and plasma is a characteristic feature of any pharmaceutical compound and is dependent on its extent of binding to plasma proteins. By comparing the distribution between Transil® and buffer with the distribution between Transil® and plasma of any species of interest, the unbound fraction in the plasma of the respective animal species can be calculated in vitro. The respective plasma and buffer concentrations were determined via a radioactivity analysis. A detailed description of the method and its validation was published by Schuhmacher et al. (2).

Protein Binding of Comparative Example 2 was Analyzed Via Ultrafiltration Assay, Described Below.

For this assay, filter membranes of 30 kDa pore size were used to separate plasma and protein free ultrafiltrate. The driving force for filtration was applied by centrifugation. Prior to protein binding studies, the adsorption (recovery) of the test compound to the ultra-filtration device and the ability of the test compound to pass the filter membrane was checked by filtration of the test compound dissolved in buffer at four concentrations. Sufficient stability of the test compound and an almost complete recovery (≥90% of the actual amount of compound used for the experiment) was a prerequisite for the use of the ultrafiltration method. The amount of organic solvent added to the plasma may not exceed 2% of the total incubation volume. Blood samples were collected in heparinized tubes either pooled (all species except human and monkey) or individually (human and monkey) and were used within 24 h for incubation experiments in blood. Plasma was prepared by centrifugation of the heparinized blood samples. Plasma was stored at −15° C. until use. Plasma stability, Compound recovery, unspecific binding to the membrane and the test device as well as partitioning between blood cells and plasma were controlled. The substance-associated radioactivity was determined by liquid scintilation counting. With this analytical method, it is not possible to distinguish between unchanged substance and radioactive metabolites. For details of the radioanalytical methods and the work up of the samples see Goeller et al. (3). A description of the ultrafiltration method in general was published by Zhang et al. In 2012 (4).

TABLE 44 protein binding of compounds

| Fraction unbound (%) | Rat Wistar | Dog Beagle | Human (male) | Monkey Cynomolgus | Minipig (female) |
|---|---|---|---|---|---|
| Comparative Example 11 | 0.224 | 0.108 | 0.0764 | 0.0485 | 0.348 |
| Comparative example 2 (Riociguat) | 15.7 | 17.1 | 4.97 | n.d. | n.d. |
| Comparative example 1 (Cinaciguat) | 0.351 | 1.12 | 0.392 | 0.0799 | n.d. | n.d. not determined

Comparative example 11 and comparative example 1 (cinaciguat) showed very high protein binding, with free fractions below 1% in all species investigated. But, example 1 showed the lowest free fractions in all tested species, where comparative results are given. In rat plasma the fraction unbound of comparative example 11 is 1.6 times lower, in human and monkey plasma free fractions is 2 times lower and in dog plasma fraction unbound is 10 times lower than comparative example 1. Comparative example 2 (Riociguat) showed much higher free fractions between 15.7 and 4.97%.

High protein binding is seen as an indicator for high lung selectivity as described by Begg et al. (5). Comparative example 11 shows therefore beneficial properties over the comparative examples 1 and 2.

REFERENCES

1. Artursson P and Karlsson J. Correlation between oral drug absorption in humans and apparent drug permeability coefficients in human intestinal epithelial (Caco-2) cells, High-throughput determination of the free fraction of drugs strongly bound to plasma proteins. Biochem. Biophys, 1991. 175 (3), 880-885.
2. Schuhmacher J, Kohlsdorfer C, Buhner K, Brandenburger T, Kruk R. High-throughput determination of the free fraction of drugs strongly bound to plasma proteins. J Pharm Sci. 2004; 93(4):816-30.
3. Goeller G, Daehler H P, Winkelmann H: Determination of Radioactivity in Liquid and Solid Biological Samples from Pharmacokinetic Experiments. 1996, Bayer Pharma Report No. 25507.
4. Zhang F, Xue J, Shao J, Jia. Compilation of 222 drugs' plasma protein binding data and guidance for study designs. Drug Discovery Today 2012; 9-10(17):475-485.
5. Begg M, Edwards C D, Hamblin N, Pefani E, Wilson R, Gilbert J, Vitulli G, Mallett D, Morrell J, Hingle M I, Uddin S, Ehtesham F, Marotti M, Harrell A, Newman C F, Fernando D, Clark J, Cahn A, Hessel E M. Translation of Inhaled Drug Optimization Strategies intoClinical Pharmacokinetics and Pharmacodynamics Using GSK2292767A, a Novel Inhaled Phosphoinositide 3-Kinase d Inhibitor. J. Pharmacol. Exp. Ther. 2019; 369: 443-453.

FIGURES

FIG. 1a+1b: capsule based single-unit dose inhaler
FIG. 2: Observed (symbols) and fitted (solid lines) pulmonary arterial pressure (=PAP) changes after administration of 0.15, 0.5, 1.5 and 5 µg/kg comparative example 11
FIG. 3: Maximal expected PAP reduction for a 60 kg human at the corresponding lung deposited dose
FIG. 4: X-Ray powder diffractogram of the amorphous residue build on salt screening experiments with L-arginine
FIG. 5: X-Ray powder diffractogram of the Semihydrate, example 6a
FIG. 6: X-Ray powder diffractogram of the Monohydrate I, example 6b
FIG. 7: X-Ray powder diffractogram of the Monohydrate II, example 6c
FIG. 8: X-Ray powder diffractogram of the 1,25-Hydrate, example 6d
FIG. 9: X-Ray powder diffractogram of the Sesquihydrate, example 6e
FIG. 10: X-Ray powder diffractogram of the Dihydrate, example 6f
FIG. 10a: X-Ray powder diffractogram of the Dihydrate after drying, example 6f
FIG. 11: X-Ray powder diffractogram of the amorphous form, example 6g
FIG. 12: Raman spectrum of the Semihydrate, example 6a
FIG. 13: Raman spectrum of the Monohydrate I, example 6b
FIG. 14: Raman spectrum of the Monohydrate II, example 6c
FIG. 15: Raman spectrum of the 1,25-Hydrate, example 6d
FIG. 16: Raman spectrum of the Sesquihydrate, example 6e
FIG. 17: Raman spectrum of the Dihydrate, example 6f
FIG. 18: Raman spectrum of the amorphous form, example 6g
FIG. 19: IR spectrum of the Semihydrate, example 6a
FIG. 20: IR spectrum of the Monohydrate I, example 6b
FIG. 21: IR spectrum of the Monohydrate II, example 6c
FIG. 22: IR spectrum of the 1,25-Hydrate, example 6d
FIG. 23: IR spectrum of the Sesquihydrate, example 6e
FIG. 24: IR spectrum of the Dihydrate, example 6f
FIG. 25: IR spectrum of the amorphous form, example 6g
FIG. 26: DSC- and TGA-thermogram of the Semihydrate, example 6a
FIG. 27: DSC- and TGA-thermogram of the Monohydrate I, example 6b
FIG. 28: DSC- and TGA-thermogram of the Monohydrate II, example 6c
FIG. 29: DSC- and TGA-thermogram of the 1,25-Hydrate, example 6d
FIG. 30: DSC- and TGA-thermogram of the Sesquihydrate, example 6e
FIG. 31: DSC- and TGA-thermogram of the Dihydrate, example 6f
FIG. 32: DSC- and TGA-thermogram of the amorphous form, example 6g, amorphous form
FIG. 33: X-Ray powder diffractogram of comparative example 11, amorphous form
FIG. 34: X-Ray powder diffractogram of example 1, monohydrate II
FIG. 35: X-Ray powder diffractogram of example 2 before micronization, monohydrate II
FIG. 36: X-Ray powder diffractogram of example 2 after micronization, monohydrate II, partial amorphization
FIG. 37: X-Ray powder diffractogram of example 3, monohydrate I
FIG. 38: X-Ray powder diffractogram of example 4, monohydrate I
FIG. 39: X-Ray powder diffractogram of example 5, monohydrate I
FIG. 40: X-Ray powder diffractogram of example 7 (storage stability): starting material for storage stability, monohydrate II
FIG. 41: X-Ray powder diffractogram of example 7 (storage stability): material after one month storage stability testing at 25° C. and 60% relative humidity in polyethylene, monohydrate I
FIG. 42: Overlay of X-ray powder diffractograms of example 8b (micronization): starting material (monohydrate II) (bottom line) and material after micronization (monohydrate II with amorphous amounts, PTFE coated jet mill, 25° C.) (top line)
FIG. 43: X-ray powder diffractogram of example 8a (micronization): material after micronization (monohydrate I with amorphous amounts, VA jet mill, 25° C.)
FIG. 44: X-ray powder diffractogram (example 8e) (micronization): material after micronization (monohydrate I)
FIG. 45: Effects of vehicle solution, comparative example 11 (10, 30 and 100 µg/kg nominal dose) and Ventavis (10 µg/kg nominal dose) after inhaled application in the PAH minipigs model. Data are expressed as % changes in PAP and BP vs baseline (10 min interval prior to start of nebulization). Data are mean f SEM. Nebulizsation interval took 5-7 min for all compounds (grey bar).

FIG. 46: Effects of lactose as well as lactose formulation I (7.5 µg/kg) after intratracheal application. Data are mean±SEM (n=3); Intratracheal application was conducted with PennCentury dry powder insufflator and Air Pump; BP: arterial blood pressure; PAP: pulmonary artery pressure; SEM: standard error of the mean FIG. 47: Effects of lactose as well as lactose formulation II (22.5 µg/kg) after intratracheal application. Data are mean±SEM (n=3); Intratracheal application was conducted with PennCentury dry powder insufflator and Air Pump; BP: arterial blood pressure; PAP: pulmonary artery pressure; SEM: standard error of the mean FIG. 48: Effects of lactose and micronized sesquihydrate, e.g. ex. 6e (375 µg/kg) after intratracheal application. Data are mean±SEM (n=3) Intratracheal application was conducted with PennCentury dry powder insufflator and Air Pump; BP: arterial blood pressure; PAP: pulmonary artery pressure; SEM: standard error of the mean FIG. 49: Effects of intratracheal application of different lactose vehicles, lactose formulation I (7.5 µg/kg), lactose formulation 11 (22.5 µg/kg) and micronized sesquihydrate example 6e (375 µg/kg). Data are shown as % changes vs. prevalues as mean±SEM (n=3)

FIG. 50: Effects of comparative example 11 after intratracheal application of different hydrates micronized monohydrate II (example 2), micronized semihydrate (example 6a) and micronized sesquihydrate (example 6e), on BP and PAP. Data are shown as absolute values [mmHg] as mean±SEM (n=3)

FIG. 51: Effects of comparative example 11 after intratracheal application of different hydrates micronized monohydrate II (example 2), micronized semihydrate (example 6a) and micronized sesquihydrate (example 6e), on BP and PAP. Data are shown as absolute values [mmHg] as mean±SEM (n=3)

FIG. 52: Means±SDs for cGMP (nmol/L)—comparison of pretreatment (day −1), first (day 1) and last (day 8) treatment days for the 480 µg (example 2) dose group (SAF, N=9)

FIG. 53: Means±SDs for cGMP (nmol/L)—comparison of pretreatment (day −1), first (day 1) and last (day 8) treatment days for the 1000 µg (example 2) dose group (SAF, N=9)

FIG. 54: Means±SDs for cGMP (nmol/L)—comparison of pretreatment (day −1), first (day 1) and last (day 8) treatment days for the 2000 µg (example 2) dose group (SAF, N=9)

FIG. 55: Means±SDs for cGMP (nmol/L)—comparison of treatment days for the placebo group (SAF, N=9)

FIG. 56: Means (N=9)±SDs for cGMP in body liquids over time (nmol/L) on baseline day (−1 d02 h-0 d00 h) first inhalation day (0 d00 h-2 d00 h), trough measurements 2 d00 h-7 d00 h) and after 7 days inhalation (7 d00 h-10 d00 h).

FIG. 57: Means (N=36, 12 each for 480, 1000 and 2000 µg, example 2) and SDs for total specific airway resistance (kPa/sec) over time: screening 1/2, baseline day (−1 d00 h-0 d00 h) first inhalation day (0 d00 h-0 d06 h), measurements after inhalations 2 d02 h-6 d04 h) and after 7 days inhalation (7 d00 h-7 d06 h).

FIG. 58: Means for cGMP difference to baseline for Placebo (N=4) and 1000 g, (N=17) example 2) over time (nmol/L) on pretreatment day (−1 d00 h--0 d09 h) first inhalation day (−0 d02 h-1 d00 h;), measurements prior and after inhalations 2 d00 h-2 d12 h, 6 d00 h-6 d12 h, 10 d00 h-10 d12 h) (profile days), at trough prior inhalation on days 3 d-5 d, 7 d-9 d, 11 d-12 d) and for last of 14 days inhalation (12 d22 h-20 d00 h).

FIG. 59: scheme of the treatments conducted to investigate lung deposition

FIG. 60: Geometric means and standard deviations for concentrations of example 4 (µg/L) in plasma, on semilogarithmic scale.

FIG. 61: Part of the dose reached the mouthpiece (emitted dose) and parts of the does remains in the capsule, in the device, the deposited lung dose and part of the dose reached the GIT tract FIG. 62: study design of clinical study in patients with PAH or CTEPH FIG. 63: summary of conducted Part A of clinical study in patients with PAH or CTEPH FIG. 64: Means and SDs for relative changes (%) from baseline (0 D 00 H00M) of pulmonary vascular resistance (PVR) over time after inhalation (0 D 00 H30M until 0 D 03 H00M) of example 4 in patients with PAH or CTEPH (N=4 each for 240, 480, 1000, 2000 and 4000 µg group, per protocol set)

FIG. 65: Means and SDs for relative changes (%) from baseline (0 D 00 H00M) of mean pulmonary arterial pressure (mPAP) over time after inhalation (0 D 00 H30M until 0 D 03 H00M) of example 4 in patients with PAH or CTEPH (N=4 each for 240, 480, 1000, 2000 and 4000 µg group, per protocol set).

FIG. 66: Manufacture flow chart for compounds of the present disclosure.

The invention claimed is:
1. A crystalline monohydrate form of Compound 1:

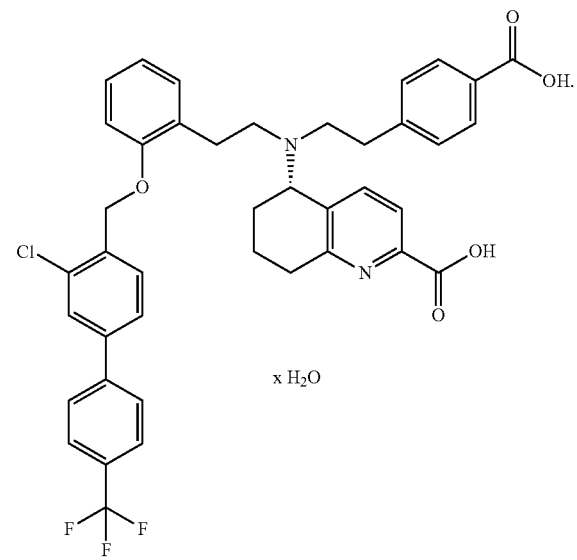 [SMILES: O=C(O)c1ccc(CCN(CCc2ccccc2OCc2ccc(-c3ccc(C(F)(F)F)cc3)cc2Cl)[C@H]2CCCc3nc(C(=O)O)ccc32)cc1]

x H$_2$O

2. The crystalline monohydrate form of claim 1, having X-ray powder diffraction reflections at 12.8±0.2 and 29.2±0.2, using Cu K alpha radiation when measured at 25° C.

3. The crystalline monohydrate form of claim 2, having at least one additional reflection at 6.9±0.2 or 7.2±0.2°2θ, using Cu K alpha radiation when measured at 25° C.

4. The crystalline monohydrate form of claim 2, having at least one additional reflection at 6.9±0.2 or 7.3±0.2°2θ, using Cu K alpha radiation when measured at 25° C.

5. The crystalline monohydrate form of claim 2, having at least one additional reflection at 6.9±0.2, 7.2±0.2, 7.3±0.2, 15.2±0.2, or 23.0±0.2°2θ, using Cu K alpha radiation when measured at 25° C.

6. The crystalline monohydrate form of claim 1, having X-ray powder diffraction reflections at 12.8±0.2, 16.0±0.2, and 25.8±0.2, using Cu K alpha radiation when measured at 25° C.

7. The crystalline monohydrate form of claim 6, having at least one additional reflection at 6.9±0.2 or 7.2±0.2°2θ, using Cu K alpha radiation when measured at 25° C.

8. The crystalline monohydrate form of claim 6, having at least one additional reflection at 6.9±0.2 or 7.3±0.2°2θ, using Cu K alpha radiation when measured at 25° C.

9. The crystalline monohydrate form of claim 6, having at least one additional reflection at 6.9±0.2, 7.2±0.2, 7.3±0.2, or 15.2±0.2°2θ, using Cu K alpha radiation when measured at 25° C.

10. The crystalline monohydrate form of claim 1, having X-ray powder diffraction reflections at 12.8±0.2, 20.5±0.2, and 25.8±0.2, using Cu K alpha radiation when measured at 25° C.

11. The crystalline monohydrate form of claim 10, having at least one additional reflection at 6.9±0.2 or 7.2±0.2°2θ, using Cu K alpha radiation when measured at 25° C.

12. The crystalline monohydrate form of claim 10, having at least one additional reflection at 6.9±0.2 or 7.3±0.2°2θ, using Cu K alpha radiation when measured at 25° C.

13. The crystalline monohydrate form of claim 10, having at least one additional reflection at 6.9±0.2, 7.2±0.2, 7.3±0.2, 15.2±0.2, or 25.1±0.2°2θ, using Cu K alpha radiation when measured at 25° C.

14. The crystalline monohydrate form of claim 1, having at least three X-ray powder reflections selected from 5.7±0.2, 6.9±0.2, 7.2±0.2, 7.3±0.2, 9.9±0.2, 10.4±0.2, 10.6±0.2, 11.1±0.2, 11.5±0.2, 12.0±0.2, 12.3±0.2, 12.4±0.2, 12.8±0.2, 13.7±0.2, 14.1±0.2, 14.3±0.2, 15.2±0.2, 15.6±0.2, 16.0±0.2, 16.9±0.2, 17.2±0.2, 17.5±0.2, 17.7±0.2, 18.0±0.2, 18.4±0.2, 18.8±0.2, 19.2±0.2, 19.9±0.2, 20.2±0.2, 20.5±0.2, 20.7±0.2, 21.3±0.2, 21.9±0.2, 22.2±0.2, 22.5±0.2, 23.0±0.2, 23.4±0.2, 23.7±0.2, 24.1±0.2, 25.1±0.2, 25.8±0.2, 26.0±0.2, 26.4±0.2, 28.9±0.2, 29.2±0.2, 29.4±0.2, 30.6±0.2, 31.1±0.2, 32.2±0.2, and 35.3±0.2°2θ, using Cu K alpha radiation when measured at 25° C.

15. The crystalline monohydrate form of claim 2, not having a reflection at 3.1±0.2 or 9.3±0.2°2θ, using Cu K alpha radiation when measured at 25° C.

16. The crystalline monohydrate form of claim 6, not having a reflection at 3.1±0.2 or 9.3±0.2°2θ, using Cu K alpha radiation when measured at 25° C.

17. The crystalline monohydrate form of claim 10, not having a reflection at 3.1±0.2 or 9.3±0.2°2θ, using Cu K alpha radiation when measured at 25° C.

18. The crystalline monohydrate form of claim 14, not having a reflection at 3.1±0.2 or 9.3±0.2°2θ, using Cu K alpha radiation when measured at 25° C.

19. The crystalline monohydrate form of claim 2, not having a reflection at 6.1±0.2 or 8.5±0.2°2θ, using Cu K alpha radiation when measured at 25° C.

20. The crystalline monohydrate form of claim 6, not having a reflection at 6.1±0.2 or 8.5±0.2°2θ, using Cu K alpha radiation when measured at 25° C.

21. The crystalline monohydrate form of claim 10, not having a reflection at 6.1±0.2 or 8.5±0.2°2θ, using Cu K alpha radiation when measured at 25° C.

22. The crystalline monohydrate form of claim 14, not having a reflection at 6.1±0.2 or 8.5±0.2°2θ, using Cu K alpha radiation when measured at 25° C.

23. The crystalline monohydrate form of claim 6, not having a reflection at one of 3.1 0.2, 6.1±0.2, 7.6±0.2, 7.9±0.2, 8.5±0.2, 9.3±0.2, 14.8±0.2, 30.0±0.2, or 31.6±0.2°2θ, using Cu K alpha radiation when measured at 25° C.

24. The crystalline monohydrate form of claim 6, not having a reflection at one of 3.1 0.2, 6.1±0.2, 7.6±0.2, 7.9±0.2, 8.5±0.2, 9.3±0.2, 14.8±0.2, 30.0±0.2, or 31.6±0.2°2θ, using Cu K alpha radiation when measured at 25° C.

25. The crystalline monohydrate form of claim 10, not having a reflection at one of 3.1 0.2, 6.1±0.2, 7.6±0.2, 7.9±0.2, 8.5±0.2, 9.3±0.2, 14.8±0.2, 30.0±0.2, or 31.6±0.2°2θ, using Cu K alpha radiation when measured at 25° C.

26. The crystalline monohydrate form of claim 14, not having a reflection at one of 3.1 0.2, 6.1±0.2, 7.6±0.2, 7.9±0.2, 8.5±0.2, 9.3±0.2, 14.8±0.2, 30.0±0.2, or 31.6±0.2°2θ, using Cu K alpha radiation when measured at 25° C.

27. The crystalline monohydrate form of claim 1, having a Raman spectrum with at least the following band maxima: 3073, 2950, 2937, 1685, 1616, 1527, 1293, 1278, and 1259 cm$^{-1}$.

* * * * *

UNITED STATES PATENT AND TRADEMARK OFFICE
CERTIFICATE OF CORRECTION

| | |
|---|---|
| PATENT NO. | : 12,202,805 B2 |
| APPLICATION NO. | : 18/506737 |
| DATED | : January 21, 2025 |
| INVENTOR(S) | : Britta Olenik et al. |

It is certified that error appears in the above-identified patent and that said Letters Patent is hereby corrected as shown below:

On the Title Page

Item (54) and in the Specification, Column 1, Lines 1-9, please replace:
"PROCESS FOR PREPARING
(5S)-{[2-(4-CARBOXYPHENYL)ETHYL]
|2-(2-{|3-CHLORO-4'-(TRIFLUOROMETHYL)
BIPHENYL-4- YL]METHOXY}PHENYL)
ETHYL]AMINO}-5,6,7,8-
TETRAHYDROQUINOLINE-2-CARBOXYLIC
ACID AND ITS CRYSTALLINE FORMS FOR
USE AS PHARMACEUTICALLY ACTIVE
COMPOUND"
With:
--CRYSTALLINE FORMS OF
(5S)-{[2-(4-CARBOXYPHENYL)ETHYL]
|2-(2-{|3-CHLORO-4'-(TRIFLUOROMETHYL)
BIPHENYL-4-YL]METHOXY}PHENYL)
ETHYL]AMINO}-5,6,7,8-
TETRAHYDROQUINOLINE-2-CARBOXYLIC
ACID--

In the Claims

At Column 188, Claim number 2, Line number 63, please replace:
"29.2±0.2, using Cu K alpha radiation when measured at 25°"
With:
--29.2±0.2°2θ, using Cu K alpha radiation when measured at 25°--

At Column 189, Claim number 6, Line number 10, please replace:
"and 25.8±0.2, using Cu K alpha radiation when measured at"

Signed and Sealed this
Twentieth Day of May, 2025

Coke Morgan Stewart
*Acting Director of the United States Patent and Trademark Office*

With:
--and 25.8±0.2°2θ, using Cu K alpha radiation when measured at--

At Column 189, Claim number 10, Line number 25, please replace:
"and 25.8±0.2, using Cu K alpha radiation when measured at"
With:
--and 25.8±0.2°2θ, using Cu K alpha radiation when measured at--

At Column 190, Claim number 23, Line number 25, please replace:
"having a reflection at one of 3.1 0.2, 6.1±0.2, 7.6±02,"
With:
--having a reflection at one of 3.1±0.2, 6.1±0.2, 7.6±0.2,--

At Column 190, Claim number 24, Line number 30, please replace:
"having a reflection at one of 3.1 0.2, 6.1±0.2, 7.6±0.2,"
With:
--having a reflection at one of 3.1±0.2, 6.1±0.2, 7.6±0.2,--

At Column 190, Claim number 25, Line number 35, please replace:
"having a reflection at one of 3.1 0.2, 6.1±0.2, 7.6±0.2,"
With:
--having a reflection at one of 3.1±0.2, 6.1±0.2, 7.6±0.2,--

At Column 190, Claim number 26, Line number 40, please replace:
"having a reflection at one of 3.1 0.2, 6.1±0.2, 7.6±0.2,"
With:
--having a reflection at one of 3.1±0.2, 6.1±0.2, 7.6±0.2,--